(12) United States Patent
Albani

(10) Patent No.: US 7,807,377 B2
(45) Date of Patent: *Oct. 5, 2010

(54) METHOD OF ISOLATING ANTIGEN-SPECIFIC T CELLS EMPLOYING ARTIFICIAL ANTIGEN PRESENTING CELLS

(75) Inventor: Salvatore Albani, 4204 Sorrento Valley Blvd., Suites A-C, San Diego, CA (US) 92121

(73) Assignee: Salvatore Albani, Tuscon, AZ (US)

(*) Notice: Subject to any disclaimer, the term of this patent is extended or adjusted under 35 U.S.C. 154(b) by 756 days.

This patent is subject to a terminal disclaimer.

(21) Appl. No.: 10/960,855

(22) Filed: Oct. 6, 2004

(65) Prior Publication Data
US 2005/0208120 A1   Sep. 22, 2005

Related U.S. Application Data

(63) Continuation-in-part of application No. 09/756,983, filed on Jan. 9, 2001, now Pat. No. 6,787,154, which is a continuation-in-part of application No. 09/421,506, filed on Oct. 19, 1999, now Pat. No. 7,022,483, and a continuation-in-part of application No. PCT/US99/24666, filed on Oct. 19, 1999.

(60) Provisional application No. 60/105,018, filed on Oct. 20, 1998, provisional application No. 60/510,645, filed on Oct. 10, 2003.

(51) Int. Cl.
*G01N 33/53* (2006.01)

(52) U.S. Cl. ............... 435/7.1; 435/7.24; 424/1.57; 424/9.34; 424/450

(58) Field of Classification Search .............. None
See application file for complete search history.

(56) References Cited

U.S. PATENT DOCUMENTS

| | | |
|---|---|---|
| 4,400,376 A | 8/1983 | Sanderson |
| 4,478,823 A | 10/1984 | Sanderson |
| 4,690,915 A | 9/1987 | Rosenberg |
| 4,885,172 A | 12/1989 | Bally et al. |
| 5,194,253 A | 3/1993 | Garrido |
| 5,216,132 A | 6/1993 | Basi |
| 5,283,058 A | 2/1994 | Faustman |
| 5,468,481 A | 11/1995 | Sharma et al. |
| 5,595,881 A | 1/1997 | Kendrick et al. |
| 5,623,056 A | 4/1997 | Tykocinski et al. |
| 5,635,363 A | 6/1997 | Altman et al. |
| 5,693,522 A | 12/1997 | Chada et al. |
| 5,734,023 A | 3/1998 | Nag et al. |
| 5,750,356 A | 5/1998 | Spack et al. |
| 5,756,666 A | 5/1998 | Takiguchi et al. |
| 5,763,585 A | 6/1998 | Nag |
| 5,773,570 A | 6/1998 | Carson et al. |
| 5,776,487 A | 7/1998 | Wilson et al. |
| 5,780,319 A | 7/1998 | Maxfield Wilson et al. |
| 5,788,963 A | 8/1998 | Murphy et al. |
| 5,827,516 A | 10/1998 | Urban et al. |
| 5,834,015 A | 11/1998 | Oleske et al. |
| 5,861,290 A | 1/1999 | Goldsmith et al. |
| 5,876,721 A | 3/1999 | Alexander et al. |
| 5,880,103 A | 3/1999 | Urban et al. |
| 5,891,689 A | 4/1999 | Takle et al. |
| 6,576,428 B1 * | 6/2003 | Assenmacher et al. ....... 435/7.1 |

FOREIGN PATENT DOCUMENTS

WO    97/46256    11/1997

OTHER PUBLICATIONS

Janeway and Travers. ImmunoBiology. 1994. 7:9-10.*
Oertli, D., et al. Cin. Exp. Immunol. 1997; 110:144-149.*
Walden, "Antigen presentation by liposomes," *Hamatologie Und Bluttransfusion* 29:481-5 (1985).
Walden et al., "Induction of regulatory T-lymphocyte responses by liposomes carrying major histocompatibility complex molecules and foreign antigen," *Nature* 315(6017):327-329 (1985).
Albani et al, "Positive selection in autoimmunity: Abnormal immune responses to a bacterial dnaJ antigenic determinant in patients with early rheumatoid arthritis," *Nat. Med.* 1:448-452 (1995).
Albani et al., "A multistep molecular mimicry hypothesis for the pathogenesis of rheumatoid arthritis," *Immunology Today* 17:466-470 (1996).
Albani et al., "Diagnostic value of a lymphocyte stimulation test in cow milk protein intolerance," *Annals of Allergy* 63(12):489-192 (1989).
Alexander et al., "Development of high potency universal DR-restricted helper epitopes by modification of high affinity DR-blocking peptides," *Immunity* 1:751-761 (1994).
Altman et al. "Phenotypic analysis of antigen-specific T lymphocytes," *Science* 274:94-96 (1996).

(Continued)

*Primary Examiner*—G. R Ewoldt
(74) *Attorney, Agent, or Firm*—Douglas C. Murdock; Daniel M. Chambers; BioTechnology Law Group

(57) ABSTRACT

The present invention concerns artificial antigen presenting cells (aAPCs) and methods of making and using the same, for example, to isolate, identify, and expand T cell populations specifically reactive against a disease-associated antigenic peptide, as well as to modulate responses of antigen-specific T cells both in vivo, ex vivo, and in vitro. Accordingly, the aAPCs of the invention can be used to treat conditions that would benefit from modulation of a T cell response, for example, autoimmune disorders, allergies, cancers, viral infections, and graft rejection. In certain preferred embodiments, the aAPCs are liposomes comprised of MHC:peptide complexes and accessory molecules. Other molecules, such as co-stimulatory molecules and adhesion molecules, can also be included in the compositions of the invention. In other embodiments, the aAPCs are comprised of a scaffold to which a plurality of MHC:peptide complexes and accessory molecules (as well as other molecules) can be attached at high density.

2 Claims, 37 Drawing Sheets
(3 of 37 Drawing Sheet(s) Filed in Color)

OTHER PUBLICATIONS

Anderson et al., "Weak peptide agonists reveal functional differences in B7-1 and B7-2 costimulation of human T cell clones," *J. Immunol.* 159(4):1669-1675 (1997).

Arimilli et al., "Refolding and reconstitution of functionally active complexes of human leukocyte antigen DR2 and myelin basic protein peptide from recombinant α and β polypeptide chains," Journal of Biological Chemistry 270(2):971-977 (1995).

Bachmann et al., "Distinct roles for LFA-1 and CD28 during activation of naïve T cells: Adhesion versus costimulation," *Immunity* 7:549-557 (1997).

Barnado et al., "Allele-specific HLA-B*15 typing by PCR-SSP and its application to four distinct ethnic populations," *Tissue Antigens* 51(3):293-300 (1998).

Blotta et al., "Cross-linking of the CD40 ligand on human CD4+ T lymphocytes generates a costimulatory signal that up-regulates IL-4 synthesis," *J. Immunol.* 156:3133-3140 (1996).

Bona et al., "Towards development of T-cell vaccines," Immunology Today (Mar. 1998).

Bonnin et al., "Mucosal modulation of immune responses to heat shock proteins in autoimmune arthritis," Biotherapy 10:213-221 (1998).

Bonnin et al., "Ontogemy of synonymous T cell populations with specificity for a self-MHC epitope mimicked by a bacterial homologue: an antigen specific T cell analysis in a non-transgenic system," *Eur. J. Immunol.* (In press) (1999).

Brian et al., "Allogeneic stimulation of cytotoxic T cells by supported planar membranes," Proc. Natl. Acad. Sci. 61:6159-6163 (1984).

Buus et al., "Isolation and characterization of antigen-la complexes involved in T cell recognition," Cell 47:1071-1077 (1986).

Carlsson et al., "Protein thiolation and reversible protein-protein conjugation," Biochem. J. 173:723-737 (1978).

Clark et al., "Antigen-specific deletion of cloned T cells using peptide-toxin conjugate complexed with purified class II major histocompatibility complex antigen," Journal of Biological Chemistry 269(1):94-99 (1994).

Crawford et al., "Detection of antigen specific T cells with multivalent soluble class II MHC covalent peptide complexes," Immunity 8:675-682 (1998).

Demotz, "DR αβ dimers released from complexes with invariant chain fail to stimulate alloreactive T cell clones," Eur. J. Immunology 23:2100-2108 (1993).

Demotz, "The ligands of the class II major histocompatibility complex-restricted T cells," Chem. Immunol. 57:18-38 (1993).

Ding et al., "Activation of CD4+ T cells by delivery of the B7 costimulatory signal on bystander antigen-presenting cells (trans-costimutation)," European Journal of Immunology 24(4):859-868 (1994).

Dubey et al., "Naïve and effector CD4 T cells differ in their requirements for T cell receptor versus costimulatory signals," *J. Immunol.* 157:3820-3289 (1996).

Eberl et al., "A simple mathematical model for the functional peptide/MHC/TCR interactions," Journal of Immunology 154:219-225 (1995).

Finger et al., "Adhesion through L-selectin requires a threshold hydrodynamic shear," Nature 379:268-269 (1996).

Flynn, "CD4 T cell cytokine differentiation: The B cell activation molecule, OX40 ligand, Instructs CD4 T cells to express interleukin 4 and upregutates expression of the chemokine receptor, Blr-1," *Journal of Experimental Medicine* 168(2):297-304 (1998).

Frumento et al., "Cellular mechanisms of artificial peptides binding to HLA, International Journal of Artificial Organs," 14:518-522 (1991).

Garboczi et al., "Structure of the complex between human T-cell receptor, viral peptide and HLA-A2," Nature 384:134-141 (1996).

Garcia et al., "Structural basis of plasticity in T cell receptor recognition of a self peptide-MHC antigen," Science 279:1166-1172 (1998).

Gaur et al, "Amelioration of relapsing experimental autoimmune enoephalomyetitis with altered myelin basic protein peptides Involves different cellular mechanisms," *J. of Neuroimmunol.* 74:149-158 (1997).

Gay et al., "The major histocompatibility complex-restricted antigen receptor on T cells," *Journal of Immunology* 136(6):2026-2032 (1986).

Gimmi et al., "Human T-cell clonal energy is induced by antigen presentation in the absence of B7 costimulation," Proc. Natl. Acad. Sci. 90:6586-6590 (1993).

Grakoul et al., "The immunological synapse: A molecular machine controlling T cell activation," Science 285:221-227 (1999).

Greten et al., "Direct visualization of antigen-specific T cells: HTLV-1 Tax11-19 specific CD8+ T cells are actvated in peripheral blood and accumulate in cerebrospinal fluid from HAM/TSP patients," *Proc. Natl. Acad. Sci.* 95:7568-7573 (1998).

Hakamada-Taguchi et al., "Expression and co-stimulatory function of B7-2 on murine CD4+ T cells,"*European Journal of Immunology* 28:865-873 (1998).

Hamad et al., "Potent T cell activation with dimeric peptide-major histocompatibility complex class II ligand: The role CD4 coreceptor," *J. Exp. Med.* 9:1633-1640 (1998).

Harder et al., "Lipid domain structure of the plasma membrane revealed by patching of membrane components," Journal of Cell Biology 141:929-942 (1998).

Hayden et al., "Costimulaiion by CD28 sFv expressed on the tumor cell surface or as a soluble bispecific molecule targeted to the L6 carcinoma antigen," Tissue Antigens 46:242-254 (1996).

Holmgren et al., "Interaction of cholera toxin and membrane $G_{M1}$ ganglioside of small intestine," Proc. Natl. Acad. Sci. 72:2520-2524 (1975).

Huby et al., "Intracellular phosphotyrosine Induction by major histocompatibility complex class II requires co-aggregation with membrane rafts," Journal of Biological Chemistry 274:22591-22596 (1999).

Hunt et al., "Peptides presented to the immune system by the murine class II major histocompatibility complex molecule I-$A^d$," *Science* 256:1817-1820 (1992).

Ignatowicz et al.; "The repertoire of T cells shaped by a single MHC/peptide ligand" *Cell* 84:521-529 (1996).

Jameson et al., "Positive selection of thymocytes," *Ann. Rev. Immunol.* 13:93-126 (1995).

Janeway, "Ligands for the T cell receptor: hard times for avidity models," Immunology Today 16(5)223-225 (1995).

Kirberg et al., "Peripheral T cell survival requires continual ligation of the T cell receptor to major histocompatibilty complex-encoded molecules," *J. Exp. Med.* 186(8):1269-1275 (1997).

Kitagawa et al., "Enzyme coupled immunoassay of insulin using a novel coupling reagent," J. Biochem. 79:233-236 (1976).

Kurosky et al., "Covalent structure of the β chain of cholera enterotoxin," Journal of Biological Chemistry 252:7257-7264 (1977).

La Cava et al, "Genetic bias in Immune response to a cassette shared by different microorganisms in patients with rheumatoid arthritis," *J. Clin. Invest.* 100:658-663 (1997).

Lai, "Determination of the primary structure of cholera toxin B subunit," Journal of Biological Chemistry 252:7249-7256 (1977).

Lehmann et al., "Spreading of T-cell autoimmunity to cryptic determinants of an autoantigen," Nature 358(6382):155-157 (1992).

Lessin et al., "Molecular diagnosis of cutaneous T-cell lymphoma: Polymerese chain reaction amplfication of T-cell antigen receptor β-chain gene rearrangements," *J. Invest. Dermatol.* 98:299-302 (1991).

Luxembourg et al., "Biomagnetic isolation of antigen-specific CD8+ T cells usable in Immunotherapy," Nature Biotech. 16:281-285 (1998).

Marsh, D.A., In: *CRC Handbook of Lipid bilayers*, pp. 183-168, CRC Press, Boca Raton, FL. (1990).

Marti et al., "Induction of antigen-presenting capacity in tumor cells upon infection with non-replicating recombinant vaccinia virus encoding murine MHC class II and costimulatory molecules," Journal of Immunological Methods 200:191-198 (1997).

Martini et al., "Recurrent juvenile dermatomyositis and cutaneous necrotizing arteritis with molecular mimicry between streptococcal type 5M protein and human skeletal myosin," *J. Peda.* 121:739-742 (1992).

McConnell at al.,"Stimulation of T cells by antigen-presenting cells is kinetically controlled by antigenic peptide binding to major histocompatibility complex class II molecules," Proc. Natl. Acad. Sci. 92:2750-2754 (1995).

McRae, "Functional evidence for epitope spreading in the relapsing pathology of experimental autoimmune encephalomyelitis," *Journal of Experimental Medicine* 182:75-85 (1995).

Merritt et al., "Crystal structure of cholera toxin B-pentamer bound to receptor $G_{M1}$ pentasaccharide," Protein Science 3:166-175 (1994).

Mitsunaga et al., "A nested PCR-RFLP method for high-resolution typing of HLA-A alleles," *Eur. J. Immunogenet.* 25(1):15-27 (1998).

Miyazaki et al., "Mice lacking H2-M complexes, enigmatic elements of MHC class II peptide-loading pathway," *Cell* 84:531-541(1996).

Murall-Krishna et al., "Counting antigen-specific CD8 T cells: A reevaluation of bystander activation during viral Infection," *Immunity* 8:177-187 (1998).

Murray, "How the MHC selects Th1/Th2 immunity," Immunology Today 19(4) (1998).

Nag et al, "Antigen-specific stimulation of T cell extracellular acidification by MHC class II-peptide complexes," Journal of Immunology 148:2040-2044 (1992).

Nag et al., "Cloned T cells Internalize peptide from bound complexes of peptide and purified class II major histocompatibility complex antigen," Journal of Biological Chemistry 288(19)14360-14366 (1993).

Nag et al., "Functionally active recombinant α and β chain-peptide complexes of human major histocompatibility class II molecules," Journal of Biological Chemistry 271(17):10413-10418 (1996).

Nag et al, "Intramolecular charge heterogeneity in purified major histocompability class II α and β polypeptide chains," Journal of Biological Chemistry 269(13)10061-10070 (1994).

Nag et al., "N-Linked oligosaccharides of murine major histocompatiblity complex class II molecule," Journal of Biological Chemistry 267(31)22624-22629 (1992).

Nag et al., "Purified β-chaln of MHC class II binds to CD4 molecules on transfected HeLs cells," Journal of Immunology 150:1358-1364 (1994).

Nag et al., "Separation of complexes of major histocompatibility class II molecules and known antigenic peptide by metal chelate affinity chromatography," Journal of Immunological Methods 169:273-285 (1994).

Nag et al, "Stimulation of T cells by antigenic peptide complexed with isolated chains of major histocompatibility complex class II molecules," *Proc. Natl. Acad. Sci. USA* 90:1604-1608 (1993).

Nag et al., "The role of N-linked oligosaccharides of MHC class II antigens in T cell stimulation," Journal of Immunological Methods 172:95-104 (1994).

Nag et al., "In vitro maximum binding of antigenic peptides to murine MHC class II molecules does not always take place at the acidic pH of the in vivo endosomal compartment," *J. Immunol.* 148:369-372 (1992).

Ogg et al., "Quantitation of HIV-1-specific cytotoxic T lymphocytes and plasma load of viral RNA," *Science* 279:2103-2106 (1998).

Peterson, "A simplification of the protein assay method of Lowry et al. which is more generally applicable," *Anal. Biochem.* 83:346-356 (1977).

Rao et al., "A trivalent system from vancomycin D-Ala-D-Ala with higher affinity than avidin-biotin," *Science* 280:708-711 (1998).

Rosenberg et al., "Observations on the systemic administraion of autologous lymphokine-activated killer cells and recombinant interleukin-2 to patients with metastatic cancer," *N. Engl. J. Med.* 313:1485-1492 (1985).

Rosenberg et al.,"Use of tumor-Infiltrating lymphocytes and interleukin-2 in the immunotherapy of patients with metastatic melanoma," *N. Engl. J. Med.* 319:1676-1680 (1988).

Rothenberg, "How T cells count," *Science* 273:78-79 (1996).

Rudensky et al., "Sequence analysis of peptides bound to MHC class II molecules," *Nature* 353:622-627 (1991).

Sebzda et al., "Positive and negative thymocyte selection induced by different concentrations of a single peptide," *Science* 263:1615-1618 (1994).

Sette et al., "Effect of pH on MHC class II-peptide interactions," *J. Immunol.* 148:844-851 (1992).

Sette, *Annals of the New York Academy of Sciences* 86:3296-3300.

Sharma et al., "Antigen-specific therapy of experimental allergic encephalomyelitis by soluble class II major histocompatibility complex-peptide complexes," Proc. Natl. Acad. Sci. 11465-11469 (1991).

Solbach et al., "Lymphocytes play the music but the macrophage calls the tune," Immunology Today 12(1):4-6 (1991).

Spack et al., "Induction of tolerance in experimental autoimmune myasthenia gravis with solubilized MHC class II: Acetylcholine receptor peptide complexes," Journal of Autoimmunity 8:787-807 (1995).

Spinozzi et al., "Local expansion of allergen-specific $CD30^+Th2$-Type γδ T cells in bronchial asthma," *Mol. Med.* 1(7):821-826 (1995).

Tang et al., "Blockade of CD40-CD40 ligand pathway induces tolerance in murine contact hypersensitivity," *European Journal of Immunology* 27:3143-3150 (1997).

Tietz et al., "$CD4^+$ T cells migrate into inflamed skin only If they express ligands for E- and P-Selectin," *J. Immunol.* 161:963-970 (1998).

Tivol et al., "Costimulation and autoimmunity," Current Opinion in Immunology 8:822-830 (1998).

Van Rensen et al., Liposomes with incorporated MHC class II/peptide complexes as antigen-presenting vesicles for T cell activation, *Pharm. Res* 16(2):198-204 (1999).

Viola et al., "T cell activaion determined T cell receptor number and tunable thresholds," *Science* 273:104-106 (1996).

Viola et al., "T lymphocyte costimulation mediated by reorganization of membrane microdomains," *Science* 283:680-682 (1999).

Voorter et al., "High-resolution HLA typing for the DQB1 gene by sequence-based typing," *Tissue Antigens* 51(1):80-87 (1998).

Walden et al., "Major histcompatibility complex-restricted and unrestricted activation of helper T cell lines by liposome-bound antigens," J. Mol. Cell. Immunol 2:191-197 (1988).

Ward et al., "Biophysical and structural studies of TCRs and ligands: Implications for T cell signaling," *Curr. Op. Immunol.* 9:97-106 (1997).

Watts et al., "Antigen presentation by supported planar membranes containing affinity-purified I-$A^d$," *Proc. Natl. Acad. Sci.* 81:7564-7568 (1984).

Witt et al., "Antigenic peptide binding to the mouse major histocompatibility complex class II protein I-$E^k$. Peptide stabilization of the quaternary structure of I-$E^k$," *J. Am. Chrm. Soc.* 114:3506-3511 (1992).

Wulfing et al., "A receptor/cytoskeletal movement triggered by costimulation during T cell activation," Science 2266-2269 (1998).

Zhong et al., "Evidence that binding site occupancy is necessary and sufficient for effective major histocompatibility complex (MHC) class II transport through the secretory pathway redefines the primary function of class II-associated Invariant chain peptides (CLIP)," *J. Exp. Med.* 284:2081-2086 (1998).

Brian, et al., "Allogeneic stimulation of cytotoxic T cells by supported planar membranes," Proc. Natl. Acad. Sci. 81:6159-6163 (1984).

Gay, et al., "The Major Histocompatibility Complex-Restricted Antigen Receptor on T Cells," The Journal of Immunology 136(6): 2026-2032 (1996).

Marti, et al., "Induction of antigen-presenting capacity in tumor cells upon infection with non-replicating recombinant vaccinia virus encoding murine MHC class II and constimulatory molecules" Journal of Immunological Methods 200:191-198 (1997).

Oertli, et al., "Artificial antigen-presenting cells engineered by recombinant vaccinia viruses expressing antigen, MHC class II, and costimulatory molecules elicit proliferation of CD4+ lymphocytes in vitro," *Clin. Exp. Immunol.* 110:144-149 (199).

Sprent, et al., "Constructing Artificial Antigen-Presenting Cells From Drosophila Cells," Dendritic Cells in Fundamental and Clinical Immunology 41:249-254 (1997).

Walden, "Antigen presentation by liposomes as model system for T-B cell interaction," *Eur. J. Immunol.* 18:1851-1854 (1988).

* cited by examiner

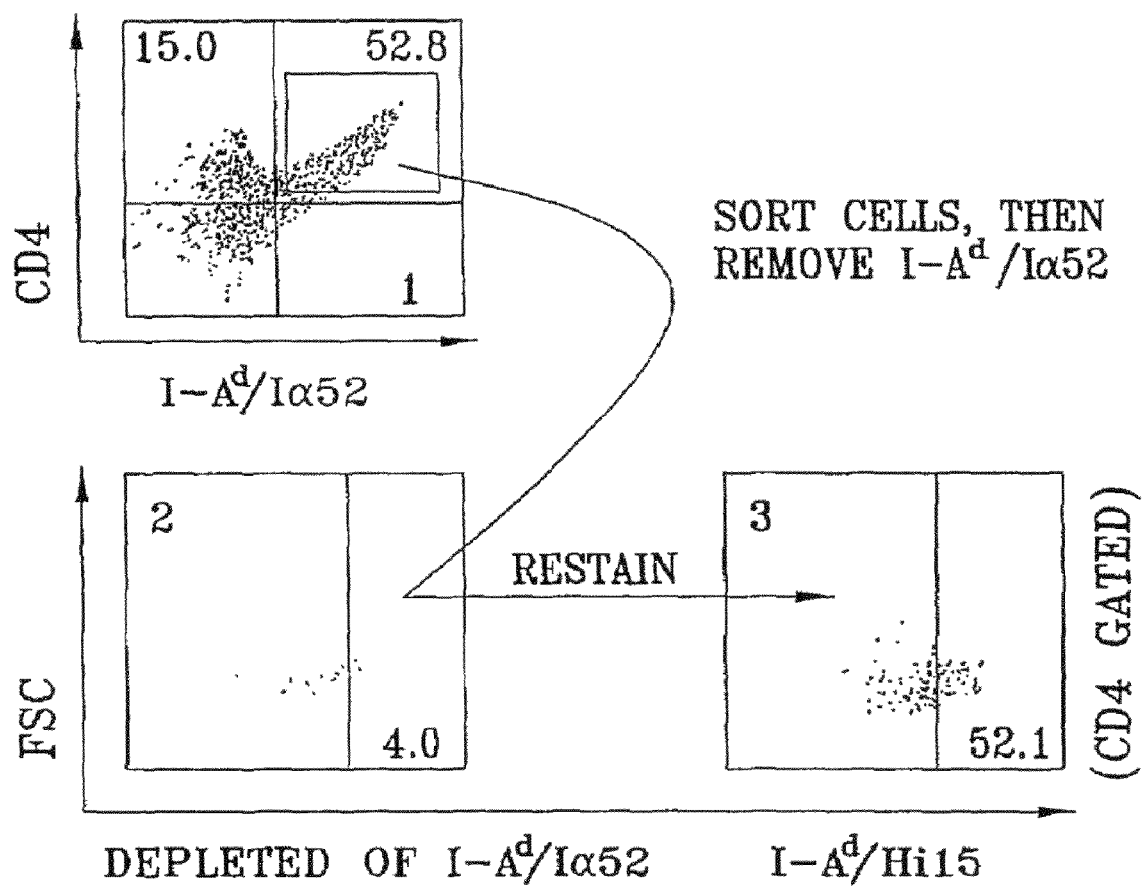
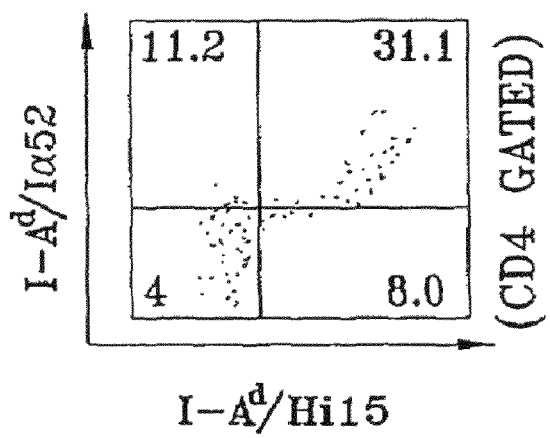
FIG. 12

B7.1-CTB construct translation DNA-PROTEIN

```
M   G   H   T   R   R   Q   G   T   S   P   S   K   C   P   Y   L   N   F   F
atg ggc cac aca cgg agg cag gga aca tca cca tcc aag tgt cca tac ctc aat ttc ttt Q   L   L   V   L   A   G   L   S   H   F   C   S   G   V   I   H   V   T   K
cag ctc ttg gtg ctg gct ggt ctt tct cac ttc tgt tca ggt gtt atc cac gtg acc aag E   V   K   E   V   A   T   L   S   C   G   H   N   V   S   V   E   E   L   A
gaa gtg aaa gaa gtg gca acg ctg tcc tgt ggt cac aat gtt tct gtt gaa gag ctg gca Q   T   R   I   Y   W   Q   K   E   K   K   M   V   L   T   M   M   S   G   D
caa act cgc atc tac tgg caa aag gag aag aaa atg gtg ctg act atg atg tct ggg gac M   N   I   W   P   E   Y   K   N   R   T   I   F   D   I   T   N   N   L   S
atg aat ata tgg ccc gag tac aag aac cgg acc atc ttt gat atc act aat aac ctc tcc I   V   I   L   A   L   R   P   S   D   E   G   T   Y   E   C   V   V   L   K
att gtg atc ctg gct ctg cgc cca tct gac gag ggc aca tac gag tgt gtt gtt ctg aag Y   E   K   D   A   F   K   R   E   H   L   A   E   V   T   L   S   V   K   A
tat gaa aaa gac gct ttc aag cgg gaa cac ctg gct gaa gtg acg tta tca gtc aaa gct D   F   P   T   P   S   I   S   D   F   E   I   P   T   S   N   I   R   R   I
gac ttc cct aca cct agt ata tct gac ttt gaa att cca act tct aat att aga agg ata I   C   S   T   S   G   G   F   P   E   P   H   L   S   W   L   E   N   G   E
att tgc tca acc tct gga ggt ttt cca gag cct cac ctc tcc tgg ttg gaa aat gga gaa E   L   N   A   I   N   T   T   V   S   Q   D   P   E   T   E   L   Y   A   V
gaa tta aat gcc atc aac aca aca gtt tcc caa gat cct gaa act gag ctc tat gct gtt S   E   F   G   G   S   G   G   S   A   T   P   Q   N   I   T   D   L   C
agc gaa ttc ggc ggc tcc ggt ggt agc gcc aca cct caa aat att act gat ttg tgt A   E   Y   H   N   T   Q   I   H   T   L   N   D   K   I   F   S   Y   T   E
gca gaa tac cac aac aca caa ata cat acg cta aat gat aag ata ttt tcg tat aca gaa S   L   A   G   K   R   E   M   A   I   I   T   F   K   N   G   A   T   F   Q
tct cta gct gga aaa aga gag atg gct atc att act ttt aag aat ggt gca act ttt caa V   E   V   P   G   S   Q   H   I   D   S   Q   K   K   A   I   E   R   M   K
gta gaa gta cca ggt agt caa cat ata gat tca caa aaa aaa gcg att gaa agg atg aag D   T   L   R   I   A   Y   L   T   E   A   K   V   E   K   L   C   V   W   N
gat acc ctg agg att gca tat ctt act gaa gct aaa gtc gaa aag tta tgt gta tgg aat N   K   T   P   H   A   I   A   A   I   S   M   A   N   *
aat aaa acg cct cat gcg att gcc gca att agt atg gca aat taa
```

FIG. 29

B7.2-CTB construct translation DNA-PROTEIN

```
M   G   L   S   N   I   L   F   V   M   A   F   L   L   S   G   A   A   P   L
atg gga ctg agt aac att ctc ttt gtg atg gcc ttc ctg ctc tct ggt gct gct cct ctg K   I   Q   A   Y   F   N   E   T   A   D   L   P   C   Q   F   A   N   S   Q
aag att caa gct tat ttc aat gag act gca gac ctg cca tgc caa ttt gca aac tct caa N   Q   S   L   S   E   L   V   V   F   W   Q   D   Q   E   N   L   V   L   N
aac caa agc ctg agt gag cta gta gta ttt tgg cag gac cag gaa aac ttg gtt ctg aat E   V   Y   L   G   K   E   K   F   D   S   V   H   S   K   Y   M   G   R   T
gag gta tac tta ggc aaa gag aaa ttt gac agt gtt cat tcc aag tat atg ggc cgc aca S   F   D   S   D   S   W   T   L   R   L   H   N   L   Q   I   K   D   K   G
agt ttt gat tcg gac agt tgg acc ctg aga ctt cac aat ctt cag atc aag gac aag ggc L   Y   Q   C   I   I   H   H   K   K   P   T   G   M   I   R   I   H   Q   M
ttg tat caa tgt atc atc cat cac aaa aag ccc aca gga atg att cgc atc cac cag atg N   S   E   L   S   V   L   A   N   F   S   Q   P   E   I   V   P   I   S   N
aat tct gaa ctg tca gtg ctt gct aac ttc agt caa cct gaa ata gta cca att tct aat I   T   E   N   V   Y   I   N   L   T   C   S   S   I   H   G   Y   P   E   P
ata aca gaa aat gtg tac ata aat ttg acc tgc tca tct ata cac ggt tac cca gaa cct K   K   M   S   V   L   L   R   T   K   N   S   T   I   E   Y   D   G   I   M
aag aag atg agt gtt ttg cta aga acc aag aat tca act atc gag tat gat ggt att atg Q   K   S   Q   D   N   V   T   E   L   Y   D   V   S   I   S   L   S   V   S
cag aaa tct caa gat aat gtc aca gaa ctg tac gac gtt tcc atc agc ttg tct gtt tca F   P   D   V   T   S   N   M   T   I   F   C   I   L   E   T   D   K   T   R
ttc cct gat gtt acg agc aat atg acc atc ttc tgt att ctg gaa act gac aag acg cgg L   L   S   S   P   F   S   I   E   L   E   D   P   Q   P   P   P   D   H   E
ctt tta tct tca cct ttc tct ata gag ctt gag gac cct cag cct ccc cca gac cac gaa F   G   G   S   G   G   S   A   T   P   Q   N   I   T   D   L   C   A   E
ttc ggc ggc tcc ggt ggt agc gcc aca cct caa aat att act gat ttg tgt gca gaa Y   H   N   T   Q   I   H   T   L   N   D   K   I   F   S   Y   T   E   S   L
tac cac aac aca caa ata cat acg cta aat gat aag ata ttt tcg tat aca gaa tct cta A   G   K   R   E   M   A   I   I   T   F   K   N   G   A   T   F   Q   V   E
gct gga aaa aga gag atg gct atc att act ttt aag aat ggt gca act ttt caa gta gaa V   P   G   S   Q   H   I   D   S   Q   K   K   A   I   E   R   M   K   D   T
gta cca ggt agt caa cat ata gat tca caa aaa aaa gcg att gaa agg atg aag gat acc L   R   I   A   Y   L   T   E   A   K   V   E   K   L   C   V   W   N   N   K
ctg agg att gca tat ctt act gaa gct aaa gtc gaa aag tta tgt gta tgg aat aat aaa T   P   H   A   I   A   A   I   S   M   A   N   *
acg cct cat gcg att gcc gca att agt atg gca aat taa
```

FIG. 30

DRA1-CTB construct translation PROTEIN-DNA

```
M   A   I   S   G   V   P   V   L   G   F   F   I   I   A   V   L   M   S   A
ATG GCC ATA AGT GGA GTC CCT GTG CTA GGA TTT TTC ATC ATA GCT GTG CTG ATG AGC GCT

Q   E   S   W   A   I   K   E   E   H   V   I   I   Q   A   E   F   Y   L   N
CAG GAA TCA TGG GCT ATC AAA GAA GAA CAT GTG ATC ATC CAG GCC GAG TTC TAT CTG AAT

P   D   Q   S   G   E   F   M   F   D   F   D   G   D   E   I   F   H   V   D
CCT GAC CAA TCA GGC GAG TTT ATG TTT GAC TTT GAT GGT GAT GAG ATT TTC CAT GTG GAT

M   A   K   K   E   T   V   W   R   L   E   E   F   G   R   F   A   S   F   E
ATG GCA AAG AAG GAG ACG GTC TGG CGG CTT GAA GAA TTT GGA CGA TTT GCC AGC TTT GAG

A   Q   G   A   L   A   N   I   A   V   D   K   A   N   L   E   I   M   T   K
GCT CAA GGT GCA TTG GCC AAC ATA GCT GTG GAC AAA GCC AAC CTG GAA ATC ATG ACA AAG

R   S   N   Y   T   P   I   T   N   V   P   P   E   V   T   V   L   T   N   S
CGC TCC AAC TAT ACT CCG ATC ACC AAT GTA CCT CCA GAG GTA ACT GTG CTC ACG AAC AGC

P   V   E   L   R   E   P   N   V   L   I   C   F   I   D   K   F   T   P   P
CCT GTG GAA CTG AGA GAG CCC AAC GTC CTC ATC TGT TTC ATC GAC AAG TTC ACC CCA CCA

V   V   N   V   T   W   R   L   N   G   K   P   V   T   T   G   V   S   E   T
GTG GTC AAT GTC ACG TGG CTT CGA AAT GGA AAA CCT GTC ACC ACA GGA GTG TCA GAG ACA

V   F   L   P   R   E   D   H   L   F   R   K   F   H   Y   L   P   F   L   P
GTC TTC CTG CCC AGG GAA GAC CAC CTT TTC CGC AAG TTC CAC TAT CTC CCC TTC CTG CCC

S   T   E   D   V   Y   D   C   R   V   E   H   W   G   L   D   E   P   L   L
TCA ACT GAG GAC GTT TAC GAC TGC AGG GTG GAG CAC TGG GGC TTG GAT GAG CCT CTT CTC

K   H   W   E   F   D   A   P   S   P   L   P   E   T   T   E   E   F   G   G
AAG CAC TGG GAG TTT GAT GCT CCA AGC CCT CTC CCA GAG ACT ACA GAG GAA TTC GGT GGT

S   G   G   S   A   Q   L   E   W   E   L   Q   A   L   E   K   E   N   A   Q
TCC GGT GGT TCC GCG CAG CTG GAA TGG GAA CTG CAG GCG CTG GAA AAA GAA AAC GCG CAG

L   E   W   E   L   Q   A   L   E   K   E   L   A   Q   G   G   S   G   G   S
CTG GAA TGG GAA CTG CAG GCG CTG GAA AAA GAA CTG GCG CAG GGC GGC TCC GGT GGT AGC

A   T   P   Q   N   I   T   D   L   C   A   E   Y   H   N   T   Q   I   H
GCC ACA CCT CAA AAT ATT ACT GAT TTG TGT GCA GAA TAC CAC AAC ACA CAA ATA CAT

T   L   N   D   K   I   F   S   Y   T   E   S   L   A   G   K   R   E   M   A
ACG CTA AAT GAT AAG ATA TTT TCG TAT ACA GAA TCT CTA GCT GGA AAA AGA GAG ATG GCT

I   I   T   F   K   N   G   A   T   F   Q   V   E   V   P   G   S   Q   H   I
ATC ATT ACT TTT AAG AAT GGT GCA ACT TTT CAA GTA GAA GTA CCA GGT AGT CAA CAT ATA

D   S   Q   K   K   A   I   E   R   M   K   D   T   L   R   I   A   Y   L   T
GAT TCA CAA AAA AAA GCG ATT GAA AGG ATG AAG GAT ACC CTG AGG ATT GCA TAT CTT ACT

E   A   K   V   E   K   L   C   V   W   N   N   K   T   P   H   A   I   A   A
GAA GCT AAA GTC GAA AAG TTA TGT GTA TGG AAT AAT AAA ACG CCT CAT GCG ATT GCC GCA

I   S   M   A   N   *
ATT AGT ATG GCA AAT TAA
```

FIG. 31

DRB1-biotag construct translation PROTEIN-DNA

```
1/1                                             31/11
M   V   C   L   K   F   P   G   G   S           C   M   A   A   L   T   V   T   L   M
ATG GTG TGT CTG AAG TTC CCT GGA GGC TCC         TGC ATG GCA GCT CTG ACA GTG ACA CTG ATG
61/21                                           91/31
V   L   S   S   P   L   A   L   A   G           D   T   R   P   R   F   L   E   Q   V
GTG CTG AGC TCC CCA CTG GCT TTG GCT GGG         GAC ACC CGA CCA CGT TTC TTG GAG CAG GTT
121/41                                          151/51
K   H   E   C   H   F   F   N   G   T           E   R   V   R   F   L   D   R   Y   F
AAA CAT GAG TGT CAT TTC TTC AAC GGG AGC         GAG CGG GTG CGG TTC CTG GAC AGA TAC TTC
181/61                                          211/71
Y   H   Q   E   E   Y   V   R   F   D           S   D   V   G   E   Y   R   A   V   T
TAT CAC CAA GAG GAG TAC GTG CGC TTC GAC         AGC GAC GTG GGG GAG TAC CGG GCG GTG ACG
241/81                                          271/91
E   L   G   R   P   D   A   E   Y   W           N   S   Q   K   D   L   L   E   Q   K
GAG CTG GGG CGG CCT GAT GCC GAG TAC TGG         AAC AGC CAG AAG GAC CTC CTG GAG CAG AAG
301/101                                         331/111
R   A   A   V   D   T   Y   C   R   H           N   Y   G   V   G   E   S   F   T   V
CGG GCC GCG GTG GAC ACC TAC TGC AGA CAC         ACC TAC GGG GTT GGT GAG AGC TTC ACA GTG
361/121                                         391/131
Q   R   R   V   Y   P   E   V   T   V           Y   P   A   K   T   Q   P   L   Q   H
CAG CGG CGA GTC TAT CCT GAG GTG ACT GTG         TAT CCT GCA AAG ACC CAG CCC CTG CAG CAC
421/141                                         451/151
H   N   L   L   V   C   S   V   N   G           F   Y   P   G   S   I   E   V   R   W
CAC AAC CTC CTG GTC TGC TCT GTG AAT GGT         TTC TAT CCA GGC AGC ATT GAA GTC AGG TGG
481/161                                         511/171
F   R   N   G   Q   E   E   K   T   G           V   V   S   T   G   L   I   Q   N   G
TTC CGG AAC GGC CAG GAA GAG AAG ACT GGG         GTG GTG TCC ACA GGC CTG ATC CAG AAT GGA
541/181                                         571/191
D   W   T   F   Q   T   L   V   M   L           E   T   V   P   R   S   G   E   V   Y
GAC TGG ACC TTC CAG ACC CTG GTG ATG CTG         GAA ACA GTT CCT CGG AGT GGA GAG GTT XXX
601/201                                         631/211
T   C   Q   V   E   H   P   S   L   T           S   P   L   T   V   E   W   R   A   R
ACC TGC CAA GTG GAG CAC CCA AGC CTG ACG         AGC CCT CTC ACA GTG GAA TGG AGA GCA CGG
661/221                                         691/231
S   E   S   A   Q   S   K   G   G   S           G   G   S   A   Q   L   K   K   K   L
TCT GAA TCT GCA CAG AGC AAG GGC GGC TCC         GGT GGT AGC GCC CAG CTG AAG AAG AAA CTC
721/241                                         751/251
Q   A   L   K   K   K   N   A   Q   L           K   Q   K   L   Q   A   L   K   K   K
CAG GCT CTG AAA AAA AAG AAT GCC CAG CTC         AAG CAG AAG CTG CAG GCC CTG AAG AAA AAG
781/261                                         811/271
L   A   Q   G   S   G   G   S   A   G           G   G   L   N   D   I   F   E   A   Q
CTG GCT CAG GGT TCC GGT GGT TCC GCG GGT         GGT GGT TTG AAC GAC ATC TTC GAA GCT CAG
841/281
K   I   E   W   H   *   *
AAA ATC GAA TGG CAC TAA TAA
```

FIG. 32

| NAME | PARAMETER | GATE | p MOLES CTB FITC | GEO MEAN | %GATED M2 |
|---|---|---|---|---|---|
| lip.001 | FL1-H | G1 | CONTROL-0 | 2.32 | 8.1 |
| lip.002 | FL1-H | G1 | 25pMOLES | 2.25 | 6.1 |
| lip.003 | FL1-H | G1 | 50pMOLES | 3.17 | 27.2 |
| lip.004 | FL1-H | G1 | 100pMOLES | 2.78 | 20.4 |
| lip.005 | FL1-H | G1 | 200pMOLES | 3.07 | 27.5 |
| lip.006 | FL1-H | G1 | 400pMOLES | 3.52 | 40.4 |
| lip.007 | FL1-H | G1 | 800pMOLES | 5.59 | 73.0 |
| lip.008 | FL1-H | G1 | 2000pMOLES | 7.57 | 82.4 |
| lip.009 | FL1-H | G1 | 5000pMOLES | 20.82 | 97.1 |

METHOD OF ISOLATING ANTIGEN-SPECIFIC T CELLS EMPLOYING ARTIFICIAL ANTIGEN PRESENTING CELLS

RELATED APPLICATIONS

This application is a continuation-in-part of U.S. patent application Ser. No. 09/756,983, filed 9 Jan. 2001 now U.S. Pat. No. 6,787,154, which is a continuation-in-part of U.S. patent application Ser. No. 09/421,506, filed 19 Oct. 1999 now U.S. Pat. No. 7,022,483, and PCT application No. PCT/US99/24666, filed 19 Oct. 1999, to which this application claims the benefit of and priority to. Additionally, this application claims the benefit of and priority to provisional application Nos. 60/105,018, filed 20 Oct. 1998, and 60/510,645, filed 10 Oct. 2003. Each of the foregoing patent applications, and any patent issuing from any of them, is hereby incorporated by reference in its entirety.

GOVERNMENT INTERESTS

This invention was made with government support under NIH Grant Nos. AR40770, AI37232, and AR41897. The government may have certain rights in this invention.

FIELD OF THE INVENTION

This invention concerns immunology. Specifically, the invention relates to methods of preparing artificial antigen presenting cells, as well as compositions comprising such artificial antigen presenting cells. Further, the invention concerns the application of such artificial antigen presenting cells to isolate antigen-specific T cells, modulating T cell responses, and treating conditions which would benefit from the modulation of a T cell response, for example, autoimmune disorders, allergies, cancers, and viral, protozoal, and bacterial infections, as well as in transplantation therapy.

BACKGROUND OF THE INVENTION

1. Introduction

The following description includes information that may be useful in understanding the present invention. It is not an admission that any such information is prior art, or relevant, to the presently claimed inventions, or that any publication or patent specifically or implicitly referenced is prior art.

2. Background

The immunologic arts have advanced markedly in recent years. The complexity of the science explaining aspects of the field is immense. Set forth below is a discussion concerning known aspects of various elements involved in immunogenic responses and concepts in the art that are related to the invention disclosed herein.

A. T Cells

T lymphocytes (i.e., T cells) are part of the immune system, which defends the body against bacterial, viral, and protozoal infection, as well as molecules that contain epitopes recognized as non-self (including aberrant forms of molecules that occur naturally in the body). The recognition of non-self molecules as well as the destruction of infectious agents carrying non-self antigens is a function of T cells, which, along with certain B lymphocytes (i.e., B cells), provide for the cell-mediated immune responses of adaptive immunity.

Infecting pathogens are generally accessible to extracellular antibodies found in the blood and the extracellular spaces. However, some infecting agents, including all viruses, replicate inside cells where they are not exposed to, and thus cannot be detected by, extracellular antibodies. In order for these foreign agents to be accessible to the cell-mediated immune response, cells harboring such pathogens must either "express" antigenic motifs of the infecting agents on the surface of the cells or the antigenic motifs must be shed from the cells, e.g., by cell death, to be accessible to and subsequently expressed on the cell membrane of phagocytic antigen presenting cells ("APCs") that participate in cell-mediated immune processes.

Antigens derived from replicating viruses, for example, are displayed on the surface of infected cells where they may be recognized by "cytotoxic" T cells or other surveillance cells such APCs, e.g., dendritic cells. T cells may then respond to the infection by recognizing the viral antigens and then killing the infected cell. The actions of such cytotoxic T cells depend upon direct interaction between the antigenic motif of the infecting agent expressed on the surface of the infected cells and T cell receptors specific for the motif.

Although T cells are important in responding to intracellular infections, some foreign agents evade such responses because they replicate in the vesicles of macrophages, as occurs with *Mycobacterium tuberculosis*, the pathogen that causes tuberculosis. Whereas bacteria that enter macrophages are usually destroyed in lysosomes (which contain a variety of enzymes and bactericidal substances), infectious agents such as *M. tuberculosis* may survive because the vesicles they occupy may not fuse with macrophage lysosomes. The immune system fights such agents using a second type of T cell, known as a "T helper cell," which helps to activate macrophages and induce the fusion of lysosomes with vesicles containing the infectious agents. The T helper cells also bring about the stimulation of other immune mechanisms of the phagocyte. T helper cells may further be involved in initiating and/or sustaining the immune system's release of soluble factors that attract macrophages and other professional APCs to the site of infection.

Additionally, specialized T helper cells play an important role in the destruction of extracellular pathogens by interacting with B cells. Depending on the type of infection being controlled, participating T helper cells may have an inflammatory, or Th1-like phenotype, or a suppressive, Th2-like phenotype. Other T helper cell types may also exist, including Treg and Th3 cells. In the case of cytotoxic T cells and Th1 cells, fragments of non-self proteins (i.e., processed antigens) are recognized on the surface of the target cell (such as an infected cell). Th2 cells, on the other hand, recognize and interact with antigen presented by professional antigen presenting cells such as dendritic cells and B cells. Dendritic cells non-specifically internalize foreign antigens while B cells may bind and internalize foreign antigens via their antigen-specific cell surface immunoglobulin. In any case, T cells recognize their targets by detecting non-self antigenic motifs (e.g., peptide fragments derived from, for example, a bacterium or virus) that are expressed either on infected cells or other immune cells, e.g., phagocytic APCs.

The actions of T cells depend on their ability to recognize antigenic motifs on cells (such as cells harboring pathogens or that have internalized pathogen-derived products). T cells recognize peptide fragments (e.g., pathogen-derived proteins) in the form of complexes between such peptides and MHC (major histocompatibility complex) molecules that are expressed on the surface of antigen presenting cells.

B. T Cell Receptors

T cell receptors (TCRs) are closely related to antibody molecules in structure, and they are involved in antigen binding although, unlike antibodies, they do not recognize free antigen; instead, they bind antigen fragments which are bound and presented by antigen-presenting molecules. An important group of antigen-presenting molecules are the MHC class I and class II molecules that present antigenic peptides and protein fragments to T cells. Other antigen presenting molecules have also been identified, including CD1, which present lipid and glycolipid antigens to T cells.

Variability in the antigen binding site of a TCR is created in a fashion similar to the antigen binding site of antibodies, and also provides specificity for a vast number of different antigens. Diversity occurs in the complementarity determining regions (CDRs) in the N-terminal domains of the disulfide-linked alpha ($\alpha$) and beta ($\beta$), or gamma ($\gamma$) and delta ($\delta$), polypeptides of the TCR. The CDR loops are clustered together to form an MHC-antigen-binding site analogous to the antigen-binding site of antibodies, although in TCRs, the various chains each contain two additional hypervariable loops as compared to antibodies. TCR diversity for specific antigens is also directly related to the MHC molecule on the APC's surface to which the antigen is bound and presented to the TCR.

C. MHC Molecules

In general, T cell responses to "non-self" peptide motifs depend on the interactions of the T cells with other cells that express or otherwise contain the proteins recognized as non-self. The molecules that associate with these peptide or antigen fragments and present them to T cells are membrane glycoproteins encoded by a cluster of genes that comprise the MHC. In general, the term MHC is used to describe generally the molecules in the mammalian immune system involved in the presentation of antigenic motifs to T cells. Here, MHC means any major histocompatibility complex class I or class II protein from any mammalian organism, including a human, mouse, rat, horse, pig, dog, cat, or sheep, that present antigens to T cells. Such molecules include full-length MHC molecules or subunits thereof, and further include MHC-encoded antigen-presenting glycoproteins having the capacity to bind a antigenic peptides. MHC proteins may comprise an amino acid sequence that is expressed and purified from natural sources, or by any synthetic techniques such as recombinant expression of a desired gene, or group of genes, in prokaryotic or eukaryotic systems, which can, for example, result in different patterns of glycosylation. The MHC sequence may comprise a natural or modified amino acid sequence, including those that are truncated at either or both the C- or N-terminus and/or include one or more amino acid insertions, deletions, or substitutions in a naturally occurring MHC sequence.

The two types of MHC molecules, i.e., MHC class I and MHC class II molecules, deliver peptides from different sources (class I MHC delivering intracellularly derived peptides, and class II MHC delivering extracellularly derived peptides) to the surface of the infected cell. The two classes of MHC molecules vary with respect to the length of peptides that they are able to present. The binding pocket of MHC class I molecules is blocked at either end, thereby imposing severe restrictions on the size of peptides it can accommodate (typically about 8-10 residues). The binding groove of the MHC class II molecules, on the other hand, allows peptides to protrude from the ends, and consequently much longer peptides (e.g., from about 8-30 residues) can bind. Rudensky, et al. Nature, vol. 353:622-27; Miyazaki, et al., Cell, vol. 84:531-41; Zhong, et al., J. Exp. Med., vol. 284:2061-66.

A naturally occurring MHC class I molecule comprises a glycosylated heavy chain non-covalently associated with $\beta$2-microglobulin. The class I heavy chain contains an extracellular portion having three domains termed $\alpha$1 (the N-terminal-most domain), $\alpha$2, and $\alpha$3, a transmembrane domain of about 25 amino acid residues, and a cytoplasmic tail comprising 30-40 residues. The extracellular domain is glycosylated, with glycosylation varying depending upon species and haplotype. Each of the three $\alpha$ domains is about 90 residues in length. X-ray crystallographic studies of the extracellular domains reveal a platform of eight anti-parallel $\beta$ strands supporting the helices in $\alpha$1 and $\alpha$2 domains (one $\alpha$-helix in each domain) arranged in an anti-parallel fashion. A long groove separates these $\alpha$-helices, which is believed to be binding site for processed antigen. The $\alpha$2 and $\alpha$3 heavy chain domains each contain intradomain disulphide bonds. The $\alpha$3 domain is structurally similar to immunoglobulin C domains. $\beta$2-microglobulin has the structure of an immunoglobulin constant region domain, and it is essential for cell surface expression of MHC class I molecules.

In contrast, the MHC class II molecules are heterodimers of heavy ($\alpha$) and light ($\beta$) chains encoded by the class genes of MHC (genes A and E in the mouse, and DP, DQ, and DR in humans), with the peptide binding groove being located between the two chains. The heavy chains vary in molecular weight between 30-34 kDa, whereas the light chains have a molecular weight of about 26-29 kDa, with much of this weight difference being due to differences in glycosylation. Despite this, the $\alpha$ and $\beta$ chains have the same overall structure, with each comprising an extracellular portion having two domains, $\alpha$1 and $\alpha$2 in the $\alpha$ chain and $\beta$1 and $\beta$2 in the $\beta$ chain, followed by short transmembrane region of about 30 residues and small cytoplasmic domain of 10-15 amino acid residues. The $\alpha$2 and $\beta$2 domains are similar to the class I $\alpha$3 domain and $\beta$2-microglobulin. The $\beta$1 domain contains a disulphide bond. The $\alpha$1, $\alpha$2, and $\beta$1 domains are N-glycosylated, whereas the $\beta$2 domain, which contains a CD4 binding site, is not. Class II molecules on APCs interact with CD4 molecules on T cells in an analogous way that that class I molecules interact with CD8 molecules. CD4 and CD8 are important in antigen presentation, which are involved in kinase recruitment that signal T cell activation.

Although the structures of class I and II molecules are similar, the groove in class II molecules is more open, and thus can accommodate longer peptides than the binding groove of class II molecules. For both class I and II molecules, the topology of the peptide-binding groove depends in part on the amino acids that comprise the groove, and peptide binding depends on the nature of the peptide's side chains and their complementarity with the binding groove. Garboczi, et al., Nature, vol. 384: 134-41; Ward and Quadri, Curr Op Immunol., vol. 9:97-106; Garcia, et al., Science, vol. 279:1166-72).

D. Antigen Processing

Antigens recognized by T cells in the context of an MHC molecule are degraded or processed so that the determinant recognized by the TCR is only a small fragment of the original antigen. Antigens are processed into peptide fragments before association with MHC molecules. TCRs are sensitive to peptides in the MHC groove, rather than the conformational determinant recognized by antibodies.

Peptides bound to MHC class I molecules are recognized by CD8+ T cells (cytotoxic T cells), and those bound to MHC class II molecules are recognized by CD4+ T cells (helper T cells). Two functional subsets of T cells can thereby be activated to initiate the destruction of cells that present, or express, the particular antigen on its surface, and thereby eliminate the source of the antigen (e.g., a pathogen or diseased cell). CD4+ T cells may also help to activate B cells, and in turn give rise to the stimulation of antibody production against the antigenic motifs of extracellular pathogens.

Infectious agents or other "non-self" antigens can reside in various intracellular compartments. Viruses and certain bacteria replicate in the cytosol or in the contiguous nuclear compartment, while many pathogenic bacteria and some eukaryotic parasites replicate in the endosomes and lysosomes that form part of the vesicular system. The immune system has different strategies for eliminating such agents from these two sites. Cells containing viruses or bacteria located in the cytosol are eliminated by cytotoxic T cells that express the cell-surface molecule CD8 and present antigens on MHC class I molecules. The function of CD8+ T cells is to kill infected cells.

Immunogenic agents located in the vesicular compartments of cells are detected by a different subset of T cells, distinguished by cell surface expression of the molecule CD4. CD4+ T cells are specialized to activate/modulate other cells and fall into at least two primary functional classes: Th1 cells, which activate various immune competent cells to destroy the intravesicular non-self antigenic agents they harbor; and Th2 cells, which help to activate B cells to, among other things, make antibodies against such antigenic agents.

To produce an appropriate response to infectious microorganisms, T cells must distinguish self from non-self (e.g., foreign) material coming from the different processing pathways. This is achieved by delivering peptides to the cell surface from these intracellular compartments using either MHC class I or II molecules. As noted above, MHC class I molecules deliver peptides that come from proteins synthesized in the cell, with the antigen being expressed in association with an MHC class I molecules (antigen:MHC complex) that can be recognized by CD8+ T cells specific for the particular antigen:MHC complex. In contrast, MHC class II molecules deliver "non-self" peptides derived from proteins that have been internalized by the cell (and are thus extracellular from the perspective of the antigen-presenting cell) and processed for presentation at the cell surface in the context of an MHC class II molecule. CD4+ T cells specific for the particular antigen:MHC class II molecule complex can then recognize the complex when presented on the surface of an APC.

E. Antigen Presenting Cells

A wide variety of cells can present antigens. In lymphoid organs, the three primary APC types are dendritic cells, macrophages, and B cells. Dendritic cells are abundant in T cell areas of lymph nodes and spleen, and are very effective in initially acitiviating naïve T cells. When naïve T cells encounter a specific antigen for the first time on the surface of an antigen-presenting cell (APC) in the context of an appropriate MHC molecule (i.e., priming), they are activated to proliferate and differentiate into cells capable of contributing to the removal of the particular antigen and its source (e.g., an infecting pathogen). The APCs are specialized in that they express surface molecules that synergize with a specific antigen in the activation of naïve T cells. APCs become concentrated in the peripheral lymphoid organs, to which they migrate after trapping antigen while circulating in the periphery. APCs present peptide fragments to recirculating T cells, some of which may be naïve. Dendritic cells are known to present processed antigens to macrophages, which are involved in the phagocytosis of cells in a first line of defense against infectious agents. Dendritic cells are also able to present internalized, processed antigens on both class I and class II MHC molecules. APCs are also known to be activated by armed effector T cells. B cells also serve as APCs under some circumstances.

One of the features of APCs is the expression of co-stimulatory molecules, including the potent B7 molecules, including B7-1 (CD80) and B7-2 (CD86). B7 are constitutively expressed on the surface of dendritic cells, and can be upregulated on monocytes, B cells, and other APCs. They are ligands for CD28, and its homologue CTLA-4 (CD 152), which is expressed after T cell activation. CD28 the primary co-stimulatory ligand expressed on naïve T cells. Anderson, et al., J. Immunol., vol. 159:4:1669-75. CD28 stimulation has been shown to prolong and augment cytokine production, and may be important in preventing induction of tolerance.

The activation of T cells by APCs leads to proliferation of the activated T cells and to the differentiation of their progeny into armed effector T cells. The proliferation and differentiation of T cells depends on the production of cytokines (such as the T cell growth factor, IL-2) and their binding to high-affinity receptors on the activated T cell. T cells whose TCRs are bound to antigens in the absence of co-stimulatory molecules may fail to make cytokines and instead may become anergic. This dual requirement for both receptor/antigenic interaction and co-stimulation helps to further mediate naïve T cell response.

Proliferating T cells develop into armed effector T cells. Once an expanded clone of T cells achieves effector function, the T cell clone progeny can act on any target cell that displays or expresses a specific antigen on its surface. Effector T cells can mediate a variety of functions. The killing of infected cells by CD8+ cytotoxic T cells and the activation of professional APC by Th1 cells together make up cell-mediated immunity. The activation of B cells by both Th2 and Th1 cells helps to produce different types of antibodies, thus driving the humoral immune response. Kirberg, et al., J. Exp. Med., vol. 186:8:1269-75.

F. T Cell Activation

T cells generally become sensitized to antigens by becoming trapped in lymphoid organs as the T cells drain into lymph nodes through which they circulate. Antigens introduced directly into the bloodstream, or that reach the bloodstream from an infected lymph node, are picked up by APCs in the spleen, for example, where lymphoid cell sensitization occurs in the splenic white pulp. The trapping of antigen by APCs that migrate to these lymphoid tissues combined with the continuous recirculation of T cells through the tissues ensures that rare antigen-specific T cells will encounter their specific antigen being presented by an APC. Overall, T cell activation has four stages: adhesion, antigen-specific activation, co-stimulation, and cytokine signaling.

The recirculation of naïve T cells through the lymphoid organs is orchestrated by non-specific, rapidly reversible adhesive interactions between lymphocytes and endothelial cells. Naïve T cells enter the lymphoid organs through a process that is thought to occur in a number of steps. The first step in this process is mediated by selectins expressed on the T cell. For example, L-selectin on naïve T cells binds to sulfated carbohydrates on the vascular addressins GlyCAM-1 and CD34. CD34 is expressed on endothelial cells in many tissues but is properly glycosylated for L-selectin binding only on the high endothelial venule cells of lymph nodes. L-selectin binding promotes a rolling interaction, which is critical to the selectivity of naïve lymphocyte homing. Although this interaction is too weak to promote extravasation, it is essential for the initiation of the stronger interactions that then follow between the T cell and the high endothelium, which are mediated by molecules with a relatively broad tissue distribution. (Finger, et al., Nature, Vol. 379:266-9).

Stimulation by locally bound chemokines activates the adhesion molecule LFA-1 on the T cell, increasing its affinity for ICAM-2, which is expressed constitutively on all endothelial cells, and ICAM-1, which, in the absence of inflammation, is expressed only on the high endothelial venule cells of peripheral lymphoid tissues. The binding of LFA-1 to its ligands, ICAM-1, ICAM-2, and ICAM-3, plays a major role in T cell adhesion to and migration through the wall of the blood vessel into the lymph nodes. Bachmann, et al., Immunity, vol. 7:549-57.

The high endothelial venules are located in the lymph nodes. This area is inhabited by dendritic cells, which have recently migrated from the periphery. The migrating T cells scan the surface of these APCs for specific antigen:MHC complexes. If they do not recognize antigen presented by these cells, they eventually leave the node via an efferent lymphatic vessel, which returns them to the blood so that they can recirculate through other lymph nodes. Rarely, a naïve T cell recognizes its specific antigen:MHC complex on the surface of an APC, which then signals the activation of LFA-1, causing the T cell to adhere strongly to the APC. Binding to the antigen:MHC complex also activates the cell to proliferate and differentiate, resulting in the production of armed, antigen-specific T cells. The number of T cells that interact with each APC in lymph nodes is very high, as can be seen by the rapid trapping of antigen-specific T cells in a single lymph node containing antigen.

G. Identification and Isolation of Antigen-Specific T Cells

In addition to their role in combating infections, T cells have also been implicated in the destruction of cancerous cells. Autoimmune disorders have also been linked to antigen-specific T cell attack against various parts of the body. One of the major problems hampering the understanding of and intervention on the mechanisms involved in these disorders is the difficulty in identifying T cells specific for the antigen to be studied. Accordingly, it is of great interest to be able to identify antigen-specific T cells. Additionally, it would be of great therapeutic benefit if T cells specific for a particular antigen could be (i) enriched and then reintroduced in a disease situation, (ii) selectively depleted in the case of an autoimmune disorder, or (iii) modified to alter their functional and/or phenotypic characteristics. Thus, identification and isolation of antigen-specific T cells is an essential requirement in immunology and medicine to understand and modulate immune responses.

Identification of antigen-specific T cell populations is generally accomplished by indirect means in animal models, such as by evaluating membrane markers correlated to activation or maturation of these cells. This has usually been accomplished using transgenic systems (Ignatowicz, et al., Cell, vol. 84:521-29; Sebzda, et al., Science, vol. 263:1615-18; Jameson, et al., Ann. Rev. Immunol., vol. 13:93-126). Analysis is generally done by means of flow cytometry, where a detector on a machine is capable of identifying cells bound to fluorescent substrates, such as fluoresceinated antibodies. Positively identified cells can be sorted for further use. Quantitation and isolation of antigen-specific T cells is usually accomplished by limiting dilution and cloning techniques. When using sorted cells, these approaches become quite cumbersome and are sometimes inaccurate, since the biological effects of antigen recognition can spread beyond the cells recognizing the antigen. For instance, upon engagement of the specific MHC:antigenic peptide complex, T cells produce cytokines that can affect expression of the same markers of activation in non-specific bystander T cells. Hence, in order to isolate and characterize cells with specificity for a given antigen, alternative procedures, such as T cell cloning, need to be applied. These techniques often require many months of technical procedures before results can be obtained. The rate of success, in particular for human systems, is quite low, and the population selected may not necessarily represent the biologically relevant component of the immune response to a given peptide. The direct interaction of a specific T cell with the antigen:MHC complex would thus be a preferred basis for T cell isolation.

H. Distinctions

Kendrick, et al., U.S. Pat. No. 5,595,881, discuss a method for the detection and isolation of MHC:antigen-restricted T cells. That method is performed by preparing a MHC:antigen complex isolated using metal chelating technology. The complex is then bound to a planar solid support (i.e., a glass coverslip), followed in turn by combining the immobilized complex with a biological sample so that the MHC:antigen complex may bind to and retain antigen-specific T cells. Determination of the presence of reactive MHC:antigen complexes is carried out by detecting cell proliferation.

The method of Kendrick, et al. substantially differs from the current invention. First, the MHC components of the complexes discussed in the Kendrick, et al. disclosure are immobilized on a planar solid support. In contrast, the MHC components of the current invention are not bound to a solid planar support. Indeed, in certain preferred embodiments of the instant invention, the MHC components are "free floating," i.e., they are capable of laterally diffusing, within the fluid lipid bilayer of a liposome membrane, preferably one comprised of phosphotidylcholine and cholesterol components, as described in greater detail below. This difference is substantial in that the MHC:antigen complexes discussed in the Kendrick, et al. disclosure are believed not to be able to participate in the migration or concentration of such complexes in "capping," which is important to improved binding and activation of bound T cells. Second, the method discussed in the Kendrick, et al. disclosure concerns detecting "natural" APCs specific for pre-selected antigen-specific T cells. Reportedly, this is accomplished by isolating antigen-specific T cells by first performing a series of steps including binding antigen via a metal chelating process to a solid support, using the antigen to capture antigen-specific MHC components, and then isolating the MHC:antigen complexes which are in turn bound to a planar solid support via a linker.

The current invention is much more versatile. It is not concerned with detecting natural APCs; instead, it concerns the isolation and manipulation of antigen-specific T cells. The manipulation of such T cells can be carried out for numerous reasons, such as to directly impact T cell function by modulating a T cell response. Such manipulations can be performed in vivo, in a column format (where artificial APCs are bound to a solid support, for example), or in solution, for example, via flow cytometry techniques such as FACS (fluorescence-activated cell sorting). The compositions of the current invention can modulate T cell function by including various functional molecules into the APC. For example, in one embodiment of the current invention, known MHC molecules may be incorporated into liposomes along with a labeled antigenic peptide for which such MHC has specificity (e.g., in the case of FACS, a biotinylated antigen). The liposome:MHC:biotinylated antigen complex may be used to bind to antigen-specific T cells. Binding can be visualized by FACS, followed by sorting the bound cells. Thus, no cell proliferation assay is necessary to identify and isolate antigen-specific T cells.

In addition to the MHC:antigen complex, the artificial APCs of this invention that are used to capture antigen-specific T cells preferably include accessory molecules to help stabilize the MHC:antigen:TCR interaction, and may also include functional molecules such as co-stimulatory molecules which, in some embodiments, may be used to activate T cells; adhesion molecules, which may be used to bind cells destined for a certain area of the body; targeting molecules that target the aAPC to a specific cell or tissue type in a patient's body; and other accessory or functional molecules such as cytokines or antibodies to cytokine receptors, which are known to have immunomodulatory effects upon T cells. Moreover, in some embodiments the current invention further provides for properly orienting these molecules in a liposome-based aAPC through the use of a novel anchoring mechanism, a preferred example of which comprises a GM-1 ganglioside molecule and the β subunit of cholera toxin. In this context, the protein of interest may be connected to a cholera toxin subunit as a fusion protein or by use of a linking moiety. By attaching the cholera toxin subunit to the molecule of interest, the cholera toxin may be bound by the GM-1 ganglioside molecule incorporated into lipid membrane of the liposome, as the GM-1 ganglioside molecule has affinity for the nonpolar region of the membrane.

In liposome-based embodiments of the invention, all of these molecules may be incorporated into the lipid bilayer of the liposome. Given the fluidity of the membrane, the molecules embedded therein can laterally diffuse and become concentrated over time, for example, at an aAPC-T cell interface, to form a structure analogous to the immunological synapse that forms between T cells and APCs. Further, other molecules may be included in the compositions that do not influence the modulation of T cell responses. Examples of such molecules include proteins useful in anchoring the artificial APC to a solid support, molecules for orienting other molecules to be included in an aAPC, as well as proteins or other molecules that target an aAPC to a cell or tissue within a patient's body. As used herein, such molecules that are not associated with modulation or T cell binding are termed "irrelevant" molecules.

Additionally, a label may be attached (covalently or non-covalently) to the antigen, an irrelevant molecule, or another aAPC component, for example, to a lipid within a liposome. The artificial APCs of the invention also allow for optional expansion of T cell populations specific for the MHC:antigen complexes using solution-based (e.g., roller bottle or bioreactor) cell culture.

The current invention represents a substantial and heretofore unrecognized advance in the MHC:antigen complex—T cell-binding art in that the artificial APC is not restricted to complexes of MHC:antigen alone or bound to a planar surface. The importance of the structural differences can not be over emphasized. The addition of accessory molecules, as well as co-stimulatory molecules, and other proteins in proper orientation (particularly in embodiments that employ liposomes) allow for substantially improved binding association and manipulation of T cells, which is very important in the identification and stimulation of antigen-specific T cells. This is especially true in solution-based FACS analysis where the functionality of antigen-specific T cells can be interpreted directly. For example, prior studies (Watts, T. H., Annals of the New York Academy of Sciences vol. 81:7564-7568.) respecting the modulation of T cells may be erroneous. There, it was demonstrated that planar membranes containing purified MHC loaded with antigen fused to glass cover slips elicited IL-2 production by T cells through the interaction of the T cell with the MHC:antigen complex. It was also shown that the same complex when formed in unilamellar vesicles (i.e., liposomes) elicited no response. Contrary to such teaching, the instant invention is based in part on the discovery that liposome vesicles containing MHC:antigen complexes can in fact elicit strong responses when combined with accessory molecules such as LFA-1, and other molecules such as co-stimulatory and adhesion molecules. We based our theory that liposomes could function without use of a planar array on the observation (by the same study cited immediately above) that crude membrane preparations of cellular material from which the MHC was purified were effective in eliciting T cell responses in both planar and vesicular forms. Subsequently, we discovered that "extraneous" matter existing in cell extracts that might be hypothesized to impart functionality to vesicular forms of lipid bilayers (as opposed to unilamellar liposomes alone) are not important to T cell binding and response. Rather, T cell binding and response is possible using vesicular forms of liposomes containing specific molecules applied in combination with liposomes (e.g., accessory molecules, co-stimulatory molecules, and adhesion molecules).

Prior research has also been inconclusive respecting the use of MHC molecules. For example, it has been shown (Buus, S., Cell, vol. 47:1071-1077) that a particular antigenic peptide binds solely to the alpha chain of the class II MHC IAd molecule, while other investigations have shown that binding interactions between T cell receptors and MHC:antigen ternary complexes use whole MHC, not just single chains of the MHC, to determine peptide sequence motifs. Exactly how much of a MHC:antigen complex must be present is not absolutely known and may vary with T cell specificity. The instant invention preferably uses either whole MHC molecules or those parts of the α and β subunits of class I and class II MHC needed to form peptide-binding cleft regions.

The current invention's use of co-stimulatory, adhesion, and other accessory molecules in a "free floating" format (in its liposome embodiments) also helps to both anchor and direct the interaction between MHC:antigen:accessory molecule and T cell receptors by providing a structure that mimics those found in the natural state. Specifically, in the liposomes used in the invention, the MHC:antigen:accessory molecule complexes in conjunction with other functional molecules are able to migrate in proper orientation in the lipid bilayer of the liposome. Such fluidity allows various components within the membrane, which may be randomly distributed prior to interaction with a T cell specific for the particular antigen being presented, to rapidly become concentrated at the T cell-liposome interface in a manner analogous to that which occurs between a T cell and an APC in situ during the formation of an immunological synapse. In preferred embodiments, the liposomes of the invention comprise preferred combinations of lipids and surfactant molecules, particularly phosphotidylcholine and cholesterol. Such aAPC embodiments provide protein presentation characteristics and protein migration properties similar to those of naturally occurring APCs, and allow the MHC:antigen complexes to easily migrate to T cell binding loci similar to "capping" events seen in natural APCs. Moreover, as representatively illustrated in the figures, the structure of the liposome-based aAPCs on the invention allows for specific "capping" of the liposomes on the surface of the T cells to which the liposomes are bound. Additionally, interaction between the T cell and aAPC-associated molecules is further enhanced by the molecules being oriented in the lipid membrane such that their active sites are positioned facing outward on the APC. Without such orientation, the ratio of properly oriented molecules to improperly oriented molecules would be expected to be around 50:50. This ratio is greatly increased using MHC, functional, and accessory proteins that have attached thereto (either by fusion protein construction or by use of a linker) an orienting moiety, a preferred example of which is cholera toxin β subunit placed in relation to the active center of the protein of interest such that upon the β subunit being bound by a GM-1 ganglioside molecule incorporated in the lipid layer of the aAPC, the protein of interest will be oriented on the outer surface of the APC, as opposed to being placed in the lumen (i.e., the internal volume defined by the liposome) of the aAPC.

Additional versatility is available with the current invention in that the artificial APCs may incorporate irrelevant molecules to be used, for example, in conjunction with separate solid support-based capture moieties for capturing generic target motifs such as irrelevant molecules. Because of the capacity for the functional molecules to migrate in the liposome, in such embodiments the irrelevant molecules can be used to anchor the aAPCs to a solid substrate (e.g., a column matrix useful for column chromatography) in a manner that will not interfere with binding of T cells having TCRs specific for the MHC: antigen complex carried by the aAPCs. As will be appreciated, such a system avoids the need for manufacturing specialized solid phase capture substrates for each antigen-specific complex.

With regard to the capture of an aAPC by a solid phase component (e.g., a column matrix having one member of a binding pair bound thereto), the target molecules used in the aAPC for binding to capture molecules (e.g., the other member of the particular binding pair) of the solid support are called "irrelevant" molecules because they do not impact the aAPC:T cell interaction. Such a design further preserves the ability of the other molecules present in the aAPC to participate in T cell capping or activation. In liposome-based embodiments, the complexes involved in such activities can diffuse away from the irrelevant molecules involved in column binding. With regard to aAPC embodiments that do not provide membrane fluidity, it is preferred that the irrelevant molecules be segregated to one region of the structure, with the complexes intended for T cell interaction being disposed in a different region.

It has been recognized that the number of receptors on a T cell is variable (Rothenberg, E., Science, vol. 273:78-79). It is also known that the number of TCRs and combination of co-stimulatory molecules and accessory molecules varies with the maturation of the T cell (Dubey, C., J. Immunol., vol. 157:3820-3289). How many such receptors are needed in any situation to elicit a T cell response is unknown. Moreover, it is known that presence of a co-stimulatory signal decreases the number of receptors necessary to activate a T cell (Viola, A. and Lanzavecchia, A., Science, vol. 273:104-106). That said, because the instant invention involves the preparation of aAPCs of defined compositions, it is now possible to control the number of MHC:antigen:accessory molecule complexes relative to other molecules, including functional molecules such as co-stimulatory and adhesion molecules, present in a given aAPC preparation. Accordingly, the binding and modulation of the T cell response at different stages of cell maturation may be "fine tuned" using the instant invention.

In another system, Nag, et al. (U.S. Pat. No. 5,734,023) disclosed MHC subunits that were complexed with antigenic peptides and "effector" molecules wherein such complexes were used to identify T cell populations that were associated with autoimmune diseases. The complexes were reportedly used to destroy and anergize such T cell populations from a patient's blood cell population. Therein, the effector molecules were disclosed as being toxins, radiolabels, etc. which may be conjugated to the MHC or antigen portion of the complexes to effectuate the identification, removal, anergy, or death of such T cell populations. Such effector molecules were not disclosed as being related to the attractive binding interactions or T cell responses to effectuate a phenotypic change in the cells. Instead, they were merely designed and intended to aid in the recognition and/or destruction of specific T cell populations. Additionally, the Nag, et al. disclosure uses lipids in the construction of micelles that are designed for intravenous injection as therapeutics.

The use of negatively charged acidic phospholipids (such as phosphatidylserine) and the lack of cholesterol or GM-1 ganglioside molecules and cholera toxin subunit in the design of such micelles differs from that of the current invention in substantial ways. For example, preferred embodiments of the instant invention use neutrally charged phospholipids such as phosphotidylcholine (Pc). It has been discovered that the aAPCs of the instant invention have substantially increased stability because of the Pc and cholesterol in environments where IL-1 is present. IL-1 is known to interact with charged phospholipids and to destabilize liposome structure. Likewise, in environments where TNF is present, the permeability of liposomes comprised of charged phospholipids (e.g., phosphotidylserine) is greatly affected. In the same manner, environments where RNase is present may also affect charged phospholipid liposome structures. In the present invention, liposome-based embodiments avoid such disruptive effects through the use of neutral phospholipids.

Additionally, the Nag, et al. disclosure provides no insight with regard to the inclusion of co-stimulatory molecules, adhesion molecules, or protein orientation mechanisms (such as the binding of cholera toxin by GM-1 ganglioside), etc.

In yet another recent disclosure, Spack, et al. (U.S. Pat. No. 5,750,356) report a method for monitoring T cell reactivity using a modified ELISPOT assay which detects various factors produced by the stimulation of T cells with numerous factors in the presence of natural antigen presenting cells. The current invention is distinguishable from the Spack, et al. disclosure in that the current invention uses artificial antigen presenting cells that, in addition to peptide loaded MHC complexes, include one more of various accessory, orienting, co-stimulatory, adhesion, cytokine, and/or chemokine molecules that can effect binding and/or modulation of T cell responses. Additionally, in embodiments that require solid support binding, the aAPCs of the invention include irrelevant molecules.

In still another disclosure, Wilson, et al. (U.S. Pat. No. 5,776,487) disclose the use of liposome structures for detecting analyte in a test sample, wherein the liposome contains only an analyte-specific ligand and a haptenated component used to bind to a receptor moiety on a solid phase, thereby allowing capture of a test analyte on a solid support for detection. Thus, it is vastly divergent from the concept of the current invention.

The present invention radically advances the art by providing synthetic compositions that enable, among other things, the stimulation and modulation of the activity of antigen-specific T cells. This has been accomplished by providing structures (e.g., liposomes and dendrimers) that allow high local concentrations of the molecules necessary to effect modulation of T cell activity to become localized at an aAPC-T cell interface and thereby facilitate binding and T cell capping. Capping is the phenomenon by which the T cell focuses the relevant molecules to the portion of the cell surface where binding has occurred, thus amplifying the binding, and subsequently the signaling of the event to the cell's other components.

SUMMARY OF THE INVENTION

An object of the invention is to provide compositions useful for identifying, isolating, modulating, and quantifying antigen-specific T cells. Other objects provide methods for isolating antigen-specific T cells using such compositions, as well as using such compositions in vivo, in vitro, and ex vivo to modulate the activity of antigen-specific T cells.

In this invention, the aAPCs present antigens complexed with MHC molecules. The MHC:antigen complexes are presented for contact with, and recognition by, a T cell receptor specific therefor. Such antigens can be selected from the group consisting of a peptide, a peptide associated with the onset of graft versus host diseases, a cancer cell-derived peptide, a peptide derived from an allergen, a donor-derived peptide, a pathogen-derived molecule, a peptide derived by epitope mapping, a self-derived molecule, and a self-derived molecule that has sequence identity with a pathogen-derived antigen in a range selected from the group consisting of between 5 and 100%, 15 and 100%, 35 and 100%, and 50 and 100%.

A. Artificial APCs and aAPC Content

An aspect of the invention concerns aAPCs and compositions comprising the same. In general, the aAPCs of the invention serve to present specific antigenic peptides to TCRs specifically reactive therewith in manner that can be used either to isolate a T cell specific for the antigen being presented, or, alternatively, to modulate the activity of such T cells and/or provide a mechanism for activating an endogenous cellular immune response for the treatment of disease. This is accomplished by providing a plurality of antigen-presenting molecules, particularly MHC class I or class II molecules, loaded, or complexed, with an antigenic peptide of interest in conjunction with a plurality of accessory molecules in a manner that allows at least some of these complexes to interact with corresponding receptors (e.g., TCRs), binding partners, or ligands on the surface of T cells. A number of other molecules can also be present on the surface of the aAPCs of the invention, including adhesion molecules and so-called "irrelevant" molecules (e.g., molecules involved in allowing an aAPC to bind to a column matrix, molecules that target an aAPC to a specific cell or tissue type in a patient, etc.). Particularly preferred additional molecules are co-stimulatory molecules, e.g., B7 molecules.

In certain preferred embodiments, the features of the invention may be provided by membrane-bound vesicles, particularly liposomes comprised of a lipid bilayer that exhibits membrane fluidity when placed under physiological conditions (i.e., those ionic, pH, temperature, and other conditions that are required in order for T cells to survive). Preferred liposomes are those wherein the fluid lipid bilayer comprises neutral phospholipids, and preferably a surfactant. A particularly preferred neutral phospholipid is phosphotidylcholine, and a particularly preferred surfactant is cholesterol. In still other embodiments, the aAPCs comprise neutral phospholipids, cholesterol, and GM-1 ganglioside molecules each present in an appropriate ratio to allow free lateral diffusion of molecules of interest through the lipid layer, i.e., a fluid lipid bilayer.

Such aAPCs further comprise on their exterior surface multiples of homo- or heterogenous combinations of MHC:antigenic-peptide complexes incorporated therein and may comprise other functional molecules including accessory molecules, co-stimulation molecules, adhesion molecules, and other immunomodulatory molecules such as cytokines, cytokine receptors, chemokines, and chemokine receptors. Such aAPCs may also include molecules to provide a desired orientation (e.g., presence on the exterior, as opposed to the interior, of the aAPC) to, or otherwise anchor, the functional molecules of interest in the aAPC. Vesicles, such as liposomes, can also serve as delivery vehicles for one or more pharmacological agent species such as nucleic acids (e.g., expression vectors encoding one or more genes of interest under the control of expression elements, anti-sense oligonucleotides, small interfering RNAs, ribozymes, and triplex-forming oligonucleotides that can function in a cell that engulfs the liposome), small molecule drugs, therapeutic proteins, proteins which serve to modulate (i.e., enhance or diminish) T cell stimulation or activation, etc.

In addition to liposomes that comprise a lipid bilayer, some embodiments comprise a lipid monolayer layered onto a non-planar, preferably a spheroid, solid support such as a plastic (e.g., polystyrene), glass, or magnetic bead. The beads may be of any suitable size depending upon application. Typically, said beads may have a diameter of about 1 um to about 300 um, although smaller beads may also be used as they provide a greater surface area relative to volume (such beads may be especially useful for in vivo applications where physical constraints, such as the internal diameter of capillaries, etc., are also important to consider). The solid support should have affinity for non-polar regions of a phospholipid. In other embodiments, the aAPCs of the invention may be synthesized on a scaffold that can be readily modified to include a plurality of different molecules of different types, e.g., MHC class I or class II molecules complexed with the corresponding antigenic peptide and associated with one or more of the various accessory molecules, co-stimulatory molecules, and irrelevant molecules (e.g., targeting molecules, tagging or detection molecules, separation molecules, etc.). Examples of such scaffolds include dendrimers and small particles (e.g., plastic or glass beads, magnetic or metal particles, etc.).

The aAPCs of the invention, in addition to a vesicle or scaffold to which may be attached multiple MHC molecules complexed with antigenic peptides, also may include a plurality of accessory molecules of the same or different species. Said accessory molecules may facilitate and stabilize the interaction between the antigen-specific T cell and the aAPC. A representative example of an accessory molecule is LFA-1. Other accessory molecules include, but are not limited to, CD11a/18, CD54(ICAM-1), CD106(VCAM), and CD49d/29(VLA-4), as well as antibodies (or antibody fragments) to ligands for each of these molecules.

With regard to co-stimulatory molecules, which function to help stimulate, prime, and/or activate (e.g., induce cell proliferation, cytokine production, etc.) an antigen-specific T cell, representative examples include, but are not limited to, B7-1, B7-2, CD5, CD9, CD2, CD40, and antibodies to their respective ligands. Such co-stimulatory molecules can be produced by recombinant methods, as is the case with regard to the other proteins included in the aAPCs of the invention. Co-stimulatory molecules can be used for a variety of purposes in addition to eliciting cell proliferation. For example, it is known that memory CD4+ T cells express B7-2, whereas naïve CD4+ T cells do not. (Hakamada-Taguchi, R., European Journal of Immunology, vol. 28:865-873). Thus, aAPCs, according to the invention, can be used to selectively target memory T cells by incorporating anti-B7-2 into the artificial APC.

Artificial APCs of the invention can also include adhesion molecules to facilitate strong and selective binding between the aAPC and antigen-specific T cells. Suitable adhesion molecules include, but are not limited to, proteins of the ICAM family, for example, ICAM-1 and ICAM-2, GlyCAM-1, as well as CD34, anti-LFA-1, anti-CD44, and anti-beta7 antibodies, chemokines, and chemokine receptors such as CXCR4 and CCR5, and antibodies to selectins L, E, and P. Such molecules may also function as homing molecules for cells destined for specific locations in vivo. For example, $\alpha 4\beta 7$ and L-selectin have been proposed as gut and peripheral lymph node homing molecules, respectively. The former is expressed mainly on memory T cells, while L-selectin is expressed mainly on naïve T cells (Abitorabi, M. A., J. Immunol., vol. 156:3111-3117). Endothelial selectins (E-selectin and P-selectin) are associated with the extravasasion of T cells into inflammatory sites in the skin (Tietz, W., J. Immunol., vol. 161:963-970). In the current invention a β7 binding molecule and gut addressin MAdCAM-1, or an anti-L-selectin antibody, can be incorporated into the aAPCs in association with the MHC:antigenic peptide complex.

It is also known that CD44, which binds hyaluronan, is involved in leukocyte extravasation. Anti-CD44 antibody binds to CD44 and strips it from the leukocyte surface. In some embodiments, anti-CD44 can be incorporated into an aAPC to strip CD44 from leukocytes as desired, thereby helping to inhibit the extravasation of the cells into extracellular spaces, for example, once the aAPC-treated cells are returned to the patient. In another embodiment, anti-CD44 can be infused into an immunomodulatory column where the leukocytes have been captured by artificial APCs for the same purpose.

In some embodiments, other functional molecules (i.e., modulation molecules) may also be incorporated into aAPCs to facilitate T cell modulation. Examples of such molecules include, but are not limited to, CD72, CD22, and CD58 (or antibodies to their ligands) antibodies to cytokine or chemokine receptors, or small molecules that mimic the actions of the various cytokines or neuropeptides. Such modulatory molecules can be used, for example, to modulate antigen-specific T cells.

In still other embodiments, aAPCs may also comprise irrelevant molecules, which are included for the purpose of providing a way to anchor the aAPC to a solid support or to carry a label. Such molecules are termed "irrelevant" because they do not participate in T cell binding, activation, or modulation.

In still further embodiments, any of the aforementioned molecules of interest (e.g., MHC, functional, accessory, irrelevant, etc.) can be bound to an anchor moiety resident in the vesicle membrane. An example of such an anchor is cholera toxin β subunit moiety, which can be linked directly or indirectly to a protein of interest by either a linking moiety or by a recombinant construction of a fusion protein wherein the toxin subunit is linked directly thereto during translation. In such embodiments, the cholera toxin subunit may be positioned with respect to the molecule of interest such that the active portion of the molecule of interest is available for contact with T cells while the toxin portion remains in the nonpolar region of the lipid layer of the aAPC. The cholera toxin moiety may remain in the aAPC's interior by binding to GM-1 that is incorporated into the APC's lipid interior.

In still other embodiments the aAPCs comprise a label. Labels can be associated with any suitable molecule type present in the aAPC, including any of the group consisting of a molecule in the lipid bilayer of a liposome, a lipid of the liposome, an antigen, an MHC molecule, a co-stimulatory molecule, an adhesion molecule, a cell modulation molecule, a GM-1 ganglioside molecules, cholera toxin β subunit, an irrelevant molecule, and an accessory molecule. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, etc. Those of ordinary skill in the art will know of other suitable labels for use in practicing the invention.

Closely related aspects of the invention concern compositions and devices that comprise aAPCs of the invention. For example, certain embodiments of the invention concern pharmaceutical compositions comprising aAPCs of the invention in a pharmaceutically acceptable carrier. Such compositions may include both liquid and dry formulations. Similarly, the aAPCs of the invention may be used to make devices to isolate, or capture, antigen-specific T cells. In such devices, aAPCs may be attached to a solid support. For example, when a solution containing T cells specific for the antigen (as may be represented by a device that contains one or more different aAPC species specific for the particular antigen) is passed over the support, the antigen-specific T cells may be retained. Later, the antigen-specific T cells may be recovered from the solid support. The T cells may then be subjected to additional manipulations, if desired, including expansion, activation, stimulation, and/or modulation, after which they may be reintroduced into a patient. Alternatively, such devices can be used to remove particular antigen-specific T cells from a sample prior to refusion of the sample back into a patient.

Kits containing such compositions and devices are also within the scope of the invention. In general, such kits contain the particular composition or device packaged in a suitable manner in an appropriate container and include required package inserts, directions for use, and the like.

B. Artificial APC Formation

Another aspect of the invention concerns making artificial APCs. Any suitable process can be used. Generally, aAPCs are assembled by first separately obtaining the various components to be included in the aAPC. Protein and peptide components can, for example, be synthesized by recombinant techniques, by synthetic chemical methods, or be purchased. Similarly, scaffolds can be synthesized or purchased, as can the components needed to make liposomes. After acquiring the various components, they can be assembled into the desired aAPC using methods well known in the art. Of course, the particular composition of a particular aAPC will depend upon many factors, including the intended application, the availability of alternative reagents, etc.

Liposome-based artificial APCs may be made by obtaining the MHC:antigen complexes of interest. These complexes are then combined with accessory molecules (e.g., ICAM-1), lipids and other components, if any (e.g., cholesterol, anchor molecules, functional molecules, irrelevant molecules, etc.), to form membrane-associated MHC:antigen:accessory molecule complexes (i.e., liposome:MHC:antigen:accessory molecule complexes). The exact order of addition of the various components will vary depending upon the desired composition, the intended application, etc. It is preferred to combine steps to increase the efficiency and yield of the assembly process. Similar methods may be used to produce aAPCs having a lipid monolayer, e.g., those having a lipid monolayer layered on a spheroid solid support.

C. Methods of Use

The invention also concerns methods for using aAPCs. In one aspect, the invention concerns methods of isolating T cells specific for particular antigens of interest. Such T cells may then be expanded, primed, stimulated, and/or modulated. Furthermore, they may be reinfused into a patient. In another aspect, the invention relates to in vivo methods for stimulating and/or modulating T cell responses. Thus, the invention concerns both in vitro, ex vivo, and in vivo methods of treating conditions that would benefit from the modulation of T cell responses, for example, transplantation therapies, autoimmune disorders, allergies, cancers, infections, and virtually any T cell-mediated disease.

Turning to embodiments of the invention that concern methods of isolating T cells specific for an antigen of interest, such methods may involve contacting a biological sample containing T cells (some of which may or may not be specific for the antigen of interest) with an aAPC, according to the invention, in which the antigen-presenting molecule presents an antigenic peptide of the antigen of interest. Any resulting aAPC:T cell complexes may then be isolated by separating the T cells from the complexes using any suitable technique. Optionally, the quantity of T cells specific for the particular antigen of interest may be determined. In addition, or alternatively, the functional phenotype of the isolated T cells may be determined. Biological samples containing T cells specific for an antigen of interest may include bodily fluids such as blood, blood plasma, and cerebrospinal fluid. Other suitable biological samples include solid tissue, for example, histological specimens.

In such methods, FACS technology may be used. Different components of the assay may be labeled e.g., the antigenic peptide may be labelled. Such labels include biotin, fluorochromes, and radioactive labels. For example, one type of label that may be used is vancomycin (Rao et al., Science, vol. 280:5364:708-11, 1998). In other embodiments of such FACS-based methods, a component of the liposome (or dendrimer or particle) may be labeled. A label may even be noncovalently enclosed within the liposome matrix, for example. If the label is within the liposome, the label may be either enclosed within the liposome or incorporated within the lipids of the outer membrane of the liposome. In other embodiments, an irrelevant molecule, if present, may be labeled. In yet other embodiments, an aAPC:T cell complex may be removed from a biological sample by capturing the complex via an irrelevant molecule. In such embodiments, a solid support may comprise an irrelevant molecule binding or capture molecule (e.g., anti-irrelevant molecule antibody) bound to the solid support.

Other methods for isolating T cells specific for an antigen of interest involve contacting a biological sample that may or may not contain T cells with a solid support to which may be attached aAPCs according to the invention. Resultant aAPC:T cell complexes specific for the antigen of interest may then be isolated, for example, by eluting the T cells that bind to the aAPCs on the column. Such affinity chromatography techniques are well known in the art, and any suitable technique can readily be adapted for use in conjunction with this invention.

A variety of kits for isolating T cells specific for an antigen of interest are provided. Certain of these embodiments comprise aAPCs according to the invention and solid supports, as well as other materials that facilitate the completion of the isolation of an antigen-specific T cell population including, but not limited to, solutions such as buffers and culture medium (which solutions may further contain cytokines, antibodies to various transmembrane or soluble molecules, chemokines, neuropeptides, and/or steroids). Other kit embodiments comprise a solid support having a capture reagent that specifically binds an irrelevant molecule present in an aAPC according to the invention. In another embodiment, the kit may comprise virtual aAPCs on solid supports comprising a single lipid layer. Still other embodiments employ aAPCs of the invention linked to particles that can easily be separated from a biological sample, such as magnetic or metal particles.

Other devices useful for isolating and modulating antigen-specific T cells are column devices. In these embodiments, the devices may comprise compartments that may be isolated from one another by way of separate entrance and exit flow ports between said compartments and between the compartments and external apparatuses. One or more compartments of such column devices may further comprise solid supports capable of binding irrelevant and other such molecules present in aAPCs or solid supports that function directly on aAPCs as described above. Such devices may be used in connection with soluble immunomodulatory molecules that are neither bound to a solid support nor incorporated into an aAPC. Examples of such molecules include cytokines, chemokines, and hormones.

In another such example, if leukopheresis is being performed with the intention of reintroducing the cells back into the patient's body, soluble factors may be introduced into a column device to induce production of IL2 in naïve T cells, IL2 being necessary for T cell growth. Likewise, IL4 or soluble IL4 receptor antibody may be introduced into an immunomodulatory column to enhance the maturation of the Th2 phenotype in specific naïve T cells of interest.

Hence, the invention further comprises a method of modulating T cell responses (i.e., altering a T cell's phenotype, activation, and/or priming). In such embodiments, methods of regulating or modifying T cell responses ex vivo, such as in a column device of the invention, are provided comprising the steps of isolating T cells which are specific for an antigen of interest and combining said isolated T cells with an artificial antigen presenting cell. The aforementioned steps may be performed simultaneously or separately. For instance, T cells specific for an antigen of interest may be isolated using the T cell isolation methods described above. The captured antigenic-specific T cells in one compartment in the device detailed above, for example, may then be introduced into another compartment into which an aAPC is introduced or already present.

The modulation of such T cell responses may comprise changing, in whole or in part, the functional pattern of cytokine receptor expression, cytokine production and secretion, chemokine production and secretion, and/or chemokine receptor expression by the isolated T cells specific for a given antigen. One of the many reasons for modulating a given population of T cell responses may be to change, in whole or in part, the functional pattern of cytokine production by the isolated T cells. For instance, a naïve T cell may be stimulated to shift its phenotype from a Th0 to a Th1, Th2, or a Th3 type helper T cell. Alternatively, the balance between Th1 and Th2 phenotypes may be shifted. Hence, using the methods described herein, a Th2 response may be increased while at the same time a Th1 response may be decreased. In this instance, the aAPC used should also express the co-stimulatory B7-2 molecule. On the other hand, a Th1 response may be increased and a Th2 response decreased. In this instance, the aAPC used preferably contains the co-stimulatory molecule B7-1.

Hence the present invention provides methods for treating various diseased conditions in a subject who would be benefited by modulating T cell production and maturity as well as the functional pattern of active factors expressed by such T cells. For example, as set forth above, production of cytokines by a T cell may be modified in certain antigen-specific T cells to increase Th2 response and/or decrease Th1 response. In such a method, a subject's T cells that are specific for an antigen capable of triggering a Th1 response are isolated by contacting said cells with an APC having an MHC:antigen complex containing an appropriate antigen. By also including a co-stimulatory molecule such as B7-2 on the aAPC, the T cells may be directed to modify their response and cytokine production to increase their Th2 response. Conditions that would benefit from altering the functional pattern of response toward a Th2 response include, for example, autoimmune diseases such as type 1 diabetes mellitus, multiple sclerosis, rheumatoid arthritis, dermatomyositis, juvenile rheumatoid arthritis, and uveitis.

Such T cell modulation, as described above, may be useful in the treatment of autoimmune diseases and asthma, as well as various cytokine-induced inflammatory diseases. For instance, a subject may benefit from altering the functional pattern of cytokine production by certain antigen-specific T cells to increase a Th1 response and/or decrease a Th2 response. Such methods comprise isolating a subject's T cells that are specific for an antigen capable of triggering the Th2 response by contacting said cells with an aAPC containing an MHC:antigen complex having an appropriate antigenic peptide, wherein said artificial APC also expresses a co-stimulatory molecule such as B7-1. For example, it is known that ST2L expression is Th2-type specific. Hence, in the current invention, ST2L may be included in an aAPC in order to identify, isolate, and extract antigen-specific T cells of the Th2 phenotype and/or enrich T cell population for antigen-specific Th1 cells. Additionally, CD30, which is known to have an association with asthma (Spinozzi, F., Mol. Med., vol. 1:7:821-826.), may be incorporated into a APCs to also identify, isolate and remove antigen-specific T cells of the Th2 phenotype and/or to induce T cell responses away from harmful Th2 helper cells in the treatment of allergic conditions. More specifically, allergic conditions that benefit by altering the functional pattern of cytokine production to increase Th1 responses and/or decrease Th2 responses including, for example, allergies to dust mites, animal skin bypass products (e.g., cat and dog dander), vegetables, fruits, pollen, and other various chemicals. Other conditions that may benefit include cancers and some types of infections (e.g., viral, protozoan, fungal, and bacterial infections).

In another example of a method of treatment according to the invention, artificial APCs may be designed to augment antigen-specific T cell responses away from the harmful helper type T cells or used to deplete offending T cells in the treatment of multiple sclerosis. Such depletion or modulation of the T cells may be carried out in combination with the infusion into a column device of either Fas, Fas Ligand, anti-Fas, or anti-Fas ligand antibody. Additionally, artificial APCs may be designed to incorporate SLAM-reactive molecules, which then function to induce a suppressive phenotype.

In another treatment example, SLAM-reactive molecules incorporated in an artificial APC may be used to treat Th2-mediated autoimmune diseases by modulating the T cell response to shift from a Th2 profile to a Th0/Th1 profile while at the same time inducing IL-2 independent co-stimulation independent proliferation.

On the other hand, the OX40 ligand is known to induce a Th2-like phenotype in naïve T cells (Flynn, S., Journal of Experimental Medicine, vol. 188:2:297-304). In this case the OX40 protein may be incorporated into an aAPC to selectively induce a Th2 phenotype.

In yet another example, cartilage degradation that is associated with rheumatoid arthritis can be treated and even in some instances prevented by use of IL-10 and IL-4 in association with an artificial APC, or by infusion of the soluble molecules into a column device, In part, the associated IL-10 and IL-4 molecules can help induce antigen-specific naïve T cells away from development into the activated Th1 state. On the other hand, IL-12 can be used, in accordance with the methods of this invention, by infusion into a column device or incorporation in an artificial APC to induce a Th1 type inflammatory response to help treat Th2 mediated autoimmune diseases.

The modulation of a T cell response may also be useful for inducing anergy and/or apoptosis. The onset of anergy is reported to be due, in part, to the presentation of MHC bound antigenic factors for T cell activation in the absence of appropriate co-stimulatory molecules. (Ding and Shevach, European Journal of Immunology, vol. 24:4:859-866) Hence, the instant invention is applicable to situations where anergy may be useful in the treatment of various maladies, such as in the induction of tolerance. For instance, various forms of Inflamatory Bowel Disease, Crohn's disease and colitis can be alleviated through tolerance mechanisms. Tolerance-inducing mechanisms may also be useful in the treatment of various forms of allergic responses. In these regards, the aAPC of the invention will process and display an appropriate antigenic epitope or allergen but will not express an appropriate co-stimulatory molecule, but may effectively express other effector molecules, e.g., Fas ligands, which may help induce allergy. Thus, an aAPC used in this method would not express a co-stimulatory molecule, but may alternatively express Fas ligand, to induce anergy or tolerance. Such tolerance may be induced orally, sub-cutaneously, intravenously, or via other suitable routes.

In another example of tolerance induction, it is known that the cross-linking of the CD40 ligand using antibodies induces cell proliferation and IL-4 production (Blotta, M., H. J. Immunol., vol. 156:3133-3140). Additionally, it is known that blockage of the CD40/CD40 ligand pathway induces tolerance in murine contact hypersensitivity studies (Tang, A., European Journal of immunology, vol. 27:3143-3150). Hence, in some embodiments of the current invention, CD40 or the anti-CD40 ligand antibody may be incorporated into an artificial APC to induce T cell modulation toward production of IL-4 and/or tolerance to alleviate inflammatory autoimmune disorders.

In other embodiments, the modulation of a T cell response may simply comprise inducing T cell proliferation in general, without regard to modifying Th1 or Th2 responses, and without regard for inducing allergy. This may be accomplished by use of an aAPC that expresses an anti-CD28 antibody. These methods of treatment can include, in addition to the use of artificial APCs, the use of a column device described herein and above.

In another example of a method of treatment, it is known that anti-B7-1 antibody will reduce the incidence of EAE, an animal model of multiple sclerosis. Anti-B7-2 antibody is known to increase the severity of EAE, while co-treatment with anti-IL4 antibody will prevent disease amelioration. Hence, the current invention provides more than one level of control with respect to this disease. For example, artificial APCs may be generated that express anti-B7-1 antibody and/or IL4 to elicit T cell responses favorable to treating this disease.

In another example, a regimen may be developed for treating melanoma by screening for T cell responses to epitopes derived from MAGE-1, MAGE-3, MART-1/melan-A, gp100, tyrosinase, gp75, gp15, CDK4 and beta-catenin, all of which are known to be associated with the disease. T cells having specificity for these molecules may be activated and modulated in various ways described herein in accordance with the invention. For example, T cells that are specific for a unique cancer related antigen can act to cause destruction of the cancerous cells and may be proliferated and infused into a patient.

In another example, T cell mediated milk intolerance as well as other various allergic responses may be treated by isolation and depletion of T cells specific for those allergens (e.g., Fel, Fel-d1, Der 1 and 2, etc.) that are incorporated as an MHC bound antigen on an artificial APC.

In still another example, T cells specific for the ras peptide, or variants thereof, may be stimulated by response to an artificial APC containing the ras peptide in the treatment of cancerous cells expressing the ras mutation.

Another aspect of the invention is that it allows for the study and use of T cell modulation in vitro, which can then be applied in an ex vivo treatment regeime. For example, due to the fact that the bioavailability of injected complexes is difficult to understand (see, Gaur, A. J of Neuroimmunol. 74:149-158.) the in vitro/ex vivo methods of the present invention allows one to follow the specific actions of peptides of interest when used either in an artificial APC or in soluble form in a column device. Hence, it has been shown that using I.V. injections of the non-encephalitogenic APL91 peptide of MBP, ameliroates disease by shifting cytokines from inducing the Th1 to the Th2 phenotype. The same type of injections using encephalitogenic superagonist APL A97 also ameliorates disease, but by causing deletion of specific T cells.

Prior studies have also indicated that the in vivo application of peptides to treat autoimmune disease states is related to epitope spreading, which results in relapsing episodes of disease (Lehmann, P. V. Nature. 358:6382:155-157.), (McRae, B. L. Journal of Experimental Medicine. 182:75-85.). The ex vivo application of the current invention allows specific peptides to be used to isolate and identify antigen-specific T cells, without exposing a patient to the danger of epitope spreading that is associated with relapses of certain autoimmune diseases.

In a further embodiment of the invention, a method of identifying T cells that express MHC epitopes important to graft versus host disease and the rejection of transplantation therapy is provided. In this embodiment, MHCs are identified and incorporated into an artificial APC. Such APCs may be used to capture and deplete the recipient's T cells having antigen specificity for such MHC:epitopes, this modulation allows a more favorable response of the recipient's immune system to the graft. More specifically, peptides derived from the MHC of a recipient are bound to the MHC of a donor that are incorporated into artificial APCs. Such APCs are used in combination with tolerogenic stimuli also on the APC or infused into an immunomodulatory column. The donor's T cells can then be screened to bind reactive T cells that can then be discarded. In a preferred embodiment, the column device of the invention can be used to carry out such immunoleukophoresis.

In another embodiment, the method contemplates treatment of an individual to cause a favorable immune response to an allograft comprising:

(a) predicting a donor's MHC to which a recipient may react;

(b) testing the predicted MHC epitopes with a recipient's T cells (in vitro) to identify antigenic epitopes;

(c) using identified epitopes in an artificial APC to deplete the recipient's antigen-specific (i.e., donor-specific) T cells, while additionally desensitizing the recipient to the epitope by contacting the recipient (as by feeding or nasal injection) with increasing doses of the donor-specific antigen (for the production of oral tolerance and anergy).

In still another embodiment, the invention provides a method of identifying a particular individuals' MHC epitopes that are of import in immunologic responses to pathogenic agents. In this embodiment, an individual's MHC is screened for epitopes that have appreciable sequence or molecular structure recognition with pathogen-derived molecules. The identified MHC epitopes can be used to elicit immunity that may be employed directly as a vaccine against such MHC epitopes that have sequence recognition with pathogen-derived peptides. For example, such a vaccine may be used to reduce natural APCs that express MHC molecules associated with autoimmune diseases including, but not limited to, multiple sclerosis, rheumatoid arthritis, and diabetes. In another embodiment, the identified MHC epitopes can be incorporated into a liposome structure along with a co-stimulatory molecule to enhance the effect of artificial APCs that express other disease related antigens.

In yet another embodiment, antigenic moieties of the pathogen which have, or are likely to have, MHC mimics may be used in artificial APC MHC:antigen complexes to isolate T cells specific for such pathogen-derived antigenic motifs or mimics thereof for the production of a T cell vaccine. Such a vaccine may be used to directly fight progression of an infection or disease caused by a pathogen, or that is the result of a pathogen-derived antigen induced autoimmune associated inflammatory response. Usually a self-derived molecule that mimics a pathogen-derived antigen comprises a polypeptide. As used herein, such a mimic has an amino acid sequence identity with said pathogen-derived antigen to an extent necessary for the MHC to bind to the mimic. The range of sequence identity may be anywhere between 5 and 100% depending upon which amino acids in a peptide sequence elicits either recognition by the MHC and/or stimulation of a T cell response. Generally, the range is between about 5 and 100%, usually, the range is between of a range of about 15 and 100%, preferably the range is between 35 and 100%, and most preferably the range is between 50 and 100%.

In still other embodiments, the invention provides a means to address other immunologic conditions relevant to a T cell response. For example, apoptosis of T cells induced by MHC molecules through the CD95/CD95 ligand pathway can be controlled by incorporating an anti CD95 molecule into an artificial APC and modulating the appropriate antigen-specific T cells.

In other applications, dendritic cells, and other similar surveillance cells, important to an immune response, may be manipulated ex vivo in the same fashion as T cells in the many examples provided above.

BRIEF DESCRIPTION OF THE DRAWINGS

The file of this patent contains at least one drawing executed in color. Copies of this patent with color drawings are provided to the Patent and Trademark Office with payment of the necessary fee. The invention will be further described with reference to the accompanying drawings, which can be briefly described as follows:

FIG. 7 is a schematic showing other embodiments of artificial APC designs, wherein

FIG. 12 shows the ability of the invention to determine the cross-reactivity of a singular group of antigen-specifically defined T cells seen first in FIG. 10, then in FIG. 11. Such a technique represents an improvement over prior art, as internalized antigen can not be removed.

FIGS. 16(A-D), 17(A-D), and 18(A-D) are color photos showing that the interaction of T cells with artificial APCs allows physiological migration of TCR proteins toward the interaction side, i.e., "capping". Resting 8DO T cells were stained with FITC-cholera toxin, incubated with artificial APCs presenting IA$^d$/OVA$^{323-339}$ complexes and analyzed by confocal microscopy. Panels A and B of each of FIGS. 16-18 show the red and green fluorescent dyes, respectively. Panel C shows the cells as seen by phase contrast. Panel D is the combination of the two fluorescent dyes with phase contrast. Panel D shows the combined fluorescence of the red and green dyes so that co-localization (FIG. 16D), and capping (FIGS. 17D, and 18D) are observed. Specifically, FIGS. 16A-D shows that the T cell receptor is associated with the cholera toxin antigen. This further shows that cholera toxin is a good tool for identifying the T cell receptor in this system. FIGS. 17A-D shows that the interaction between T cells and artificial APCs allows physiologic migration and capping of the T cell receptor in the T cell membrane.

FIGS. 19A-D are PAGE photos showing optimization of peptide (antigen) loading of human and mouse MHC class II molecules wherein detergent solubilized MHC class II molecules were incubated with biotinylated peptides at the designated pH and temperature for 16 and 24 hrs. Peptide loading was analyzed through ECL. FIGS. 19A and B show binding of biotinylated PADRE peptide to HLA-DR4. FIGS. 19D and C show binding of biotinylated OVA$^{323-339}$ to mouse IA$^d$. The photos show output signal of the level of binding of the peptides to MHC. Results indicate that an incubation of 16 hrs at room temperature and pH 7 and a molar ratio of 200 to 1 provide for optimal results with respect to the human MHC and 1000 to 1 for the mouse.

FIG. 25A shows IFA only-immunized mice.

FIG. 29 shows DNA (Seq. Id. No. 15) and its amino acid translation sequence (Seq. Id. No. 16) wherein the DNA sequence encodes B7-1 from its 5' initiation codon to its 3' codon for the carboxy terminal Serine which is connected to a sequence encoding a spacer/linker peptide, which is connected in turn by a nucleic acid sequence encoding the full length mature cholera toxin β subunit. Sequence for the linker section is underlined.

FIG. 30 shows a DNA sequence (Seq. Id. No. 17) and its amino acid translation sequence (Seq. Id. No. 18) comprising a fusion protein encoding B7-2 from its initiation codon to its 3' codon for the carboxy terminal Histidine followed by a sequence encoding a spacer/linker peptide, followed in turn by a nucleic acid sequence encoding the full length mature cholera toxin 13 subunit. Sequence for the linker is underlined.

FIG. 31 shows the DNA sequence (Seq. Id. No. 21) and its translated reading frame for the encoded amino acid sequence (Seq. Id. No. 22) of the a domain of HLA DRB 1*0401 (comprising α1 to α2) fused to a linker sequence, a protein binding Leucine zipper A, followed in turn by a second linker sequence and the cholera toxin 13 subunit.

FIG. 32 shows the DNA sequence construct (Seq. Id. No. 23) and amino acid sequence translation (Seq. Id. No. 24) of the HLA DRB1*0401 β domain (comprising β1 to β2) fusion with a linker sequence, followed by Leucine zipper B, followed in turn by a second linker sequence, which is followed by a biotag peptide sequence (and an irrelevant molecule).

FIG. 39A shows that in the non-raft system only 7% of cells were stimulated as opposed to the raft system (FIG. 39B) wherein 16.2% of the cells were stimulated.

DETAILED DESCRIPTION OF THE INVENTION

Figure 1:
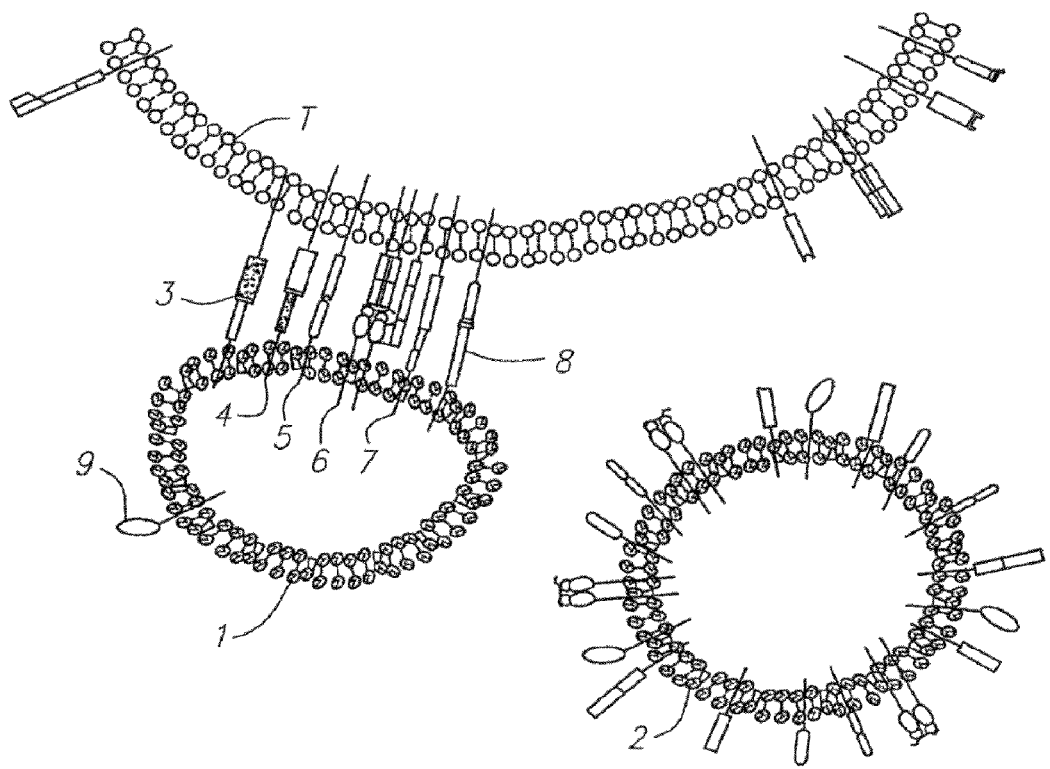
FIG. 1 is a schematic representation of the basic features of the invention and it's interaction with various molecules on a T cell, where (1) is an artificial APC in which embedded molecules have conformed to the capping of the T cell, where (2) is an artificial APC that has not interacted with a T cell and who's molecules are randomly dispersed through the membrane, where (T) is a T cell who's molecules have capped in response to the interaction with the artificial APC, where (3) is an accessory molecule for stabilizing the binding between the TCR and MHC:antigen complex, where (4) may be T cell accessory or adhesion molecule ligands, where (5) may be T cell co-stimulatory molecule ligands, where (6) may be an MHC:antigenic peptide complex, where (7) may be cytokine related molecules, where (8) may be chemokine related molecules, where (9) may be an irrelevant molecule used in binding of the artificial APC to a solid support or a molecule which is tagged with a molecule used in visualization.

The immunoregulation art has advanced steadily in recent years. The scientific literature contains many studies reporting interactions and modulation effects between specific molecules and cell types. However, no discovery has been presented that is able to apply the knowledge that has been gained by the extensive research in the field toward methods, compositions, or devices that can be used in a comprehensive package for carrying out the identification, isolation, and modulation of immunoregulatory cells for the purpose of advancing the ultimate goal of such knowledge, i.e, improved treatment regimens for various states of disease.

Here, the invention concerns a platform technology for advancing treatment regimens requiring the immunoregulation of immune cells that centers around the use of an artificial antigen presenting cell (aAPC). This platform technology may be designed or programmed on demand for use in the treatment of a broad spectrum of specific disease states. Moreover, this system is versatile and applicable to all situations where the isolation, identification, and modulation of T cells is of clinical import. The invention is based on the recognition of the relevance of several types of molecular entities to the stimulation/activation, modulation, and response of T cells in their role within the immune system, which molecules can be used to produce artificial APCs. Such artificial APCs can then be used, for example, to capture and/or manipulate antigen-specific T cells in vitro, and well as to therapeutically or prophylactically treat diseases in vivo or ex vivo. For example, they can be used in vivo to modulate T cell activity.

Historically, programming and using T cells therapeutically has been hampered by the problem of finding a means by which the cells can be handled for such manipulation and observation of the effectiveness of the manipulation applied. This invention solves this problem by adopting the theory that a T cell can best be manipulated by using APC-like structures and incorporating into such structures molecules that (1) bind the "artificial" APC to specific T cell types and (2) stimulate or modulate only specifically bound T cells for any desired response. For in vitro applications, if desired, the artificial APCs can be bound to a solid support.

Prior to the instant invention, no comprehensive system has been disclosed, nor was it obvious that such a system would function as desired in a universally applicable manner to activate and modulate T cells.

Accordingly, the present invention is directed to novel aAPCs, compositions comprising these aAPCs, as well as various methods, including methods of making the aAPCs of the invention and methods of isolating T cells specific for particular antigens of interest, and modulating T cell function ex vivo or in vitro. Methods for modulating T cell function in vivo are also provided. Among the methods of the invention are those for treating conditions that would benefit from the modulation of T cell responses, for example, transplantation therapies, autoimmune disorders, allergies, cancers and viral infections, and virtually any T cell mediated disease. The present invention is further directed to T cell modulation column devices as well as kits for isolating and modulating antigen-specific T cell populations.

Artificial APC Compositions

According to preferred embodiments of this invention, an artificial APC may comprise MHC:antigen complexes, accessory molecules, and other functional molecules including, but not limited to, co-stimulatory molecules, adhesion molecules, modulation molecules, irrelevant molecules, anchoring components such as GM-1 ganglioside molecules and subunits of cholera toxin attached to any of the aforementioned molecules, and labels, some or all of which may collectively assembled into functional aAPCs. In certain preferred embodiments, the above components are incorporated within or are associated with the lipids of a liposome or other membrane-based vesicle such as depicted in FIG. 1. Such incorporated or associated molecules may also include GPI anchored proteins. In other embodiments, these components are attached to an underlying scaffold such as a dendrimer or a particle.

In preferred embodiments of liposome-based aAPCs, the lipid membrane component comprises neutral phospholipids such as phosphotidylcholine and surfactant elements such as cholesterol. These materials are provided in a ratio that allows the other molecules of interest to freely migrate, or diffuse laterally, in the membrane layer. Other lipid membrane components include anchoring moieties such as GM-1 ganglioside molecules, which is a transmembrane pentasaccharide protein and associates in part with nonpolar regions of the liposome matrix. GM-1 ganglioside molecules can be used in association with proteins such as cholera toxin β subunits to orient molecules of interest in the liposome matrix.

Accessory molecules may be included for the purpose of stabilizing the interaction between a TCR and an MHC:antigen complex. Suitable accessory molecules may include, but are not limited to, LFA-1, $CD49^d/29$(VLA-4), CD11a/18, CD54(ICAM-1), and CD106(VCAM) and antibodies to their ligands. In a preferred embodiment, the artificial APC includes ICAM-1 as such an accessory molecule.

Co-stimulatory molecules may be included for the purpose of stimulating or activating a TCR. Suitable co-stimulatory molecules may include, but are not limited to, B7-1, B7-2, CD5, CD9, CD2, CD40, and antibodies to their ligands such as anti-CD28.

Adhesion molecules may be included for the purpose of enhancing the binding association between the artificial APC and a T cell. Suitable adhesion molecules may include, but are not limited to, members of the ICAM family such as ICAM 1, ICAM 2 and GlyCAM-1, as well as CD 34, anti-LFA-1, anti-B7, and chemokines such as CXCR4 and CCR5, and antibodies to selectins L, E, and P.

Modulation molecules may be included for the purpose of modulating the phenotype of a T cell. Suitable modulation molecules may include, but are not limited to, CD72, CD22, and CD58 and antibodies to their ligands, antibodies to cytokine or chemokine receptors or small molecules that mimic the actions of the various cytokines or neuropeptides.

Irrelevant molecules may be included for the purpose of either carrying a label or serving as a scaffold for binding to a solid support. Such a molecule can be any peptide or other molecule having characteristics that make it suitable for use with a liposome and antigen carrier. Such molecule should not interfere with the binding of a T cell to the artificial APC.

With respect to the incorporation of each of the aforementioned MHC, accessory, co-stimulatory, adhesion, modulation, and irrelevant molecules in the artificial APC, proper orientation of these molecule's active centers may be provided by combining the molecules with, for example, the β subunit of cholera toxin so that the cholera toxin subunit can be recognized and bound by GM-1 ganglioside molecules incorporated into the liposome membrane matrix. The incorporation of the cholera toxin and orientation mechanism markedly increases the ability of the artificial APC to interact with T cells and other cells and molecules due to the proper orientation of incorporated molecules from about 50% without such orienting to 90% or more with such orienting.

In preferred embodiments, the aforementioned molecules of interest may be produced by recombinant technology as is well known to those skilled in the art. Use of recombinantly produced molecules further provides the opportunity to produce such molecules as fusion molecules comprising the molecule of interest attached to the β subunit of cholera toxin. In another embodiment, the recombinantly produced (or for that matter a purified natural molecule) may be linked to cholera toxin by a commercial linker.

In still other embodiments, an aAPC of the invention comprises one or more labels, wherein the label(s) is (are) associated with at least one of the group selected from the group consisting of a lipid bilayer of the liposome components, a lipid of the liposome, an antigen, an MHC molecule, a co-stimulatory molecule, an adhesion molecule, a cell modulation molecule, a GM-1 ganglioside molecule, cholera toxin β subunit, an irrelevant molecule, and an accessory molecule.

Artificial APC Formation

The MHC:antigenic peptide complexes of the aAPCs of the invention comprise at least two components: an antigenic peptide or other antigenic sequence with the relevant effect on the immune system; and at least a portion of a subunit of a MHC-encoded protein involved in antigen presentation. The association between the peptide antigen and the antigen binding sites of the MHC subunit(s) can be by covalent or non-covalent bonding.

In other embodiments, the aAPCs of the invention may contain a compound that is toxic, or which can become toxic upon activation (e.g., a prodrug). Toxic agents include naturally occurring toxins, chemotherapeutic agents, and radio-active compounds. For example, a number of protein toxins are well known in the art including ricin, diphtheria, gelonin, *Pseudomonas* toxin, and abrin. Chemotherapeutic agents include, for example, doxorubicin, daunorubicin, methotrexate, cytotoxin, and anti-sense RNA. Antibiotics can also be used. In addition, radioisotopes such as yttrium-90, phosphorus-32, lead-212, iodine-131, or palladium-109 can be used. The emitted radiation destroys the target T-cells. In vesicle-based embodiments, the toxic compound may be carried inside the vesicle, and is released into a T cell upon membrane fusion. In other embodiments, the compound may be conjugated to the scaffold or another component of the aAPC.

Each of the components of the aAPCs of the invention is described below, followed by a description of some of the preferred methods by which these aAPCs can be prepared and employed.

MHC-Derived Components

The glycoproteins encoded by the MHC have been extensively studied in human and murine systems. In general, there are two classes: class I glycoproteins, found on the surfaces of all cells and primarily recognized by cytotoxic T cells; and class II molecules, which are found on the surfaces of several cell types, including accessory cells such as macrophages, and are involved in presentation of antigens to helper T cells. Many of the histocompatibility proteins have been isolated and characterized in the scientific literature.

The Class I MHC in humans has three loci, HLA-A, HLA-B, and HLA-C, all of which reside on chromosome 6. HLA-A and HLA-B have a large number of alleles encoding alloantigens. Class I molecules consist of a 44 kD (kilodalton) heavy chain subunit and a 12 kD B2-microglobulin subunit which is common to all antigenic specificities. Isolation of these detergent-soluble HLA molecules has been described. See, e.g., Springer, T. A., et al., Proc. Natl. Acad. Sci. USA (1976), vol. 73:2481-2485; and Clementson, K. J., et al., in "Membrane Proteins" Azzi, A., ed.

Further work has resulted in a detailed picture of class I three-dimensional structure. See Bjorkman, P. J., et al., Nature (1987), vol. 329:506-518. It is believed that the B2-microglobulin protein and alpha-3 domain of the heavy chain are associated, while the alpha-1 and alpha-2 domains of the heavy chain form antigen-binding sites. Science (1987), vol. 238:613-614.

Class II glycoproteins have a general domain structure similar to that of class I molecules. The antigen binding sites of class II MHC are located on the N-terminal domains of the two subunits, the alpha and beta chains. A separate antigen binding site is located on each subunit. Luescher, et al., J. Biol. Chem. (1990), vol. 265:11177-11184. The alpha and beta subunits are held together by non-covalent forces. Each chain contains two globular domains, designated alpha-1, alpha-2, beta-1, beta-2, respectively. Except for alpha-1, each of these domains is stabilized by disulfide bonds.

MHC glycoproteins (or portions thereof) can be isolated from appropriate cells or can be recombinantly produced. Methods for purifying class II proteins are well known. (see, e.g., Turkewitz, A. P., et al., Molecular Immunology (1983), vol. 20:1139-1147), as are methods for cloning the genes encoding these proteins (or their functional domains). Herein, an MHC molecule refers to entire molecule (such as it occurs in nature), as well as functional subunits or domains thereof (e.g., an alpha or beta chain of MHC II, a heavy chain of MHC I, the extracellular domains of such subunits, etc.). In any event, a functional subunit comprising an antigen binding site and sequences necessary for recognition by the appropriate TCR. Typically, they comprise at least about 50-80%, preferably 90-95%, of the amino acid sequence of the full-length protein. Again, MHC molecules may be recombinantly produced or be isolated from the membranes of a suitable cell type. Notwithstanding the foregoing, it is well known that native forms of "mature" MHC proteins and subunits vary somewhat in length because of deletions, substitutions, and insertions or additions of one or more amino acid residues in the sequences. Thus, MHC components are subject to substantial natural modification, yet are still capable of retaining their respective activities. Modified MHC molecules can also be readily designed and manufactured utilizing various well known recombinant DNA techniques. For example, MHC molecules can vary from naturally occurring sequences at the primary structure level (i.e., amino acid sequence) due to the substitution, addition, deletion, and the like of one or more amino acid residues. These modifications can be used in a number of combinations to produce the final modified protein chain.

In general, modifications to genes encoding MHC molecules can be readily accomplished by a variety of well-known techniques, such as site-directed mutagenesis (see, Gillman and Smith, Gene (1979), vol. 8:81-97; Roberts, S. et al., Nature (1987), vol. 328:731-734). While the effect of many mutations is difficult to predict, their effect can be evaluated by routine screening in a suitable assay for the desired characteristic. For instance, a change in the immunological character of an MHC molecule can be detected by competitive immunoassay with an appropriate antibody. Similarly, the effect of a mutation in the binding site for an antigenic peptide may be evaluated by testing the modified MHC molecule's ability to bind a particular antigenic peptide. Modifications of other properties can also be assayed by standard techniques.

This invention provides amino acid sequence variants of MHC molecules engineered for different reasons, for example, to alter the affinity of the molecule for antigenic peptides and/or T cell receptors, to facilitate stability, and to ease purification of the molecules. The modified MHCs can result in aAPCs with different plasma half lives, improved therapeutic efficacy, and fewer side effects. Preferably, the variants will exhibit at least the same, and preferably enhanced, biological activity (for example, antigenic peptide binding) as compared to the naturally occurring analogue. However, the variants and derivatives that are not capable of binding to their ligands may be useful nonetheless, for example, as reagents for purifying anti-MHC antibodies from antisera or hybridoma culture supernatants and as immunogens for raising antibodies to MHC.

Insertional variants of the present invention are those in which one or more amino acid residues are introduced into a predetermined site in the MHC subunit and which displace the preexisting residues. For instance, insertional variants can be fusions with heterologous proteins or polypeptides. Substitutions involve the replacement of one amino acid type with a different amino acid type (including amino acids and amino acid derivatives not normally found in native proteins) at a particular amino acid position in a protein. Deletional variants are characterized by the removal of one or more amino acid residues from a MHC protein (or portion thereof). In certain preferred embodiments, the transmembrane and cytoplasmic domains of MHC molecules are deleted. This facilitates not only recombinant production, but also provides polypeptides that are preferred for use in aAPC embodiments where it is not essential for a part of an MHC molecule to reside in a lipid bilayer, for example, when a biotinylated MHC molecule is associated via a liposome through a membrane-anchored complex that presents one or more streptavidin moieties above the exterior surface of the membrane, or, alternatively, when a dendrimer is used as the scaffold for making the aAPC.

Other protein modifications can also be made. For example, MHC proteins having different patterns of glycosylation as compared to native MHC molecules can be synthesized, including variants completely lacking in glycosylation (unglycosylated) and variants having at least one less glycosylated site than the native form (deglycosylated) as well as variants in which the glycosylation has been changed. For example, substitutional or deletional mutagenesis can be employed to eliminate, add, or replace N- or O-linked glycosylation sites. Glycosylation variants can also be made by using different host cells. Yeast, for example, glycosylate proteins significantly differently than mammalian systems. Similarly, mammalian cells of a different species (e.g., hamster, murine, insect, porcine, bovine, or ovine) or tissue origin (e.g., lung, liver, lymphoid, mesenchymal, or epidermal) than the original MHC source can provide for variant glycosylation, as characterized, for example, by elevated levels of mannose or variant ratios of mannose, fucose, sialic acid, and other sugars. In vitro processing e.g., neuraminidase digestion, may also be employed to alter glycosylation.

MHC molecules can be isolated from MHC-bearing cell types using any suitable technique. Suitable techniques include solubilization by treatment with papain, by treatment with 3M KCl, and by treatment with detergent. Isolation of individual MHC subunits is easily achieved using standard techniques. For instance, in the case of class I molecules, the heavy chain can be separated using SDS/PAGE and electroelution of the heavy chain from the gel (see, e.g., Hunkapiller, et al. (1983), Methods in Enzymol., vol. 91:227-236). Separate alpha and beta subunits of MHC II molecules can also be isolated using SDS/PAGE followed by electroelution, as described, for example, by Gorga, et al. (J. Biol. Chem. (1987), vol. 262:16087-16094) and Dornmair, et al. (Cold Spring Harbor Symp. Quant. Biol. (1989), vol. 54:409-416). Other standard techniques for separating molecules can also be used, such as ion exchange chromatography, size exclusion chromatography, and affinity chromatography.

Alternatively, as the genes and amino acid sequences many class I and II proteins are known (or can be determined using techniques known in the art), MHC molecules useful in practicing the invention can also be synthesized using recombinant methods. These techniques enable numerous modifications to MHC molecules, e.g., site directed mutagenesis, fusion with other proteins (or protein domains), addition of amino acid residues to facilitate purification, deletion of transmembrane and cytoplasmic domains, etc. Typically, a gene encoding a particular MHC polypeptide will include restriction sites to aid insertion into expression vectors and manipulation of the gene sequence. Genes encoding a desired protein are then inserted into suitable expression vectors, expressed in an appropriate host, such as E. coli, yeast, CHO or other mammalian cell line, and insect cells. Cell-free expression systems can also be employed. Indeed, if the desired protein is less than about 100 amino acids in length, synthetic chemistry methods may be employed in its synthesis.

Construction of expression vectors and recombinant production from the appropriate nucleic acid sequences are well known in the art. Such techniques and various other techniques are generally performed according to Sambrook, et al., Molecular Cloning—A Laboratory Manual, Cold Spring Harbor Laboratory, Cold Spring Harbor, N.Y., 1989. Desired MHC molecules from recombinant sources are recovered and preferably purified prior to further use.

Antigenic Peptides

The antigenic proteins or tissues for a number of deleterious immune responses are known. For example, in experimentally induced autoimmune diseases, antigens involved in pathogenesis have been characterized in arthritis in rat and mouse, native type-II collagen is identified in collagen-induced arthritis, and mycobacterial heat shock protein in adjuvant arthritis; thyroglobulin has been identified in experimental allergic thyroiditis (EAT) in mouse (Maron et al. (1988), J. Exp. Med., vol. 152:1115-1120); acetyl choline receptor (AChR) in experimental allergic myasthenia gravis (EAMG) (Lindstrom et al. (1988), Adv. Immunol., vol. 42:233-284); and myelin basic protein (MBP) and proteolipid protein (PLP) in experimental allergic encephalomyelitis (EAE) in mouse and rat. In addition, for example, target antigens have been identified in humans: type-II collagen in human rheumatoid arthritis (Holoshitz et al. (1986), Lancet ii:305-309); and acetyl choline receptor in myasthenia gravis (Lindstrom et al. (1988), supra) all of the above are incorporated herein by reference.

Antigens are presented on MHC molecules on the surface of antigen-presenting cells subsequent to the hydrolysis of antigenic proteins into smaller peptide units. The location of these smaller segments within an antigenic protein can be determined empirically. See, e.g., U.S. Pat. No. 5,734,023. These segments are thought to be about 8 to about 20 residues in length, and contain both a region recognized by the MHC molecule and an epitope recognized by a TCR on the T cell. Once determined, the relevant antigenic peptides can readily by synthesized, preferably using standard automated methods for peptide synthesis. In the alternative, they can be made recombinantly using isolated or synthetic DNA sequences.

In preferred embodiments, the aAPC comprises antigens wherein the antigens are presented by MHC components for contact with and recognition by a T cell receptor. Such antigens may be selected from the group consisting of a peptide, a peptide derived from the recipient for graft versus host diseases, a cancer cell-derived peptide, a peptide derived from an allergen, a donor-derived peptide, a pathogen-derived molecule, a peptide derived by epitope mapping, a self-derived molecule, a self-derived molecule that has sequence identity with said pathogen-derived antigen, said sequence identity having a range selected from the group consisting of between 5 and 100%, 15 and 100%, 35 and 100%, and 50 and 100%.

Examples of some antigens noted above include the peptide QKRAAYDQYGHAAFE (Seq. Id. No. 10) which is derived from *E. coli* dnaJp1 heat shock protein. A human self-derived peptide is QKRAAVDTYCRHNYG (Seq. Id. No. 11) derived from the HLA. This peptide also has sequence identity with the pathogen Sequence Id. No. 10. Peptides derived from epitope mapping include human peptides from the HA I matrix GILGFVFTL (Seq. Id. No. 12), VKLGEFYNQ (Seq. Id. No. 13) which is a HA I nucleoprotein, and PKYVKQNTLKLAT (Seq. Id. No. 14) derived from the HA II locus.

Formation of the MHC Molecule:Antigenic Peptide Complexes

Complexes between antigen-presenting molecules (e.g., MHC molecules) and antigenic peptides can be formed using any suitable technique. The antigenic peptides can be associated non-covalently with the antigen binding sites of the MHC molecules by, for example, mixing the two components. They can also be covalently bound using any suitable linkage chemistry. In many embodiments, the antigenic peptides are mixed with the desired MHC molecules.

Making aAPCs

APCs may be made, for example, by:

(a) obtaining an MHC:antigen complex of interest;

(b) combining said MHC:antigen complex with an artificial lipid membrane to form a membrane-associated MHC:antigen complex, (i.e., a liposome:MHC:antigen complex); and (c) combining said liposome:MHC:antigen complex resulting from step (b) with any of the following: accessory molecule, a co-stimulatory molecule, an adhesion molecule, a modulation molecule, and an irrelevant molecule to form an artificial APC comprising a liposome:MHC:antigen:functional molecule:complex. Steps (b) and (c) may be performed simultaneously. In one embodiment of this method, step (c) is optional in whole or in part with respect to any of co-stimulatory, adhesion, modulation, irrelevant molecules or GPI proteins. In another embodiment, any of the molecules of interest (MHC, accessory, co-stimulatory, adhesion, modulation, irrelevant molecules) can be bound to the β subunit of cholera toxin and GM-1 can be included in the APC lipid matrix to provide a means for proper orientation of the molecules of interest such that their active centers are oriented to facilitate interaction with T cells and other components external to the APC.

By "membrane-associated" is meant the non-covalent attraction between the lipid molecules of a liposome and MHCs, antigens, accessory molecules, co-stimulatory molecules, adhesion molecules, modulation molecules, irrelevant molecules, GM-1 ganglioside molecules, and cholera toxin β subunit.

In another preferred embodiment, the artificial APCs may be made by:

(a) obtaining a spheroid solid support of interest having affinity for non-polar regions of a phospholipid; and (b) combining MHC:antigen complexes, accessory molecules such as ICAM-1, and functional molecules (i.e., other accessory molecules, co-stimulatory molecules, modulation molecules, irrelevant molecules and adhesion molecules) with the phospholipid and solid support to form a solid support associated:membrane-bound:MHC:antigen:accessory molecule:functional molecule complexes (i.e., solid support:phospholipid:MHC:antigen:accessory molecule:functional molecule complex).

In this embodiment, the solid support is preferably a glass bead or magnetic bead. It is also preferred that the phospholipid be phosphotidylcholine. In one embodiment of this aspect, the functional molecules are individually optional. In another preferred embodiment, the molecules may be properly oriented by inclusion of a molecule bound to cholera toxin and GM-1 in the APC membrane matrix. In another embodiment the complex may include an irrelevant molecule for carrying a label. In still other embodiments, the antigen may have a label. In still other embodiments, a label may be noncovalently associated with the lipid layer.

In yet more embodiments of this solid-support APC construct, the solid support is a glass or magnetic bead having a diameter of about between about 25 to about 300 um. In still another embodiment, the solid-support APC construct has only lipids, cholesterol and a molecule having affinity for binding to an irrelevant molecule that is located on another APC (either solid-support based or non-solid support bases). This construct allows for such molecule (which is also an "irrelevant" molecule) to float freely in the lipid layer for proper migration to aid binding of APCs that have bound to T cells.

Artificial APC Uses and Methods

In another aspect, the present invention is directed to a method of isolating T cells specific for an antigen of interest comprising:

(a) obtaining a biological sample containing T cells which are specific for an antigen of interest;

(b) preparing an artificial APC as described herein comprising an MHC:antigen component, wherein the antigen in said component is said antigen of interest;

(c) contacting the biological sample obtained in step (a) with the artificial APC obtained in step (b) to form an artificial APC:T cell complex;

(d) removing said complex formed in step (c) from said biological sample; and (e) separating T cells specific for said antigen of interest from said complex.

Any suitable biological sample which contains T cells specific for the antigen of interest may be used in the method. Suitable biological samples containing T cells specific for an antigen of interest include fluid biological samples, such as blood, plasma and cerebrospinal fluid, and solid biological samples, such as tissue, for example, histological samples. In one embodiment of the above example, the artificial APC may be complexed to a solid support in addition to the T cell. The complexing of the APC to the solid support provides a means to anchor the APC so that it and any T cell binding to it can be preferentially captured and isolated from extraneous matter. In such case, the solid support may be a glass or magnetic bead that is coated with a lipid mono layer that is bound to the bead by, for example, a linker. The solid support may additionally have noncovalently bound accessory molecules associated with the lipid layer such as binding molecules that recognize and bind to irrelevant molecules associated with the artificial APC. In another embodiment, the binding molecules may be covalently bound to the solid support by a linker. Additionally, the lipid layer may further include GM-1 for binding to a molecule of interest that is connected to cholera toxin subunit for orienting said molecule of interest.

By "T cells specific for an antigen of interest" is meant the T cells expressing receptors for a relevant target of an immune response. As noted above, the specificity of the T cell receptor (TCR) determines which antigens bind to the TCR with sufficient affinity to activate a particular T cell. Optionally, the above outlined method of isolating T cells specific for a particular antigen of interest may include determining the quantity of such T cells that bind to the artificial APC, or may include characterizing the functional phenotype of such T cells. Such method may also include the use of a solid support containing a molecule which is able to recognize and bind to the irrelevant molecule located in the lipid layer of the APC. Such solid support may further be confined to an accessible chamber of a column device.

By "MHC:antigen component" is meant MHC molecules that have affinity for antigens of interest which antigens are associated with such MHC and together form a complex of molecules that are inserted into or are associated with the lipid membrane. Artificial lipid membranes such as liposomes may be prepared in a fashion similar to methods known in the art, (e.g., Watts, et al., PNAS, vol. 81:7564-68; Buus, et al., Cell, vol. 47; 1071:77). In a preferred embodiment, the liposome forms a bilayer having eukaryotic cell-like properties in that non-lipid molecules (e.g., MHC:antigen complexes, GM-1 bound to cholera-molecule of interest) may freely migrate within the matrix of the lipid molecules of the liposome's lipid bilayer. An example of a liposome:MHC:antigen combination is provided in FIG. 1 and such a complex may also be prepared, for example, as described in Example 1 below. Moreover, the lipid bilayer may also include accessory molecules such as cholesterol to provide elasticity in the bilayer and GM-1 to provide an anchor for orientation of cholera p subunit comprising molecules of interest.

In one embodiment, a biological sample derived from a tissue sample of interest in the form of a single cell suspension is contacted with an artificial APC followed by incubation of the artificial APC tissue sample mixture with antigen-specific staining compounds (i.e. for example, fluorochrome conjugated antibodies against T cell surface markers of interest e.g., CD3, CD4, or CD8). The cells may also be stained prior to incubation with the complexes. The resulting artificial APC:T cell complex may be separated from the cell suspension by, for example, flow cytometry, capture by a solid support in a column device, or centrifugation of such complexes bound to a solid support such as glass beads or magnetic beads.

Figure 2:
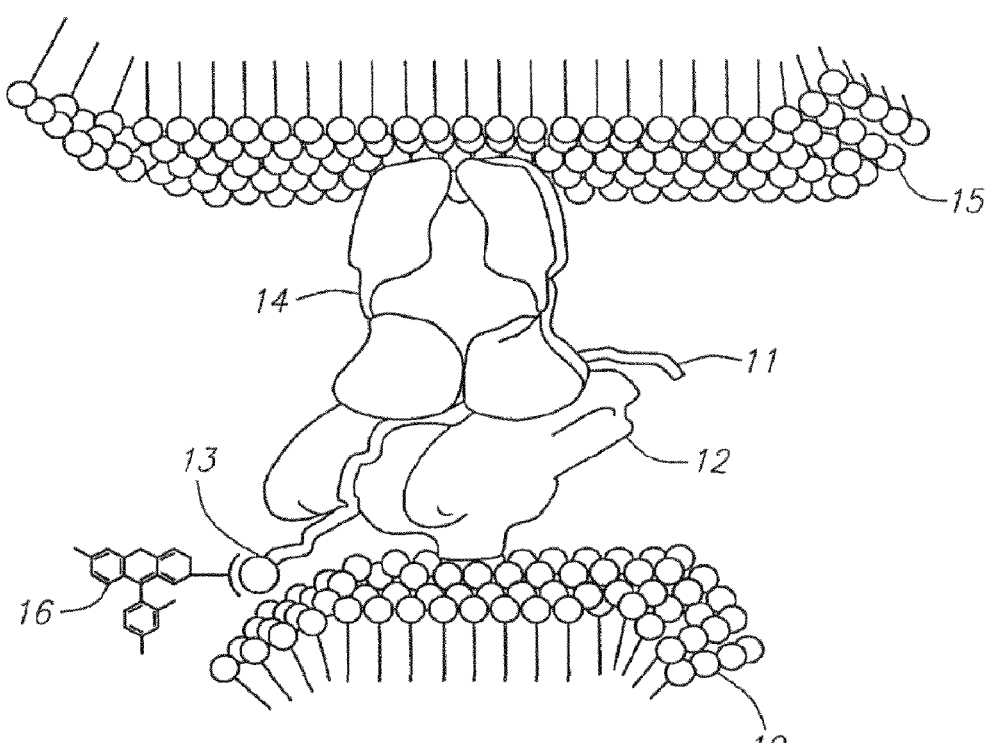
FIG. 2 is a schematic representation of an embodiment of the invention representative of a portion of an artificial APC (10) in which the peptide (11) complexed to the MHC (12) is tagged, wherein the tag, for example, is biotin (13). The visualization of the complex comprising the above components may occur (while a TCR (14) on a T cell (15) is bound to the APC) by FACS through the addition of a streptavidin molecule complexed to a fluorochrome (16).
Figure 3:
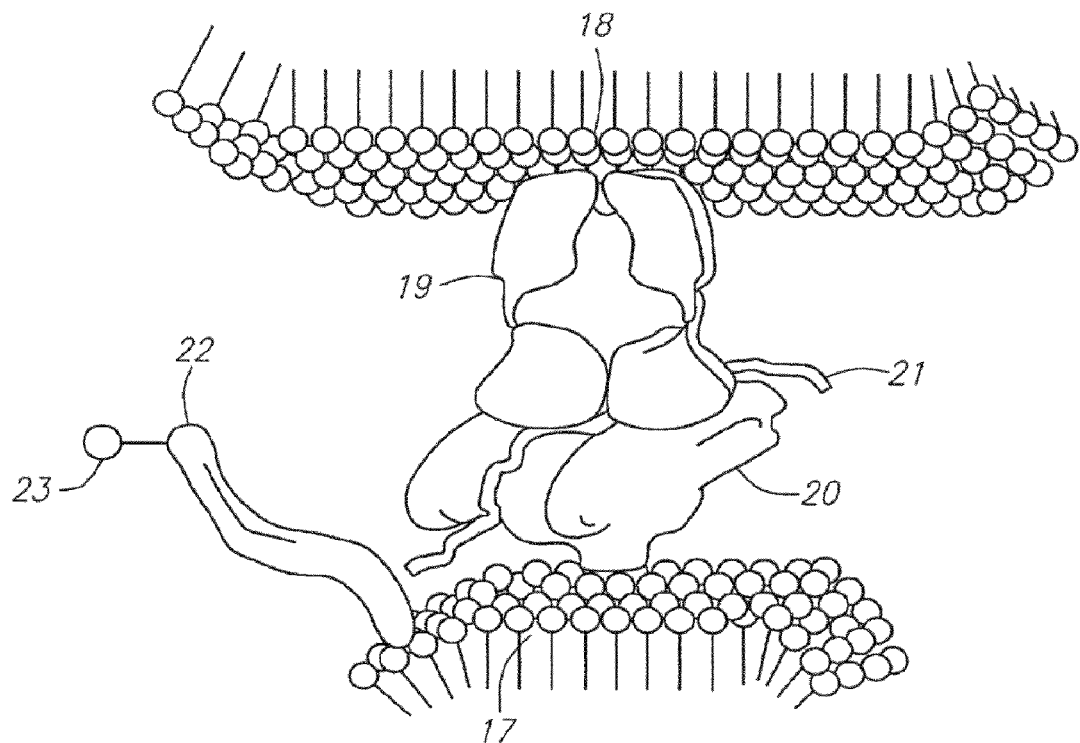
FIG. 3 is a schematic representation of an embodiment of the invention represented by a portion of an artificial APC (17) interacting with a T cell (18) through the TCR (19), using the artificial APC's MHC (20) and unlabeled peptide (21). The visualization by FACS is performed by the inclusion of an irrelevant molecule (22) having an attached label (23). The irrelevant molecule minus the label may also be used to bind the liposome to a solid support.
Figure 4:
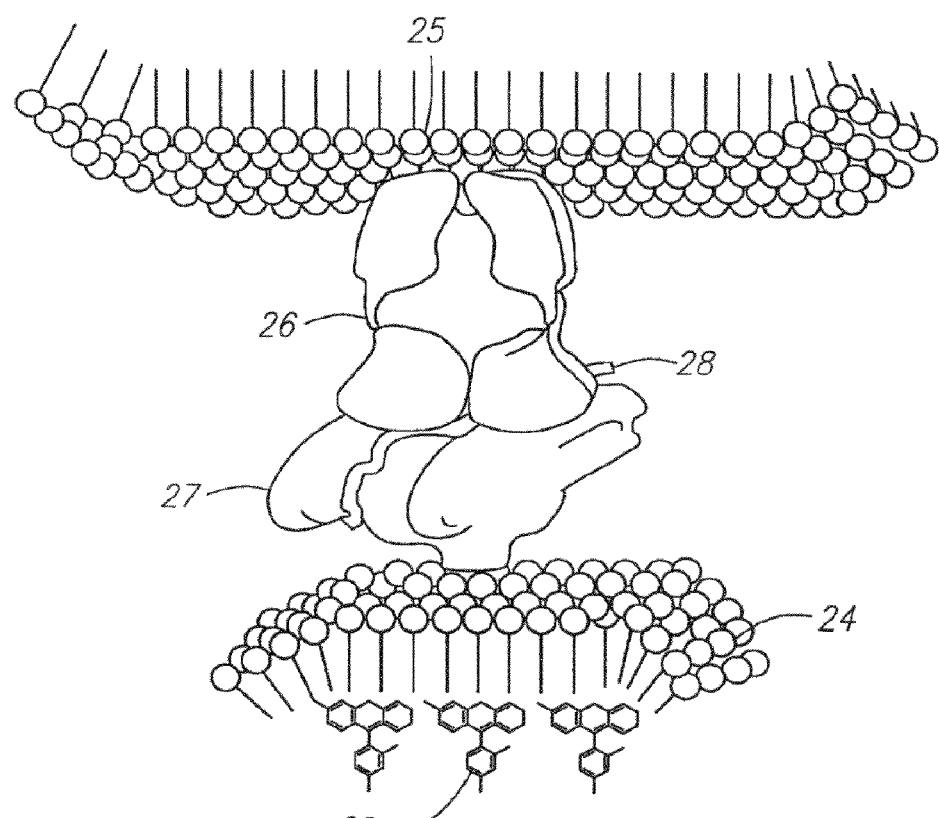
FIG. 4 is a schematic representation of an embodiment of the invention represented by a portion of an artificial APC (24) interacting with a T cell (25) through the TCR (26), using the artificial APC's MHC (27) and unlabeled peptide (28). A fluorochrome (29) may be added to the dialysis buffer during the formation of the liposomes so that visualization may be carried out by FACS.

In one embodiment of the T cell isolation method, the antigen is labeled (FIG. 2). In another embodiment, the irrelevant molecule may be labeled (FIG. 3). In another embodiment of the method, label is associated either covalently or non-covalently with the lipid molecules making up the liposome (FIG. 4). Preferred labels include biotin, fluorochromes such as FITC, radioactive labels and vancomycin. Use of such labels is well understood in the art. In embodiments where the label is associated with lipids of the liposome, the label may be either enclosed within the liposome or incorporated within the lipids of the outer membrane of the liposome. Preferably, the label is a fluorochrome, for example FITC. Such labeled liposomes may be made by mixing FITC with lipids during liposome formation, or may be obtained from commercial sources (e.g., polar lipids).

In another embodiment, the present invention provides an alternate method of isolating T cells specific for an antigen of interest. This alternate method comprises:

(a) contacting an artificial APC comprising a MHC:antigen:accessory molecule component of interest with a solid support to form a solid support:artificial APC (The liposome of the APC contains a binding molecule i.e., an "irrelevant" binding molecule. The capture molecule that binds to the irrelevant molecule may be bound to said solid support via a linker or may be associated with a phospholipid layer on the solid support). In this embodiment, the antigen binding region of said MHC:antigen component is available for binding to a T cell receptor without steric hindrance because the MHC:antigen component is free to move within the liposome membrane of the APC while the irrelevant binding protein allows the APC to be anchored to the solid support;

(b) contacting said solid support:artificial APC with a biological sample containing T cells specific for an antigen of interest to form a solid support:artificial APC:T cell complex;

(c) removing said solid support:artificial APC:T cell complex from said biological sample; and (d) separating the T cells specific for said antigen of interest from said complex.

In this embodiment, the T cells are separated by either the physical removal of the T cell bound solid support from the biological sample, or separation may occur by retention of the bound T cells in a solid support containing compartment of a column device.

In another embodiment, the present invention is directed to other alternate methods of isolating T cells specific for an antigen of interest. One such method comprises:

(a) obtaining a solid support of interest having affinity for non-polar regions of a phospholipid;

(b) combining the solid support and MHC:antigen complexes, accessory molecules such as LFA-1, and functional molecules (i.e., other accessory molecules, co-stimulatory molecules, modulation molecules, adhesion molecules, and irrelevant molecules) with the phospholipid support to form a solid support associated:membrane-bound:MHC:antigen:accessory molecule:functional molecule complexes (i.e., solid support:phospholipid:MHC:antigen:accessory molecule: functional molecule complex;

(c) contacting said solid support:phospholipid:MHC:antigen:accessory molecule:functional molecule complex formed in (b) with a biological sample containing T cells specific for an antigen of interest to form a solid support: phospholipid:MHC:antigen:accessory molecule:functional molecule:T cell complex;

(d) removing said complex formed in (c) from said biological sample; and (e) separating the T cells specific for said antigen of interest from said complex.

In this embodiment, the solid support is preferably a glass bead or magnetic bead of about 25 to about 300 um in diameter. Additionally, the MHC, accessory, and functional molecules are not covalently bound directly to the solid support but are noncovalently associated with the lipid layer having the capacity to migrate on the surface of the solid support. Moreover, in a preferred embodiment of this example, the molecule of interest (e.g., MHC, accessory and functional molecules) are connected to cholera toxin β subunit. Further, GM-1 protein is incorporated into the lipid layer matrix providing a means by which the cholera toxin portion can be bound and the molecule of interest properly oriented in the lipid layer.

In still another aspect, a spheroid solid support may comprise lipid monolayer coating the solid support with only a irrelevant molecule having affinity for bonding another irrelevant molecule located on an APC that either does not have a solid support interior or does have a solid support interior. This aspect adds versatility to the capture process for isolation of APCs that are bound to antigen-specific T cells.

In a further preferred aspect of the invention, kits are provided for the isolation of T cells specific for an antigen of interest comprising any of the following: solid supports, phospholipids, antigen-specific artificial APCs, TCR-specific artificial APCs, solid supports containing lipid associated capture molecules for capturing irrelevant molecules, solid supports containing capture molecules bound to the solid support buffers, media, labels and column devices.

In another embodiment, the invention contemplates a method of characterizing the functional state of antigen-specific T cells comprising:

(a) isolating T cells;
(b) extracting mRNA from said isolated T cells;
(c) obtaining cDNA corresponding to said extracted mRNA;
(d) evaluating the mRNA encoding proteins that govern function and phenotype of the antigen-specific T cells wherein the evaluation is carried out by a method selected from the group consisting of (1) mRNA translation of the proteins and testing such proteins using antibodies against the proteins, and (2) rtPCR of the mRNA using primers specific for the proteins.

In this method, the evaluation of the mRNA encoding proteins that govern function and phenotype of the antigen-specific T cell may be used to determine efficacy of an immunomodulation treatment regimen such as the administering of a vaccine. The immunomodulation treatment can comprise inducing tolerance in autoimmunity, reducing allergic response, inducing an immune response against cancer cells. Additionally, the proteins that govern function and phenotype of the antigen-specific T cells include cytokines, chemokines, chemokine receptors, and cytokine receptors.

The genes encoding antigens may also be identified. In another aspect, the invention contemplates a method for identifying a gene which is expressed by a T cell specific for an antigen of interest comprising:

(a) obtaining a biological sample containing T cells which are specific for an antigen of interest;
(b) labeling with a first label at least the intracellular gene product of interest produced by T cells in said biological sample;
(c) preparing a liposome:MHC:antigen complex, wherein the antigen in said liposome:MHC:antigen complex is said antigen of interest;
(d) contacting the biological sample obtained in step (a), as labeled in accordance with step (b), with the liposome:MHC:antigen complex obtained in step (c) to form a liposome:MHC:antigen:T cell complex;
(e) labeling with a second label the liposome:MHC:antigen:T cell complex obtained in step (d); and
(f) discriminating, according to antigen specificity, cells producing the intracellular gene product of interest, which cells have both the first label and the second label.

In such method, the first and said second label may be selected from the group consisting of biotin, a fluorochrome, FITC, and a radioactive label; provided that the first and second labels are not the same.

In yet another preferred embodiment, methods are provided for modulating T cell responses. In this embodiment, T cells are isolated from a subject which are specific for an antigen of interest followed by combining said isolated T cells with an artificial APC having functional molecules specific for modulating a T cell. In a preferred embodiment, the T cells specific for an antigen of interest are isolated using any of the T cell isolation methods described herein. In one preferred embodiment, modulation to activate T cells generally is caused by contacting said T cells with an artificial APC that expresses the co-stimulatory molecule B7 or anti-CD28, as well as MHC:antigen.

By "modulating T cell response" is meant the intentional intervention in the functional characteristics of antigen-specific T cells, including, but not limited to, functional pattern of cytokines produced, change in phenotype of T cells, and modulation in the expression of activation markers, cytokines and their receptors and chemokines and their receptors. Such modulations can be carried out for numerous purposes as discussed in the numerous examples above.

The modulation of T cell response may further comprise changing in whole or in part the functional pattern of cytokine production by the isolated T cells specific for a given antigen from a Th1 response to a Th2 response. In a preferred embodiment, modification of a T cell response for the purpose of increasing its Th2 response and/or decreasing its Th1 response includes the expression by the artificial antigen presenting cell used in such method of a co-stimulatory molecule, such as B7-2.

In another embodiment, the modulation of T cell response may comprise changing in whole or in part the functional pattern of cytokine production by said isolated T cells from a Th2 response to a Th1 response. Preferably, modulation of a T cell response for the purpose of increasing its Th1 response and/or decreasing its Th2 response includes the expression by the artificial APC used in such method of a co-stimulatory molecule such as B7-1.

The two subsets of CD4 T cells represented by Th1 and Th2 cytokine markers, have very different functions from one another. These two CD4 T cell subsets can also regulate each other. Once one subset becomes dominant, it is often difficult to shift the response of the T cell (i.e. expression of the cytokine) to the other type. One reason for this is that expressed cytokines of one type of CD4 T cell will inhibit the activation of the T cell to expression of another cytokine. For example, IL-10, a product of Th2 cells, can help to inhibit the development of a Th1 response. Therefore, in one embodiment, IL-10 is incorporated into artificial APCs and the resulting APC may be used to inhibit development of Th1 response.

In another example, interferon-γ (INF-γ), a product of Th1 cells, can help to prevent the activation of a Th2 response. If a particular CD4 T cell type is activated preferentially in a response so that the cytokine (Th1 or 2) is highly expressed, such high expression can suppress the development of the other subset. The overall effect of T cell populations expressing one or the other subset is that various tissues become either suppressive (Th2) or inflammatory (Th1). Thus, INF-γ can be incorporated into artificial APCs and the resulting APC used to modulate cell populations to become either suppressive or inflammatory.

The ability to manipulate T cell response (as exemplified by the Th1/Th2 subsets) provides a novel method by which treatment can be provided for numerous disease states. For example, a response to an allergen can be manipulated so as to shift the antibody response away from an IgE-dominated response. Such a shift will prevent the allergen from activating IgE-mediated effector pathways. For example, a technique that has been used for many years to generate a desensitization response is carried out by contacting patients with escalating doses of the allergen (such as by feeding, nasal delivery, or by injection). This immunization schedule appears to gradually divert an IgE-dominated response, which diversion is driven by Th2 cells, to one driven by Th1 cells, with the consequent down-regulation of IgE production. Thus, the activation of a Th2 response in such a manner may be of use in the treatment of allergy.

Similarly, other conditions that are associated with a Th2 T cell response, as for example, responses in which the functional phenotype of cytokine secretion is tolerogenic to viral infections and some types of cancer, may also benefit from a modification of the Th2 T cell response so that Th2 is reduced and/or a Th1 T cell response is increased.

Autoimmune conditions, in which the functional phenotype of cytokine secretion is pro-inflammatory (as is the case with Th1), will benefit from a modification of the Th1 T cell response so that it is reduced and/or a Th2 T cell response is increased. As noted above, cytokines are cell-derived soluble mediators associated with immune responses that may act both within a microenvironment and/or systemically. Immune cells secrete specific cytokine profiles, each having markedly different effects. Th2-type cells secrete low levels of TGF-β, no IFN-γ and high levels of IL-4 and IL-10, the presence of which in turn produce an immunosuppressive or tolerogenic immune environment. Th1-type cells on the other hand secrete very low TGF-β, high IFN γ and no IL-4 or IL-10. High expression of INF-γ is associated with cell mediated proinflammatory immune environments. As discussed herein, the artificial APC of the current invention can be used to modulate T cell responses by affecting these and other cytokines. Moreover, such cytokines as well as other soluble factors to which a T cell responds may be used in conjunction with a column device as described below.

In yet another embodiment, the regulation of T cell responses may comprise inducing anergy. Specifically, T cell responses may be modified for the purpose of inducing anergy through the Fas/Fas Ligand pathway.

In yet another aspect, the present invention provides methods of treating a condition in a subject who would be benefited by modulating the functional patterns of cytokine production by certain of such subject's antigen-specific T cells to increase Th2 response and/or decrease Th1 response, comprising:
  (a) isolating T cells capable of triggering a Th1 response from a subject;
  (b) combining said isolated T cells with artificial APCs which express MHC capable of binding an antigen recognized by said T cells wherein said artificial APC also expresses the co-stimulatory molecule B7-2;
  (c) separating T cells that have bound to said artificial APCs in step (b); and
  (d) administering said T cells isolated in step (c) to said subject.

T cells that have been in contact with an artificial APC as described above will be stimulated to shift their Th1 response to a Th2 response. Conditions which would be benefited by modulating the functional pattern of cytokine production to increase Th2 response and/or decrease Th1 response include autoimmune diseases such as, for example, type 1 diabetes mellitus, multiple sclerosis, rheumatoid arthritis, dermatomiosytis, juvenile rheumatoid arthritis and uveitis.

In yet another aspect, the present invention provides methods of treating a condition in a subject that would be benefited by altering the functional pattern of cytokine production by certain antigen-specific T cells to increase Th1 response and/or decrease The response comprising:
  (a) isolating T cells that are specific for an antigen capable of triggering a Th2 response from a subject;
  (b) combining said isolated T cells with an artificial APC which expresses an MHC capable of binding an antigen that is recognized by said T cells so that the functional pattern of said T cells may be modulated, wherein said artificial APC also expresses the co-stimulatory molecule B7-1;
  (c) separating the T cells modulated in step (b); and
  (d) administering said T cells isolated in step (c) to said subject.

Conditions which would be benefited by modulating the functional pattern of cytokine production to increase Th1 response and/or decrease Th2 response include for example, allergy, allergy to dust, animal skin bypass products, vegetables, fruits, pollen, chemicals, and some infections (e.g., viral, fungal, protozan and bacterial).

As noted above, the present invention provides methods for isolating antigen-specific T cells. It is desirable to isolate antigen-specific T cells in a variety of contexts. For example, in adoptive immunotherapy, lymphocytes are removed from a patient, expanded ex vivo, and then reinfused back into the patient to augment the patient's immune response. See Rosenberg et al., N. Engl. J. Med. 313:1485-1492 (1985); U.S. Pat. No. 4,690,915. This approach has been effective in the treatment of various cancers (see, e.g., Rosenberg et al., N. Engl. J. Med. 319:1676-1680 (1988). Isolation and expansion of T cells specific for a particular antigen will increase the specificity and effectiveness of adoptive immunotherapeutic approaches. Such expansion may be benefited by obtaining a population of monoclonal T cells. Thus, the invention contemplates a method of obtaining a monoclonal population of T cells specific for an antigen of interest comprising:
  (a) isolating T cells specific for an antigen of interest; and
  (b) culturing the isolated T cells in an individual well with the antigen of interest and an artificial APC.

Isolated T cells specific for a particular antigen may also be used as a diagnostic to screen for the presence of, or amount of a particular antigen and thus detect the presence, absence, or status of an immune response. Early detection of an immune response will facilitate selection of a particular treatment regimen in a variety of pathological conditions such as autoimmune diseases, allergies, allograft rejection, and infectious diseases. In a diagnosis of this type, the isolated T cells are used both as a means of detection and as reporters. The T cells proliferate when contacted with the antigen for which they are specific. This proliferation is easily detected as an increase in cell number or as an increase in growth rate measured, for example, by the rate of uptake of a label (e.g., observation of the uptake of tritiated thymidine or bromodeoxyuricyl (BrdU)). Thus, the presence or absence of target antigen can be detected by exposing the isolated T cells to a tissue sample (e.g., peripheral blood) and monitoring their proliferation rate. In the current invention, a preferred embodiment includes the observation of bound T cells using a FACS which allows the avoidance of time consuming proliferation experiments.

Isolation of antigen-specific T cells also provides a homogenous source of T cell receptors. A homogenous source of T cell receptors is an aid to the elucidation of structure-function relationships of particular receptors. A homogenous source of T cell receptors also facilitates the development of solubilized T cell receptors that are of use in a number of therapeutic applications (See, e.g., U.S. Pat. No. 5,283,058). In the current invention, solubilized receptors may be used in conjunction with an immunomodulation column device.

In another preferred embodiment, the invention provides for a method of identifying epitopes expressed on the MHC that are of import to acceptance or rejection of grafts in transplantation therapy. In this embodiment, a donor's MHC is examined by computer modeling to identify peptide moieties likely to be recognized by a recipient's T cells. The recipient's T cells are tested by FACS analysis for binding against the peptides. Upon positively identifying reactive peptides, such peptides may then be used to deplete the recipient's graft rejecting T cells thereby modulating the recipient's immune response in the transplantation regimen. This modulation is carried out within a comprehensive treatment that includes further modulating the recipient's sensitivity to the graft epitopes by exposing the recipient to the donor's epitopes by feeding, nasal delivery, or injection of increasing concentrations of the peptides.

In another aspect, the invention provides for a method to identify antigenic motifs of pathogens that are recognized by the MHC. In this embodiment the identification of such motifs allows the development of anti-pathogen vaccines comprising either pools of such motifs in the form of peptides that are recognized by T cells in the general human population i.e., the pathogen's antigenic moieties responsible for generating immune responses are identified so that for any disease, a vaccine comprising such antigens may be produced. Additionally, a vaccine may be produced against such antigenic moieties comprising a population of a patient's pathogen-specific T cells that have been expanded ex vivo.

Figure 6:
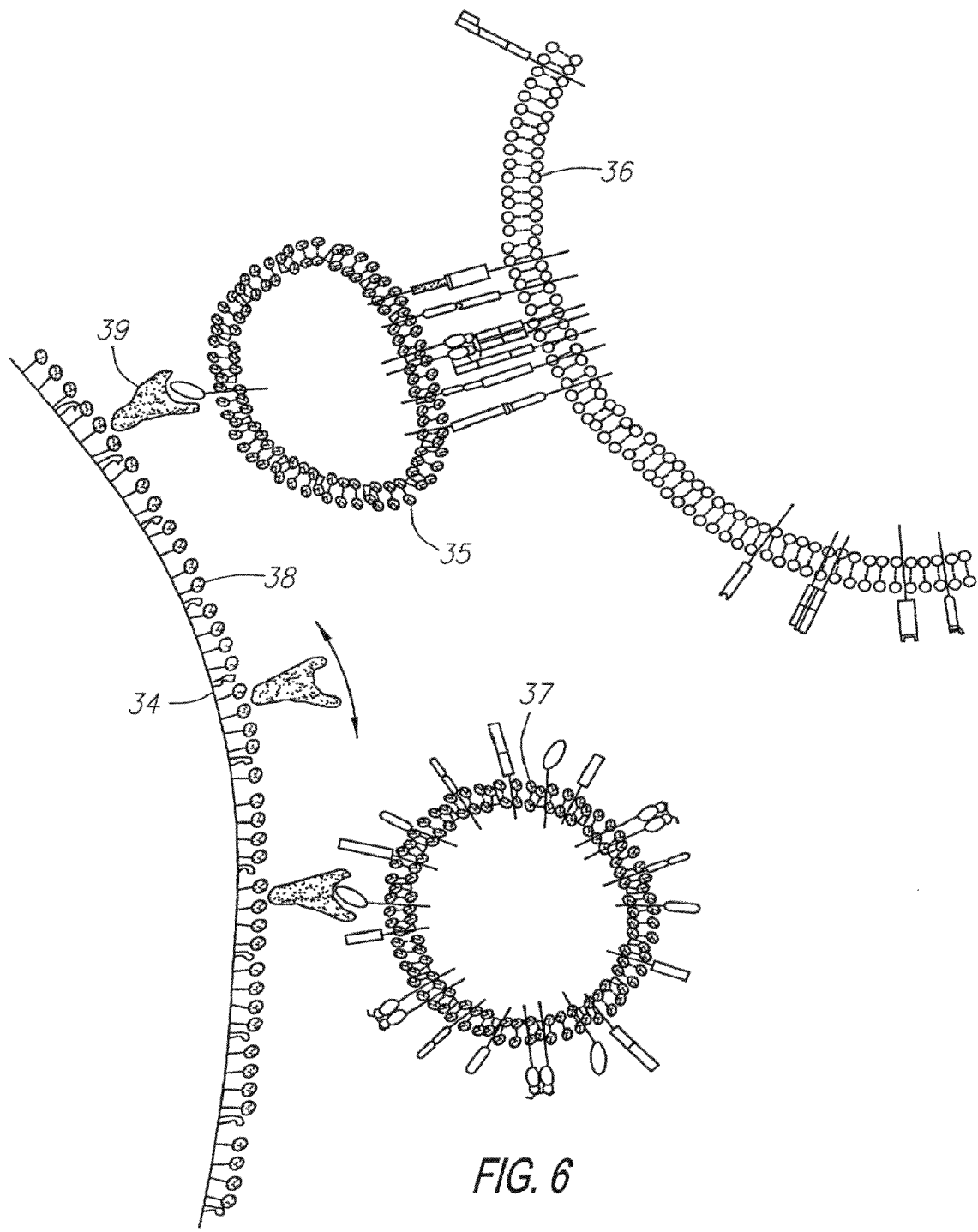
FIG. 6 is a schematic showing the capture of artificial APCs (35) and (37) by capture molecules (39) that are noncovalently associated with a lipid layer (38) (e.g., a neutral phospholipid) attached to a solid support (34).
Figure 7A:
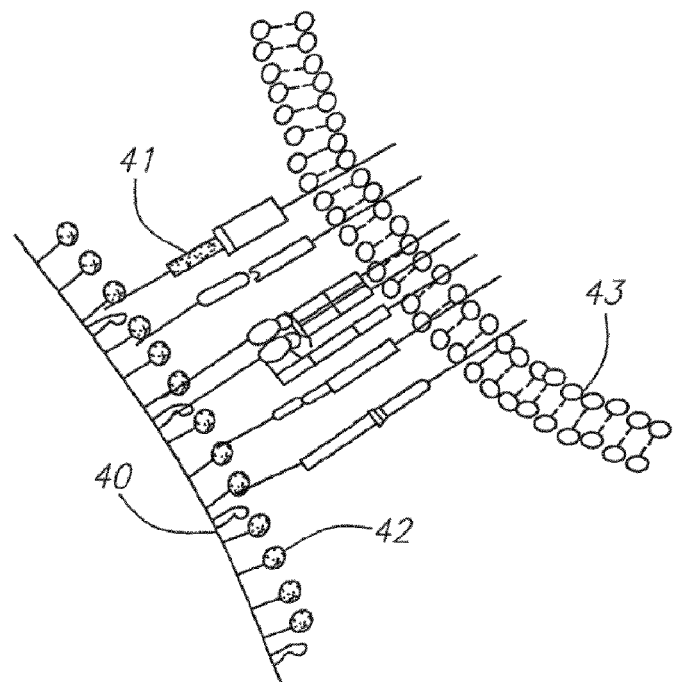
FIG. 7a represents a solid support (40) having a non-covalently associated lipid layer (42) containing various components of artificial APCs (41) that can bind a T cell (43).
Figure 7B:
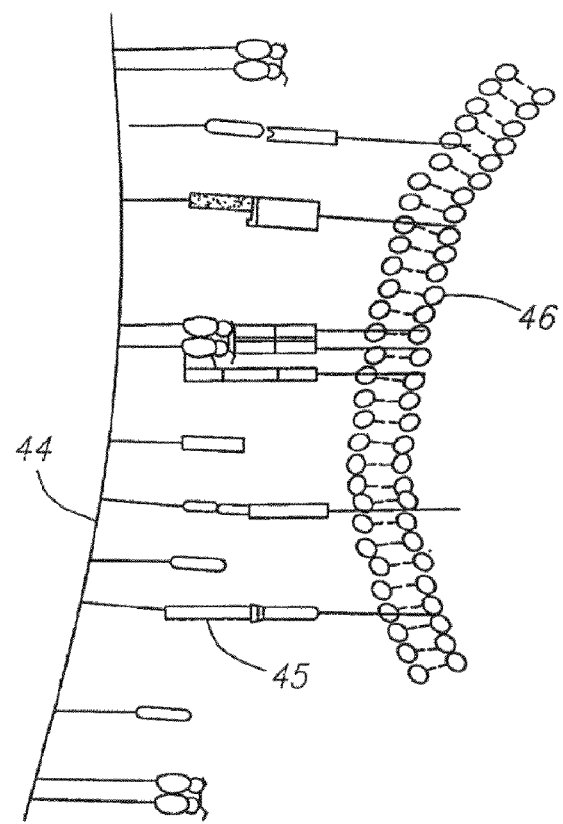
FIG. 7b shows a solid support (44) having the various components of artificial APCs (45) without a lipid component that can bind to a T cell (46).
Figure 8:
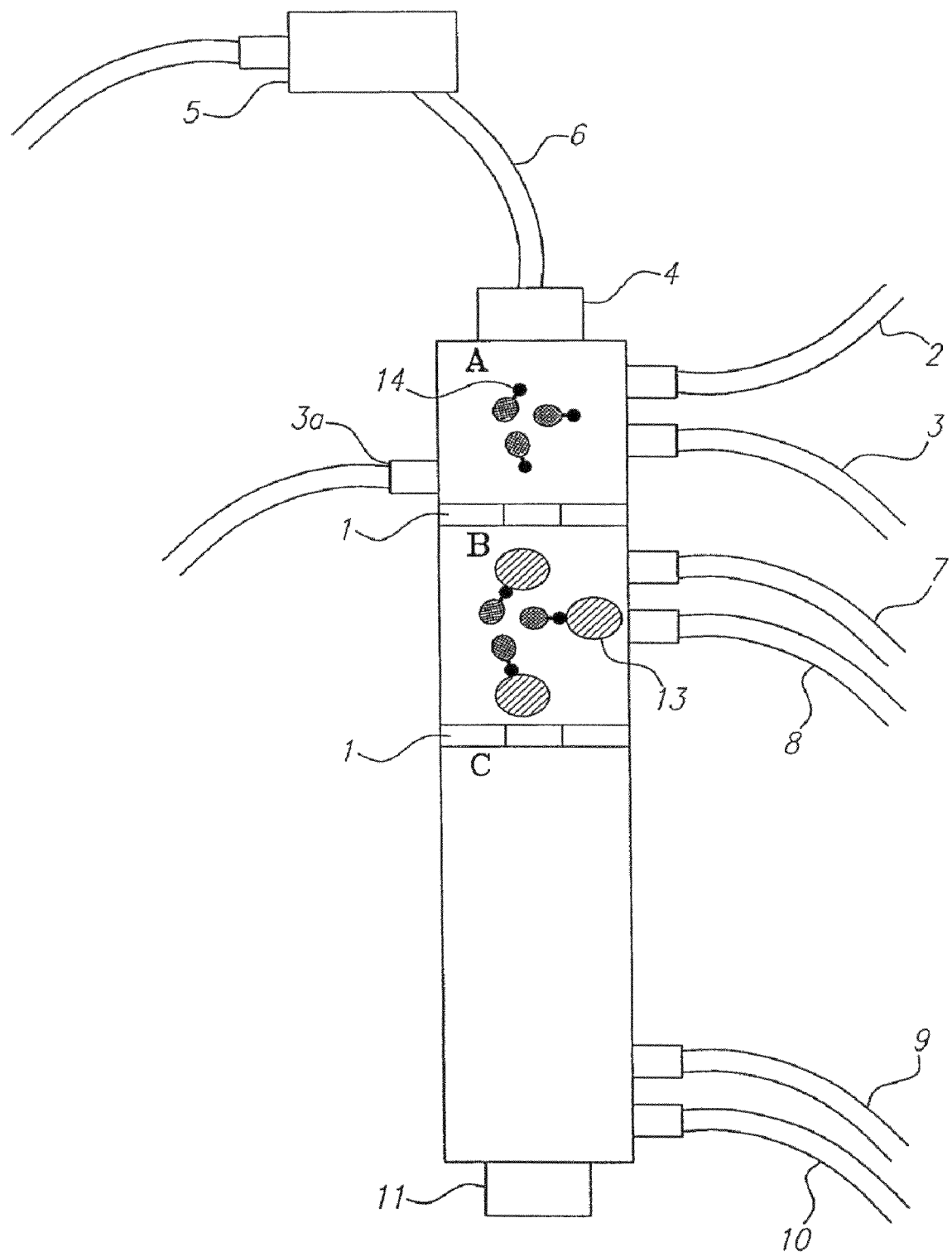
FIG. 8 shows a column device having a multiplicity of compartments for processing antigen-specific T cells. The column, as shown, also contains aAPCs and various embodiments of solid supports.

In yet another aspect of the invention, a column device is provided comprising a multiplicity of compartments that are arranged in series. As shown in FIG. 8, one embodiment of such device has compartments A, B, and C. Each compartment is contiguous with the adjacent compartment by a valve 1. The valve between each compartment may be opened or closed. Compartment A also has entrance ports 2 and exit ports 3 for receiving a flowable medium. Any of the compartments may contain solid supports as seen in FIGS. 6, and 7 for binding either a molecule that can bind to an irrelevant molecule for immobilizing an artificial APC, or for binding directly MHC:antigen:functional molecule complexes. The entrance port 4 of compartment A is attached to an external device 5 (e.g., a device where a patient's T cells are separated from whole blood and concentrated) prior to export through a sterile tube 6 to entrance port 4. Once the patient's enriched T cell population is transported into compartment A via entrance port 4, the T cells containing TCR specific for the MHC:antigen complexes bind to MHC:antigen complexes that are themselves attached either directly to the solid supports or are associated with an artificial APC which is bound to a solid support via an irrelevant molecule. In the configuration demonstrated in FIG. 8, artificial APCs 14 are attached to solid supports in compartment A awaiting interaction with incoming cell through interance port 4. Compartment A thus provides a chamber wherein the APCs and cells can interact so that antigen-specific T cells can be isolated while non-binding T cells are allowed to wash out of the compartment A via exit port 3a. After the non-binding cells are removed (and either discarded or returned to the patient's circulatory system, or addressed to a device for monitoring the cells such as a FACS), the bound antigen-specific T cells may be released from the solid supports in A and allowed to channel or flow through valve 1 located between compartment A and B and into compartment B. The artificial APC-cell bound complexes or just the antigen-specific T cells alone may be released from solid support of compartment A by adjusting the temperature of the medium in the compartment A. Once the antigen-specific T cells are in compartment B, they may again be captured as shown in FIG. 8, or simply be treated without recapture in any number of ways to induce cell modulation. For example, artificial APCs containing antigen-specific MHC:antigen:functional molecule complexes may be infused into compartment B via entrance port 7. With the infusion of the antigen-specific APCs into compartment B, the antigen-specific T cells may then bind and be induced to modulate their respective response or be acted upon otherwise as desired. FIG. 8 shows T cells 13 that have been released from compartment A and are shown bound to APCs that are in turn bound to solid supports. As described above, and hereinafter, numerous types of modulation of the T cells may occur. For example, the T cells maybe modulated to (1) increase a Th1 and/or decrease a Th2 response, (2) increase a Th2 and/or decrease and Th1 response, (3) be generally induced to proliferate regardless of Th1 or Th2 response, (4) enter a state of anergy, (5) become apoptotic, (6) shed certain adhesion molecules known to those skilled in the art to be involved in the entry of cells into specific diseased areas, (7) upregulate/downregulate chemokine or cytokine receptors associated with a Th1-type response, (8) upregulate/downregulate chemokine or cytokine receptors associated with a Th2-type response. The T cells may also be captured on such APCs for the purpose of (1) depleting allo-antigen-specific T cells from a donor's T cell population in transplantation oriented therapy, such as bone marrow transplant therapy or (2) from a patient's T cell population such as to facilitate a graft of allogenic solid organs, or (3) used in identifying TCRs that bind to pathogen-recognizing MHCs or self-derived pathogen-mimic antigenic motifs. Moreover, soluble molecules may be added to the device for inducing such modulation including cytokines, adjuvants, and hormones.

Once isolation or other modulation has been performed in compartment B, the T cell:artificial APC complex may be addressed to compartment C via the valve 1 between compartments B and C. The entrance port 7 of compartment B may be additionally connected to external units for supplying buffers and the like that may be necessary for carrying out manipulations of the T cells in compartment B. The exit port 8 of compartment B may also be used to transport modulated T cell:artificial APC complexes to sampling devices such as FACS or to other devices for such things as cell proliferation and the like.

Compartment C may also contain solid supports and the like for binding artificial APC:T cell complexes and further treatment. In compartment C, the modulated and isolated T cells may be eluted from the APCs (via the adjustment of the medium's temperature) and addressed to other devices through ports 9 and 10, or addressed out of the column through exit port 11 to, for example, the patient, a FACS, a culture device, or to another location for further manipulation.

Formulation and Administration

For in vivo application, aAPCs of the invention are administered by any suitable route, preferably by injection. For systemic administration, intravenous injection is preferred. Suitable formulations are found in Remington's Pharmaceutical Sciences, Mack Publishing Company, Philadelphia, Pa., 17th ed. (1985). A variety of pharmaceutical compositions comprising aAPCs of the present invention and pharmaceutically effective carriers can be prepared. The pharmaceutical compositions are suitable in a variety of drug delivery systems.

In preparing the pharmaceutical compositions of the present invention, it is frequently desirable to modify the aAPCs to alter their pharmacokinetics and biodistribution. For a general discussion of pharmacokinetics, see, Remington's pharmaceutical sciences, supra. A number of methods for altering pharmacokinetics and biodistribution are known. For instance, methods suitable for increasing serum half-life of aAPCs include treatment to remove carbohydrates which are involved in the elimination of substances from the bloodstream. Also, conjugation to soluble macromolecules, such as proteins, polysaccharides, or synthetic polymers, such as polyethylene glycol, is also effective. Preferred macromolecules include those that target aAPCs complexed therewith to a specific tissue (e.g., a lymphoid organ) or cell type. A number of such targeting molecules are known in the art, and they include proteins and carbohydrates.

Liposomes can be prepared according to any suitable method known in the art. Following liposome preparation, the liposomes may be sized to achieve a desired size range and relatively narrow distribution of liposome sizes. One preferred size range is about 0.2-0.4 um, which allows the liposome suspension to be sterilized by filtration through a conventional filter, typically a 0.22 micron filter.

Several techniques are available for sizing liposome to a desired size. These include sonicating a liposome suspension either by bath or probe sonication to produce a progressive size reduction. Homogenization is another method, and it relies on shearing energy to fragment large liposomes into smaller ones. In a typical homogenization procedure, multilamellar vesicles are recirculated through a standard emulsion homogenizer until selected liposome sizes, typically between about 0.1 and about 0.5 microns, are observed. In such methods, particle size distribution can be monitored, for example, by conventional laser-beam particle size discrimination.

Extrusion of liposomes through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size.

Even under the most efficient encapsulation methods, the initial sized liposome suspension may contain various components that have not been incorporated into a liposome. If desired, any suitable available for removing non-entrapped compounds from a liposome suspension may be employed. In one such method, liposomes are pelleted by high-speed centrifugation, leaving free compounds and other contaminants in the supernatant. Another method involves concentrating a liposome suspension by ultrafiltration, then resuspending the concentrated liposomes in a replacement medium. Alternatively, gel filtration can be used to separate large liposome particles from solute molecules.

After arriving at a desired aAPC composition based on liposomes, the liposome suspension may be brought to a desired concentration for administration. This may involve resuspending the liposomes in a suitable volume of injection medium, where the liposomes have been concentrated, for example by centrifugation or ultrafiltration, or concentrating the suspension, where the drug removal step has increased total suspension volume. The suspension may then be sterilized by filtration. The composition may then be administered, for example, parenterally or locally in a dose which varies according to, e.g., the manner of administration, the particular disease being treated, etc.

For pharmaceutical compositions which comprise aAPCs of the present invention, the dose will vary according to, e.g., the particular aAPC composition complex, the manner of administration, the particular disease being treated and its severity, the overall health and condition of the patient, and the judgment of the prescribing physician.

The pharmaceutical compositions are intended for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, and capsules.

Preferably, the pharmaceutical compositions are administered intravenously. Thus, this invention provides compositions for intravenous administration that comprise a solution of aAPCs dissolved or suspended in a pharmaceutically acceptable carrier, preferably an aqueous carrier. A variety of aqueous carriers may be used, e.g., water, buffered water, 0.4% saline, and the like. For instance, phosphate buffered saline (PBS) is particularly suitable for administration of aAPCs of the present invention. These compositions may be sterilized by conventional, well-known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of the aAPCs in the composition can vary widely, i.e., from less than about 0.05%, usually at or at least about 1% to as much as 10 to 50% or more by weight and will be selected primarily by fluid volumes, viscosities, etc., in accordance with the particular mode of administration selected. Preferred concentrations for intravenous administration are about 0.02% to about 0.1% or more in PBS.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient.

For aerosol administration, the aAPCs are preferably supplied in finely divided form along with a surfactant and propellant. The surfactant must, of course, be nontoxic, and preferably soluble in the propellant. Representative of such agents are the esters or partial esters of fatty acids containing from 6 to about 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides may also be employed. The surfactant may constitute 0.1%-20% by weight of the composition, preferably 0.25-5%. The balance of the composition is ordinarily propellant. Liquefied propellants are typically gases at ambient conditions, and are condensed under pressure. Among suitable liquefied propellants are the lower alkanes containing up to five carbons, such as butane and propane. Mixtures of the above may also be employed. In producing the aerosol, a container equipped with a suitable valve is filled with the appropriate propellant, containing the finely divided compounds and surfactant. The ingredients are thus maintained at an elevated pressure until released by action of the valve.

The compositions containing aAPCs can be administered for therapeutic, prophylactic, or diagnostic applications. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient. As discussed above, this will typically be between about 0.5 mg/kg and about 25 mg/kg, preferably about 3 to about 15 mg/kg.

In prophylactic applications, compositions containing aAPCs of the invention are administered to a patient susceptible to or otherwise at risk of a particular disease. Such an amount is defined to be a "prophylactically effective dose." In this use, the precise amounts again depend on the patient's state of health and weight. The doses will generally be in the ranges set forth above.

Kits can also be supplied for in vivo uses. Often, the subject composition of the present invention will be provided, usually in a lyophilized form, in a container. The aAPC-containing compositions are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of complex and usually present in total amount of at least about 0.001% wt. based again on the protein concentration. Frequently, it will be desirable to include an inert extender or excipient to dilute the active ingredients, where the excipient may be present in from about 1 to 99% wt. of the total composition. A suitable buffer for reconstituting the dry composition is also provided in the kit.

Specific embodiments of the present invention are exemplified in the following Examples. These Examples are not to be interpreted as limiting the scope of the invention in any way, the scope being disclosed in the entire specification and claims.

Example 1

Liposome Assay for Detection of Antigen-Specific T Cells

In this example, experiments are described which demonstrate the capacity of T cells to bind to liposomes containing cholesterol having MHC:antigen complexes inserted into the liposome membrane. The capacity of T cell binding was quantified by flow cytometry analysis (FACS). Negative controls for the binding include the use of a control T cell line (i.e., non-reactive) having specificity for an irrelevant peptide, incorrect MHC restriction, peptide and antibody inhibitions, limiting dilutions, and the use of MHC without peptide.

The ability of the method to provide for discrimination between antigen-specific T cells was facilitated by use of two T cell hybridomas specific for the same peptide. These hybridomas were $OVA_{323-336}$ (which correspond to residues 323-326 of ovalbumin) (obtained from Research Genetics, Huntsville Ala.) which were restricted by two different MHCs, I-A$^s$ and I-A$^d$. Specifically, the designations for the restrictions were I-A$^s$ restricted $OVA^{323-336}$ specific T cell hybridoma, AG 111.207, and the Iα52-restricted $OVA^{323-336}$ specific T cell hybridoma 8D051.15. A peptide containing 2 identities and one conservative substitution, Hi15 (Research Genetics), which corresponds to residues 15-31 of *H. influenzae* isoleucyl tRNA transferase, was used as a negative control.

Materials and Methods

Preparation of Liposome:MHC:Antigen Complexes

Liposomes were prepared similarly to that described by Brian et al., PNAS, 81:6159-63. Briefly, cholesterol (Ch) and L-α-phosphotidylcholine (PC) (Sigma) were mixed at a molar ratio of 2:7 of Ch and PC respectively. The mixture was placed under an argon stream for 30 minutes to evaporate chloroform used in the preparation, and resuspended in 140 mM NaCl, 10 mM Tris HCl, and 0.5% deoxycholate at pH 8. The suspension was sonicated for three minutes or until clear.

Complexes of affinity-purified MHC molecules I-A$^s$ and I-A$^d$ (each expressed in a B cell lymphoma and purified via immunoaffinity column) were inserted into liposomes by a 72 hour 4° C. dialysis against three changes of PBS (Slidalyzer, Pierce) at a 1:10 molar ratio of MHC to liposomes to form liposome:MHC complexes.

The $OVA^{323-326}$ peptide and the control peptide, Hi15, were biotinylated, (post synthesis, Sigma), and the biotinylated peptides (b-peptides) were incubated with the liposome:MHC complexes for 18 hours at room temperature at a physiologic pH to form liposome:MHC:b-peptide complexes.

Flow Cytometry

Viable cells were separated from debris using a ficol-hypaque gradient. (Lymphocyte M) Cells were blocked with 10% FCS in PBS for 10 minutes on ice, then washed in PBS. Incubations with antibodies (used at concentrations of 400-600 ng/ml) were performed on ice in the dark for 20 minutes. The antibodies used included anti-CD3e (clone 145-2C11), anti-CD4 (clone GK 1.5), anti-CD8a (clone 53-6.7), anti-HSA (clone M1/69), and anti-CD69 (H1.2F3) (Pharmingen, San Diego, Calif.). Liposome:MHC:b-peptide complexes were preincubated with fluorescent streptavidin molecule (f-strep) at room temperature for ½ hour. When two peptides were used in the same assay, the liposome:MHC:b-peptide complex was preincubated with streptavidin molecules of differing fluorescence prior to addition to cells. Sorted cells were either (a) cultured (using a 3:1 ratio of irradiated BALB/c spleen cells, 20 U/ml rIL-2, 10 ug/ml Hi15 or Iα52, 10% FCS, 1% Penicillin/Streptomycin/Glutamine (P/S/G), in RPMI 1640 at 37° C. and 6% $CO_2$), (b) processed for variable beta chain (Vb) analysis by PCR, or (c) reanalyzed by a fluorescent antibody cell sorter (FACS).

Yields ranged from 2,000 to 16,000 events. Bulk-sorted cells used for reanalysis were incubated for ½ hour on ice and spun down through 100% FCS at 325.times.g for 10 minutes to remove liposome:MHC:b-peptide complexes, prior to restaining with liposome:MHC and a different b-peptide. Single-cell sorts were dispersed in 96-well culture plates containing fresh irradiated APCs obtained from the spleen of a syngeneic BALB/c mouse. Generally 8-12 wells showed proliferation over six weeks. Cells were visualized with a Becton Dickinson FACS Star equipped with LYSIS II software.

As shown in FIG. 9, specific recognition of MHC/peptide complexes by T-T hybridomas AG111.207 (1-A$^s$/OVA$^{323-336}$ specific) and 8D051.15 (IA$^d$/OVA$^{323-336}$ specific) were observed. Cultured AG111.207 or 8D051.15 cells were analyzed by flow cytometry using anti-CD4 antibodies and I-A$^d$/b-peptide or I-A$^s$/b-peptide combinations complexed into liposomes and visualized by addition of f-strep. The ratio of cells specific to either the I-A$^d$/antigen or A$^s$/antigen was constant between experiments. (All figures are gated on CD4+ cells unless otherwise stated.) FIG. 9 (*a*) shows AG111.207 cells which were stained with anti-CD4 antibody and differing combinations of MHC/antigen including an irrelevant peptide known to bind to I-A$^d$ (Hi15). Cellular specificity is shown by use of a B cell hybridoma (FIG. 9-*a*4). FIG. 9(*b*) shows 8D051.15 cells which were analyzed with differing combinations of MHC:antigen. Included is a control using biotinylated I-A$^d$ alone to detect the T cell hybridoma (FIG. 9-*b*4).

Results

Figure 9A:
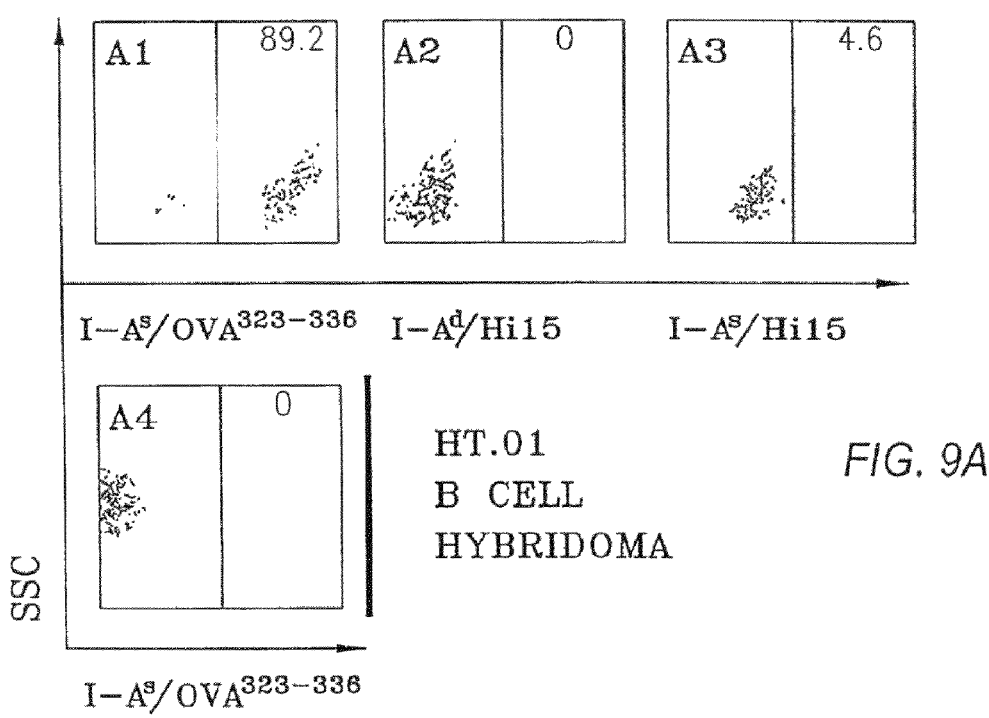
FIGS. 9A and B is a series of FACS figures detailing the specificity of the embodiment of the method diagramed in FIG. 2 using two different murine hybridomas specific for the OVA peptide in the context of either Iα52 or I-A$^s$. The Hi15 peptide has two identities and one conservative substitution with the OVA peptide; thus being a stringent control of specificity.
Figure 9B:
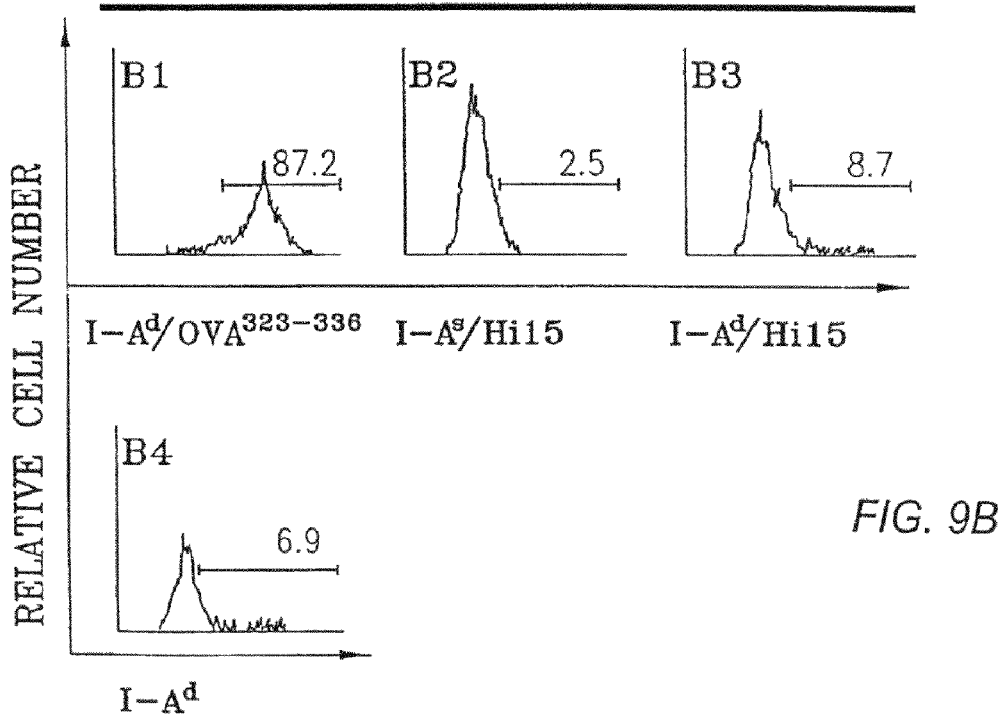

In the series of experiments for which results are shown in FIG. 9, purified I-A$^s$ or I-A$^d$ MHCs were inserted into liposomes and then complexed to the biotinylated OVA$^{323-336}$ peptide. These complexes were incubated with streptavidin- FITC, and then with a standard amount of AG 111.207 or 8D051.15 cells (final MHC concentration of 66 ug/ml). When analyzed by flow cytometry, nearly 90% of the AG111.207 (FIG. 9a1) and 87.2% of 8D051.15 (FIG. 9b1) cells stained positive when using the correct restriction and peptide.

The specificity of the entire interaction was demonstrated by lack of staining of AG111.207 and 8D051.15 cells when incubated with anti-CD4 antibodies and complexes of the incorrect restriction for each hybridoma, I-$A^d$ and I-$A^s$ respectively, and Hi15 which has two identities (p2, p10) and one conservative substitution (p5) with $OVA^{323-336}$ (0% positive cells FIG. 9a2; 2.5% positive cells, FIG. 9b2). The peptide specificity of the interaction was demonstrated when AG111.207 and 8D051.15 cells were incubated with anti-CD4 antibody, the correct restriction element, but irrelevant peptide for each hybridoma, I-$A^s$/b-Hi15 or I-$A^d$/b-Hi15 respectively (4.6% positive cells, FIG. 9a3; 8.7% positive cells, FIG. 9b3). The binding between MHC:b-peptide complexes and AG111.207 T cells was also concentration dependent. Only 13.1% of AG111.207 cells tested positive when the I-$A^s$/$OVA^{323-336}$ concentration in the assay was reduced five fold to 13 ug/ml (not shown). The signal was also reduced by the addition of 300 ug/ml of the same, non-biotinylated $OVA^{323-336}$ peptide as a competitive inhibitor during preparation of the I-$A^S$/OVA complexes (5.1% of CD4+ cells positive, not shown). This finding suggests that biotinylation of the peptide does not interfere with the trimolecular interactions among peptide, MHC and TCR. Moreover, this assay was seen to be dependent on both TCR and MHC:peptide complexes, insofar as binding can be inhibited by simultaneous addition of anti-TCR and anti-1-A antibodies (6.9% of CD4+ cells positive). As shown in FIG. 9a4, no binding to TCR-negative cells, such as B cell hybridoma HT.01, was detected (0% of cells positive). Using biotinylated I-$A^d$ in liposomes without peptide, 6.9% of 8D051.15 cells bound the MHC alone (FIG. 9b4). Hence, the interaction requires the presence of the specific peptide.

Figure 15:
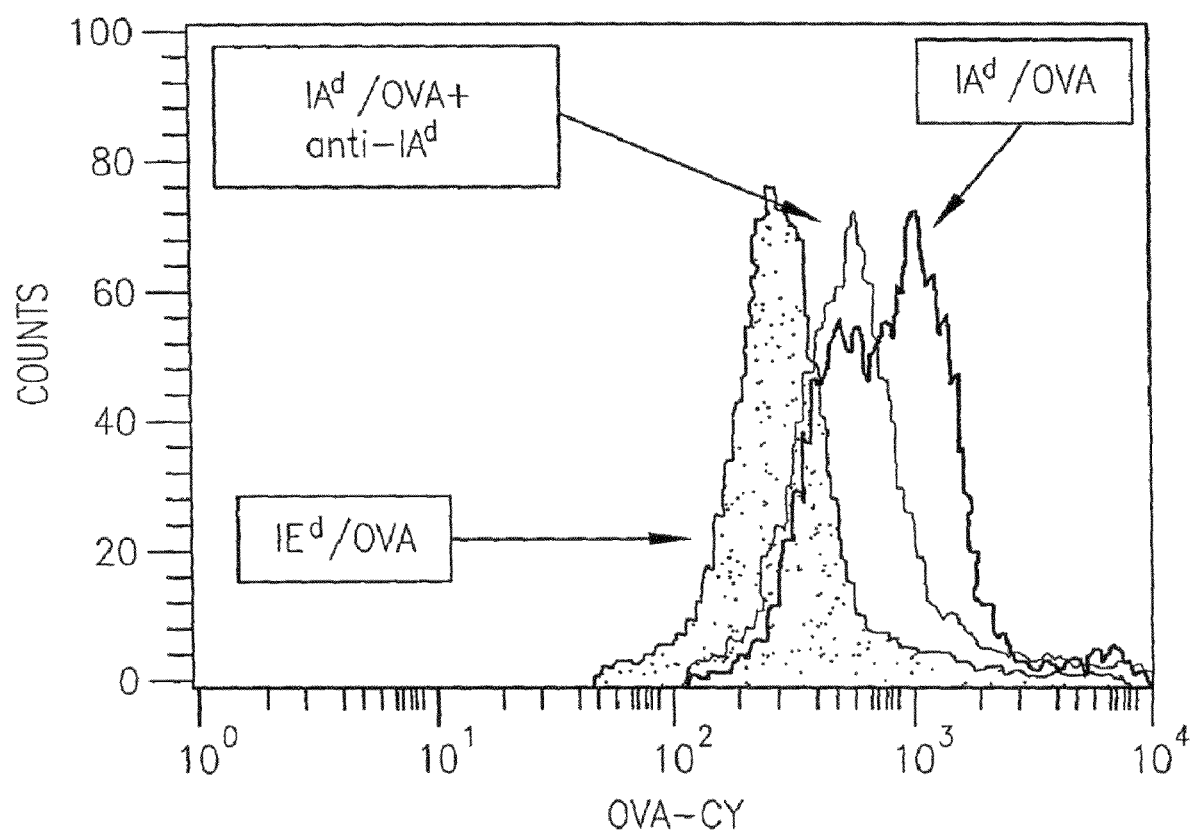
FIG. 15 shows the identification of antigen specific cells with T cell capture in a monoclonal TCR population wherein OVA$^{323-339}$/IA$^d$ specific T cell hybridoma 8D0 cells were incubated with artificial APCs complexed with IA$^d$ and biotinylated OVA$^{323-339}$. Prior to the incubation, the hybridoma cells were stained with CD4 PE (phycberithrin, i.e., a fluorochrome) and the artificial APCs, complexed with IA$^d$ and biotinylated OVA$^{323-339}$, were stained with streptavidin labeled with CY. As control for specificity of the binding, T cells of the same hybridoma were incubated with liposomes complexed with IE$^d$ and biotinylated OVA$^{323-339}$. Binding of hybridoma T cells to artificial APCs could be inhibited by co-incubation with monoclonal anti IA$^d$ antibody. The histograms show the intensity for staining for streptavidin CY in CD4 gated hybridoma cells. Gates were set on irrelevant isotype controls for CD4, and on binding of cychrome-conjugated streptavidin to T cells/artificial APC with unbiotinylated OVA$^{323-339}$ peptide.
Figure 16A:
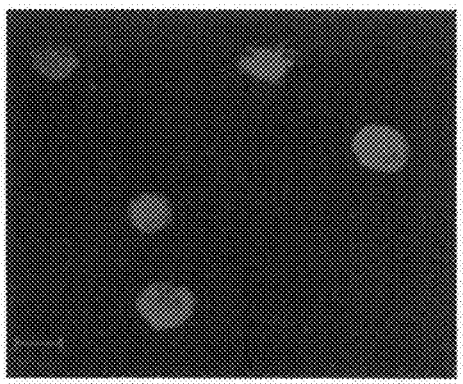
FIGS. 16A-D shows 8DO cells alone stained with Alexa 568-anti CD3 (red) bound to the T cell receptor and FITC-cholera toxin (green) bound to the cholera toxin. Thus.
Figure 16B:
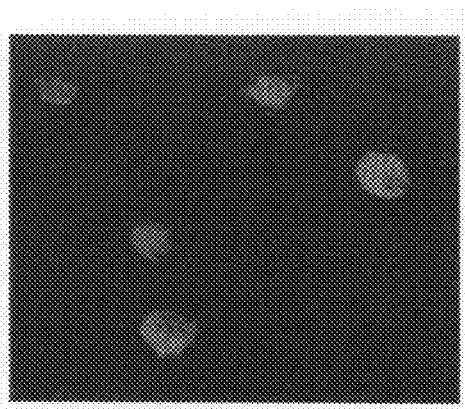
Figure 16C:
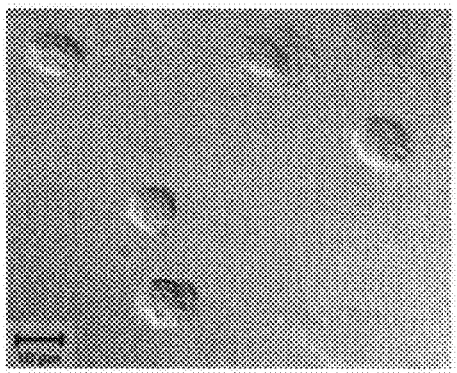
Figure 16D:
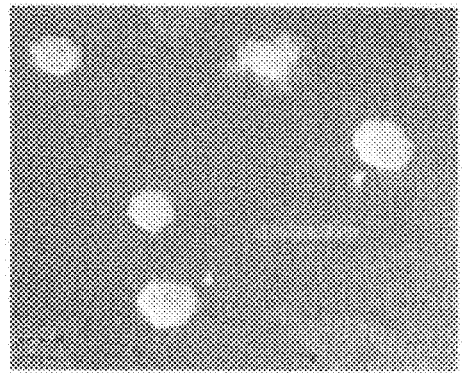
Figure 17A:
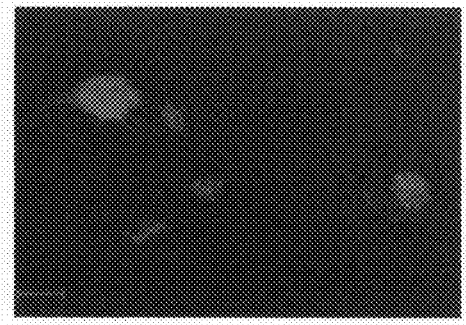
FIGS. 17A-D shows 8DO cells incubated for 20 minutes with artificial APCs expressing IA$^d$/OVA$^{323-339}$ complexes. Artificial APCs were stained with Alexa568 anti MHC (red) (i.e., the MHC is labeled red), and FITC cholera toxin (green) (i.e., the cholera toxin bound to the T cell receptor is labeled green). Thus.
Figure 17B:
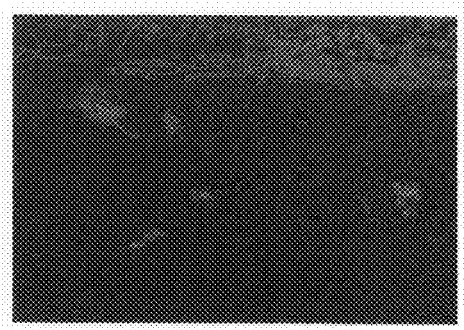
Figure 17C:
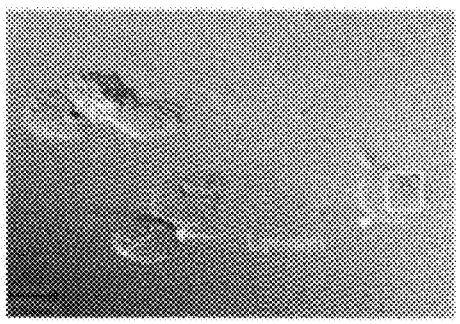
Figure 17D:
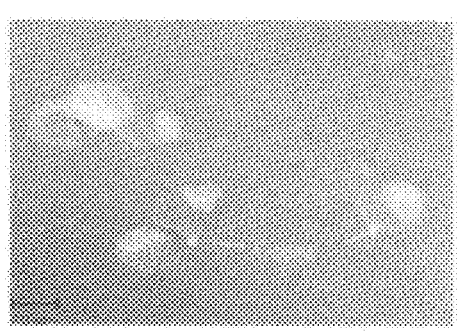
Figure 18A:
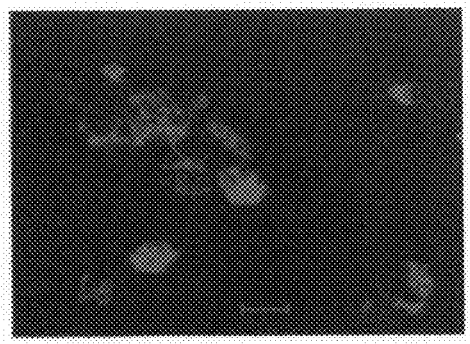
FIGS. 18A-D shows 8D0 cells incubated for 20 minutes with artificial APCs expressing IA$^d$/OVA$^{323-339}$ complexes. Artificial APCs lipid membranes were labeled using FITC (green). The T cell receptor were labeled with Alexa568 anti CD3 (red). Thus, FIGS. 18A-D further confirms the data shown in FIGS. 17A-D.
Figure 18B:
Figure 18C:
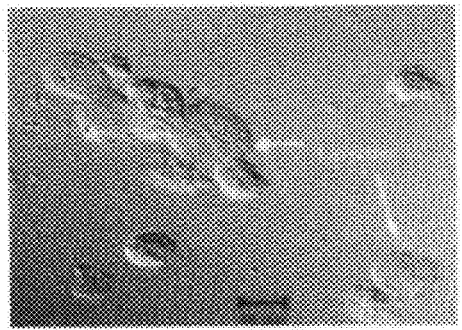
Figure 18D:

Artificial APCs Identify T Cell Hybridoma 8DO, Specific for IA$^d$/OVA Combination In another experiment we evaluated the capability of artificial APC, presenting synthetic biotynilated peptide OVA in the context of IA$^d$, to visualize by FACS analysis hybridoma 8D0, which is OVA/IA$^d$ specific. As shown in FIG. 15, the percentage of hybridoma cells was visualized by binding with cychrome-tagged artificial APC. This interaction was specific, insofar as TCR binding was dependent on the availability of the MHC/peptide complexes. The interaction was inhibitable by addition of antibodies interfering with such interaction (% positive cells, FIG. 15 middle graph), and 8D0 hybridoma cells did not bind to the artificial APC presenting the correct peptide in the context of IE$^d$ (% positive cells, FIG. 15 left graph). The result indicates that highly specific and sensitive interaction occurs between T cells and artificial APCs. Moreover, addition of competitive inhibitors in reducing the specific binding proves that the labeling of this method does not interfere with the APC/T cell interaction.

Example 2

Identification of Antigen Specific T Cells in Mouse Embryonic Thymuses

In this example, a murine model is used to investigate the effects of a naturally processed self-peptide on the maintenance and proliferation of T cells which may cross-react with homologous peptides of exogenous origin, all performed in a non-transgenic system. The example emphasizes the fact that without a method such as that of the current invention to capture T cells, it is not possible to evaluate polyclonal antigen specific chimeric T cell selection in a non-transgenic system. This is because conventional methods that examine cytokine presence or cell proliferation cannot identify cells specific for relevant antigen.

The self-peptide Iα52 (ASFEAQGALANIAVDKA) (Seq. Id. No. 1), used in these experiments corresponds to residues 52 to 68 of the a chain of the I-E molecule. It represents one of the most abundant peptides naturally processed and presented in the context of 1-$A^d$ (Hunt, et al. (1992), Science, vol. 256:1817-20; Rudensky, et al. (1991), Nature, vol. 353:622-27). These experiments demonstrate that T cells specific for a particular antigen can be identified from a polymorphic population of cells. In addition, functional and genetic characteristics of the cell population were demonstrated (Table 1).

1TABLE I Phenotypic and Functional Characteristics of Thymocytes Before and After Fetal Thymic Organ Culture Day 6 of Day 16 FTOC+ of Day 6 of $10^{-2}$ mM Gestation FTOC Iα52 CD3$^{lo}$CD4+/CD8+6% 1.3% 1.1% CD3$^{lo}$HSA$^{hi}$ 99 3.9 4.1 CD3$^{lo}$CD69+2<1<1 CD3$^{hi}$<1 47 34 CD4+ CD8+ CD3$^{hi}$HSA$^{hi}$<1 82 84 CD3$^{hi}$CD69+<1 10 11 Cell Number N/D1.55×10$^5$#1.65×10$^5$#Iα52 N/D 0.5x+/−0.1 6.2x+/−2.7 Stimulation Index Hi15 N/D 0.1x+/−0.06 2.5x+/−1.1 Stimulation IndexBALB/c embryonic thymus lobes were made into single cell suspensions, and analyzed by flow cytometry. Cell numbers are an average of eight to ten thymus lobes from FTOC. Data in the table represent between two and four experiments. #Standard deviations are 3.1×10$^4$ and 1.5×10$^5$ respectively.

Materials and Methods

Antigens

The I-$A^d$-derived peptide Iα52 (ASFEAQGALANIA-VDKA) (Seq. Id. No. 1) was synthesized (Research Genetics) using standard solid phase peptide synthesis method. Peptides used for flow cytometry were biotinylated (b-peptides) using a kit (Sigma) and were separated from free biotin by HPLC.

Generation of Lymphocytes from Fetal Thymic Organ Cultures (FTOC)

BALB/c embryonic thymi were harvested day 16 of gestation and placed onto 0.4 um cell culture inserts (Fisher) in six-well plates containing RPMI 1640, 10% FCS, 1% P/S/G, with or without Iα52 ($10^{-1}$ mM to $10^{-10}$ mM), at 37° C. and 6% $CO_2$ for six days. Cells were dissociated with a glass grinder (Kontes). Cell recovery was between 1.0×10$^5$ and 2.8×10$^5$ cells/lobe. Post-FTOC cultures were performed using a 3:1 ratio of irradiated BALB/cspleen cells, 20 U/ml rIL-2, 10 ug/ml H±15 or Iα52, 10% FCS, 1% P/S/G, in RPMI 1640 at 37° C. and 6% $CO_2$.

Preparation of Liposome:MHC:Antigen Complexes

Liposomes were prepared as described in Example 1.

Flow Cytometry

Flow cytometry was performed as described in Example 1.

Results

It has been shown previously that different concentrations of the same peptide have strong implications for T cell selection (see Sebzda, et al., Science, vol. 263:1615-18). We confirmed this phenomenon using various concentrations of Iα52 peptide to demonstrate its influence upon peptide-mediated positive selection and to define, directly, the antigen specificity of a positively selected T cell population in a non-transgenic BALB/c model.

Figure 10A:
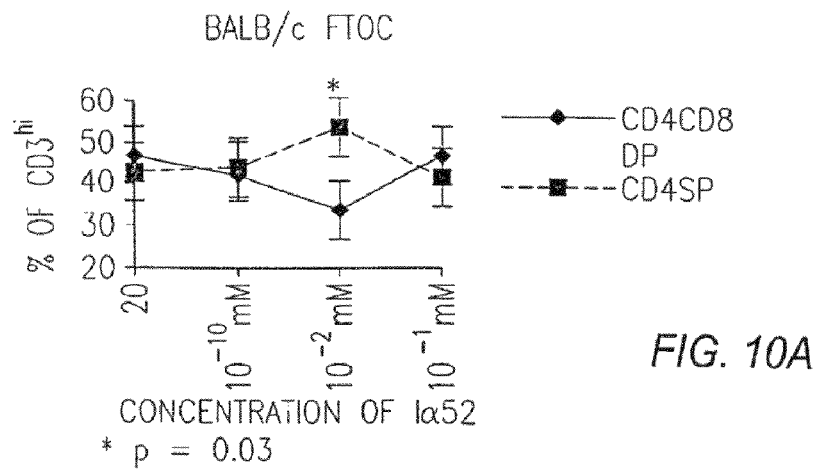
FIGS. 10A, B, and, C show a series of experiments from a non-transgenic murine model in which the characterization of the antigen specificity (the Iα52 peptide) of a T cell population without the use of the current invention was attempted.
Figure 10B:
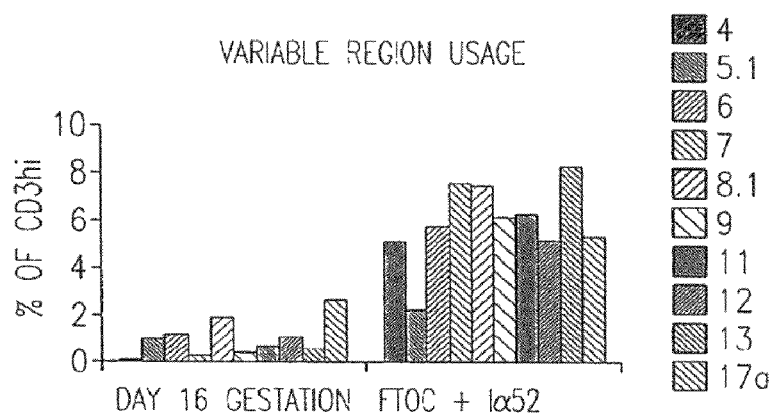
Figure 10C:
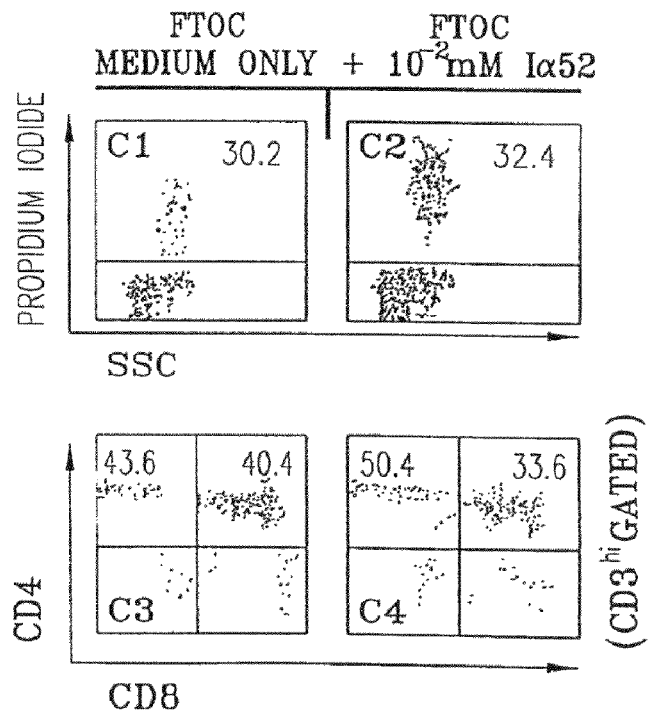

FIG. 10 shows the influence of Iα52 on the maturation of antigen specific thymocytes in fetal thymic organ cultures. FIG. 10(a) represents differing concentrations of Iα52 added to 6-day FTOC using day 16 of gestation BALB/c embryonic thymus lobes. Thymocytes were analyzed by three color flow cytometry to determine the percentages of CD3H1, CD4, and CD8 double positive and CD3HI CD4 single positive cells. With FTOC alone in the absence of any added peptide, 20.7% of CD4+ cells bound liposome: Iα52:biotinylated-Iα52 complexes during one week. This finding reflects the availability of Iα52 as an abundantly represented, naturally processed peptide available for thymic selection.

FIG. 10(b) shows Vβ analysis by FACS of cells taken directly from day 16 of gestation embryonic thymus lobes, and from FTOC supplemented with $10^{-2}$ mM Iα52.

FIG. 10(c1) represents thymocytes from FTOC without antigen, or with addition of the Iα52 peptide (c2), which were analyzed by FACS using propidium iodide to measure cell viability. Analysis of CD4, CD8 ratios from the two cell cultures (c3,4) is representative of those used in the above titration.

Figure 11:
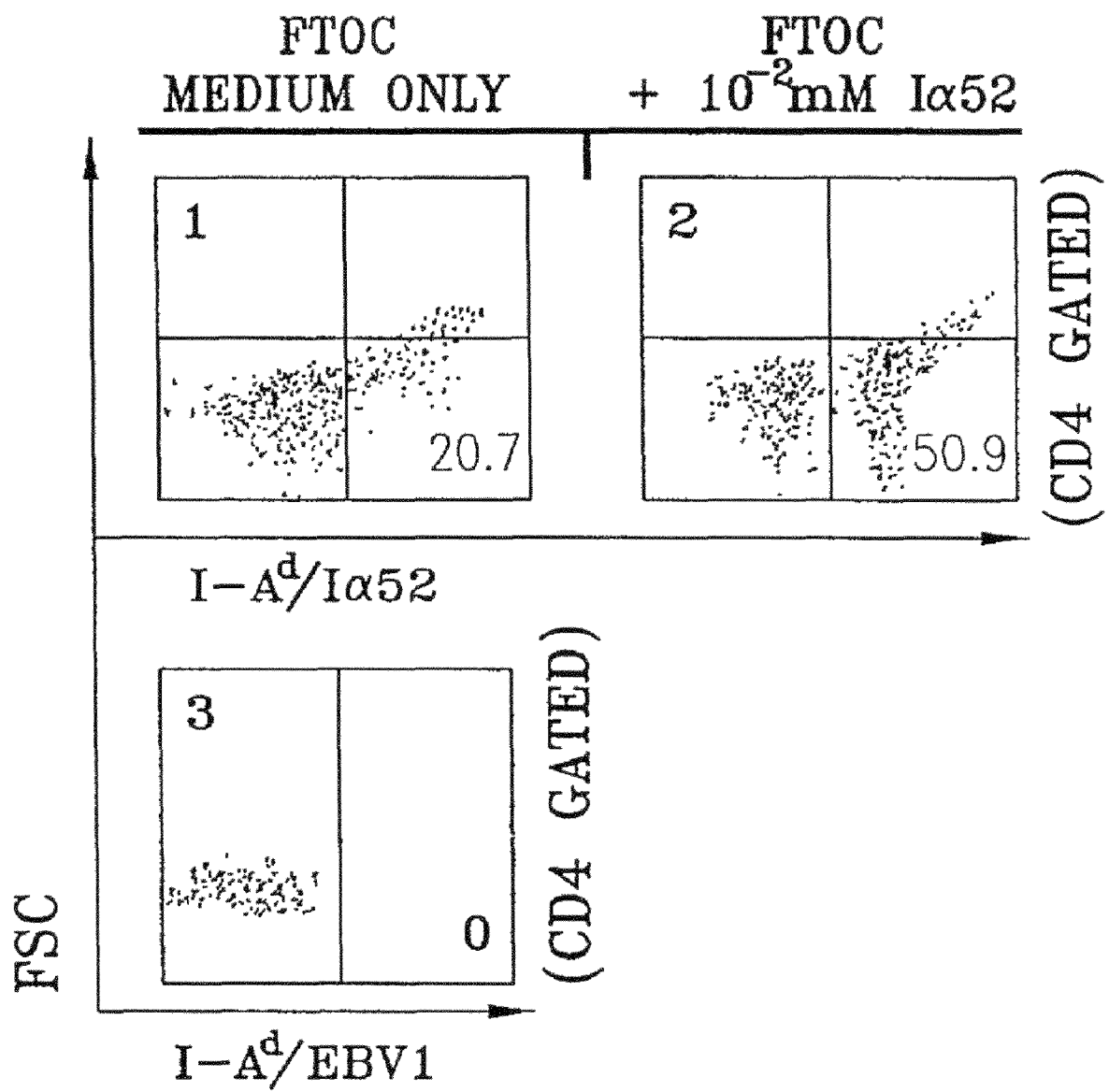
FIG. 11 shows the ability of the invention to determine directly the antigen specificity of a T cell population in the non-transgenic mouse model that could only be inferred in FIG. 10.
Figure 13A:
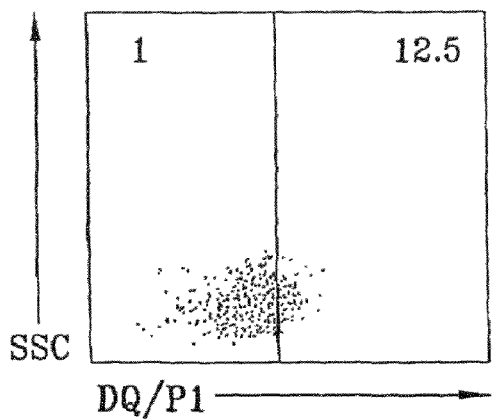
FIGS. 13A-E. is a series of FACS figures showing the use of the invention to identify T cells based on the specificity of the TCR in the PBMC of a patient with RA.
Figure 13B:
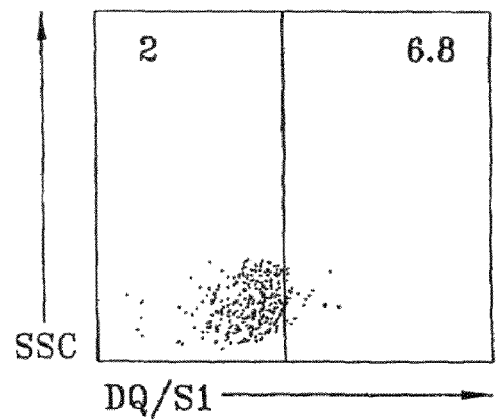
Figure 13C:
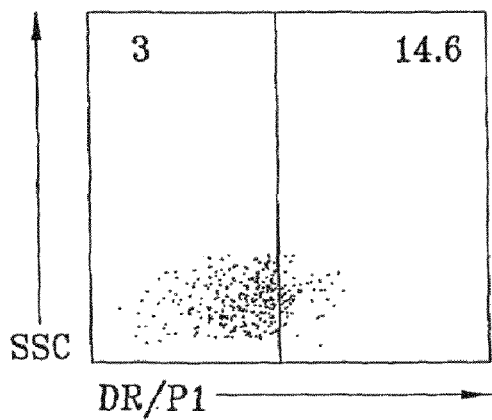
Figure 13D:
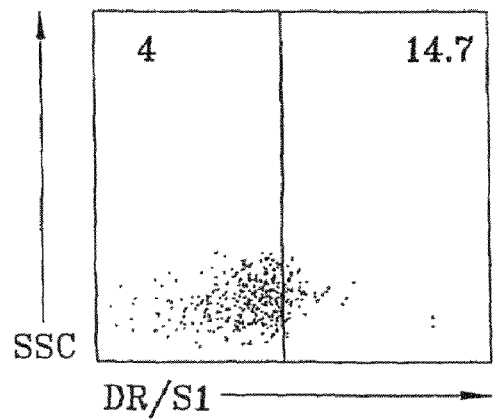
Figure 13E:
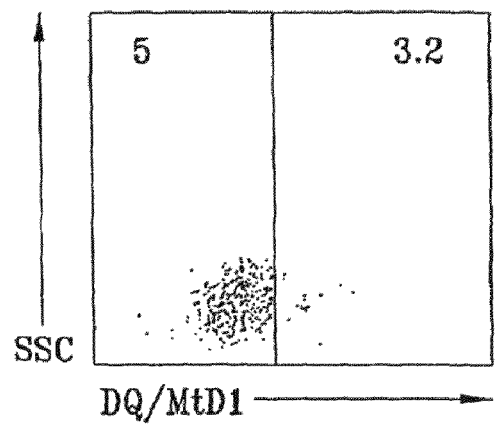
Figure 14A:
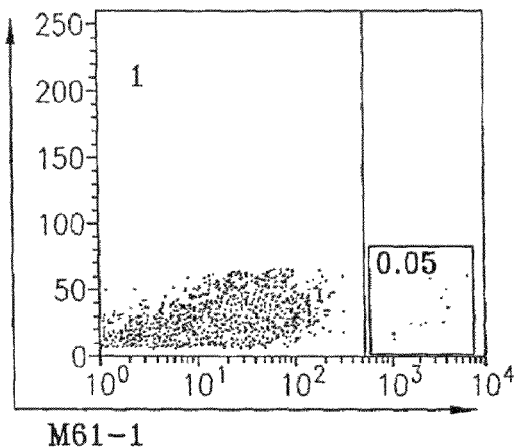
FIGS. 14A-D is a series of FACS figures showing the use of the invention to identify T cells based on the specificity of the TCR in the PBMC of a patient with JDM.
Figure 14B:
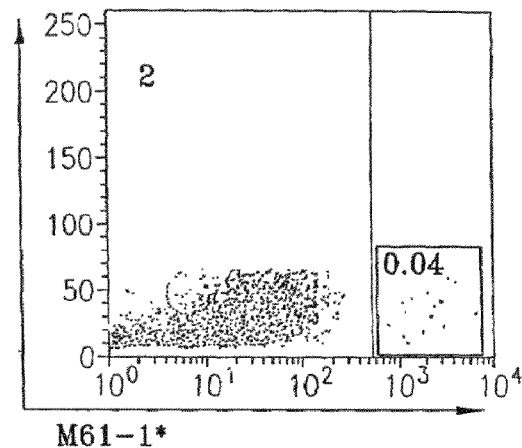
Figure 14C:
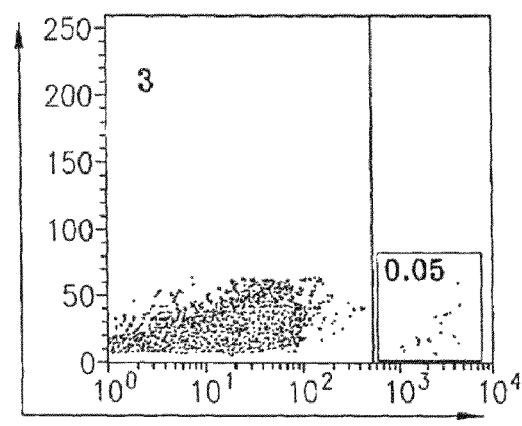
Figure 14D:
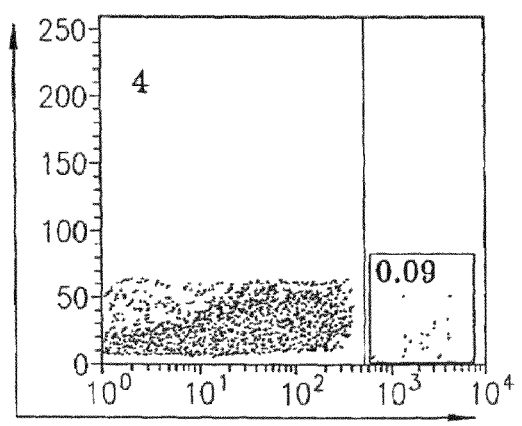

Performance of the detection of antigen specific thymocytes by FACS using anti-CD4 antibody and liposome: Iα52:b-Iα52 complexes bound to f-strep is shown in FIG. 11. When thymic lobes were cultured for one week without the presence of $10^{-2}$ mM Iα52 (FIG. 11-1), a relative increase (to 50.9%, FIG. 11-2) of liposome:Iα52:biotinylate-d-Iα52, CD4+ cells was seen in the presence of $10^{-2}$ mM Iα52. These data demonstrate for the first time that a self-derived peptide can induce positive selection in a non-transgenic system. As a control for antigen specificity in the T cell capture assay, the unrelated, biotinylated peptide EBV1 (TRDDAEYLLGRESVL), (Seq. Id. No. 2) derived from the EBV protein balf2 (residues 1030-1045) was used. EBV1 binds efficiently to Iα52 and is a good immunogen in adult BALB/c mice (La Cava et al, submitted). Biotinylated EBV1 peptide complexed to Iα52 in liposomes bound 0% of CD4+ cells from FTOC (FIG. 11-3).

Example 3

Identification of Cross Reactive T Cells with Specificity for Homologous Peptides The method of the invention was used to further examine the capacity for closely related antigenic moieties to cross-react, in this case using the murine model seen in Examples 1 and 2. Evidence of such cross-reaction provides the basis for an explanation of some autoimmune disease states. In this Example, the ability of T cells selected by the self-MHC-derived peptide Iα52 to cross-react with the homologous peptide of non-self origin Hi15, was examined by performing antigen-specific T cell analysis.

Materials and Methods
Antigens

The Iα52 derived peptide Iα52 was synthesized as described in Example 2. Hi15 (TSFPMRGDLAKREPDK) (Seq. Id. No. 3) was synthesized by standard solid phase peptide synthesis technique (Research Genetics). Hi15 was identified among 20 candidates with an arbitrary homology score of 20, based on homologies including potential MHC-binding residues. The search was performed on the non-redundant database scanned by Blast 2 program, available on the NCBI website. Peptides were >90% pure (Research Genetics). Peptides used for flow cytometry were biotinylated (b-peptides) using a commercial kit (Sigma) and were separated from free biotin by HPLC. Experiments were performed to determine the possible interference of the biotin label on the specificity of T cell receptors for the Hi15 peptide using the post-synthesis biotinylated Hi15 and N-terminus biotinylated peptide separately complexed to MHC molecules in liposomes and labeled with different colors of conjugation to streptavidin molecules. Results showed equal binding of the two preparations to a T cell line having specificity for both Iα52, and Hi15 (not shown).

Generation of Lymphocytes from Fetal Thymic Organ Cultures (FTOC)

FTOC was prepared as described in Example 2.
Preparation of Liposome:MHC:Antigen Complexes
Liposomes were prepared as described in Example 1.
Flow Cytometry
Flow cytometry was performed as described in Example 1.

Results

These experiments show that a T cell population derived from Iα52-supplemented FTOC can be determined, characterized and expanded. Essentially, an artificial APC will comprise MHC:peptide complexes stabilized into liposomes, with the addition of transmembrane proteins which accomplish stabilizing, co-stimulatory, and/or modulatory functions. These accessory and co-stimulatory molecules comprise, but are not limited to, any or all of the following:

(i) ICAM1 as adhesion molecule to facilitate initial interaction between the T cell and the APC.

(ii) anti-CD28 transmembrane antibody facilitates the propagation of antigen-specific T cells isolated by T cell capture using artificial APCs such that up to 20 replicative cycles have been obtained, which represents a valid alternative to T cell expansion and cloning using autologous APC systems, often an insurmountable hurdle in human systems.

(iii) B7-1 maybe used instead of anti-CD28. The cells obtained from this treatment may exert immunoregulatory function in autoimmunity.

(iv) B7-2 may be used instead of anti-CD28. Cells obtained from this treatment may have immunomodulatory properties in settings such as cancer or infectious disease.

All of the aforementioned molecules are transmembrane proteins which can be incorporated into liposomes according to above examples, or as an alternative, bound to a solid support as in above examples.

Isolation and Immunomodulation of Antigen Specific T Cells

Antigen-specific T cells isolated according to above examples are incubated with the appropriate variant of the artificial antigen presenting cells according to the desired objective, i.e. expansion, functional phenotype switch, etc. Day 16 of gestation BALB/c embryonic thymus lobes were harvested and cultured on 0.4 um filters in medium supplemented with $10^{-2}$ mM Iα52. Lobes were dissociated and cultured with autologous, irradiated APC, IL-2 and the Hi15 peptide. After two weeks of incubation with 10 ug/ml of Hi15, FACS analysis showed that 52.8% of cells bound anti-CD4 and the self-derived Iα52:Iα52 peptide complexes (FIGS. 12-1). The liposome: Iα52:biotinylated Iα52+:CD4+ cell complexes were sorted and depleted of their liposome:I-A$^d$: Iα52+ components by incubation at 4° C. for thirty minutes followed by centrifugation at 325×g for 10 minutes through 100% FCS (FIGS. 12-2). The sorted cells were then restained with liposome:I-A$^d$ and the exogenous, biotinylated peptide Hi15 that was complexed to a streptavidin molecule conjugated to a fluorochrome. The restained T cells were then reanalyzed by three-color flow cytometry using anti-CD4 antibody, liposome:I-A$^d$:b-Hi15 complexes, and liposome:I-

$A^d$:b-Iα52 complexes bound to different color f-strep molecules. Results showed that 52% of the cells tested positive (FIGS. 12-3). To further demonstrate the ability of TCRs selected by Iα52 to recognize the exogenous antigen Hi15, T cell populations derived from Iα52 FTOC were expanded with Hi15 and incubated with anti-CD4 antibodies and liposome:I-$A^d$ complexes bearing either biotinylated-Iα52 or Hi15 bound to streptavidin molecules labeled with different fluorochromes. The results indicated that 31.1% of the CD4+ cells were positive for both peptides (double positive) (FIGS. 12-4). The results of this Example 3 show that positive selection by a self-peptide generates CD4+ T cells that can recognize a homologous, exogenous peptide.

Example 4

Identification of TCR Usage by Antigen Specific T Cells

Variable regions of TCRs on the cross-reactive cells identified in Example 3 were evaluated in order to demonstrate the absolute ability of the method of the current invention to evaluate TCR specificity and potential cross-reactivity seen at a molecular level.

Materials and Methods
  Antigens
  The Iα52 (ASFEAQGALANIAVDKA) (Seq. Id. No. 1) peptide (Research Genetics) and the Hi15 (TSFPMRGD-LAKREPDK) (Seq. Id. No. 3) peptide (Research Genetics) were >90% pure. Peptides used for flow cytometry were biotinylated (b-peptides) using a commercial kit (Sigma) and were separated from free biotin by HPLC.
  Generation of Lymphocytes from Fetal Thymic Organ Cultures (FTOC)
  FTOC were prepared as described in Example 2.
  Preparation of Liposome:MHC:Ag Complexes
  Liposomes:MHC:antigen complexes were prepared as described in Example 1.
  Flow Cytometry
  Flow cytometry was performed as in Example 1.
  Analysis of T Cell Receptor Gene Usage
  To analyze the TCR-Vβ repertoire, 500 FACS-sorted cells were washed twice and poly (A) mRNA was isolated with the Invitrogen Micro Fast Track mRNA Isolation kit (Invitrogen, San Diego). The resulting mRNA was quantified with DNA DipStick kit (Invitrogen) and equal amounts of mRNA from each source were reverse transcribed using Invitrogen's cDNACycle kit. The cDNA was then submitted to a first PCR by using specific Vβ sense primers and a common Cβ antisense primer (Lessin, et al. (1991), J. Invest. Dermatol. vol. 96:299-302). PCR conditions were 200 uM dNTPs, 1×Taq polymerase buffer, cDNA, 20 uM each primer, 0.6 U Taq DNA polymerase (Boehringer Mannheim) in a 25 ul total reaction volume. After 3 minute hot start at 94° C. and addition of Taq DNA polymerase at 80° C. using a Perkin Elmer 2400 thermal cycler, reactions were cycled 40 times consisting of 30 seconds at 94° C., 30 seconds at 55° C. and 40 seconds at 72° C., last extension 6 minutes. Five microliters were used as template for a second PCR, whose conditions were identical to the previous PCR, except that reactions were cycled 35 times and 0.125 U of Taq DNA polymerase was used. Twenty-five microliters of the resulting PCR products were then analyzed by electrophoresis through a 4% agarose gel and ethidium bromide staining. DNA sequencing was performed at The Scripps Research Institute Core Facility using an ABI system.

Results

T cell lines obtained from either FTOC supplemented with $10^{-2}$ mM Iα52, or from peripheral lymph nodes of animals immunized with Iα52, were subsequently expanded in the presence of Hi15 and IL-2. Cells were sorted by FACS, as described in Example 1 using cytometry based on anti-CD4, liposome: Iα52:biotinylated-Hi15 and liposome:Iα52:biotinylated-α52 triple binding. Then, RT-PCR specific for the known TCR Vβ families was performed.

The results of these experiments showed almost exclusive use of Vβ1 by cells that recognized both the selecting self-peptide Iα52 and the cross-reactive, non-self homologue Hi15 (Table II). We also obtained DNA sequences from three representative clones. This analysis showed only modest differences in amino acid sequence for various representative clones, which all utilized Vβ1 genes (Table II). Molecular modeling showed that these amino acid sequences had little effect on the predicted conformation of the Vβ chain used by the different clones (FIG. 9).

TABLE II CDR3Sequence Comparison and Variable Region Gene Usage of Iα52 and Hi15 Cross-Reactive T Cell Receptors T Cell Isolated VDJ Line sequences R3F17 LHISAVDPEDSAVYFCASSQEFFSSYEQYFGPGTRL* R3F16 I R3F15 T Variable Region (Vβ) Gene Usage F7d 1, 8 Lines were generated from single cell sorting by flow cytometry using the T cell capture assay. Detection in the assay was based upon I-Ad/b-Iα52 and I-$A^d$/b-Hi15 double binding. These sequences contain the Vβ1 region of murine TCR in positions 78-107. *Seq. Id. No. 4.

Example 5

Identification, Isolation, and Characterization of T Cells Specific for Rheumatoid Arthritis-Related Antigens Initiation of autoimmune diseases such as rheumatoid arthritis is thought to be dependant on the recognition by T cells of one or more "pathogenic" antigens which may be responsible for triggering proinflammatory events which lead to chronic autoimmune damage. Several different hypotheses and experimental approaches have led to the identification of a pool of potential pathogenic antigens.

In this Example 5, it is demonstrated how T cells specific for rheumatoid arthritis-related antigens can be identified and enumerated starting from polymorphic T cell populations with very diverse specificities. Peripheral blood mononuclear cells (PBMC) from a patient with rheumatoid arthritis are incubated with a peptide called dnajp1 (U.S. Pat. No. 5,773, 570) corresponding to certain positions of the *E. coli* heat shock protein dnaJ. Certain peptides derived from dnaJ are homologous to rheumatoid arthritis-associated HLA alleles, and have been shown to be immunogenic in patients with rheumatoid arthritis. (Albani et al., "Positive selection in autoimmunity: Abnormal immune responses to a bacterial dnaJ antigenic determinant in patients with early rheumatoid arthritis," Nat. Med. 1:448-452 (1995); Albani & Carson, "A multistep molecular mimicry hypothesis for the pathogenesis of rheumatoid arthritis," Immunology Today 17:466-470 (1996); La Cava et al., "Genetic bias in immune response to a cassette shared by different microorganisms in patients with rheumatoid arthritis," J. Clin. Invest. 100:658-663 (1997). Each of the above references are herein incorporated by reference).

Materials and Methods

Preparation of DNA

Genomic DNA is prepared from white blood cells by methods known to those skilled in the art utilizing ammonium acetate and isopropyl alcohol precipitation with resuspension in TE (1 mM Tris, 0.1 mM EDTA, dH2O, pH 7.5).

PCR Amplification

DNA is enzymatically amplified by the polymerase chain reaction and amplification primers that have previously been reported for DQA1 and DQB1, for level I DRB typing, for level 2 allele assignment of DRB1 specificities associated with DR52, and for DR4 and DR1 (Vooter, C. E. Tissue Antigens. 51:1:80-87.; Barnardo, M. C. Tissue Antigens. 51:3:293-300.; Mitsunaga, S. Eur J. Immunogenet. 25:1:15-27.). Genomic DNA (5-10 ul at 80-150 ug/ml) is added to PCR mix consisting of 5 ul of 2 mmole/ul dNTPs, 3 ul of each primer at 10 pmole/ul, 5 ul of 10×PCR buffer, 0.5 ul of Taq polymerase (5 U/ul) and 23.5 ul sterile dH2O. Total reaction volume is 50 ul. DNA is amplified for 30 cycles in a DNA Thermal Cycler (Perkin Elmer Cetus) with denaturation, annealing, and extension parameters that vary depending upon the locus studied. In general, annealing is at 53° C. for DQ and DRB level I, and at 60° C. for DRB1-specific families. Positive and negative controls are included with each run and care is taken to avoid any source of contamination.

SSOP Hybridization and Detection

After amplification, 5.0 ul samples (10% of total PCR mixture) are run on a 1.0% agarose gel to verify sufficient quantity of amplified product. The remaining portion of the samples (90% of total PCR mixture) are denatured prior to blotting and hybridization using chem-luminescence using methods known to those skilled in the art. Membranes are washed twice with 2.times.SSC+0.1% SDS (0.3 M NaCl, 0.03 M Na-citrate, 0.1% SDS, dH$_2$O, pH 7.0) for five minutes at room temperature, and then twice with 3 M TMAC buffer in the appropriate temperature for the length of the probe. Fifteen-base pair probes are washed at 50-52° C. and 18-base pair probes are washed at 59-61° C. Membranes are wetted with Lumi-Phos (Boehringer Mannheim), sealed in acetate sheets, and exposed to X-ray film for 1 to 5 minutes. Results are graded using 11th International Workshop criteria as follows: 1:negative (definite) 2:negative (probable) 4:indefinite 6:positive (probable) 8:positive (definite) 9:positive (definite, more than double intensity). If unique hybridization patterns are found in the course of these studies sequence analysis is done. The patient employed in the example was HLA typed by PCR.

HLA Purification

Lymphoblastoid cell lines from RA patients are used as a source of HLA molecules, as known to those skilled in the art. Allele and species-specific monoclonal antibodies, whose corresponding hybridomas are already available, are produced as ascites liquid from BALB/c mice and purified on protein A, and covalently bound to a solid support (AffiGel, Bio-Rad, Richmond, Calif.). HLA molecules are purified by immunoaffinity chromatography from lysates of $10^8$ lymphoblastoid cells. The yield ranges from 1 to 4 mg/preparation. Purity is assessed by SDS/Page and Western blotting. Molecules in an elution buffer containing 0.2% octasilglucoside are stable for more than 4 months at 4° C.

Preparation of Liposome:MHC:Antigen Complexes

Liposomes are prepared as described in Example 1.

Flow Cytometry

Flow cytometry is performed as described in Example 1.

Results

T cells specific for the various combinations of the HLA, DR/DQ, and Si or dnaJp1 peptides were enumerated. T cells binding the S1 or dnaJp1 peptides in the context of HLA DR are more abundant (FIGS. 13A-E). Seen in the figure are PMBC from an RA patient expressing disease associated alleles DRB* 10401 and DQ*30301 captured with DQ/P1 (FIG. 13-A), DQ/S1 (FIG. 13-B), DR/P1 (FIG. 13-C), DR/S1 (FIG. 13-D), and DQ/Mtd1 (FIG. 13-E).

In order to demonstrate cross-reactivity, T cells specific for the various HLA/peptide combinations are sorted and RT-PCR for TCR Vβ gene usage is performed. The results, shown in Table III, demonstrate that T cells specific for the self-HLA derived peptide Si cross-react with the homologous peptide dnaJp1. Identification and isolation of T cells with a high pathogenic potential, as described in this Example 5 allows manipulation ex vivo to induce tolerization.

3TABLE III TCR VP Usage of T cells Isolated by Detection with RA Associated HLA Molecules Bound by Self or Exogenous Peptides. HLA DQ HLA DR dnaJP1 1, 8, 12 8, 14 Si 4, 12, 21 1, 9, and 14.

Peripheral blood mononuclear cells were isolated from an RA patient expressing the RA associated HLA alleles DRB*10401 and DQB*30301. The cells were cultured for five days in the presence of IL-2 and the bacterial heat shock protein peptide dnaJP1 then sorted by flow cytometry using HLA/Antigen combinations complexed into liposomes. RT-PCR was performed on sorted cells using primers specific for the known Vβ regions. Data are representative of two separate experiments.

The numbers in the above Table III show that of the 23 genes of the VP gene family, crossreaction occurs with only a few even though the family is highly related. Additionally, the results show that individual members of the family can be detected using the T cell capture method of the invention using artificial APCs.

Example 6

Identification, Isolation, and Characterization of T Cells Specific for Juvenile Dermatomiosytis-Related Antigens Juvenile Dermatomiosytis is a chronic autoimmune disease of unknown etiology. It has been reported that in several patients there is an association between relapse of the disease and documented *Streptococcus pyogenes* infection (Martin, A., Ravelli, A., Albani, S., J. Peds, 121:739-742 1992). Sequences shared between *Streptococcus* M5 protein and the human skeletal myosin, the target of the autoimmune process have been reportedly identified. It has also been demonstrated that the shared sequences contain epitopes which elicit cross-reactive T cell responses. In this Example 6, it is demonstrated that the homologous sequences are actually recognized by T cells which bear the same TCR Vβ gene.

Materials and Methods

Sequence-specific oligonucleotide probe HLA typing was performed as described in Example 5.

Preparation of Liposome:MHC:Antigen Complexes

Liposome:MHC:antigen complexes are prepared as described in Example 1.

Flow Cytometry

Flow Cytometry is performed as in Example 1.

Two alternative methods for visualization of the antigen-specific T cells were employed. In the first method, affinity-purified HLA molecules were stabilized by incorporation within the interior of liposomes using a method similar to that described in Examples 1-5 and then incubated with biotinylated peptides which were labeled using a method similar to that described in Examples 1-5. In a second alternate method, a label, in this case fluorescent (FITC), was incorporated directly into the liposomes themselves. Thus, the liposomes, rather than the peptides were labeled. FIGS. 14A-D shows data representing PBMC from a patient with JDM capture with a class I HLA and M61-1, M61-1*, M61-2, and M61-2*(FIGS. 14-A to 14-D respectively).

Results from these experiments show that T cells which recognize homologous peptides of either self or bacterial origin use the same TCR Vβ genes, confirming cross-reactivity at a molecular level. In addition, a direct identification and enumeration of CD3+ antigen-specific T cells is possible without detectable differences in sensitivity between the two labeling methods used. These results also suggest that direct incorporation of a label, e.g., FITC, into the liposomes themselves, or incorporation of a labeled (e.g., biotinylated) transmembrane protein which may or may not interfere with the TCR:antigen:MHC interactions, represent valid methods as alternatives in labeling of the liposome. This may be advantageous in that a label (e.g., a biotin molecule) when complexed with the peptide, may interfere with the interactions among agretopes and epitopes within the TCR:antigen:MHC complex. This may be especially true with class I MHC molecules, in which the antigen binding groove is open only at one end. Our diverse approaches bypass these potential limitations.

Example 7

Identification and Enumeration of T Cells Specific for Peptides from Pathogenic Organisms Physiologic, as well as vaccine-induced, immune responses to infectious agents are based on T cell recognition of, and reactivity to, immunogenic epitopes of the infectious agents. In several instances, immunogenic epitopes of microorganisms employed in vaccines, and their HLA restrictions, have been identified. One example is the influenza vaccine.

In this Example, quantitative and qualitative T cell response abnormalities in response to influenza vaccination can be identified. Peptides encompassing the major epitopes of the influenza virus are employed for analysis. Antigen specific T cells are identified and isolated as described in Example 1. The population to be screened is comprised of elderly persons who are vaccinated and then screened for immune responses. Antigen specific T cells are quantified and isolated from both the responder and non-responder groups. Phenotypical and functional characteristics are then evaluated, and the results compared between the two groups to analyze whether hyporesponsiveness in some of the vaccinated subjects is related to lack of specific T cells.

PBMC are incubated with the relevant and control peptides for five days in order to increase precursor frequency. Cells are then incubated with HLA-peptide complexes, and positive cells are enumerated by FACS. Commercially available cell lines are the source of soluble HLA molecules (Corriel Cell Repository).

Antigen specific T cells are evaluated for the production of cytokines which are related to either effective responses to viruses (IFN, IL-2) or associated with anergy (as in the case of using, for example, IL-10). This analysis elucidates differences, if any, between antigen specific T cells of responders versus non-responders. Hence, important functional differences are evaluated at an antigen-specific T cell level. Membrane phenotype of the isolated antigen specific T cells is evaluated, with particular attention to early activation markers, such as CD69, and memory, such as CD45RO. This test helps distinguishing anamnestic from recently induced responses. mRNA is purified and RT-PCR using Vβ chain for the T cell receptor specific primers is performed. The definition of the T cell receptor (TCR) used by the various subjects may help in pointing out differences between responders and non-responders due to genetic differences in the TCR repertoire. This shows the potential for the technology of the current invention to discriminate between anamnestic and recall immune responses at the level of antigen-specific T cells Materials and Methods
 Lymphocyte Proliferation Assays
 Preliminary experiments are performed to identify the optimal conditions for culture. Initially, cell cultures are performed in duplicate for three to seven days, using 5 million cells/well. (All antigens have shown a range of optimal responses between 1 and 10 ul/ml). The proliferation assays are conducted as controls to compare against the T cell capture specificity of the invention.
 Lymphocyte Cytotoxicity Tests
 Cytotoxic responses are measured using a LDH-release kit (Promega). The tests are performed according to manufacturer's instructions. Effectors are incubated for 5 days with IL2 and the relevant peptides or with irrelevant antigens. Targets are irradiated autologous PBMC or, when available, EBV-transformed lymphoblastoid cell lines. Targets are pulsed with the relevant antigens overnight. The cytotoxicity assays are conducted as controls to compare against the T cell capture specificity of the invention.
 Antigens
 Synthetic peptides (Matrix 58-66:GILGFVFTL (Seq. Id. No. 5); Nucleoprotein 82-94:VKLGEFYNQ (Seq. Id. No. 6)) are purchased from Research Genetics.
 MHC Purification
 Commercially available lymphoblastoid cell lines (Corriel Cell Repository) are used as a source of MHC molecules and purified by immunoaffinity chromatography using anti-HLA class I antibodies in a manner similar to that shown in Example 5.
 Liposome:MHC:antigen complexes are prepared as described in Example 1. Antigen specific T cells are prepared as described in Example 1. Intracellular immunofluorescence staining of cytokines was performed as described in Example 10.
 Cytokine Measurement by RT/PCR
 Messenger RNA is extracted from approximately $7 \times 10^6$ cells by using Oligotex Direct mRNA Kit (Qiagen, Chatsworth, Calif.). mRNA is reverse-transcribed into cDNA with the oligo dT primer (RT-PCR Kit, Stratagene, La Jolla, Calif.). Two ul of single strand cDNA are amplified using the cytokine specific forward and reverse primer sets, IL-2, IL4, INF-γ. Quantitative measurement of various cytokines using competitive PCR is performed (Biosource reagents). In this method, a known copy number of an exogenously synthesized DNA used as an internal control sequence (ICS) is mixed with the sample prior to amplification. The ICS is constructed to contain identical primer binding sites as the cytokine to be analyzed, and a unique binding site that allows the resulting amplicon to be distinguished from the cytokine product. Detection of the amplification product is by non-radioactive microplate techniques.
 T Cell Receptor Analysis by PCR
 Messenger RNA is extracted from a minimum of 70 cells by using Micro-FastTrack Kit (Invitrogen, Carlsbad, Calif.). The yield of mRNA is about 2 ul that is resuspended into 20 ul of water. Two ul of mRNA for each reaction is reverse-transcribed into single strand cDNA with the oligo dT primer (cDNA Cycle Kit, Invitrogen, Carlsbad, Calif.). 1.5 ul of single strand cDNAs are amplified with constant primer and various V region primers (Vb1-Vb24), the sequences of which may be designed by those knowledgeable in the art. For example, 20 pico moles of each primer and 1.25 units of Taq polymerase (Boehringer Mannheim, Germany) are used. The total volume is 25 ul. The cycling parameters for PCR is indicated as: heat PCR reaction mixture without Taq and dNTPs at 94° C. for 4 min, then perform 40 cycles of 30 seconds at 94° C., 30 seconds at 58° C. and 30 seconds at 72° C. The final elongation is 7 minutes at 72° C. Add 0.5 ul of 100 mM dNTPs and 0.25 ul of Taq Polymerase (1.25 units, Boehringer Mannheim) at end of 58° C. of first cycle. The PCR-amplified products are analyzed on 4% agarose gel.

In summary, the experiments described in this Example 7 are accomplished according to the following steps:

(i) MHC typing by PCR of the test sample derived from a test subject, (e.g. a patient that is to receive treatment against an infectious agent);

(ii) Purification by immunoaffinity chromatography or by other methods known to those skilled in the art, of MHC molecules corresponding to that of the test subject's. The source for these molecules may be directly from an individual or from cell lines homozygous for the HLA alleles.

(iii) Synthesis of liposomes containing MHC:peptide complexes. (These liposomes may be tagged according to any of the methods described herein or known by those in the art.);

(iv) Incubation of PBMC from the test subject with the MHC:peptide tagged liposomes, and;

(v) counting of the binding T cells for the purpose of determining which peptides have bound thereby indicating the specific peptides effective in binding antigen-specific T cells.

Methods described in this Example are useful in determining the number of vaccine-specific T cells in peripheral blood, both in normal and immune compromised individuals, for example, as a tool for decisions regarding the opportunity for vaccination in immune compromised subjects, and in determining the efficacy of vaccination, measured as increase in the number of vaccine-specific T cells after vaccination.

Example 8

Diagnosis and Immunomodulation of Allergic Disease

Allergy is mediated by release of pro-inflammatory and vasoactive mediators triggered by binding of allergen specific immunoglobulins with receptors of inflammatory cells at the site of allergen contact with cellular tissues. The production of allergen specific immunoglobulins appears to be mediated by strong interactions between B and T cells, an example being Casein in the pathogenesis of lactose intolerance (Albani, S. Annals of Allergy. 63:12:489-492.). It is therefore of importance to have the possibility to identify allergen specific T cells, isolate them and manipulate them ex vivo. An outline of the strategy to be employed is:

(i) MHC typing of the test subject by PCR technology;

(ii) Identification of candidate "allergenic" peptides, based on current knowledge of the field. (When a candidate epitope on a given proteic allergen will not be already available, computerized analysis of MHC binding motifs will enable the identification of candidate peptides to be used.)

(iii) Synthesis of liposomes containing relevant MHC:peptide complexes. (Such liposomes can be tagged using any of the techniques described herein or known by those in the art.);

(iv) Incubation of PBMC of the test subject with the MHC:peptide:tagged liposomes complexes;

(v) Identification and enumeration of allergen specific T cells;

(vi) manipulation ex vivo of such cells, by stimulation in culture with the antigenic peptide in the presence of stimuli related to induction of TH-1 phenotype Materials and Methods Lymphocyte proliferation assays are performed as described in Example 7.

Lymphocyte cytotoxicity tests are performed as described in Example 7.

Antigens

Peptides are identified based on scanning the sequences of the proposed allergens for MHC-binding motifs and synthesized according to standard peptide synthesis methods know to those in the art.

MHC purification is performed as described in Example 7.

Liposome MHC:antigen complexes are prepared as described in Example 1.

T cells, generated as described in Example 1, are captured by separation using flow cytometry as described in Example 1.

Intracellular immunofluorescence staining of cytokines, is performed as described in Example 5.

Cytokine measurement by RT/PCR is performed as described in Example 7.

T cell receptor analysis by PCR is performed as described in Example 7.

This Example therefore shows that artificial APCs may be used to diagnose and monitor progress of therapies and modulation level of specific responses in a patient's T cells.

Example 9

Identification of Cancer-Specific T Cells Epitopes

It is commonly accepted that lack of immunity to cancer (e.g., melanoma), depends on low antigenicity of the neoplasm, as well as on functional and/or numerical deficiencies of antigen-specific T cells.

Several therapeutical approaches are currently underway to improve the efficiency of recognition of and reactivity to cancer antigens by T cells. Unfortunately, the efficiency of the treatment can be measured, to date, only in terms of clinical outcome. This Example 9 describes a solution to this problem, by enabling identification, enumeration, characterization and possible manipulation of cancer-specific T cells. Hence, efficiency of the treatment will be measured in terms of increase in antigen-specific precursor frequency, and also in terms of functional outcome of antigen recognition. This latter aspect is of particular importance in those instances where the therapy is aimed at activation of otherwise dormant T cells.

(i) The following protocol is applied:

MHC typing by PCR of the test subject;

(ii) Identification of candidate peptides. For example, sources for antigen in the treatment of melanoma include MAGE-1, MAGE-3, MART-1/melan-A, gp100, tyrosinase, gp75, gp15, CDK4 and beta-catenin. When a candidate epitope on a given protein allergen will not be already available, computerized analysis of MHC binding motifs will enable the identification of candidate peptides to be used;

(iii) Synthesis of liposomes containing relevant MHC:peptide complexes;
(iv) Incubation of PBMC of the test subject with the MHC:peptide:tagged liposomes complexes;
(v) Identification and enumeration of antigen specific T cells.

Materials and Methods

Lymphocyte proliferation assays are performed as described in Example 7.

Lymphocyte cytotoxicity tests are performed as described in Example 7.

Antigens

Synthetic peptides will be identified based on scanning the sequences of the proposed allergens for HLA-binding motifs., MHC Purification MHC purification is performed as described in Example 7. Commercially available lymphoblastoid cell lines (Corriel Cell Repository) are used as a source of MHC molecules, and purified by immunoaffinity chromatography using anti-MHC class I antibodies, available in our laboratory.

Liposome MHC:antigen complexes are prepared as described in Example 1.

T cells, generated as described in Example 1, are captured by separation using flow cytometry as described in Example 1.

Intracellular immunofluorescence staining of cytokines, is performed as described in Example 5.

Cytokine measurement by RT/PCR is performed as described in Example 7.

T cell receptor analysis by PCR is performed as described in Example 7.

As shown, a peptide based method for monitoring cancer therapy is established using antigen-specific artificial APCs. This methods allows for studying the progress of the therapy and the state of the cancer.

Example 10

Methods for Distinguishing "Bystander T Cells" from Antigen-Specific T Cells

The experiments described in this Example demonstrate that antigen-specific T cells can be identified and enumerated and distinguished from antigen non-specific T cells present in the same tissue. These latter cells (so-called "bystander T cells") may participate in pathogenic processes. This has particular relevance for autoimmune and allergic diseases, where the initiating event may be the recognition of a pathogenic antigen by a specific T cell population. This interaction leads to production of pro-inflammatory or pro-allergic mediators (i.e., cytokines) by the antigen-specific T cells. The cytokine cascade will subsequently involve T cells that are not specific for the antigen (bystander T cells), which may then participate in the pathogenic processes, amplifying significantly the degree of the damage. It is important in a clinical or research setting to discriminate between the antigen-specific and bystander populations in order to evaluate, for instance, the efficacy of a treatment. The strategy may be summarized as follows;

(i) Identification of candidate peptides, based on current knowledge of the field. When a candidate epitope on a given protein antigen is not already available, computerized analysis of MHC binding motifs will enable the identification of candidate peptides to be used in the "T cell capture". Such analysis is standard practice to those skilled in the art;

(ii) Synthesis of liposomes containing relevant MHC:peptide complexes. Such liposomes can be tagged using any of the techniques described herein;
(iii) Incubation of PBMC of the test subject with the MHC:peptide:tagged liposomes complexes;
(iv) Identification and enumeration of antigen specific T cells.

Materials and Methods

Lymphocyte Proliferation Assays

Preliminary experiments may be performed to identify the optimal conditions for culture. Cell cultures may be performed in duplicate for three to seven days, at 5 million cells/well. All antigens have shown a range of optimal responses between 1 and 10 ul/ml.

Lymphocyte Cytotoxicity Tests

Cytotoxic responses may be measured using a LDH-release kit (commercially available). The tests may be performed according to manufacturer's instructions. Effectors may be incubated for 5 days with IL2 and either the relevant peptides or with irrelevant peptide antigens. Targets may be irradiated autologous PBMC or, when available, EBV-transformed lymphoblastoid cell lines. Targets may be pulsed with the relevant antigens overnight.

Antigens

Synthetic peptides are identified based on scanning the sequences of the proposed allergens for MHC-binding motifs.

MHC Purification

Commercially available lymphoblastoid cell lines (Corriel Cell Repository) may be used as a source of MHC molecules and purified by immunoaffinity chromatography using anti-MHC class I antibodies.

Preparation of Liposome MHC:Ag Complexes

Preparation of APCs are the same as that performed for Example 1.

FACS

A Beckton Dickenson FACS Star with LYSIS II software was used to visualize cells. Sortings were performed using standard procedures.

T Cell Capture

T cells, generated as described, are captured by separation using flow cytometry. Bulk sorted cells are either cultured as described, immediately used for DNA analysis, or used directly for reanalysis using FACS. Yields from bulk sortings range from 2000-16,000. Single cell sorts utilized 96 well culture plates containing media previously described. Fresh irradiated APCs are added to the single cell cultures once per week, at which time analysis of clonal expansion is performed. Of 96 wells of sorted "events", generally 8-12 show good expansion over a six week period.

Intracellular Immunofluorescence Staining of Cytokines

Human PBMC are isolated by density centrifugation and stimulated for 36 hours with peptides at 10 ul/ml in the presence of 2 uM monensin. Cells are washed in PBS with 2% FCS and incubated with Fc-block for 5 min. at 4° C. PE-conjugated anti-CD3 monoclonal antibodies (mABs) are added and cells are incubated for 30 min. at 4° C. Cells are washed, fixed 20 min. at 4° C., and resuspended in a solution containing either FITC conjugated anti-IFN-γ mAbs or FITC conjugated anti-IL4 or IL2 mAbs. Cells are incubated for 30 min at 4° C., washed twice in PBS with 2% FCS and their fluorescence measured using a Becton Dickinson FACScan. Flow data are analyzed using Lysis II software (Becton Dickinson).

Cytokine Measurement by RT/PCR

Messenger RNA is extracted from approximately 7×10$^6$ cells by using Oligotex Direct mRNA Kit (Qiagen, Chatsworth, Calif.). The mRNA is reverse-transcribed into cDNA using oligo dT primer (RT-PCR Kit, Stratagene, La Jolla, Calif.). Two ul of single strand cDNA are amplified using the cytokine specific forward and reverse primer sets for IL-2, IL4, TNF-α, and INF-γ. Quantitative measurement of the various cytokines was carried out using competitive PCR (Biosource). In this method, a known copy number of an exogenously synthesized DNA (ICS) is mixed with the sample prior to amplification. The ICS has been constructed to contain identical primer binding sites as the cytokine to be analyzed, and a unique binding site that allows the resulting amplicon to be distinguished from the cytokine product. Detection of amplicons is allowed by non-radioactive microplate techniques.

T Cell Receptor Analysis by PCR

Messenger RNA is extracted from a minimum of 70 cells by using Micro-FastTrack Kit (Invitrogen, Carlsbad, Calif.). The yield of mRNA is about 2 ul that is resuspended into 20 ul of water. Two ul of mRNA for each reaction is reverse-transcribed into single strand cDNA with the oligo dT primer (cDNA Cycle Kit, Invitrogen, Carlsbad, Calif.). 1.5 ul of single strand cDNAs are amplified with constant primer and different V region primers (e.g., Vb1-Vb24). 20 pico moles of each primer and 1.25 units of Taq polymerase (Boehringer Mannheim, Germany) were used. The total volume is 25 ul. The cycling parameters for PCR are: heat PCR reaction mixture without Taq and dNTPs at 94° C. for 4 min, performance of 40 cycles for 30 seconds at 94° C., 30 seconds at 58° C. and 30 seconds at 72° C. The final elongation is 7 minutes at 72° C. Add 0.5 ul of 100 mM dNTPs and 0.25 ul of Taq Polymerase (1.25 units, Boehringer Mannheim) at end of 58° C. of first cycle. The PCR-amplified products were analyzed on 4% agarose gel. The sequences of Vβ-specific primers that may be used may be designed by those knowledgeable in the art.

This example therefore shows that antigen-specific immunotherapy can be used to influence populations of T cells having different specificity that participate in the pathogenic process.

Example 11

Immunoaffinity Chromatography for Positive Selection of Antigen-Specific T Cells As demonstrated in this Example, MHC:antigen complexes may be incorporated into liposomes as described in certain embodiments of the invention above and bound to a solid support. By orienting the complexes so as to optimize the chance of interaction between the T cell receptor and the complexes, antigen-specific T cells may be isolated from biological samples.

Immunoaffinity Chromatography Columns

MHC:peptide complexes may be bound to hydrazide coated glass beads. Alternatively, molecules having affinity for irrelevant molecules may be bound to glass beads coated with a hydrazide linker and may be used to bind a irrelevant molecule-containing liposome:MHC:peptide complexes. A slurry of either of the above coated bead solid supports is incorporated into a compartment of a column such as that shown in FIG. 8 in a controlled fashion. Polymorphic T cell populations contained in a liquid medium are then introduced into the column, and the mixture is incubated at room temperature for 30 minutes, with gentle turning of the column. T cells with irrelevant specificity are not bound by the slurry and will flow through. Peptide or antigen-specific T cells that bind during mixing are then removed from the solid supports by incubating the column at 4° C. for 30 minutes.

Example 12

Ex Vivo Depletion of Cells Related to a Pathogenic Process: Antigen-Specific Leukapheresis In certain situations, it is desirable to deplete living systems of T cells having specificity for a given antigen. In the case of autoimmunity or allergy, these T cells may be involved in pathogenic processes and their depletion may therefore induce clinical improvement. Likewise, in the case of transplantation, recognition of a donor's epitopes and ideotopes as non-self will cause graft vs. host rejection of a transplanted organ. In such instances, depletion of the recipient's T cell population that recognize the foreign epitopes/ideotopes is beneficial. Depletion of such reactive T cells may be accomplished by connecting in line with the general circulation of a patient a device comprising MHC:antigen complexes bound to a solid support and oriented to optimize TCR:complex interaction. For example, MHC:peptide complexes may be associated in liposomes containing irrelevant molecules which may themselves be captured by glass beads coated with molecules having specificity for the irrelevant molecules. Appropriate filters, sterilization and heating procedures may be used in a manner similar to that currently employed in conventional leukaphoresis procedures. In operation, whole blood or blood enriched for T cells is allowed to flow through the device. Antigen-specific T cells are bound and eliminated from solution. The slurry is continuously stirred, and after appropriate time periods portions of it are incubated at 4° C. in order to elute the antigen-specific T cells that have bound to the solid support associated MHC:antigen complexes. For clinical conditions where such antigen-specific T cells are harmful, such cells can be simply discarded.

The specific procedure with respect to autoimmunity comprises:

(i) Preparing a column in which the MHC:antigen:accessory molecule:other molecule complex is designed to interact with T cells which may be involved in the pathogenesis of autoimmune disease using methods described in Example 11.

(ii) Allowing blood from the patient to flow through the column containing artificial APC prepared in step (i), by which means antigen specific T cells will be retained.

The specific procedure with respect to transplantation comprises:

(i) Preparing a column in which the MHC:antigen:accessory molecule:other molecule complex is designed to interact with T cells which may be involved in either the graft vs. host disease of bone marrow transplant or the pathogenesis of graft destruction in allogenic solid organ transplant using methods described in Example 11.

(ii) Allowing blood from the patient to flow through the column containing artificial APC prepared in step (i), by which means antigen specific T cells will be retained.

Example 13

Ex Vivo Manipulation of Antigen Specific T Cells: Bidirectional Switch from Th1 to Th2-Type Functional Phenotype In the case of infectious disease or cancer, it may be beneficial to isolate cells with a given antigen specificity in order to change their functional phenotype, for example, by manipulating such cells using the artificial antigen presenting cells described in this Example. Manipulated cells can then be reintroduced for immunomodulation.

Antigen-specific T cells, isolated according to Example 1 or Example 2, are incubated with the appropriate variant of the artificial antigen presenting cells according to the following examples.

Expansion of Antigen-Specific T Cells

Isolated cells (10,000/ml) are incubated in standard culture medium with APC expressing the relevant MHC:peptide combination, ICAM1 as adhesion molecule to facilitate initial interaction, and anti-CD28 transmembrane antibody. The latter is employed as a co-stimulatory molecule to induce T cell proliferation without affecting Th bias. This type of approach is the antigen-specific equivalent of the recent approach at T cell expansion using anti-CD3/anti-CD28 molecules. Up to 20 replicative cycles have been obtained in this system, which represents a valid alternative to T cell expansion and cloning using autologous APC systems, often an insurmountable hurdle in human systems.

Expansion and Immunomodulation of Cells from a Th1 to a Th2 Functional Phenotype (i) In one expansion, B7-1 may be used as a co-stimulatory molecule instead of anti-CD28. The cells obtained from this treatment may exert an immunoregulatory function in the autoimmunity condition.

(ii) In another expansion, B7-2 may be used as a co-stimulatory molecule instead of anti-Cd28: Cells obtained from this treatment may have immunomodulatory properties in settings such as cancer or infectious disease.

Specifically, an artificial APC comprises MHC:peptide complexes stabilized into liposomes, with the addition of transmembrane proteins which accomplish co-stimulatory functions. The molecules may comprise any or all of the following:

(a) ICAM1 as adhesion molecule to facilitate initial interaction between the T cell and the APC.

(b) anti-CD28 transmembrane antibody is employed as a co-stimulatory molecule which may induce T cell proliferation without affecting Th bias. This type of approach is the antigen-specific equivalent of T cell expansion using anti-CD3/anti-CD28 molecules. Up to 20 replicative cycles have been obtained in this system, which represents a valid alternative to T cell expansion and cloning using autologous APC systems.

(c) B7.1 may be used instead of anti-CD28. The cells obtained from this treatment may exert immunoregulatory function in autoimmunity.

(d) B7.2 may be used instead of anti-CD28. The cells obtained from this treatment may have immunomodulatory properties in settings such as cancer or infectious disease.

All of the aforementioned molecules are transmembrane proteins which can be incorporated into liposomes according to above examples, or as an alternative, bound to a solid support as in above examples.

Isolation and Immunomodulation of Antigen Specific T Cells

Antigen-specific T cells isolated according to the above examples are incubated with the appropriate variant of the APC according to the desired objective, i.e. expansion, functional phenotype switch, etc.

Example 14

Monitoring Immunological Outcome of Intervention of Antigen-Specific T Cells by Correlation of Clinical Outcome with T Cell Phenotype In this example, the invention is applied to evaluating the clinical outcome of treatment regimens by correlating the phenotype of antigen-specific T cells with clinical outcome. Specifically, the invention is applicable to clinical monitoring and clinical trials where there is a need to evaluate the effectiveness of artificial APC induced T cell responses. The antigen-specific T cells associated with a response (or disease state) are identified followed by the identification of their functional phenotype. The phenotype identified is then correlated and monitored against the progression of a patient's response to various treatment regimens.

Example 15

Interaction of Artificial APCs with T Cells to Induce Capping of Transmembrane Proteins The immune synapse is the cluster of transmembrane molecules which ensures specific interaction between antigen specific T cells and antigen presenting cells. The outcome of these interactions is antigen specific response by the T cells, mediated by signaling through the TCR. Several factors contribute to significant quantitative and qualitative differences in the response provided by the T cell. These factors include affinity of interaction between MHC and peptide, and between the TCR and the MHC/peptide complex, the number of moieties available for interaction, and the relative concentration of the moieties available for interaction. In a physiological situation, the triggering number of interacting molecules is achieved by "capping", a phenomenon, which occurs when transmembrane molecules are allowed to freely migrate to definite zones of the membrane, usually upon initial interaction between two of the ligands involved, in this case the TCR and the MHC/peptide complex. In order to emulate such physiologic mechanisms, we employed artificial APCs loaded with the combination $IA^d$/OVA, and hybridoma 8D0 as the specific T cells. To visualize free movement of the TCR in the T cell membrane, we employed a system where FITC-conjugated cholera toxin, a molecule known to combine with the intracellular portion of transmembrane proteins, is introduced into the T cells. We show here for the first time that artificial APCs can effectively emulate the physiologic interactions between T cells and APC, particularly with respect to allowing migration of molecules whose proper density is an essential requirement to induce T cell activation. Our system has also the potential to be a tool to study physiological mechanisms of T cell activation, and to manipulate the intensity and quality of T cell response. This could be accomplished by controlling the affinity of the interaction, and by adding the proper co-stimulatory and adhesion molecules to the artificial APC.

Approximately 100 MHC/peptide binding sites are available on each artificial APC for interaction with a single T cell, increasing therefore the likelihood that artificial APCs will engage, through multiple interactions, low-affinity T cells. This may provide a significant advantage over current methods for the identification of low affinity, class II restricted antigen-specific T cells, such as the ones often involved in physiologic regulatory mechanisms or in disease related autoimmune responses.

We first identified the optimal incubation times for the artificial APC with the T cells, (i.e., about 20 minutes) at different stages of evolution in the capping mechanism. Unlike systems where the interacting molecules are fixed on planar membranes, interactions between T cells and artificial APCs occur in culture medium, and rely on random movement for molecular interactions. This results in the optimal period for a result to be based on formation of "capping" of the TCR in the cell membrane rather than just binding of the TCR and target moieties. In the experiments shown in FIGS. 16-18, we incubated the artificial APC with 8D0 cells for 20 minutes, and evaluated the capping by confocal microscopy. In FIGS. 16A-D, we visualized comigration of the colera raft and the TCR, by incubating T cells with PE-conjugated monoclonal antibody (Pharmigen). TCR molecules are uniformely distributed in the cells membrane, as expected for cells, which are not interacting with stimulatory triggers. In experiments described in FIGS. 17A-D, we visualized interaction of TCR by using the cholera toxin raft, and the MHC in the artificial APC membrane using a specific anti-MHC (Pharmigen) monoclonal, Alexa-red conjugated. In the field shown, the phenomenon of progressive migration of the TCR molecules toward the point of initial interaction of the artificial APC with the TCR is evident at different stages for different cells. In experiments described in FIGS. 18A-D, we visualized the TCR using an Alexa red-conjugated anti CD3 monoclonal (source) and the liposomes using FITC-conjugated streptavidin which bound to the biotin at the N-terminal of the OVA peptide. The results of this visualization procedure in FIG. 18 are overlapping with those shown in FIG. 17. Hence, we show here for the first time that artificial APCs can effectively emulate the physiologic interactions between T cells and APCs, particularly with respect to allowing migration of molecules whose proper density is an essential requirement to induce T cell activation. Our system also provides for studying physiological mechanisms of T cell activation and the manipulation of the intensity and quality of T cell response. This "modulation" of T cell response could further be accomplished by controlling the affinity of the interaction by adding the proper co-stimulatory and adhesion molecules to the artificial APC. An additional preferred advantage of the system of the invention is that it allows free movement of transmembrane proteins, enabling the sequential order of interactions among ligands, which occur upon first contact of the TCR with the APC in the immune system.

Immunohistochemistry Methods for FIGS. 16-18

Liposomes and $0.5 \times 10^5$ cells were cytospinned at 300×g for 5 min on poly-L-lysine coated slides (Sigma, St. Louis, Mo.). The cells were fixed for 10 minutes in 4% Paraformaldehyde, washed in PBS and then incubated for 1 hours with the antibodies anti-CD3 IAd (Pharmingen, San Diego, Calif.), at a concentration of 2-10 ul/ml in I-Block blocking buffer (Tropix, Bedford, Mass.). Alexa 568 (red) species-specific secondary antibodies (Molecular Probes, OR) were used to visualize the proteins. Coverslips were washed successively in PBS and deionized $H_2O$ for 5 min and mounted in Fluoromount (Fisher, Calif.). Images were obtained with a Zeiss Confocal Laser Microscope.

Example 16

Identification of Class II Restricted T Cells in Polymorphic Populations

Identification of antigen-specific, class II restricted T cells is much more difficult than the same identification analysis for class I restricted T cells. These difficulties stem from the lower affinity of interaction of TCR/peptide/MHC for class II restricted responses, when compared to class I. Known methodologies have identified only high affinity antigen specific T cells based on soluble recombinant molecules that provide anywhere from one to four interaction sites for TCR binding, wherein steric hindrance problems are thought to affect correct folding of the recombinant molecules and their interactions with the TCR. In contrast, our results show that MHC/biotynilated peptide complexes can effectively visualize class II-restricted hybridoma T cells regardless of affinity.

Figure 5:
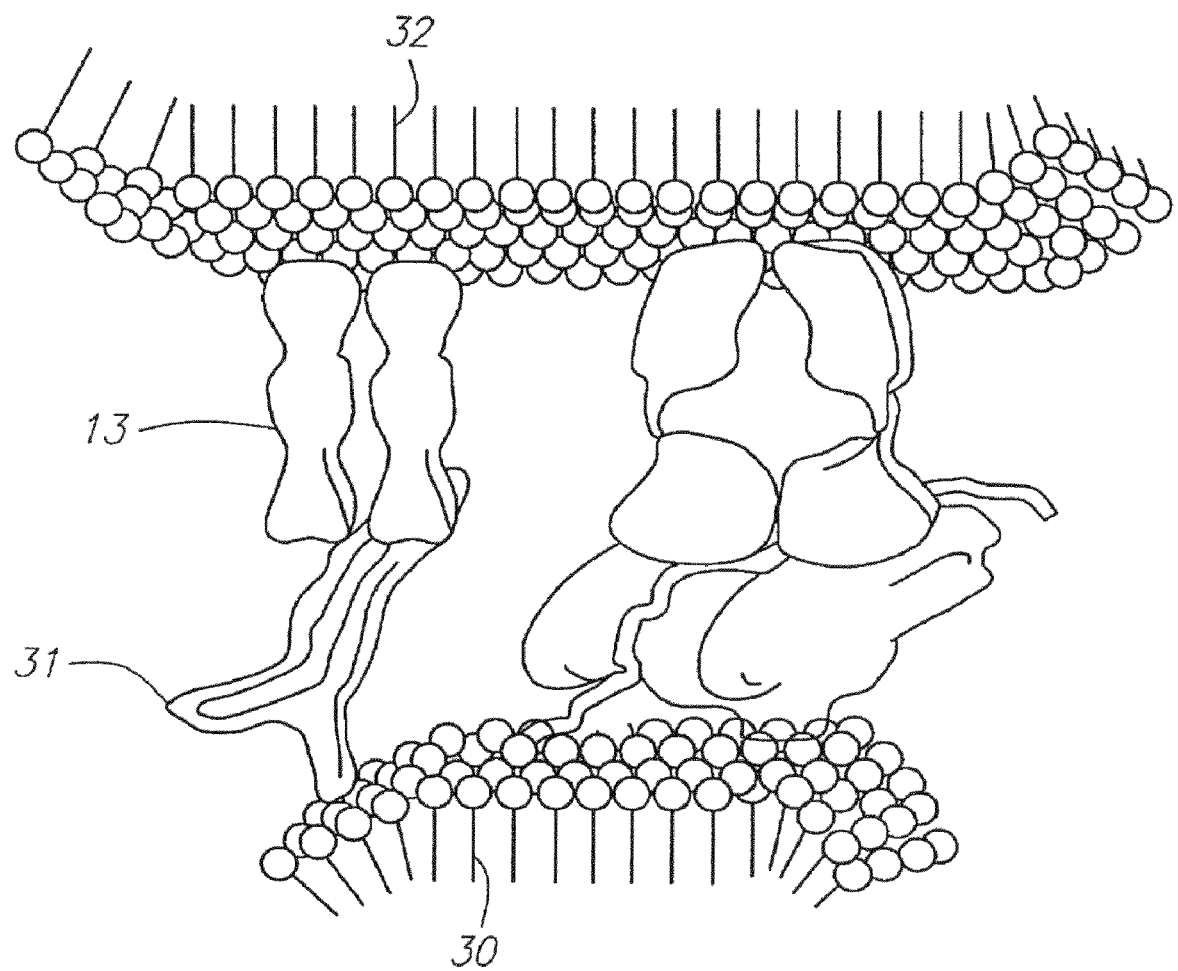
FIG. 5 is a schematic representation of an embodiment wherein the artificial APC (30) includes a functional molecule (31) (such as an accessory, co-stimulatory, adhesion, modulation, cytokine, or chemokine molecule) that interacts with a molecule (33) expressed by a T cell 32.
Figure 25A:
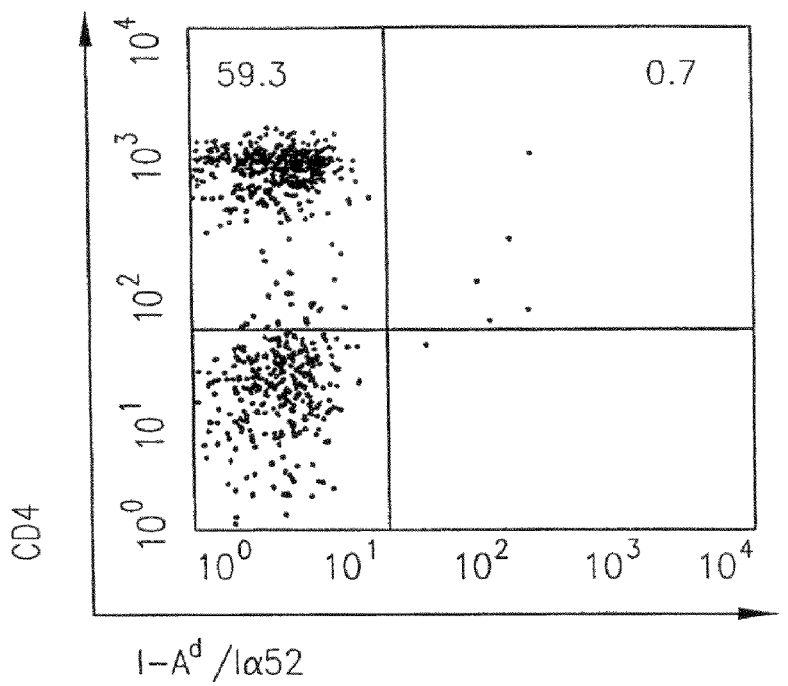
FIGS. 25A and B are FACS plots showing identification by T cell capture using artificial APCs of class II-restricted antigen specific mouse T cells upon immunization and shows increase of $IA^d/I\alpha52$ specific cells measured after immunization of the mice (at the base of the tail) with $I\alpha52$ or IFA (adjuvant) alone. Cells were harvested three days after the last immunization from inguinal draining lymphnodes, stained with anti-mouse CD4 PE and incubated with fluorescein labeled artificial APCs complexed with $IA^d/I\alpha52$.
Figure 25B:
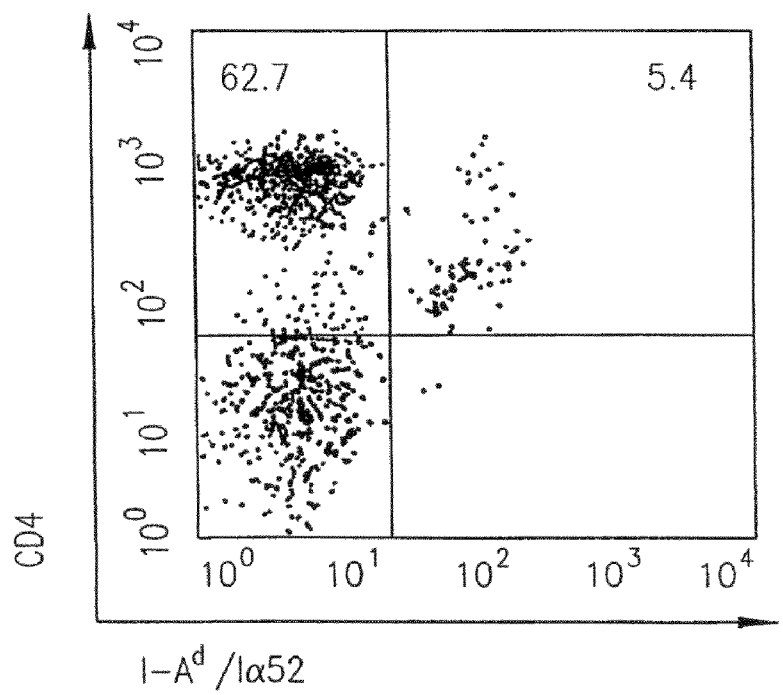
FIG. 25B shows $IA^d/I\alpha52$ specific CD4 cells. Y axis: CD4; X axis: $IA^d/I\alpha52$ specific T cells. The result indicates that the adjuvant immunized cells showed only 0.7% specific cells whereas the IA52 immunized cells comprised 5.4%. Thus, T cell capture using artificial APCs is useful to show antigen specificity.
Figure 26:
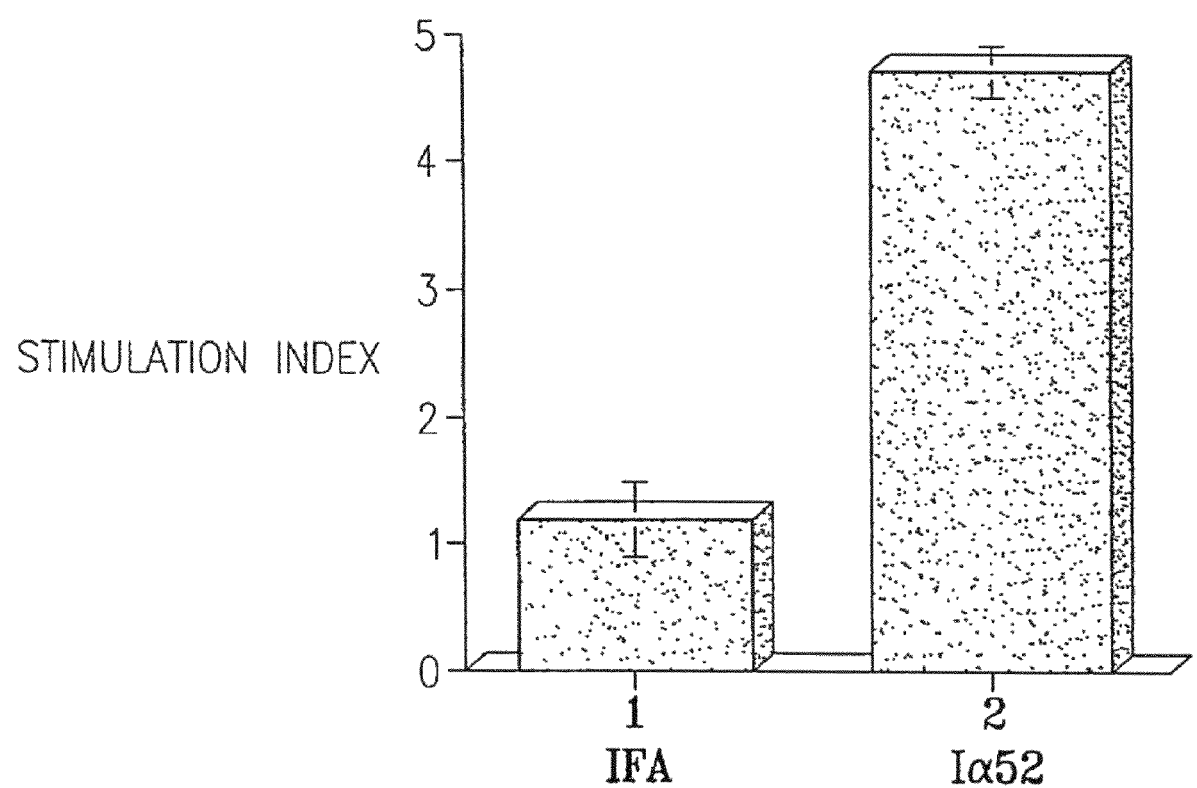
FIG. 26 is a bar graph showing T cell proliferation to $I\alpha52$ after immunization. Cells were harvested from inguinal lymphnodes and incubated for three days with 10 mg/ml of $I\alpha52$ peptide. Proliferation was measured by thymidine incorporation and is expressed as stimulation index "SI": cpm of stimulated/unstimulated cultures. The result indicates that conducting T cell proliferation tests to determine specificity is effective in measuring the specificity of T cell populations. However, the specificity is not to the same extent as that using the current invention shown in FIG. 25.

To evaluate the efficiency of our artificial APC system to identify Class II restricted antigen specific T cells, we immunized BALB/c mice with the peptide Iα52. Iα52, is a naturally processed, abundantly presented $IE^d$-derived peptide, which has previously been described as antigenic in BALB/c mice. Cells from regional draining lymphnodes, both from AFA only and Iα52 immunized mice, were harvested. These cells were then incubated with artificial APC presenting $IA^d$/Iα52 complexes. As shown in FIG. 25B, 5.4% of CD4+ T cells were Iα52 specific, while in comparison, only 0.7% CD4 cells were specific for the peptide in the IFA-only immunized mice (FIG. 25A). These data related well to antigen-specific T cell proliferation, measured by standard thymidine incorporation assay (FIG. 26).

Capture of T Cells by Artificial APCs is Effective in Identifying Polyclonal Class II Restricted Human T Cells To identify human antigen-specific T cells, we employed as model antigens a system comprising Pan-DR binder peptides (PADRE) of comparable affinity, and the influenza hemoagglutinin HA peptide. The peptides used were pan-DR binding peptide 965.10 PADRE (K(X) VAAWTLKAA Seq. Id. No. 7), HA 307-319 (PKYVKQNTLKLAT Seq. Id. No. 8), and IAd binding peptide $OVA^{323-339}$ (ISQAVHAAHAEINEAGR Seq. Id. No. 9). Peptides were synthesized as C-terminal amides, purified by reversed-phase HPLC, and checked by fast atom bombardment mass spectrometry. For use in MHC-binding assays and the T cell capture, peptides were biotinylated during peptide synthesis (only one biotin molecule, at the n-terminus, 100% biotinylation).

Figure 23A:
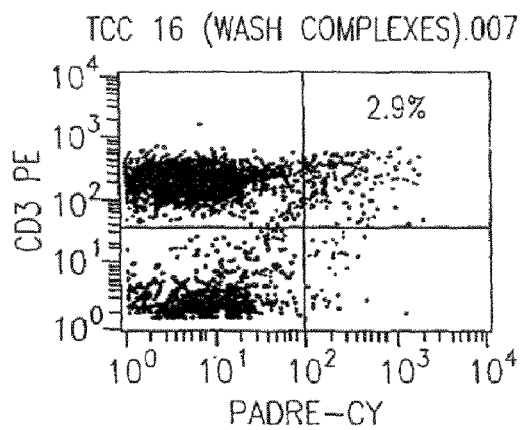
FIGS. 23A-F show plots of FACS analysis showing that T cell capture is an effective method to identify class II restricted human polyclonal T Cells. The panels show a comparison of CD3+ cells binding PADRE/HLA or HA/HLA (HA is hemoglutinin A) complexes. PADRE is used as positive control because it will bind many MHC molecular species thereby providing an easy means to visualize populations of specific cells. HA is also a pan DR binding peptide but because cells in this example are expanded using PADRE peptide, use of HA for binding should serve as a negative control. The Y axis represents CD3+ cells. The x axis represents HLA/PADRE or HLA/HA complexes. Panels A and B show the % of PADRE antigen specific T cells at day 0 of culture (A) (i.e., 2.9%), and the % of antigen-specific T cells at day 10 of culture with PADRE (B) (i.e., 8.1%). Thus, cells appear to be expanding as an antigen specific fashion. To test the specificity of the cell population, the % of HA cells are tested. As shown in panels C and D respectively, the % of HA specific T cells after 0 days of culture with PADRE/HA (C) (i.e. 1.0%) drops to 0.3% HA specific T cells after 10 days of culture with PADRE (D). Panels E and F show the % of antigen specific T cells at day 10 of culture wherein T cell capture using aAPCs was inhibited with an equimolar ratio of non-biotynilated PADRE. Panel E shows that 50% of inhibition was achieved, (i.e., the label does not interfere with testing of specificity using the APC). Panel F shows that 50% of inhibition was also achieved showing that the T cell/aAPC binding depends on the specific interaction of the T cell receptor, i.e., inhibition of binding using anti-HLA DR antibody at a molar ratio of 0.5:1 antibody to HLA. The FACS plots show results from an experiment wherein PBMC from a HLA-DR40401+ donor were stimulated with 10 ug/ml of PADRE peptide, K(X) VAAWTLKAA (Seq. Id. No. 7) where X is a derivatized amino acid such as cyclohexylalanine. At days 4 and 7.10 ng/ml IL-2 was added. At day 10 cells were harvested for T Cell capture. HLADR4 was complexed with NBD-labeled liposomes (1:7 ratio HLA to liposomes) through 48 hours dialysis against PBS in 10.000 M cutoff dialysis membrane (Pierce). Complexes were then incubated for 48 hours at RT with n-terminus biotinylated peptides at a molar ratio of 10:1 for peptide/HLA. Excess of unbound peptide was removed through 24 hours of dialysis against PBS. Liposome-HLA-peptide complexes were incubated for 30 minutes with streptavidin-Cy before adding to the cells. The liposome-HLA-peptide complexes were then incubated with the stained cells and run on a Becton Dickinson FACS Star. Gates were set on viable cells, isotype controls and cells incubated with streptavidin CY alone.
Figure 23B:
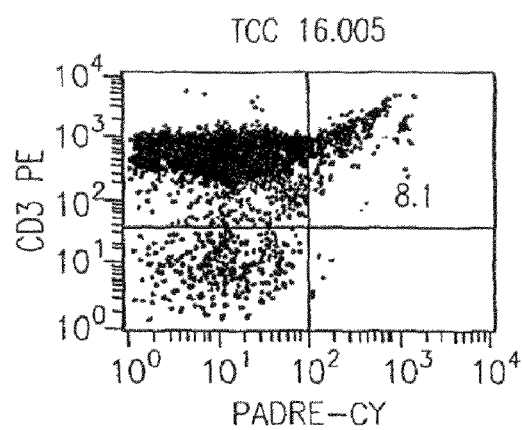
Figure 23C:
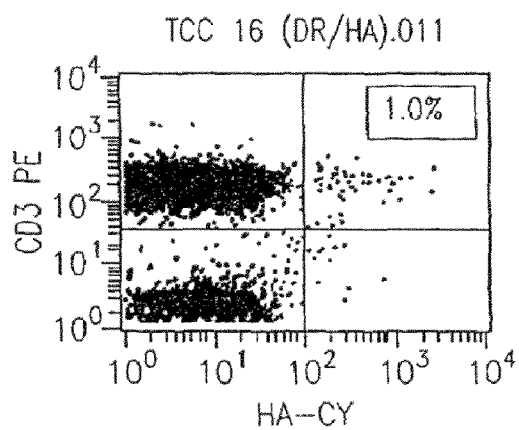
Figure 23D:
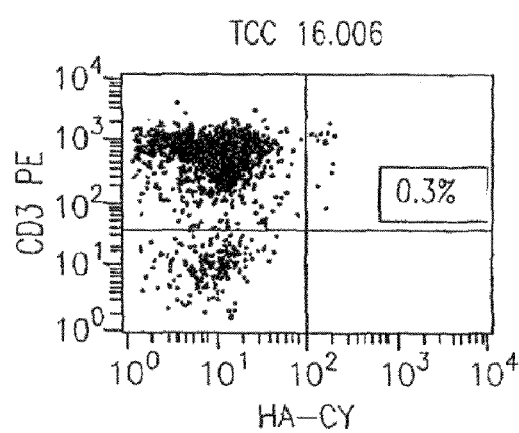
Figure 23E:
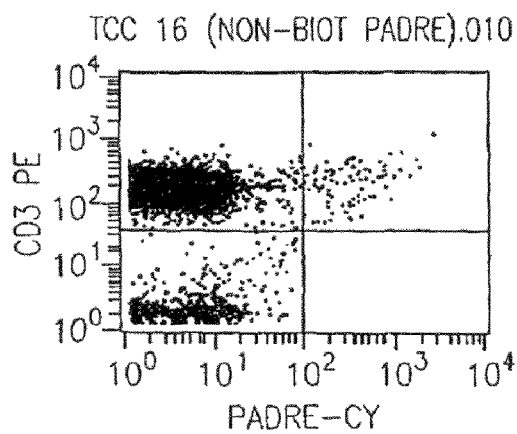
Figure 23F:
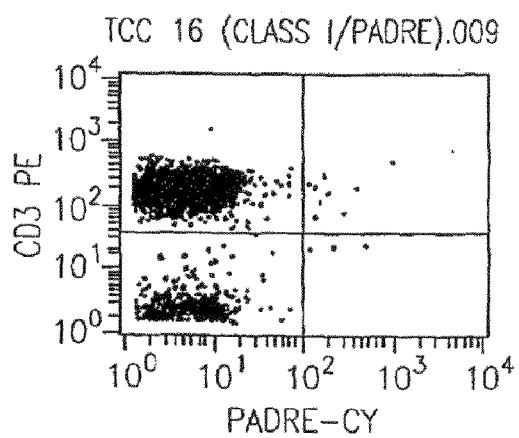

The choice of such antigens was based on the concept that a high number of polyclonal T cells could be found in PBMC if a peptide with high affinity would be employed in the assay. We first defined the optimal molar concentration to employ in loading PADRE pan-DR peptide KXVAAWTLKAA Seq. Id. No. 7, and showed the specificity of interaction between the PADRE peptide and the HLA molecules. T cells from a normal HLA DRB1*401 donor were first tested for the number of PADRE and HA-specific T cells (FIG. 23A), and then cultured with 10 ul/ml of PADRE for ten days. As shown in FIG. 23B, PADRE-specific T cells were expanded to 8.1%, while the number of cells specific for the control HA peptide actually decreased from 1.0 to 0.3% (FIG. 23D). Interaction between antigen-specific T cells and artificial APC was, as expected, depending on availability of TCR and HLA/peptide molecules. Our experiment further showed that binding was inhibited by addition of anti-HLA antibody prior to incubation of artificial APCs with the T cells. Moreover, both total cell number and MFI were reduced by 62% when compared with panel 23B upon competition between biotynilated and non-biotynilated PADRE peptides. This control further supports the specificity of the interactions between the various components of the system, and rules out the possibility of steric hindrance from the biotin at the n-terminal of the peptide in interfering with the necessary molecular interactions.

Figure 24:
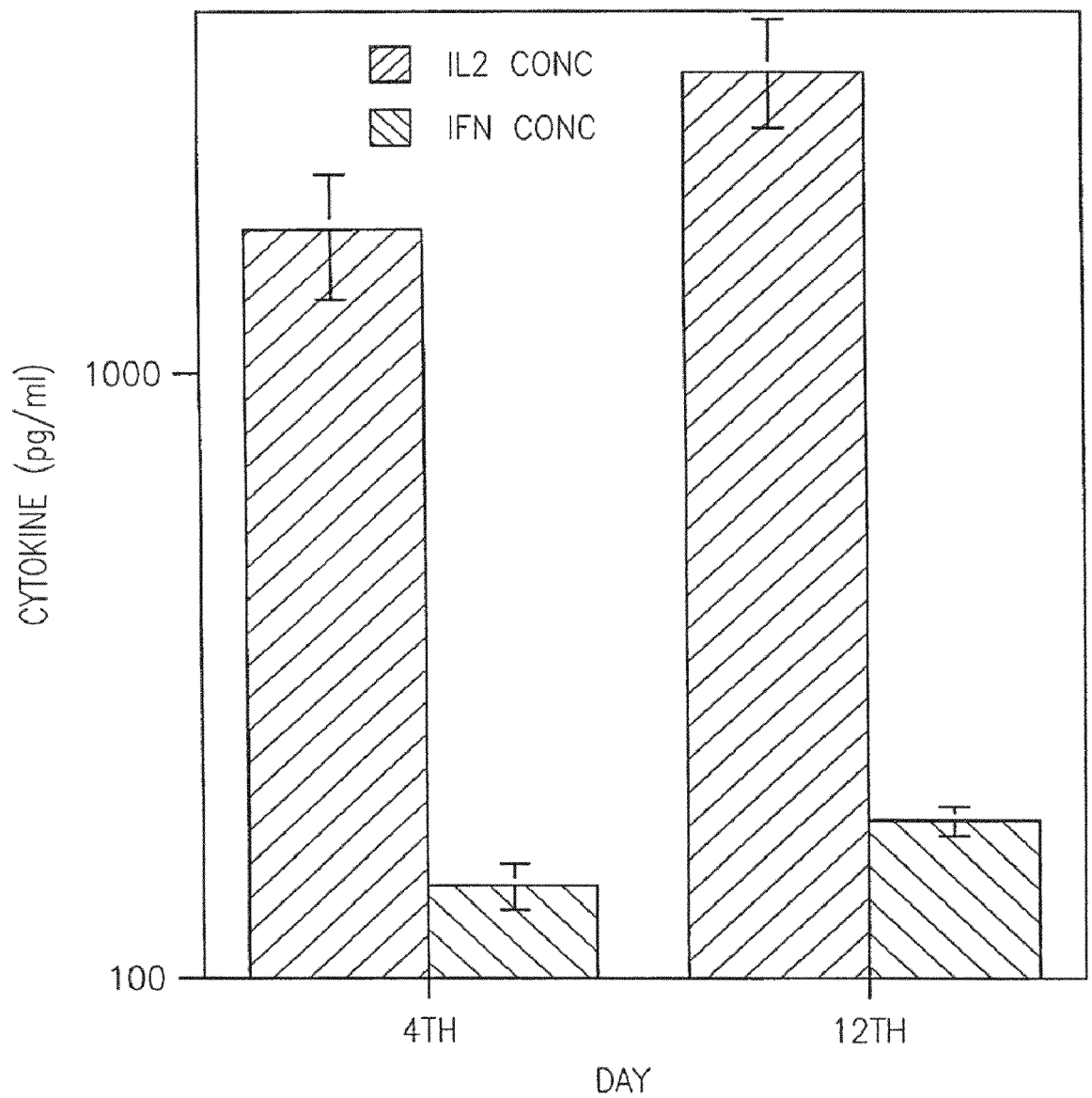
FIG. 24 is a bar graph showing cytokine production by PADRE-stimulated cells. Production of IL-2 and IFN in vitro of PBMC from HLA-DR 0401 healthy adults. PBMCs were initially stimulated with 10 ug/ml of Pan DR Epitope binding peptide (PADRE) and cultured for 10 days. The cells were restimulated with autologous APCs and 10 ug/ml of peptide. Culture supernatants were collected at different days and measured for cytokine production by capture ELISA method. The result indicates that cell specificity can be shown by measuring cytokine production as cells proliferate. However, measuring cytokine production is actually less specific than the method of the invention as demonstrated in FIG. 23.

T cell Capture by Artificial APCs is More Sensitive than Measurement of Cytokine Production to Assess the Number of Antigen Specific T Cells in a Culture Measurement of production of cytokines in response to an antigen is often used to estimate the number of antigen specific T cells. To compare sensitivity of measuring cytokine production against T cell capture by artificial APCs, we harvested culture supernatants from PADRE-stimulated cultures, at the fourth and sixteenth day of culture and measured concentrations of IL-2 and IFN-γ by sandwich ELISA. As shown in FIG. 24, the differences in IL-2 and IFN-γ production between the two time points were not as evident as the increase in PADRE-specific T cells, as measured by our T cell capture method (FIGS. 23A-F). Hence, from the comparisons of the T cell capture using artificial APCs with antigen induced T cell proliferation (FIGS. 25 and 26) and cytokine production (FIG. 24) it appears evident that T cell capture using artificial APCs is a tool for sensitive measurement of antigen-specific responses. The advantage of identifying specific T cells by T cell capture is also important for the fact that T cells may not directly participate in antigenic responses while retaining antigen specificity. This phenomenon may also provide an important tool for the understanding of the regulation of T cell responses to antigens.

Methods

Short Term T Cell Line

Peripheral Blood Mononuclear Cells (PBMC) from healthy donors were stimulated in vitro with the PADRE peptide. PBMC were isolated using a Ficoll-Isopaque gradient and stimulated in vitro with 10 ul/ml PADRE peptide in a 24 well tissue culture plate (Costar, Cambridge, Mass.) at $4 \times 10^6$ cells per well. The cells were cultured in RPMI containing 15% AB serum, at 37° C. and 5% $CO_2$. At days 4 and 7, media were replaced with fresh medium containing recombinant human Interleukin-2 (IL-2) at a final concentration of 10 ng/ml. Culture supernatants taken at day 4 were analyzed for production of IL-2 and Interferon-γ by ELISA. At day 10 viable cells were harvested and analyzed in a T cell capture as described below.

Animals

Balb/C mice were obtained from Harlan. Mice were 4-6 weeks old at the beginning of each experiment.

Immunizations

Balb/C mice were immunized with 100 mg of $OVA^{323-339}$ in Complete Freundis Adjuvant (CFA) subcutaneous, followed by immunizations with 100 mg of $OVA^{323-339}$ in Incomplete Freundis Adjuvant (IFA) at days 7, 14, and 21 after the initial immunization. A subgroup of mice was sacrificed 5 days after each immunization.

Preparation of MHC

Balb/C MHC class II molecules I-Ad and I-Ed were purified from the lysate of B cell lymphoma A20.11 by immunoaffinity chromatography using anti-IAd monoclonal antibody MKD6 (Pierce) and anti-IEk monoclonal antibody 14-4-4S, essentially as previously described.

Human MHC Class II DRB1*0401 and MHC Class I molecules were purified from the lysate of the Epstein Barr virus transformed B cell lines. Affinity purified MHC molecules were solubilized in a TRIS buffer containing 50 mM diethylamine and 0.2% n-acetyl-octyl-glucopyranoside (Calbiochem, San Diego). Conditions tested: pH5 and 7, RT and 37° C., 16-24-40 hr peptide loading.

Competition/Inhibition of Non-Biotinylated PADRE Peptide on Binding to HLA DR4*0401

A modified ELSA using soluble HLA-DR 0401 assessed the competition/inhibition of biotinylated and non-biotinylated PADRE peptide. A ten-fold molar excess of biotinylated PADRE peptide was incubated with affinity purified DR4*0401 at pH 7.0 for 16 hrs in room temperature. In addition, a 250 fold molar excess of non-biotinylated PADRE was added. After 16 hours the complexes were transferred to a 96-well flat bottom ELISA plate (Costar) coated with an anti-DR capture antibody. The excess of unbound peptides and complexes were removed trough extensive washing with buffer. A 1:20,000 solution of Neutravidin-HRP was then added to the wells and incubated for 40 minutes in room temperature. After washing, a TMB developing solution was added and developed for approximately 15 minutes. 1M $H_3PO_4$ was used as a stop solution. The optical density was read at 450-650 nm using a micro-plate reader. Delta Soft program was used to analyze the data.

Preparation of Cells

Cells were washed twice in staining buffer (PBS with 2% FCS and 0.05% sodium azide) and then incubated at 4° C. for 20 minutes in blocking buffer (staining buffer with 10% FCS, for mouse cells FcBlock (Pharmingen) is used). The cells were stained for the surface markers and isotype controls for 20 minutes at 4° C., and washed twice and resuspended in staining buffer. The following monoclonal antibodies were used: PE-, CY- and FITC-labeled anti-mouse and anti-human CD3 and CD4.

T Cell Capture

The cells were incubated with the MHC-peptide liposomes for 20 minutes at room temperature. Before acquisition on the FACScan, cells were washed twice (5 minutes, 500 g) and resuspended in staining buffer. Partial inhibition of the interaction of cells to the liposomes was achieved with monoclonal antibodies against T cell receptor or MHC. For inhibition through partial blocking of the T cell receptor, cells were incubated for 20 minutes with 50 ul/ml unlabeled anti-TCR antibody (Pharmingen), prior to the incubation with the liposomes. For inhibition through partial blocking of MHC, the liposomes were incubated with unlabeled anti-MHC at a molar ratio of 1:1 to incorporated MHC. For competition/inhibition with non-biotinylated peptide, non-biotinylated peptide was added together with the biotinylated peptide, and at the same molar ratio to the MHC.

Example 17

Characterization of Artificial APCs

Figure 20:
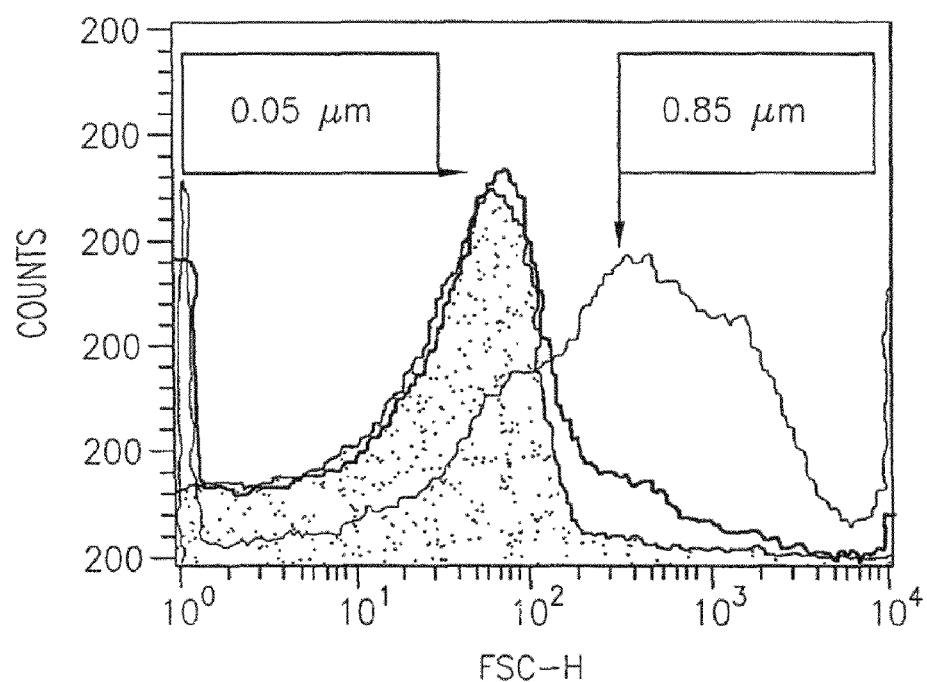
FIG. 20 is a graph showing characterization of the artificial APCs by flow cytometric analysis wherein the approximate size of the fluorescent-labeled liposomes was determined through comparison with single size fluorescent particles with a mean size between 0.05 um and 0.85 um. The 0.85 um labeled curve represents beads of 0.85 um diameter, while the curve labeled 0.05 represents beads of 0.05 um in diameter, the shaded curve represents the size of APC.
Figure 21:
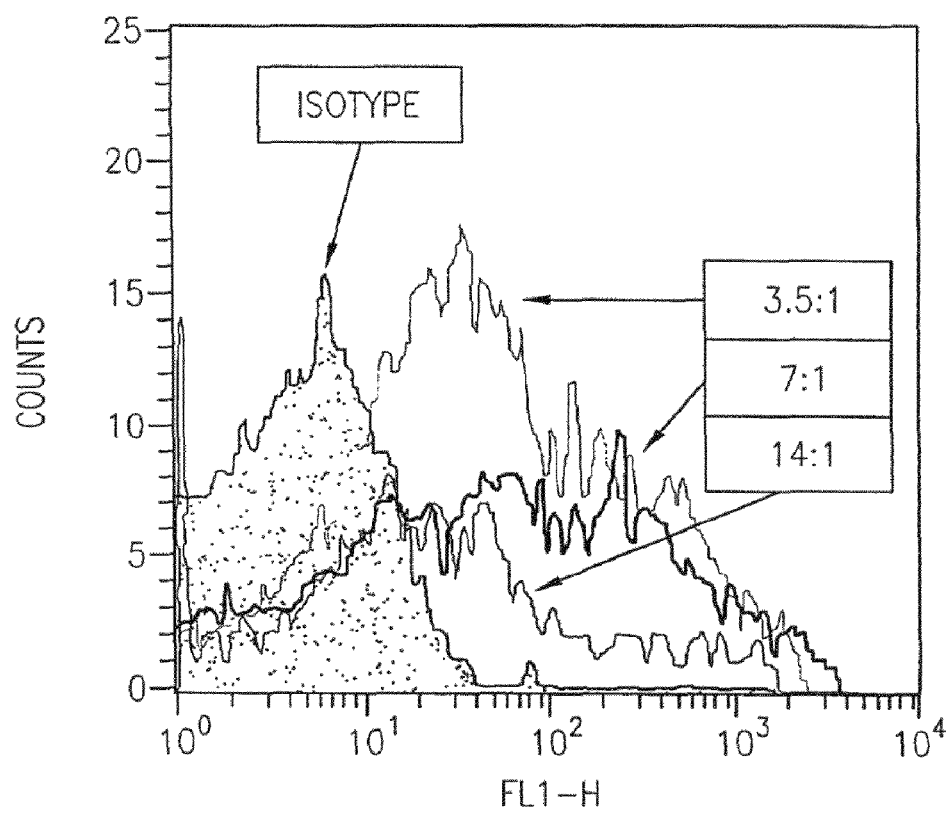
FIG. 21 is a graph showing determination of the optimum incorporation of MHC class II in liposomes. Optimum incorporation is a factor of the ratio of the phospholipid and cholesterol. The ratio of the lipid components were tested such that fluorescent labeled liposomes were complexed with HLA DR4 where the ratio was from 3.5:1 (w/w) to 14:1 and stained with anti-HLA DR PE. The incorporation of DR4 was measured by means of flow cytometric analysis of the signal for HLA DR-PE in FL2 (X-axis). As shown the number of incorporating events is highest (x axis) at a lipid/cholesterol ratio of 7:1.
Figure 22:
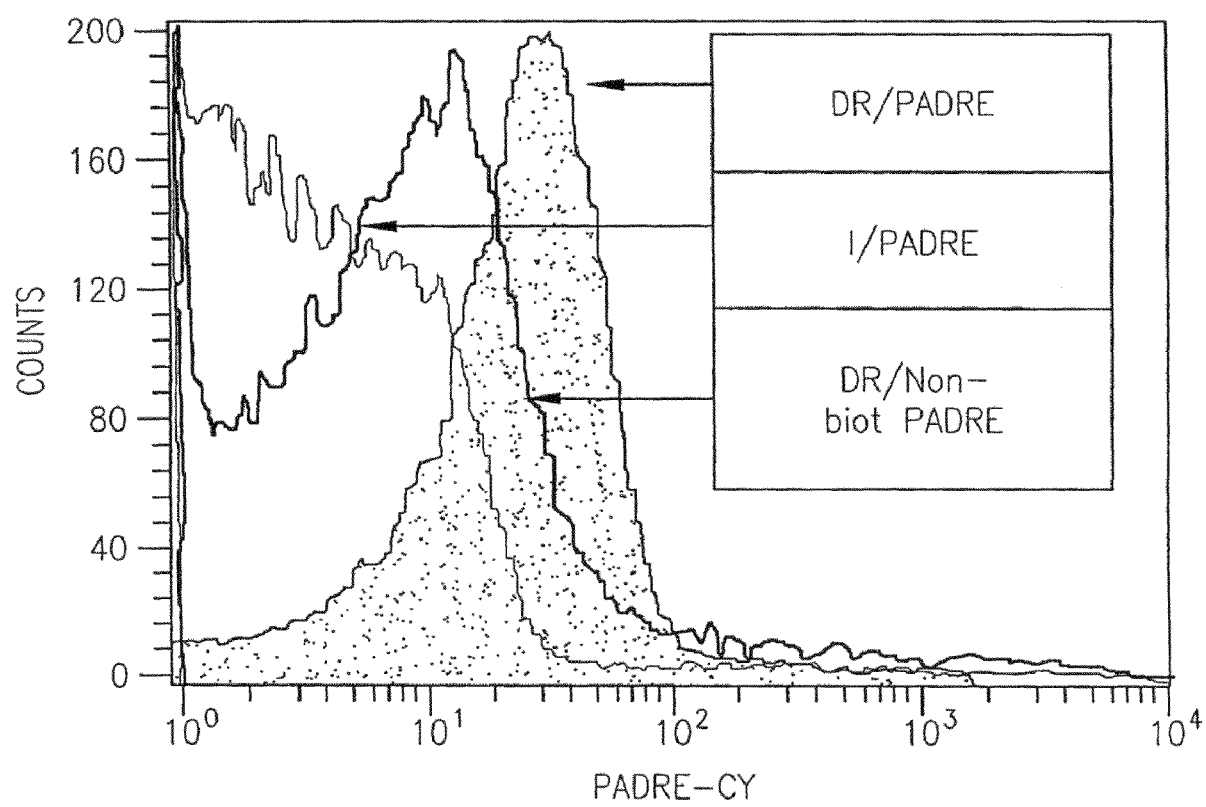
FIG. 22 is a graph showing incorporation of biotinylated PADRE in fluorescent labeled liposomes, complexed with HLA DR4 and specificity of the binding of biotinylated PADRE peptide to HLA DR4 complexed with liposomes. Biotinylated PADRE peptide is incubated with HLA DR4 or MHC Class I, both at a molar ratio of 10:1 (peptide to MHC) prior to incorporation in artificial APCs with fluorescent lipids. As an additional control, non-biotinylated PADRE peptide and biotinylated PADRE peptide (at a 1:1 w/w ratio) were incubated with HLA DR4 before incorporation in artificial APCs. The PADRE is a pan DR binding peptide. The graph indicates specificity and that label bound to the PADRE does not interfere with binding to the MHC component. Specifically, where non-biotinylated peptide is used at the same time, it will compete out biotinylated. The Class I binding shows that there must be specificity for such binding as use of the Class I fails to bind PADRE.

Mean particle sizes of the MHC-containing liposomes were determined through dynamic light scattering analysis with a Malvern 4700 system, using a 25 mW Ne—He laser and the automeasure version 3.2 software (Malvern, Ltd.). For refractive index and viscosity the values for pure water were used. The particle size distribution was reflected in the polydispersity index (p.i.: 0, which ranges from 0.0 for a monodisperse to 1.0 for a polydisperse dispersion). Besides DLS analysis, liposomes were visualized through flow cytometric analysis as described before herein. Briefly, FITC-labeled liposomes were gated according to their FL1 fluorescence by placing a threshold at the FL1 channel, while for forward and side scattering the most sensitive settings were selected. The size of the FITC-liposomes was compared with the FSC of 2 types of FITC-labeled calibration beads ranging in sizes from 40 to 60 nm and from 700 to 900 nm (Pharmingen). The results are shown in FIG. 20 wherein the shaded area shows that the artificial APCs size peak is in the range of 0.05 uM.

For qualitative analysis of the MHC class II incorporation efficiency as explained in Example 16, MHC class-II liposomes were incubated with PE-labelled anti-MHC class II mAbs (anti-DR4 (Parmogen); anti-1-Ad (clone OX-6, Harlan)) or PE-labelled isotype controls and analyzed for PE-staining on the FACS calibur. MHC incorporation was quantitatively analyzed by a Petterson modification of the Lowry protein assay. Briefly, a standard curve (0-1-2-4-6-8-12 ug of MHC) was made with the same detergent solubilized MHC batch as used for the preparation of the artificial APC. A reliable range for protein determination was between 2-12 mg of MHC. All samples were analyzed in duplicate and linear regression was performed on the standard curve to evaluate the amount of protein incorporated in the liposome preparation. To calculate the number of MHC molecules per liposome, the amount of MHC, as determined by the Petterson modified Lowry method, and the size of the liposomes, as determined by DLS, were used to convert the amount of incorporated MHC into the number of MHC per liposome, assuming that a 100 nm liposome contains approximately 80,000 phospholipid molecules/vesicle, and assuming that the average area per phospholipid molecule is 75 $uM^2$.

For qualitative analysis of peptide loaded MHC class II molecules, MHC molecules were preloaded with biotinylated-peptide using the optimized peptide-MHC loading conditions. After MHC incorporation, the artificial APC were incubated with Streptavidin-CY (Pharmingen), and analyzed for FL3 staining using the FACS calibur. The quantitative analysis of occupancy of the number of MHC molecules with the desired peptide was performed in 2 different ways, namely, soluble ELISA and by the analysis of unbound biotinylated peptide after SDS-PAGE and blotting of MHC molecules incubated with peptide.

Figure 19A:
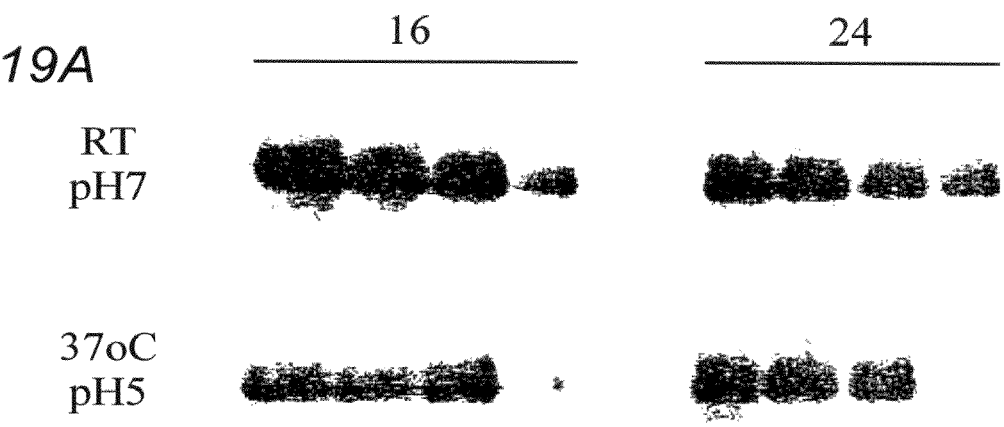
Figure 19C:
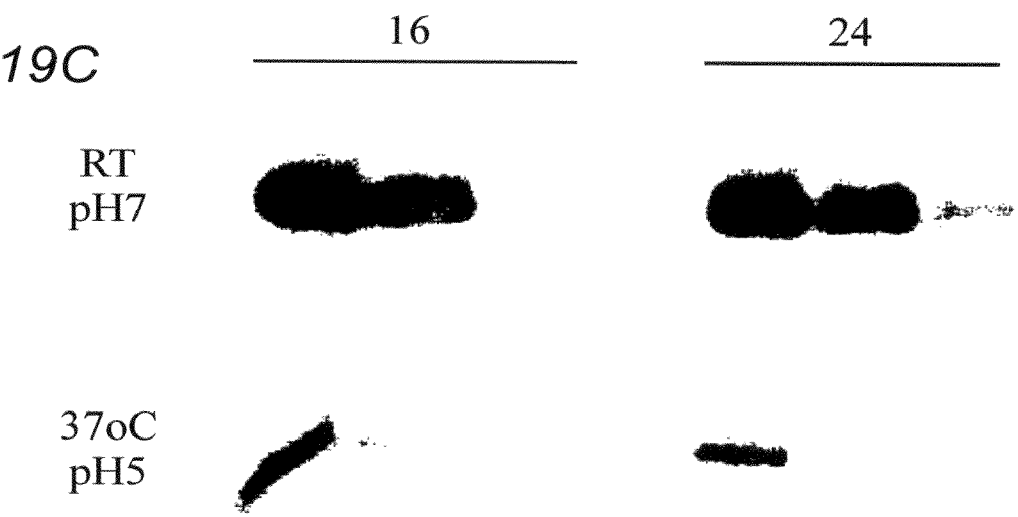

In addition to the MHC samples incubated with a dose range of biotinylated peptide, the same dose range of biotinylated peptide was incubated under exactly the same experimental conditions without the addition of MHC. After 24 hrs., two gels were run under identical conditions in one minigel-system (Biorad). One gel was loaded with the MHC-peptide samples, while the other gel was loaded with the peptide samples. The fronts of the gels were scanned by using the Molecular Analyst software (Maxsott), and a standard curve was made by linear regression of the peptide loaded gel. After front analysis of the MHC-peptide gel the decrease of the peptide signal was quantified by comparison with the standard curve and consequently, the amount of MHC bound peptide could be determined. See FIG. 19.

Methods

Peptide Loading of MHC Class II Molecules

To determine optimal loading conditions for MHC class II molecules a MHC class II binding assay was performed, essentially as described before with minor modifications. Briefly, detergent solubilized MHC class II molecules (0.5-1 uM) were incubated with a 50-250-fold molar excess of biotinylated peptide for the designated time, pH and temperature without the addition of protease inhibitors. The following conditions were tested; pH 5 and pH 7; Room Temperature and 37° C.; 16, 24 and 40 hours of peptide loading; 0.05-, 1-, 10-, 100-fold molar excess of peptide. For DRB1*0401 0.5 uM, for I-Ad 3 uM of MHC was used in binding assays.

MHC-peptide complexes were analyzed via a non-reducing SDS-polyacrylamide gel electrophoresis (SDS-PAGE). Following Western Blotting (Highland-ECL, Amersham), the biotinylated peptides were visualized on preflashed films (Hyperfilm, Amersham) through enhanced chemiluminescence (Western blot ECL kit, Amersham). Optimal binding conditions were established by evaluation of the density of the spots at the position of the MHC class II dimer-peptide complexes. The presence of the MHC Class II dimer under the tested conditions was checked with a non-reducing SDS-PAGE followed by silver staining (Biorad). (see FIGS. 19A-D)

Preparation of Liposomes

Liposomes were prepared as follows. Stock solutions of egg Phosphatidyl Choline (Sigma) and Cholesterol (Sigma) were combined in a glass tube at a molar ratio of 7:2. N-(fluorescein-5-thiocarbamoyl)-1,2-d-ihexadecanoyl-sn-glyvero-3-phosphoethanolamine, triethylammonium salt (fluorescein-DHPE, Molecular ProbesEugene, Oreg.) was added at a final concentration of 1 mol % of Phosphatidyl Choline. The solvent was evaporated under an Argon stream for 30 minutes and the lipids were dissolved at a final concentration of 10 mg/ml in a buffer containing 140 mM NaCl, 10 mM TrisHCl (at pH 8) and 0.05% deoxycholate (Buffer A). The solution was sonicated until clear, and aliquoted in 500 ul Eppendorf tubes and stored at minus 200° C.

Incorporation of MHC-peptide in Liposomes

After preincubation of biotinylated peptides and MHC at conditions based on in vitro MHC binding, MHC-peptide complexes were added to the lipids in Buffer A at a ratio (w/w) of MHC: liposomes of 1:7 (DR4) or 1:10 (IAd and IEd). Additionally, for each T cell capture sample a ratio of 1 ul MHC per 6000 cells was used.

The lipids and MHC-peptide complexes were dialyzed at 4° C. against PBS in a 10K Slide A Lyzer (Pierce) for 48 hours with two buffer changes. The formed liposomes were then recovered from the Slide A lyzers and incubated with streptavidin-CY for 20 minutes before adding the liposomes to the cells. For MHC staining, liposomes were stained with a PE-labeled anti-MHC antibody at the same time.

Where other molecules of interest are to be incorporated into the artificial APC (i.e., accessory, adhesion, co-stimulatory, cell modulation, irrelevant, GM-1 ganglioside molecules, and cholesterol molecules), such molecules can be added simultaneously with the incorporation of the MHC: antigen complexes.

Quantification of HLA-DR and PADRE Peptide Bound to Liposomes

A modified ELISA was used to assess the amount of HLA-DR bound to the liposomes. Briefly, liposomes containing HLA DR4*0401 and biotinylated PADRE peptide were formed as described above. The resulting liposomes were counted and sorted by FACS on (FITC) fluorescence and forward scatter. The sorted samples were then divided into two lots for HLA and peptide quantification by ELISA.

DR Quantification

The sorted liposome sample was initially incubated with 10×M excess of neutra-avidin (Pierce) to cap the biotin on the peptide. This was followed by an extensive dialysis with a 300 k MWCO membrane (Pierce) to remove excess unbound neutra-avidin. The sample was then incubated with biotinylated mouse anti-DR (Parmagen) at 1:1 molar ratio, which was again followed by extensive dialysis. The tagged complex was incubated with neutra-avidin-HRP at 1:20,000 and the excess dialyzed as before. A known amount of soluble DR pre-incubated with non-biotinylated PADRE peptide (standard) was incubated with the same antibody used for detecting the DR in the liposomes. Multiple epitope recognition by the antibody assured retention of the complex during dialysis steps. Both the sorted sample and the standard were then developed with TMB-HRP substrate and read at 450-650 nm.

PADRE Peptide Quantification

The sorted liposome sample was incubated with non-biotinylated anti-DR (Pharmagen) at a 1:1 molar ratio. The sample was treated and developed in the same manner as for DR quantification described above. The peptide was quantified based on its biotin tag. Analysis of the data was adjusted to background and to appropriate negative controls.

Example 18

Methods for Orienting Molecules of Interest in as Artificial APC

We have shown that incorporation of molecules of interest into the artificial APC liposome matrix yields insertion of such molecules in an orientation wherein the active center of the molecules face outward on the APC at a rate of about 50%. We have found that proper orientation can be dramatically increased to over 90% by applying a mechanism to direct the insertion of the molecules. This mechanism uses GM-1 ganglioside, which is a pentasaccharide that acts like a transmembrane protein and has an affinity for binding the β subunit for cholera toxin. When the GM-1 is associated with the liposome membrane of the APC, it can be used to bind cholera toxin which in turn can be attached to the molecule of interest. By attaching the cholera toxin to a point distal to the active site of the molecule of interest, we can direct the orientation of the molecule of interest such that the active site will be placed in the artificial APC in an orientation favorable to interaction with T cells and various molecules. In a preferred embodiment, proper orientation is obtained using a recombinant fusion between the molecule of interest and the β subunit of cholera toxin the construction of which will be well understood by those skilled in the art of making recombinant fusion proteins. The β subunit can also be connected to a molecule of interest using a linker.

Methods

GM-1 Gangliosie Pentasaccharide Anchors

The structure of GM-1 gangliosides has been elucidated and shown to be pentasaccharide. The molecule is branched having terminal sugars, galactose and sialic acid (n-acetyl neuraminic acid), which exhibit substantial specific binding interactions with the βsubunit of cholera toxin. A smaller contribution to binding is derived from the N-acetyl galactose residue of the molecule. This binding interaction is mediated through hydrogen bonding. Each of the five identical binding sites are primarily within a single monomer of the B-pentamer. GM-1 ganglioside may be purchased from commercial sources (Sigma #G7641).

Cholera β Subunit (CTB)

Cholera toxin (mw=84 kda) is comprised of two subunits; a (mw=27 kda) and β(mw=11.6 kda). The amino acid sequence has been determined at about 11,604 da. The primary structure of the β subunit, which is responsible for binding of the toxin to the cell receptor ganglioside GM1, has been determined. Cholera toxin's ability to bind well to such transmembrane structures makes it very attractive anchor for membrane proteins (e.g. molecules of interest as disclosed herein). Since the β subunit is primarily involve in the binding to the GM1 ganglioside pentasaccharide, the α subunits are not necessary. The use therefore of only the βsubunit makes issues respecting toxicity less important with respect to use of the toxin protein subunits in therapeutic applications such as drug delivery or transport and manipulation of T cells ex vivo.

The receptor binding site on the CTB is found to lie primarily within a single β-subunit, with a solvent-mediated hydrogen bond involving the two terminal sugars of GM1 (galactose and sialic acid). The binding of GM1 to cholera toxin thus resembles a 2-fingered grip. Cholera toxin β-subunit may be purchased from commercial sources (Sigma #C9903 or C7771) or synthesized by recombinant methodology.

Linkers for Attaching Cholera Toxin to Molecules of Interest

Linkers may be used to attach the cholera toxin subunit to the molecule of interest. In a preferred embodiment, a linker such as N-succinimidyl[3-(2-pyridyl) dithio) propionate (SPDP, Sigma Prod. No. P3415). NHS-esters such as this yield stable products upon reaction with primary or secondary amines. Coupling is relatively efficient at physiological pH. Accessible-amine groups present on the N-termini of proteins react with NHS-esters and form amides. In this regard, reaction with side chains of amino acids can also occur. A covalent amide bond is formed when the NHS-ester cross-linking agent reacts with primary amines, releasing N-hydroxysuccinimide.

In another preferred embodiment, pyridyl disulfides can be used to react with sulfhydryl groups to form a disulfide bond. Pyridine-2-thione is released as a by-product of this reaction. These reagents can be used as cross-linkers and to introduce sulfhydryl groups into proteins. Conjugates prepared using these reagents are cleavable. Pyrimidine-2-thione groups are released upon reaction with free —SHs and the concentration can be determined by measuring the absorbance at 343 nm (Molar extinction coefficient=$8.08 \times 10^{-3}$ $M^{-1}$ $cm^{-1}$).

Results

Figure 27A:
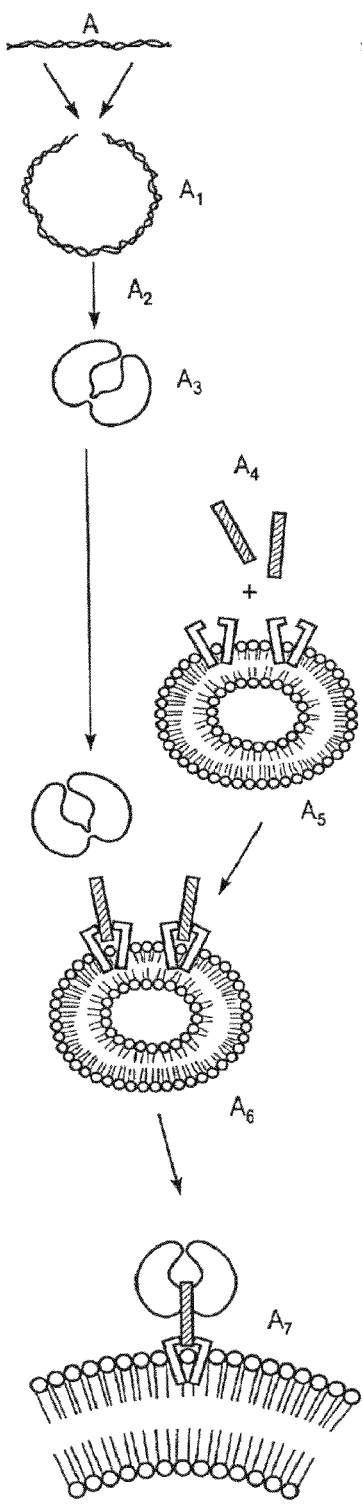
FIGS. 27A-C is a schematic showing methodology for orienting molecules of interest in the APC liposome matrix. In 27A, a molecule of interest such as MHC, functional, accessory, adhesion, or irrelevant molecule, may be synthesized by recombinant methods well known to those skilled in the art and linked to GM-1 by a linker and properly oriented in the APC membrane. In 27B, a molecule of interest may be constructed as a fusion protein with cholera toxin β subunit and the fusion protein anchored in proper orientation in the APC membrane by the cholera toxin moiety binding to GM-1. In 27C, a cholera toxin subunit may be chemically linked to SPDP linker (Pierce) and then attached to a molecule of interest followed by anchoring to a GM-1 containing aAPC. In any of the above, the cholera toxin, GM-1, linkers may be synthetically produced. In the figure, A represents a gene for a molecule of interest, B represents the gene for the β subunit of cholera toxin, A1 is an expression vector, A2 represents expression and isolation of the cloned gene, A3 is an expressed molecule of interest, B1 is a fusion protein of a molecule of interest and cholera toxin, A4 is a linker, A5 is an artificial APC containing GM-1 protein, A7 is a partial view of an artificial APC wherein the molecule of interest is directly linked to the GM-1, C is choler toxin subunit, C1 is a linker, C2 is a molecule of interest, C3 is a choler toxin subunit attached to a linker, C4 is a molecule of interest linked to a choler toxin subunit, E represents a liposome bilayer, E1 shows GM-1 molecules, E2 is an artificial APC containing GM-1, and F is a partial view of an artificial APC having a molecule of interest bound to the APC by the binding interaction of the GM-1 and cholera moiety.
Figure 27B:
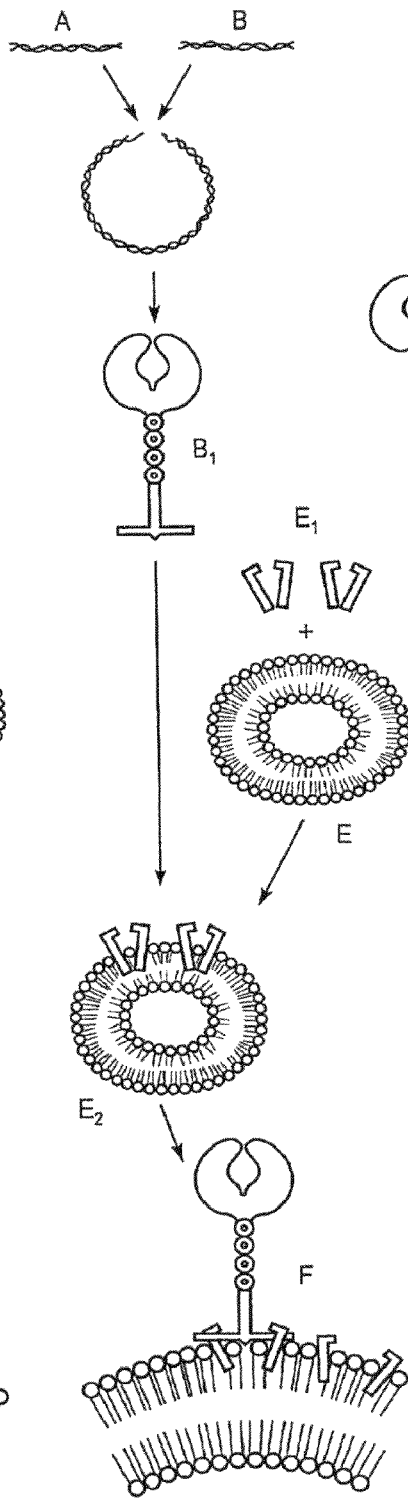
Figure 27C:
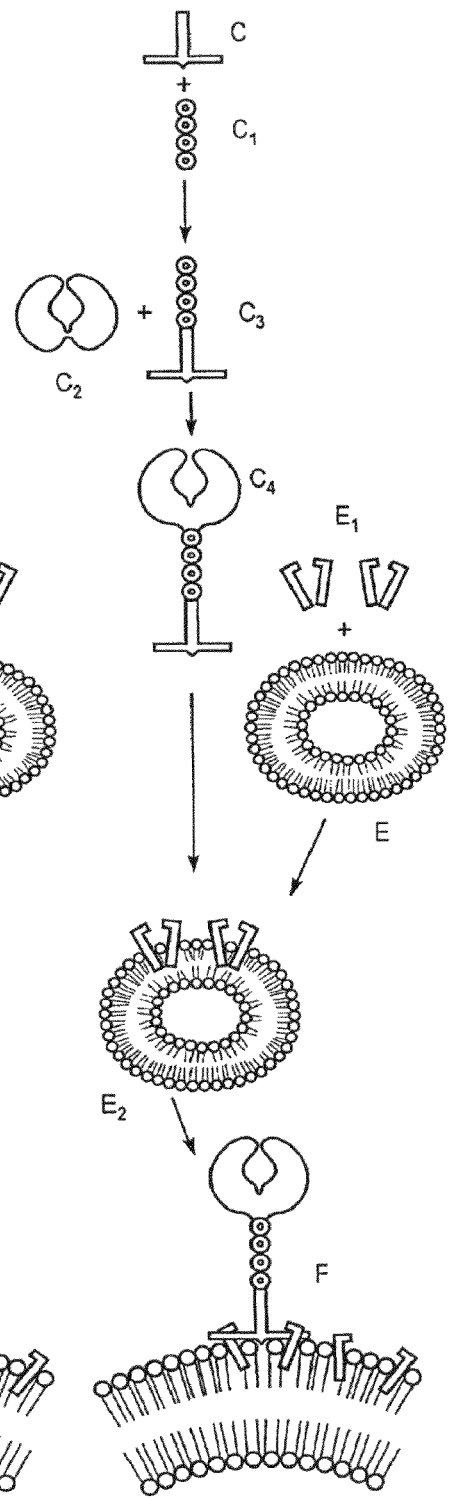

The GM-1 ganglioside molecule acts like a transmembrane protein by anchoring itself in the lipid bilayer. It can be associated with the "raft" or freely mobile molecules of interest in the lipid membrane. GM-1 ganglioside has been used in studying movement and interactions of co-stimulatory molecules through cross-linking the molecule with flourescinated-tagged cholera toxin. This cross linking can be carried out in several ways as shown in FIG. 27. For example, in FIG. 27A, a synthetic gene encoding a molecule of interest is cloned into a commercial vector such as a generic expressions vector (for example, DES Expression Vector, Invitrogen) and expressed. The recombinant product can be purified and linked to GM-1 protein that is in an artificial APC. In a similar fashion (FIG. 27B) the molecule of interest can be cloned into an expression vector as a fusion protein with cholera toxin β subunit. The fusion product can be purified and mixed with an artificial APC containing GM-1 ganglioside where the cholera moiety will bind to the GM-1 ganglioside. Additionally, as shown in FIG. 27C, the cholera toxin (whether natural or recombinant) can be attached to a linker, such as N-succinimidyl [3-(2-pyridyl) dithio]propionate, either to a complete (3 subunit molecule or during synthesis of a recombinant toxin molecule, the product of which can be then mixed with a GM-1 ganglioside containing artificial APC.

We have found that cross-linkers are useful as "flexible hinges" where protein molecules can be covalently linked to allow for intercellular interaction with transmembrane proteins (e.g., B7-CD28, ICAM-1-LFA-1, MHCs, TCRs, etc.). Once the GM-1 ganglioside protein is incorporated into the liposome of the aAPC, cholera toxin-conjugated surface proteins can then be cross-linked. The system containing properly oriented molecules of interest can then be tested through ELISA, WESTERN, and by FACS analysis.

Example 19

High Density Expression on aAPC of Molecular Rafts Comprising GM and Molecules Active in T-Cell/aAPC Interactions Stable interactions between aAPCs and T-cells depends on several factors. These include the absolute affinity between TCRs and their respective ligands, as well as the relative density of molecules available for interaction at the binding site. Under normal physiologic conditions, ligand density is achieved in part by migration of the relevant molecules in the cell membrane toward the site of initial T cell-APC interaction, i.e., capping as described earlier, the outcome of which is stable cell-cell binding. Clustering ensures specific interaction between T-cells and APCs.

The molecular interaction between the clustered transmembrane molecules taking part in T-cell/APC recognition has been termed the "immune synapse". The outcome of forming the immune synapse is an antigen specific response by the T-cell mediated by signaling through the TCR.

Several factors contribute to significant quantitative and qualitative differences in the response provided by the T-cells. These factors include TCR affinity for the MHC/peptide complex and the number of ligands available for interaction. The threshold of response is achieved when enough ligands have migrated to the initial interaction site on the cell surface. Prior to the current invention, known conceptions concerning liposome formation and uses thereof precluded the ability to achieve high threshold immune responses. However, as shown by the results obtained for responses induced by aAPC of the current invention, use of GM-1 based raft structures in liposomes of the particular design of the current invention provide a markedly and unexpectedly superior response result.

The current invention as shown in this example recognizes that modulation of antigen specific T cell response is affected and can be directed by the ability to control the affinity and molarity of the molecules involved in T-cell binding and activation. Our unique construction of GM-1 containing aAPC allow for control of the content and relative ratios of molecules used on the aAPC for interaction with T-cells. We are further able to produce the aAPC with relative high densities of such molecules. Additionally, we provide examples of the effectiveness of such aAPC in binding and activation of T-cells. By "high density" is mean that the aAPC of the current invention possess substantially elevated numbers of immunologically active molecules on freely mobile rafts per each aAPC sufficient to support at least binding between aAPC and a T cell and/or immunmodulation of a T cell.

Artificial APCs are constructed with free floating rafts in the lipid membrane of the aAPC wherein the rafts contain high density of molecules thereby providing hundreds of molecules that are available for binding by the T-cell which collectively are capable of comigration, as in the capping process, mimicking the physiologic interaction between T-cell and natural APC. Hence, both high absolute numbers and relative concentrations of interacting molecules are achieved on a uniquely designed freely migratable raft using the aAPC of the present invention.

aAPC Raft Composition

In this embodiment, rafts, also referred to as "micromembrane domains" are formed in the bilayer lipid membranes of aAPCs. By "rafts" or "micromembrane domains", is meant the free-floating molecular complex which interacts with the transmembrane molecules of the T cell that in part form the immune synapse as is understood by one of skill in the relevant art. In a preferred embodiment, the rafts comprise multiples of GM-1 bound to molecules that interact with the T cell. In a preferred embodiment, each unit of the GM-1 for example is bound to a cholera toxin β subunit which is in turn fused with a molecule of interest such as a molecule that is active in some manner with the T cell/aAPC binding or T cell modulation. Generally, the T cell interacting proteins may be fusion proteins comprising at least three components. These components are (1) an immunologically active component for binding or otherwise interacting with T-cells, (2) a variety of linker components that can comprise short peptides or functional peptides (such as an amino acid sequences capable of binding other peptide sequences), and (3) an anchor component comprising the cholera toxin subunit β itself. By "immunologically active molecule/protein", is meant molecules that are used to bind to T cells and/or participate in the immunomodulation of T cells, or that can be used to detect location of molecules either on the T cell surface or surface of the aAPC.

Figure 28:
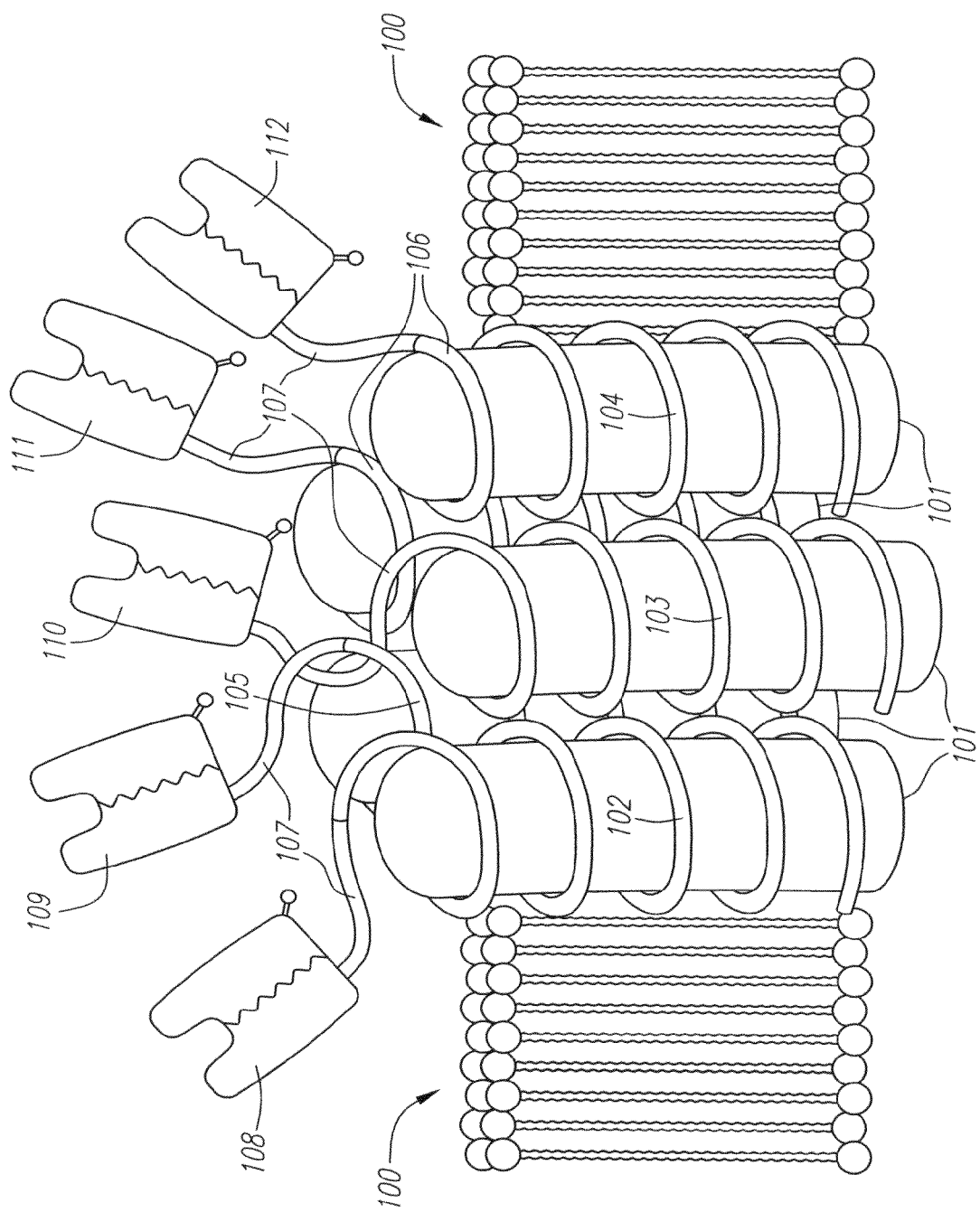
FIG. 28 shows a diagram wherein aAPC lipid bilayer 100 contains a pentameric GM-1 raft 101 that is bound to five cholera toxin β subunits 102-106 (each unit of the pentamer bound to a single toxin subunit). As indicated, each of 20 the toxin subunits comprise a fusion of a complete cholera β subunit and an immunologically active protein sequence of interest 108-112 connected through a linking sequence 107.

Fusion protein constructs expressed in appropriate host expression systems well known to those of skill in the art may be isolated for use in the rafts. In forming the rafts, each of the cholera subunits making up the carboxyterminal portion of the fusion proteins becomes bound by one GM-1. Thus, for every raft, due to natural aggregation of GM-1 within the lipid bilayer (typically to form a pentameric structure), at least five immunologically active molecules can be associated with each raft present on the aAPC. As shown below, the immunologically active molecules can be mixed and matched as desired to create a specific ratio and density of molecules for binding to and modulation of the T cells. FIG. 28, shows the high density expression concept described above.

In one embodiment, the fusion proteins can be designed as cassettes in expression plasmids comprising the various components (i.e., cholera toxin, linker, immunologically active molecule). Generally, the cholera toxin anchor component can be constructed as a cDNA cassette in an expression plasmid comprising sequence encoding, from 5' to 3', a short linker sequence followed by the toxin sequence. The linker sequence codes for appropriate restriction endonuclease sites and a stretch of amino acids to provide spacing between the toxin subunit and the immunologically active component that is desired for attachment to the cassette. Alternatively, both a linker sequence and an additional nucleic acid sequence coding for an amino acid sequence having a binding function for binding additional molecules important in T cell binding and modulation can be constructed into the cassette. The cassette can then be manipulated, through recombinant technology well known to those of skill in the art, such that the linker sequence is fused to a sequence coding for an immunologically active protein of interest. Once so constructed, the expression plasmid may be processed for ultimate production and isolation of the resulting fusion protein. The fusion protein may then be used in forming high density rafts for insertion into the aAPC.

Generally, the immunologically active portion of the fusion proteins can be any sequence recognized by the T-cell and/or important to T cell binding and/or immunmodulation, or detection of the binding process. Examples of such proteins are, without limitation:

(a) MHC molecules;
 (b) Antibody molecules that interact directly with the TCR;
 (c) Co-stimulatory molecules including, but not limited to, B7-1, B7-2, OX40, chemokine receptors, CD30, CD5, CD9, CD2, and CD 40, and many other receptors, ligands, and antibodies thereto as would be understood as important to one of skill in the art;

(d) Antibodies directed against CD4 and CD8 receptors, tissue specific receptors, syalic acid;

(e) Cytokines such as interferon and IL-4;

(f) Accessory molecules as delineated throughout this disclosure including, but not limited to, LFA-1, CD11a/18, CD54(ICAM-1), CD106(VCAM), and CD49d/29(VLA-4).

(g) Antibodies to accessory molecules;

(h) Antibodies against CD28 and CTLA4;

(i) Adhesion molecules including, but not limited to, ICAM-1, ICAM-2, GlyCAM-1, CD34, anti-LFA-1, anti-CD44, anti-beta 7 antibodies, and chemokine receptors such as CXR4, and CCR5;

(j) T cell modulatory molecules including, but not limited to, CD72, CD22, and CD58; and (k) Irrelevant molecules for binding the aAPC to solid supports or for use as a label.

Immunologically active molecules such as those provided above when presented in the high density component rafts of the invention aid in the binding and/or modulation of the T-cells which come into contact with the aAPCs.

For example, FIG. 29 shows a fusion construct wherein a nucleic acid sequence encoding the B7-1 molecule has been attached to the cholera β subunit nucleic acid sequence through a linking sequence (underlined).

Specifically, the B7-1 portion makes up the immunologically active portion which comprises the N-terminal region of the fusion protein while the cholera subunit (fused through the linker to its N-terminal amino acid) makes up the C-terminal portion.

In another example, shown in FIG. 30, a very similar construct can be created for the B7-2 molecule.

As will be understood by those skilled in the art, appropriate makeup of the fusion proteins is amenable to computer analysis for determining sequences for fusion constructs so as to predict and avoid steric hindrance and undesirable tertiary interactions of the amino acid moieties on the immunologic portion with that of the cholera toxin anchor portion.

In yet another embodiment, in addition to the cholera toxin anchor portion, the immunologic portion, and linker portion, the fusion construct may also be designed to incorporate a protein binding peptide sequence. Such sequence can be, without limitation, a peptide such as a leucine zipper sequence as shown below:

Leucine Zipper A: SAQLEWELQALEKENAQLEWELQALEKELAQ (Seq. Id. No. 19)

Leucine Zipper B: AQLKKKLQALKKKNAQLKQKLQALKKKLAQ (Seq. Id. No. 20)

As shown in FIGS. 31 and 32, immunologically active proteins such as the HLA FRA1 and DRB1*0401 sequences comprising α and β domains can be engineered into a fusion protein constructs. In FIG. 31, the α domain (comprising α1 to α2) forms the N terminal portion of the fusion which is then linked by a short amino acid sequence to Leucine zipper A followed by a second linker sequence which is followed in turn by the cholera toxin β subunit making up the carboxy-terminal portion of the fusion.

FIG. 32 shows the construction of the HLA DRB1*0401 β domain (comprising β1 to β2) fused to a short amino acid linker, followed by Leucine zipper B, followed in turn by a second linker, which is followed yet again by a biotag peptide sequence. As described earlier, the biotag moiety comprises an irrelevant molecule in that it does not participate in binding between T cells and the aAPC or in immunmodulation but does provide a means for visualization of the T cell-aAPC binding process.

Figure 33:
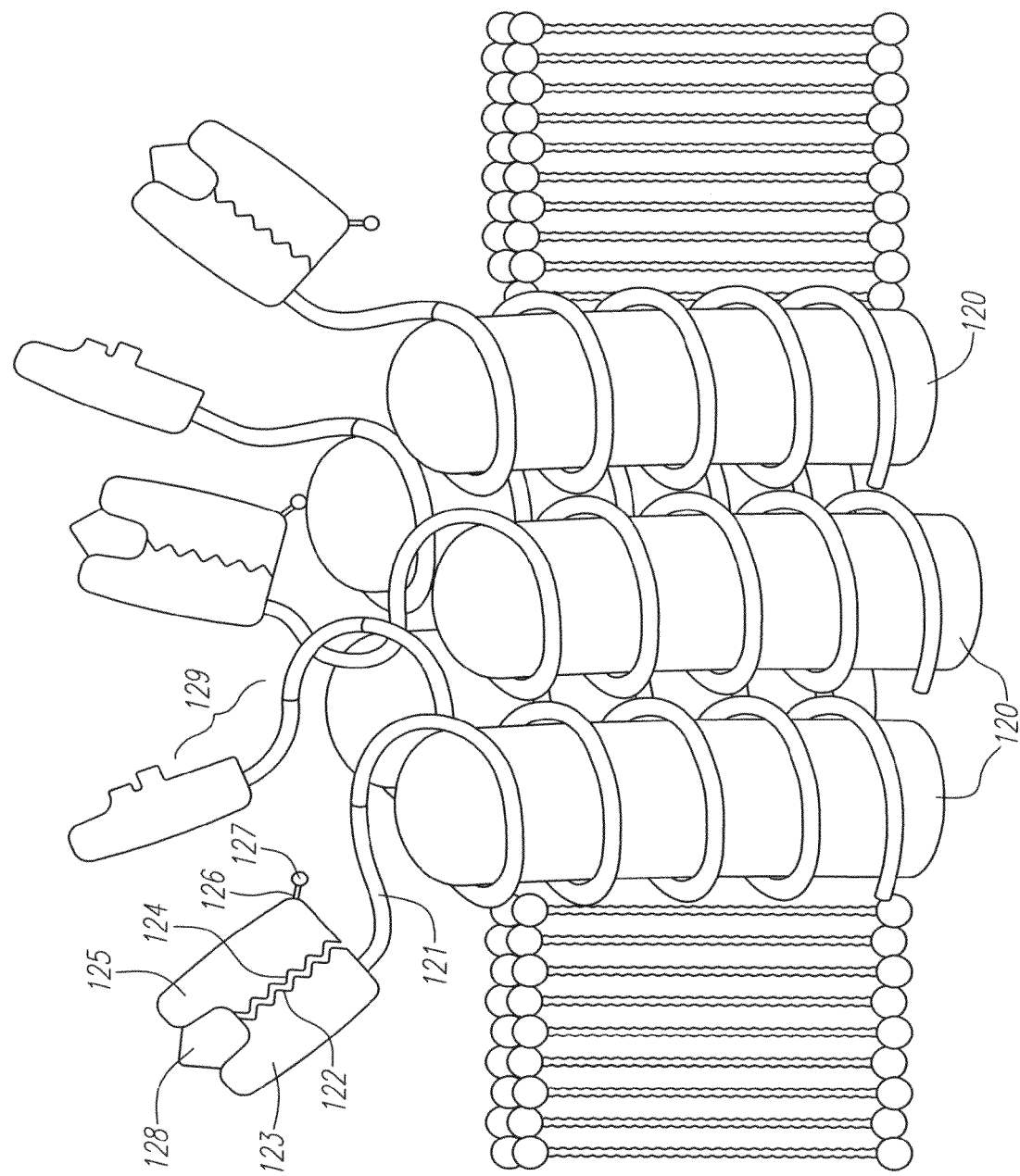
FIG. 33 is a schematic showing a pentameric aggregation of GM-1 binding to five cholera toxin subunits 120. Each cholera toxin β subunit comprises a fusion protein wherein the toxin moiety is connected to a linker 121, followed by a Leucine zipper A sequence 122, followed in turn by HLA DRB1*0401 α123. The Leucine zipper A 122 is bound to the Leucine zipper B component 124 of a second fusion protein construct comprising the β domains of HLA DRB1*0401 125 which is fused to a linker, followed by the Leucine zipper B 124, followed in turn by another linker 126 and finally to a biotag moiety 127. Also, depicted is antigen peptide 128 bound to the HLA α and β moieties, as well as accessory fusion constructs 129 depicting the variable nature of the GM-1 ganglioside-based rafts of the invention.

In the embodiment comprising DRA and DRB fusion proteins, we demonstrate the ability to create highly complex rafts wherein one fusion protein construct possessing a cholera anchor segment that is bound to a GM-1 moiety of the raft, is able to carry with it another fusion protein that has no cholera anchor component. Specifically, as shown in FIG. 33, the A and B Leucine zippers bind to one another allowing the rafts to carry fusion proteins comprising both a and domains. This allows for insertion of complex molecular structures into the raft without using a cholera toxin anchor for at least one molecule making up the complex structure. Further, the use of binding sequences (such as the leucine zipper) allows for the proper orientation and tertiary structure between molecules that must form a specific three dimensional structure (as is the case with the HLA-DRB1) to achieve its immunologic usefulness.

From the above examples of fusion protein constructs, it can readily be understood that aAPC can be generated containing high density rafts comprising any combination and/or ratio of immunologically active molecules. The ability to control raft structure contrasts substantially with current methods for 'detection' of antigen specific T-cells. For example, existing systems used in binding assays rely on absolute affinity between the T cell and the molecular complexes. Moreover, current binding assays are limited in the nature of the binding interaction between T cells and binding complexes comprising immunologically active molecules because they do not allow the physiologic phenomenon of capping. Such systems must rely only on high affinity binding which limits the use of such complexes to the detection of binding but not manipulation of T cell modulation. Additionally, such limited methodologies may not have the capacity to detect "low affinity" binding interactions, which can be important to T cell education/stimulation such as the induction of autoimmunity.

The current invention sharply contrasts with less capable methods by, for example, allowing active clustering of TCR-MHC molecules at the immune synapse, which clustering occurs after the initial interaction between aAPC and T cells. The capability for this multivalent system for strong binding aids low affinity interactions thereby providing for both simultaneous stimulation and modulation responses of antigen specific T cells even in cases where the molecules comprising the immune synapse interact with low affinity binding.

Figure 34:
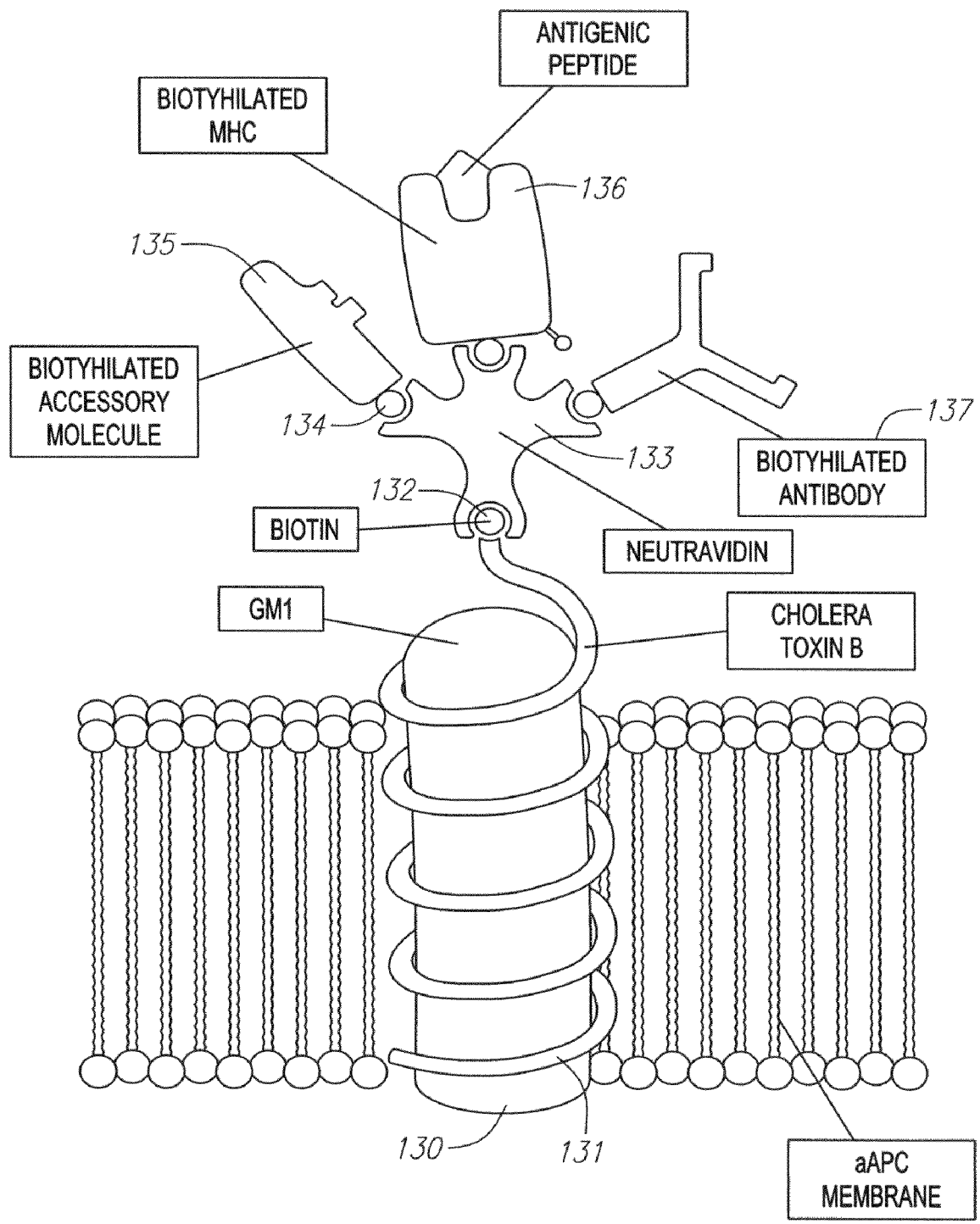
FIG. 34 depicts a GM-1 molecule 130 bound by a cholera toxin molecule 131 that has been biotinylated 132 at its 5' end. The biotin is bound to one of the binding centers of neutravidin 133 that is in turn bound through its remaining three binding centers 134 to any immunologically active molecule of interest. Specifically depicted are binding to an accessory molecule 135, MHC with its antigen peptide 136, and anti-CD 28 antibody 137.

Besides the fusion protein concept described above, we have also engineered liposomes containing high density rafts by binding neutravidin (also known as tetravidin) to the cholera toxin through a biotin moiety (FIG. 34). Since neutravidin has four binding centers capable of binding four biotin molecules, each cholera anchor molecule (bound to a GM-1 molecule) can provide for binding three immunologically active molecules through the neutravidin moiety. Specifically, as shown in FIG. 34, biotinylated cholera toxin is bound to GM-1 ganglioside. The biotin of the cholera toxin is bound to neutravidin that is in turn bound to any variety of biotinylated immunologically active molecules of interest. Hence, each GM-1 molecule of the rafts has three valences available for interaction with T cells. Since the GM-1 molecules aggregate to form generally pentameric rafts, it is possible for at least 15 immunologically active molecules and as many as 30 immunologically active molecules to be present on any pentameric GM-1-based raft. This raft construct method ultimately results in the possibility to provide several thousand immunologically active molecules on several hundred high density rafts on each aAPC. FIG. 34 depicts the structure of a hypothetical individual GM-1 raft in the aAPC membrane.

Figure 35A:
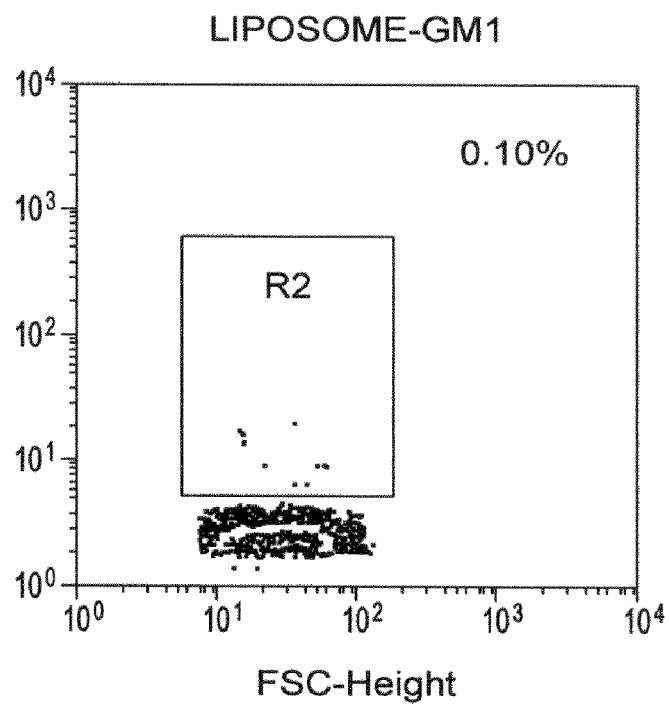
FIGS. 35A and B shows FACS analysis wherein GM-1 rafts in liposomes are shown to bind to cholera toxin-conjugated with FITC label.
Figure 35B:
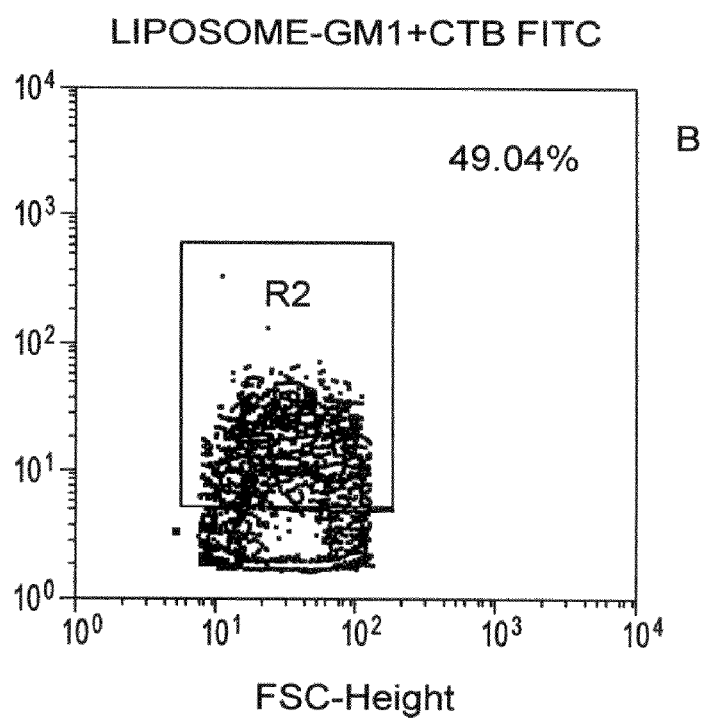
Figures 36, 37:
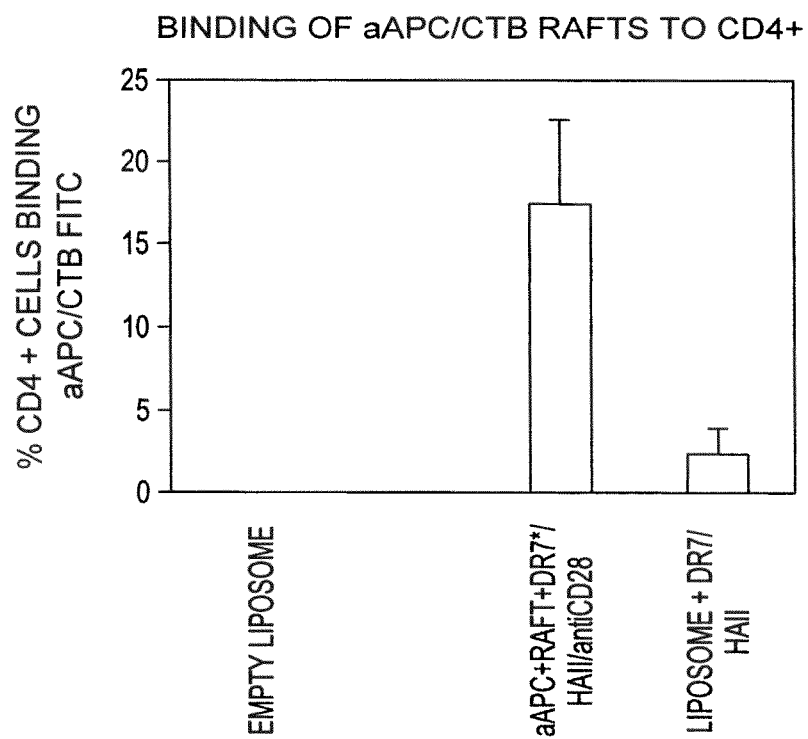
FIG. 36 shows a saturation curve wherein increasing amounts of cholera toxin is added to a fixed GM-1 population (approximately 6,374 pico moles) on the aAPC. FACS analysis visualizes cholera toxin bound on the aAPC showing saturation is obtained by addition of at least 5,000 picomoles of the toxin. The table shows GEO, which represents the mean fluorescent intensity observed for each condition which translates into the % of aAPCs containing toxin, the percent saturation expressed by the % gated M2 column.
FIG. 37 shows binding of GM-1 raft based aAPC containing HLA, HA and anti-CD28 vs. non-GM-1 raft based liposome containing randomly distributed HLA and HA. Identification of HA-positive CD4+ cells was significantly more efficient when both biotinylated HLA/HA and anti CD28 molecules were present on the micromembrane domains on the aAPC (17.8+5.2% CD4+ cells. In comparison, only a small proportion of antigen specific T cells was visualized when only HLA/HA complexes were deployed on the aAPC using non-GM-1 based rafts for visualization of the antigen specific T cells. Only 2.4+1.6% of CD4+ cells was bound by aAPC in which HLA/peptide complexes were randomly distributed on the lipid bilayer as previously described.

To show raft density on the aAPCs, FIG. 35 provides FACS analysis of raft densities wherein various raft components are added using the tetravidin construct method. The data shows binding of biotinylated cholera toxin to GM-1 in the aAPC. In this experiment, the cholera toxin is conjugated with FITC to allow visualization of the binding of the cholera toxin to the aAPC. FIG. 35A depicts the liposome containing only GM-1 molecules. FIG. 35B depicts binding of the cholera toxin to the GM-1 molecule at substantially high levels. These levels, as shown in FIG. 36 correspond to a binding efficiency approaching 100% saturation of all GM-1 molecules on the aAPC. Specifically, the aAPC, which were created using 230 ug of total lipid and 10 ug of the GM-1 (i.e., approximately 6374 pico moles), were incubated with various amounts of FITC conjugated cholera toxin for 20 minutes, washed, and read for density. Saturation of the GM-1 with cholera toxin begins to occur at levels in the area of 5,000 pico moles of cholera toxin showing that each aAPC can contain hundreds of GM-1/cholera toxin raft forming microdomains expressing even more hundreds of immunologically active molecules available for binding (i.e., high density rafts).

To show the efficiency of aAPC of the current invention and method over conventional liposome art, high density rafts incorporating HLA, HA (antigen peptide) and anti CD28 were tested for binding with CD4+ T cells from a healthy individual previously immunized with flu vaccine. The percent of CD 4+ cells bound by the aAPC was observed by FACS analysis. Visualization of binding was obtained by adding FITC conjugated cholera toxin to the aAPC prior to incubation with PBMC.

As shown in FIG. 37, the GM based raft containing aAPC exhibited a significant increase of bound CD4+ cells over that of non-raft liposomes. Specifically, GM-1 based raft aAPC containing HLA/HA and a costimulous anti CD28 molecule was presented to CD4+ cells and compared to liposomes prepared only with HLA and HA. In the non-raft liposomes, the HLA and HA are randomly distributed throughout the liposome lipid bilayer. These results show that the aAPC of the current invention are substantially superior in binding T cells over the binding capability of prior liposome construct concepts.

Figure 38A:
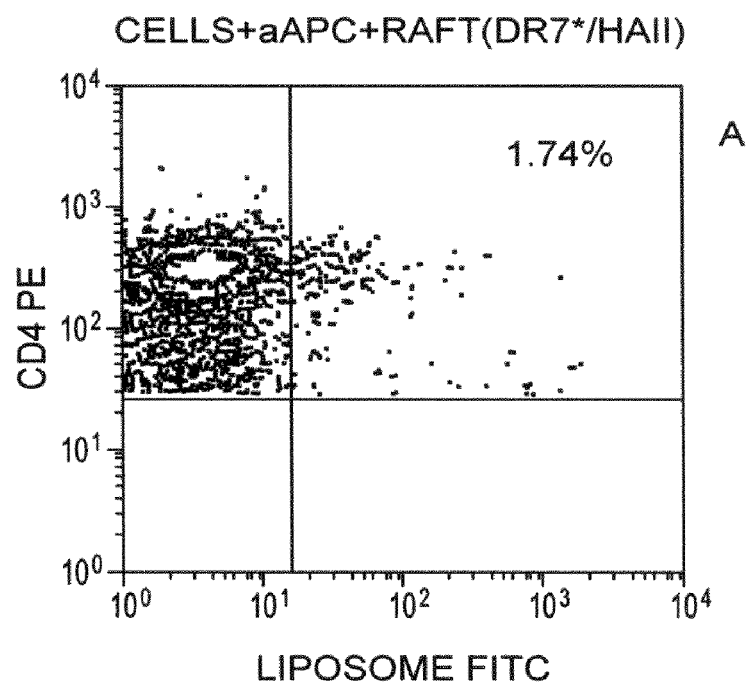
FIG. 38 shows relative binding of CD 4+T cells by GM-1 raft based aAPC containing HLA and HA and anti CD28 vs. non-GM-1 raft liposomes containing HLA and HA. As indicated, the GM-1 based aAPC of the current invention exhibited approximately an eight fold increase in the binding efficiency.
Figure 38B:
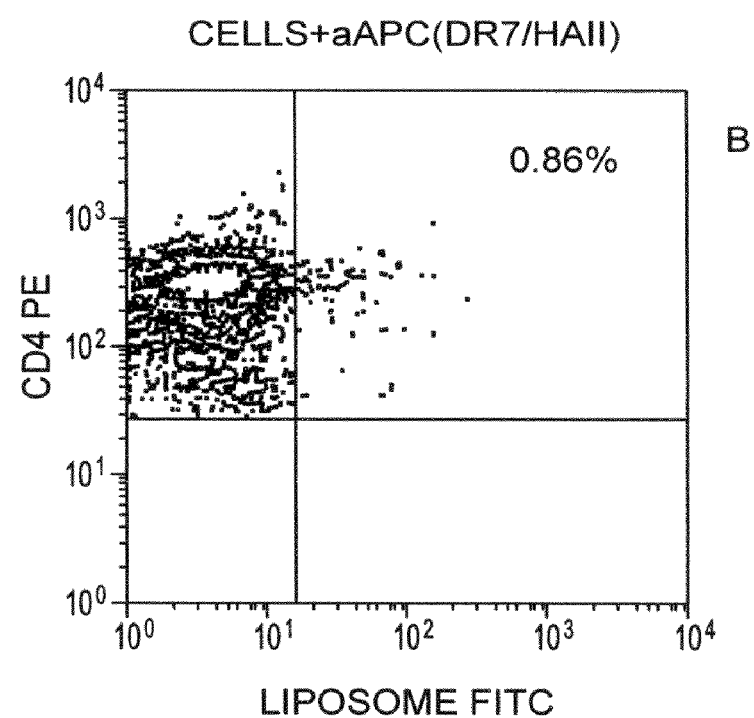

Additionally, as shown in FIGS. 38A and B, binding to T cells by aAPC containing GM-1 rafts with HLA and HA alone is compared to binding of cells by non-raft liposomes containing only randomly distributed HLA and HA. Here, the costimulatory effect of anti CD28 is not present. Thus, the results show that the raft based aAPC provided at least a 100% greater efficiency of binding to T cells. Therefore, the aAPC of the current invention is proven substantially superior to prior liposome methods and further indicates that the current invention's employment of GM-1 based rafts bearing immunologically active molecules provides unexpected and significantly improved binding to T cells over that of prior liposome construct methodologies.

Example 20

T Cell Modulation by Aapc

One of the most important and original advantages of the technology herein disclosed is that it provides a tool to control exactly the affinity and molarity of molecules on the aAPC surface at the level of micromembrane domains. This is an essential and, to date, unfulfilled requisite for controlling T cell responses. Below are provided two examples of such control. In the first, the GM-1 based raft containing aAPC is compared with liposome constructs of previous methods, in stimulation of T cells in a non-antigen specific fashion. In the second example, the capability of the aAPCs of the present invention to modulate ex vivo T antigen specific T cell responses is demonstrated.

To compare our raft technology with prior art in stimulation of T cell in a non antigen specific fashion, CD4+ cells were sorted from PBMC (using PBMC from the same donor as described above) followed by incubation for 72 hours with either aAPC containing anti CD3 and anti CD28 antibodies on GM-1 based rafts, or with anti CD3 and anti CD28 that had been bound to a planar surface of a tissue culture plate well as disclosed in prior applications. The CD4+ cells were tested for expression of IL-2, a cytokine associated with T cell proliferation and activation. Analysis was performed by FACS.

Figure 39A:
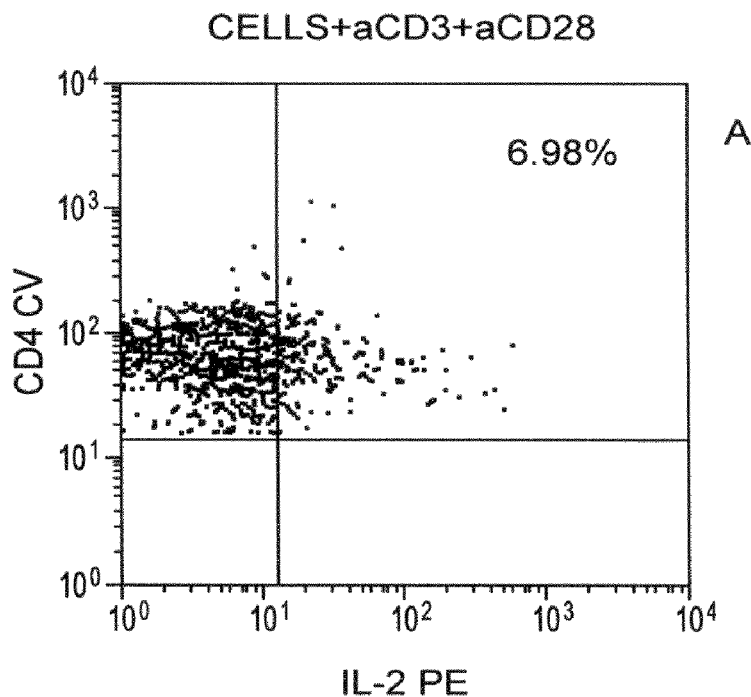
FIGS. 39A and B show efficiency of activation of IL-2 production in CD4+ cells by FACS analysis using either GM-1 based rafts containing anti-CD3 and anti-CD28, or a non-GM-1 raft system (e.g., a planar array format).
Figure 39B:
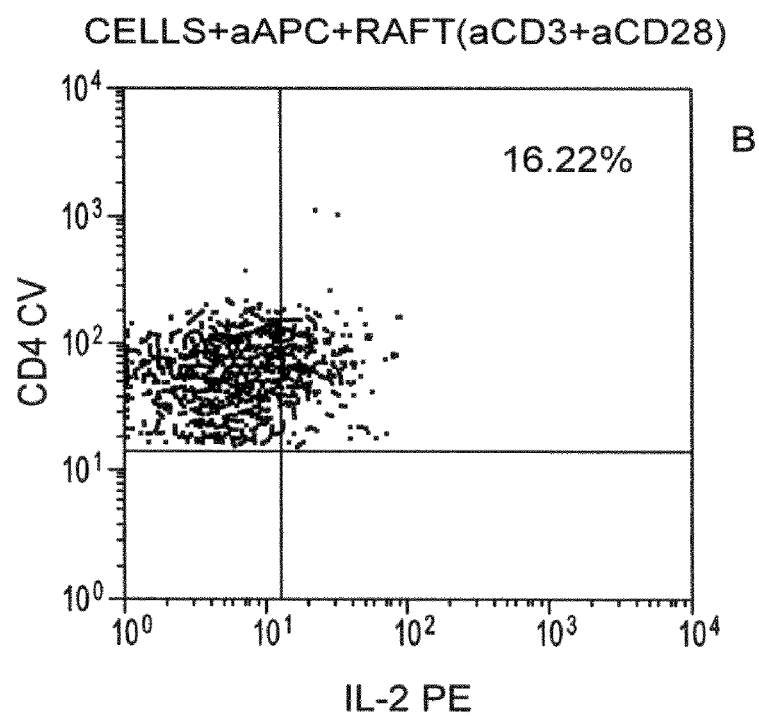

As shown in FIGS. 39A and B, activation of CD4+ cells using GM-1 based aAPC of the current invention provided significantly higher efficiency in expression of IL-2 than that of the solid phase methodology. The results further indicate that efficiency of stimulation was strictly dependant not upon the engagement of the CD28 receptor by the anti CD28 antibody but on the organization of the immunologically active molecules comprising the high density raft constructs of the current invention aAPCs.

Figure 40:
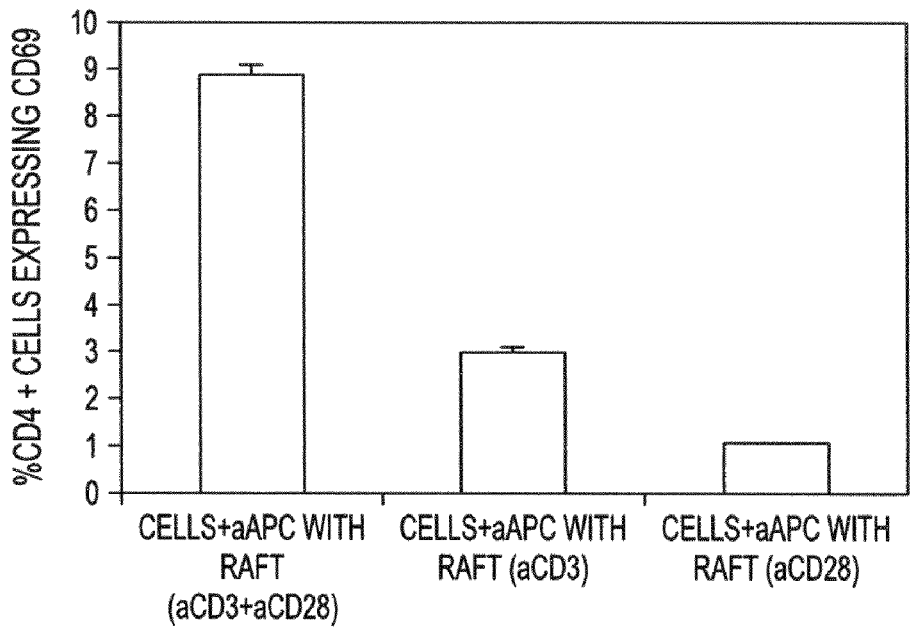
FIG. 40 shows that CD4+ T cells can be modulated to express CD69 using of a combination of anti-CD3 and anti-CD28. This combination provides a significantly higher stimulation of expression of CD 69 than when either anti-CD3 or CD28 are used in the aAPC alone.
Figure 41:
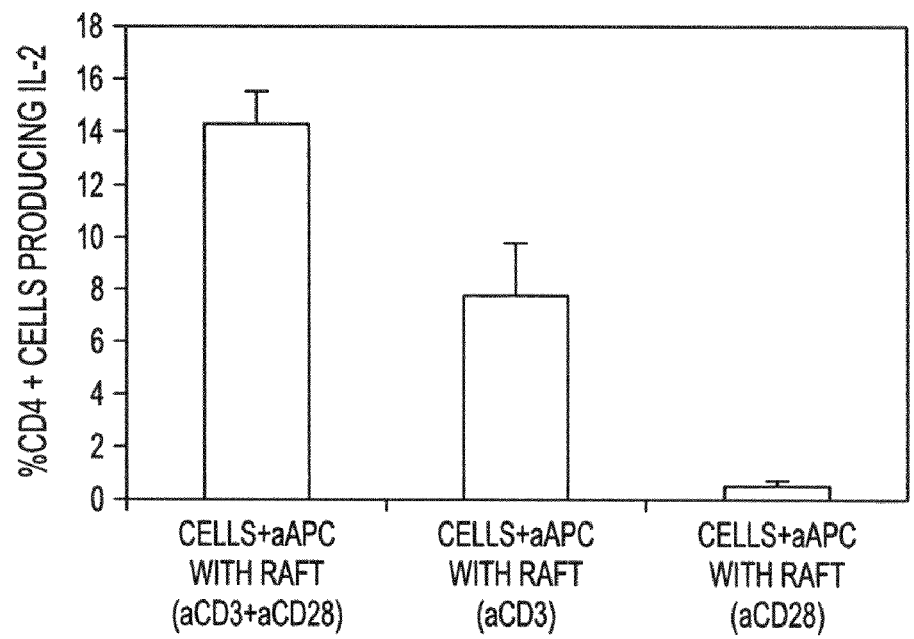
FIG. 41 shows IL-2 production by CD4+ cells following stimulation with GM-1 based aAPC. As indicated, use of a combination of anti-CD3 and anti-CD28 provides stimulation of significantly higher IL-2 production.

In another experiment the ability to modulate T cells was tested by comparing CD69 (FIG. 40) and IL-2 (FIG. 41) production in CD4+ sorted cells incubated with aAPC containing either CD3 or CD28, or both CD3 and CD28. When both CD3 and CD28 are present, IL-2 and CD69 production are substantially stimulated. This shows that the aAPC of the current invention are capable of providing an effective means for modulation of T cell response in vitro.

Figure 42:
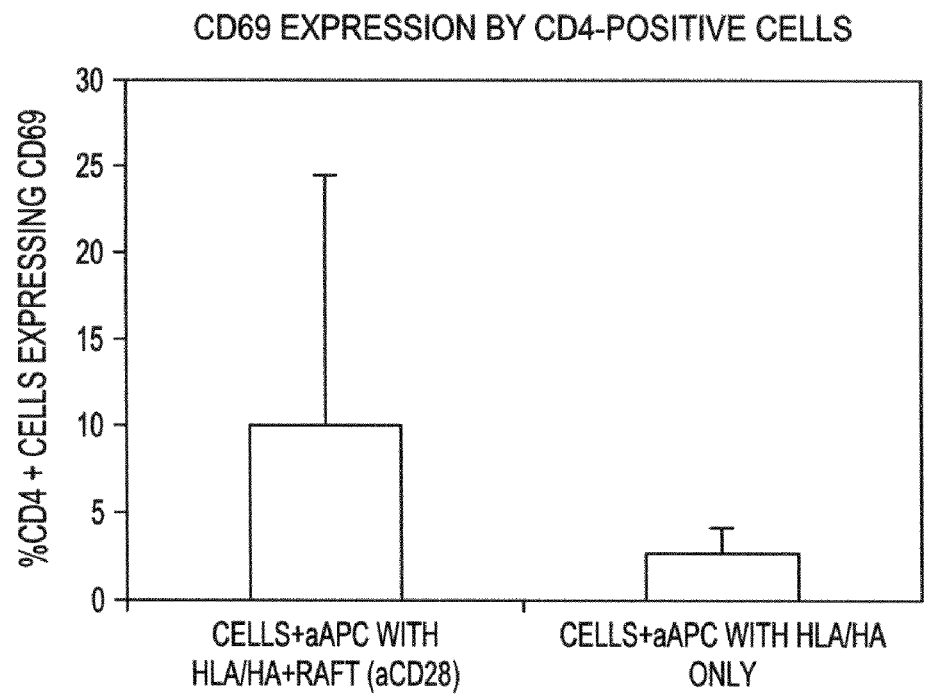
FIG. 42 shows specific activation of CD4+ cells to express CD69. Particularly, aAPC of the current invention provide a three-fold increase in stimulation over liposome constructs not containing GM-1 based rafts.
Figure 43:
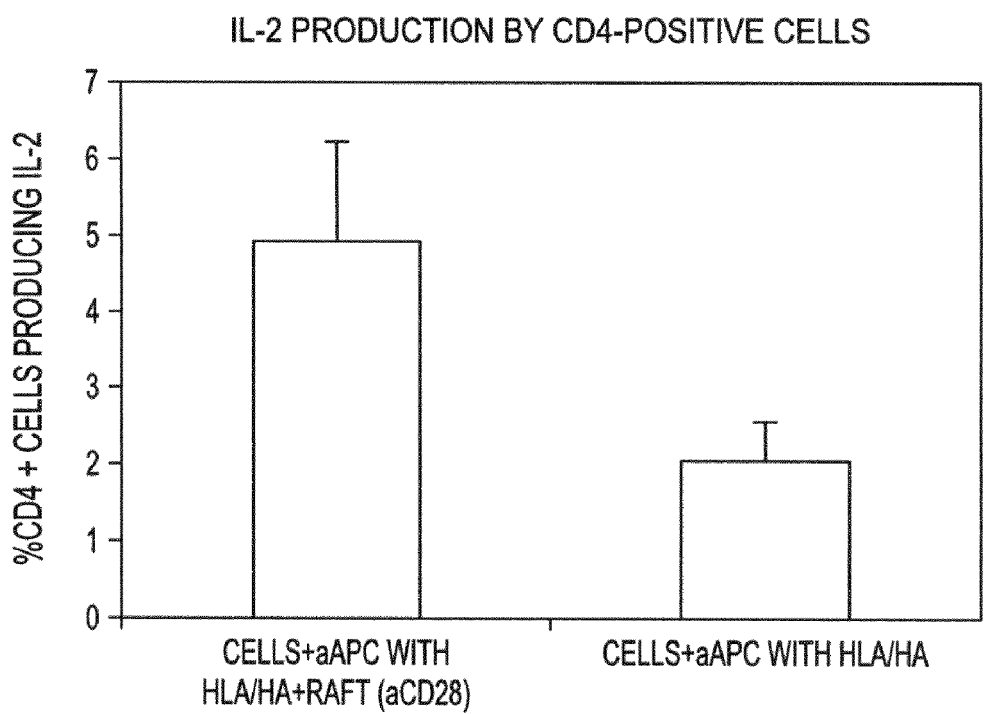
FIG. 43 shows specific activation of CD4+ cells to express IL-2. Particularly, aAPC of the current invention provide almost a three-fold stimulation over liposome constructs not containing GM-1 based rafts.

To demonstrate the capability of our invention to modulate antigen specific T cell responses, we incubated CD4+ cells from a flu-vaccinated donor with aAPC containing high density micromembrane domains expressing HLA/HA complexes, with or without costimulatory molecules, and compared CD69 expression and IL-2 production with prior art (i.e. liposomes in which HLA/HA peptide complexes were randomly distributed on the surface). as shown in FIGS. 42 and 43 such responses can be specific in nature. In FIG. 42 CD69 production by CD4+ cells is significantly greater using aAPC of the current invention wherein the aAPC contain HLA and HA and anti CD28 as compared to non-GM-1 based liposomes. FIG. 43 provides similar results for IL-2 expression. In both cases, specific stimulation using the aAPC of the current invention is approaching 3 fold increases in stimulation over that of non raft liposomes.

These results therefore demonstrate the superiority of our technology over prior approaches. aAPC engineered to contain micromembrane domains can modulate in a specific fashion antigen specific T cells responses, thus providing an important tool for ex vivo therapeutic, diagnostic and research applications.

Modifications and other embodiments of the invention will be apparent to those skilled in the art to which this invention relates having the benefit of the foregoing teachings, descriptions, and associated drawings. The present invention is therefore not to be limited to the specific embodiments disclosed but is to include modifications and other embodiments which are within the scope of the appended claims. All references are herein incorporated by reference.

All patents and patent applications, publications, scientific articles, and other referenced materials mentioned in this specification are indicative of the levels of skill of those skilled in the art to which the invention pertains, and each of which is hereby incorporated by reference to the same extent as if each reference had been incorporated by reference in its entirety individually. Applicants reserve the right to physically incorporate into this specification any and all materials and information from any such patents and patent applications, publications, scientific articles, electronically available information, and other referenced materials or documents.

The specific methods and products described in this specification are representative of preferred embodiments and are exemplary and not intended as limitations on the scope of the invention, and it is understood that the terminology used herein is for the purpose of describing particular embodiments only and is not intended to limit the scope of the present invention which will be limited only by the appended claims. Other objects, aspects, and embodiments will occur to those skilled in the art upon consideration of this specification and are encompassed within the spirit of the invention as defined by the scope of the claims. It is understood that this invention is not limited to the particular materials and methods described, and it will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Also, the terms "comprising", "including", "containing", etc. are to be read expansively and without limitation. It must be noted that as used herein and in the appended claims, the singular forms "a", "an", and "the" include plural reference unless the context clearly dictates otherwise.

The terms and expressions that have been employed are used as terms of description and not of limitation, and there is no intent in the use of such terms and expressions to exclude any now-existing or later-developed equivalent of the features shown and described or portions thereof, but it is recognized that various modifications are possible within the scope of the invention as claimed. Thus, it will be understood that although the present invention has been specifically disclosed by preferred embodiments and optional features, modification and/or variation of the disclosed elements may be resorted to by those skilled in the art, and that such modifications and variations are within the scope of the invention as claimed.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of isolating antigen-specific T cells, comprising:

a) providing to a sample comprising T cells capable of binding a specific antigen of interest a population of artificial APC's comprising said antigen of interest bound to an MHC component to form an MHC antigen component, said artificial APC further comprising a liposome comprising a lipid bilayer, wherein the lipid bilayer is comprised of neutral phospholipids and cholesterol; at least one GM-1 ganglioside molecule disposed in the lipid bilayer; a cholera toxin beta subunit bound to a GM-1 ganglioside molecule; wherein said MHC:antigen component is bound to the cholera toxin beta subunit; and an accessory molecule that can stabilize an interaction between a T cell receptor and the MHC:antigen component;

b) allowing said artificial APC to bind to T cells specific for said antigen of interest to form a T cell/artificial APC complex; and c) isolating the antigen-specific T cell from the T cell/aAPC complex thereby isolating an antigen-specific T cell.

2. A method of claim 1 wherein said accessory molecule is selected from the group consisting of LFA-1, CD11a/18, CD54(ICAM-1), CD 106(VCAM), CD49d(VLA-4).

* * * * *

SEQUENCE LISTING

<160> NUMBER OF SEQ ID NOS: 24

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide derived from third hyper V region of IE
      molecule Mus musculus

<400> SEQUENCE: 1

Ala Ser Phe Glu Ala Gln Gly Ala Leu Ala Asn Ile Ala Val Asp Lys
  1               5                  10                  15

Ala

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide derived from bole I protein of Epstein
      Barr virus

<400> SEQUENCE: 2

Thr Arg Asp Asp Ala Glu Tyr Leu Leu Gly Arg Glu Ser Val Leu
  1               5                  10                  15

<210> SEQ ID NO 3
<211> LENGTH: 16
<212> TYPE: PRT

```
<213> ORGANISM: Artificial Sequence
<220> FEATURE:
<223> OTHER INFORMATION: Description of Artificial Sequence: Synthetic
      peptide derived from the hemophilus influenza
      virus

<400> SEQUENCE: 3

Thr Ser Phe Pro Met Arg Gly Asp Leu Ala Lys Arg Glu Pro Asp Lys
 1               5                  10                  15

<210> SEQ ID NO 4
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide derived from the TCR receptor gene of Mus
      musculus

<400> SEQUENCE: 4

Leu His Ile Ser Ala Val Asp Pro Glu Asp Ser Ala Val Tyr Phe Cys
 1               5                  10                  15

Ala Ser Ser Gln Glu Phe Phe Ser Ser Tyr Glu Gln Tyr Phe Gly Pro
             20                  25                  30

Gly Thr Arg Leu
         35

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide derived from the influenza virus

<400> SEQUENCE: 5

Gly Ile Leu Gly Phe Val Phe Thr Leu
 1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide derived from the influenza virus

<400> SEQUENCE: 6

Val Lys Leu Gly Glu Phe Tyr Asn Gln
 1               5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (2)
<223> OTHER INFORMATION: cyclohexylalanine

<400> SEQUENCE: 7

Lys Xaa Val Ala Ala Trp Thr Leu Lys Ala Ala
 1               5                  10
```

-continued

```
<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide derived from the influenza virus

<400> SEQUENCE: 8

Pro Lys Tyr Val Lys Gln Asn Thr Leu Lys Leu Ala Thr
 1               5                  10

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide derived from the ovalbumin of Mus musculus

<400> SEQUENCE: 9

Ile Ser Gln Ala Val His Ala Ala His Ala Glu Ile Asn Glu Ala Gly
 1               5                  10                  15

Arg

<210> SEQ ID NO 10
<211> LENGTH: 15
<212> TYPE: PRT
<213> ORGANISM: Escherichia coli

<400> SEQUENCE: 10

Gln Lys Arg Ala Ala Tyr Asp Gln Tyr Gly His Ala Ala Phe Glu
 1               5                  10                  15

<210> SEQ ID NO 11
<211> LENGTH: 15
<212> TYPE: PRT
<213> ORGANISM: Homo sapiens

<400> SEQUENCE: 11

Gln Lys Arg Ala Ala Val Asp Thr Tyr Cys Arg His Asn Tyr Gly
 1               5                  10                  15

<210> SEQ ID NO 12
<211> LENGTH: 9
<212> TYPE: PRT
<213> ORGANISM: Homo sapiens

<400> SEQUENCE: 12

Gly Ile Leu Gly Phe Val Phe Thr Leu
 1               5

<210> SEQ ID NO 13
<211> LENGTH: 9
<212> TYPE: PRT
<213> ORGANISM: Homo sapiens

<400> SEQUENCE: 13

Val Lys Leu Gly Glu Phe Tyr Asn Gln
 1               5

<210> SEQ ID NO 14
<211> LENGTH: 13
<212> TYPE: PRT
<213> ORGANISM: Homo sapiens
```

-continued

```
<400> SEQUENCE: 14

Pro Lys Tyr Val Lys Gln Asn Thr Leu Lys Leu Ala Thr
1               5                   10

<210> SEQ ID NO 15
<211> LENGTH: 313
<212> TYPE: PRT
<213> ORGANISM: Artificial Sequence
<220> FEATURE:
<223> OTHER INFORMATION: Description of Artificial Sequence: Synthetic
      fusion construct with human and bacterial
      sequences

<400> SEQUENCE: 15

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
                20                  25                  30

Ser Gly Val Ile His Val Thr Lys Glu Val Lys Glu Val Ala Thr Leu
            35                  40                  45

Ser Cys Gly His Asn Val Ser Val Glu Leu Ala Gln Thr Arg Ile
        50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Glu Phe Gly Gly Ser Gly Gly
        195                 200                 205

Ser Ala Thr Pro Gln Asn Ile Thr Asp Leu Cys Ala Glu Tyr His Asn
    210                 215                 220

Thr Gln Ile His Thr Leu Asn Asp Lys Ile Phe Ser Tyr Thr Glu Ser
225                 230                 235                 240

Leu Ala Gly Lys Arg Glu Met Ala Ile Ile Thr Phe Lys Asn Gly Ala
                245                 250                 255

Thr Phe Gln Val Glu Val Pro Gly Ser Gln His Ile Asp Ser Gln Lys
            260                 265                 270

Lys Ala Ile Glu Arg Met Lys Asp Thr Leu Arg Ile Ala Tyr Leu Thr
        275                 280                 285

Glu Ala Lys Val Glu Lys Leu Cys Val Trp Asn Asn Lys Thr Pro His
    290                 295                 300

Ala Ile Ala Ala Ile Ser Met Ala Asn
305                 310

<210> SEQ ID NO 16
```

<211> LENGTH: 942
<212> TYPE: DNA
<213> ORGANISM: Artificial Sequence
<220> FEATURE:
<223> OTHER INFORMATION: Description of Artificial Sequence: Synthetic fusion construct with human and bacterial sequences

<400> SEQUENCE: 16

```
atgggccaca cacggaggca gggaacatca ccatccaagt gtccatacct caatttcttt     60
cagctcttgg tgctggctgg tctttctcac ttctgttcag gtgttatcca cgtgaccaag    120
gaagtgaaag aagtggcaac gctgtcctgt ggtcacaatg tttctgttga agagctggca    180
caaactcgca tctactggca aaaggagaag aaaatggtgc tgactatgat gtctggggac    240
atgaatatat ggcccgagta caagaaccgg accatctttg atatcactaa taacctctcc    300
attgtgatcc tggctctgcg cccatctgac gagggcacat acgagtgtgt tgttctgaag    360
tatgaaaaag acgctttcaa gcgggaacac ctggctgaag tgacgttatc agtcaaagct    420
gacttcccta cacctagtat atctgacttt gaaattccaa cttctaatat tagaaggata    480
atttgctcaa cctctggagg ttttccagag cctcacctct cctggttgga aaatggagaa    540
gaattaaatg ccatcaacac aacagtttcc caagatcctg aaactgagct ctatgctgtt    600
agcgaattcg gcggctccgg tggtagcgcc acacctcaaa atattactga tttgtgtgca    660
gaataccaca cacacaaat acatacgcta atgataaga tattttcgta tacagaatct    720
ctagctggaa aaagagagat ggctatcatt acttttaaga atggtgcaac ttttcaagta    780
gaagtaccag gtagtcaaca tatagattca caaaaaaag cgattgaaag gatgaaggat    840
accctgagga ttgcatatct tactgaagct aaagtcgaaa agttatgtgt atggaataat    900
aaaacgcctc atgcgattgc cgcaattagt atggcaaatt aa                       942
```

<210> SEQ ID NO 17
<211> LENGTH: 1056
<212> TYPE: DNA
<213> ORGANISM: Artificial Sequence
<220> FEATURE:
<223> OTHER INFORMATION: Description of Artificial Sequence: Synthetic fusion construct with human and bacterial sequences

<400> SEQUENCE: 17

```
atgggactga gtaacattct ctttgtgatg gccttcctgc tctctggtgc tgctcctctg     60
aagattcaag cttatttcaa tgagactgca gacctgccat gccaatttgc aaactctcaa    120
aaccaaagcc tgagtgagct agtagtattt tggcaggacc aggaaaactt ggttctgaat    180
gaggtatact taggcaaaga gaaatttgac agtgttcatt ccaagtatat gggccgcaca    240
agttttgatt cggacagttg gaccctgaga cttcacaatc ttcagatcaa ggacaagggc    300
ttgtatcaat gtatcatcca tcacaaaaag cccacaggaa tgattcgcat ccaccagatg    360
aattctgaac tgtcagtgct tgctaacttc agtcaacctg aaatagtacc aatttctaat    420
ataacagaaa atgtgtacat aaatttgacc tgctcatcta tacacggtta cccagaacct    480
aagaagatga gtgttttgct aagaaccaag aattcaacta tcgagtatga tggtattatg    540
cagaaatctc aagataatgt cacagaactg tacgacgttt ccatcagctt gtctgtttca    600
ttccctgatg ttacgagcaa tatgaccatc ttctgtattc tggaaactga caagacgcgg    660
cttttatctt caccttctc tatagagctt gaggaccctc agcctccccc agaccacgaa    720
ttcggcggct ccggtggtag cgccacacct caaaatatta ctgatttgtg tgcagaatac    780
```

```
cacaacacac aaatacatac gctaaatgat aagatatttt cgtatacaga atctctagct    840
ggaaaaagag agatggctat cattactttt aagaatggtg caacttttca agtagaagta    900
ccaggtagtc aacatataga ttcacaaaaa aaagcgattg aaaggatgaa ggataccctg    960
aggattgcat atcttactga agctaaagtc gaaaagttat gtgtatggaa taataaaacg   1020
cctcatgcga ttgccgcaat tagtatggca aattaa                             1056
```

<210> SEQ ID NO 18
<211> LENGTH: 351
<212> TYPE: PRT
<213> ORGANISM: Artificial Sequence
<220> FEATURE:
<223> OTHER INFORMATION: Description of Artificial Sequence: Synthetic
      fusion construct with human and bacterial
      sequences

<400> SEQUENCE: 18

```
Met Gly Leu Ser Asn Ile Leu Phe Val Met Ala Phe Leu Leu Ser Gly
 1               5                  10                  15

Ala Ala Pro Leu Lys Ile Gln Ala Tyr Phe Asn Glu Thr Ala Asp Leu
            20                  25                  30

Pro Cys Gln Phe Ala Asn Ser Gln Asn Gln Ser Leu Ser Glu Leu Val
        35                  40                  45

Val Phe Trp Gln Asp Gln Glu Asn Leu Val Leu Asn Glu Val Tyr Leu
    50                  55                  60

Gly Lys Glu Lys Phe Asp Ser Val His Ser Lys Tyr Met Gly Arg Thr
65                  70                  75                  80

Ser Phe Asp Ser Asp Ser Trp Thr Leu Arg Leu His Asn Leu Gln Ile
                85                  90                  95

Lys Asp Lys Gly Leu Tyr Gln Cys Ile Ile His His Lys Lys Pro Thr
            100                 105                 110

Gly Met Ile Arg Ile His Gln Met Asn Ser Gly Leu Ser Val Leu Ala
        115                 120                 125

Asn Phe Ser Gln Pro Glu Ile Val Pro Ile Ser Asn Ile Thr Glu Asn
    130                 135                 140

Val Tyr Ile Asn Leu Thr Cys Ser Ser Ile His Gly Tyr Pro Glu Pro
145                 150                 155                 160

Lys Lys Met Ser Val Leu Leu Arg Thr Lys Asn Ser Thr Ile Glu Tyr
                165                 170                 175

Asp Gly Ile Met Gln Lys Ser Gln Asp Asn Val Thr Glu Leu Tyr Asp
            180                 185                 190

Val Ser Ile Ser Leu Ser Val Ser Phe Pro Asp Val Thr Ser Asn Met
        195                 200                 205

Thr Ile Phe Cys Ile Leu Glu Thr Asp Lys Thr Arg Leu Leu Ser Ser
    210                 215                 220

Pro Phe Ser Ile Glu Leu Glu Asp Pro Gln Pro Pro Asp His Glu
225                 230                 235                 240

Phe Gly Gly Ser Gly Gly Ser Ala Thr Pro Gln Asn Ile Thr Asp Leu
                245                 250                 255

Cys Ala Glu Tyr His Asn Thr Gln Ile His Thr Leu Asn Asp Lys Ile
            260                 265                 270

Phe Ser Tyr Thr Glu Ser Leu Ala Gly Lys Arg Glu Met Ala Ile Ile
        275                 280                 285

Thr Phe Lys Asn Gly Ala Thr Phe Gln Val Glu Val Pro Gly Ser Gln
    290                 295                 300
```

His Ile Asp Ser Gln Lys Lys Ala Ile Glu Arg Met Lys Asp Thr Leu
305                 310                 315                 320

Arg Ile Ala Tyr Leu Thr Glu Ala Lys Val Glu Lys Leu Cys Val Trp
                325                 330                 335

Asn Asn Lys Thr Pro His Ala Ile Ala Ala Ile Ser Met Ala Asn
            340                 345                 350

<210> SEQ ID NO 19
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Ala Gln Leu Glu Trp Glu Leu Gln Ala Leu Glu Lys Glu Asn Ala
1               5                   10                  15

Gln Leu Glu Trp Glu Leu Gln Ala Leu Glu Lys Glu Leu Ala Gln
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Gln Leu Lys Lys Lys Leu Gln Ala Leu Lys Lys Lys Asn Ala Gln
1               5                   10                  15

Leu Lys Gln Lys Leu Gln Ala Leu Lys Lys Lys Leu Ala Gln
            20                  25                  30

<210> SEQ ID NO 21
<211> LENGTH: 1095
<212> TYPE: DNA
<213> ORGANISM: Artificial Sequence
<220> FEATURE:
<223> OTHER INFORMATION: Description of Artificial Sequence: Synthetic
      fusion construct with human and bacterial
      sequences

<400> SEQUENCE: 21
atggccataa gtggagtccc tgtgctagga ttttcatca tagctgtgct gatgagcgct     60
caggaatcat gggctatcaa agaagaacat gtgatcatcc aggccgagtt ctatctgaat   120
cctgaccaat caggcgagtt tatgtttgac tttgatggtg atgagatttt ccatgtggat   180
atggcaaaga aggagacggt ctggcggctt gaagaatttg gacgatttgc cagctttgag   240
gctcaaggtg cattggccaa catagctgtg acaaagcca acctggaaat catgacaaag   300
cgctccaact atactccgat caccaatgta cctccagagg taactgtgct cacgaacagc   360
cctgtggaac tgagagagcc caacgtcctc atctgtttca tcgacaagtt caccccacca   420
gtggtcaatg tcacgtggct tcgaaatgga aaacctgtca ccacaggagt gtcagagaca   480
gtcttcctgc caggaagga ccaccttttc cgcaagttcc actatctccc cttcctgccc   540
tcaactgagg acgtttacga ctgcagggtg gagcactggg gcttggatga gcctcttctc   600
aagcactggg agtttgatgc tccaagccct ctcccagaga ctacagagga attcggtggt   660
tccggtggtt ccgcgcagct ggaatgggaa ctgcaggcgc tggaaaaaga aaacgcgcag   720

```
ctggaatggg aactgcaggc gctggaaaaa gaactggcgc agggcggctc cggtggtagc    780
gccacacctc aaaatattac tgatttgtgt gcagaatacc acaacacaca aatacatacg    840
ctaaatgata agatattttc gtatacagaa tctctagctg aaaaagaga gatggctatc      900 attactttta agaatggtgc aacttttcaa gtagaagtac caggtagtca acatatagat    960
tcacaaaaaa aagcgattga aaggatgaag gataccctga ggattgcata tcttactgaa    1020
gctaaagtcg aaaagttatg tgtatggaat aataaaacgc ctcatgcgat tgccgcaatt    1080
agtatggcaa attaa                                                      1095
```

<210> SEQ ID NO 22
<211> LENGTH: 364
<212> TYPE: PRT
<213> ORGANISM: Artificial Sequence
<220> FEATURE:
<223> OTHER INFORMATION: Description of Artificial Sequence: Synthetic
      fusion construct with human and bacterial
      sequences

<400> SEQUENCE: 22

```
Met Ala Ile Ser Gly Val Pro Val Leu Gly Phe Phe Ile Ile Ala Val
 1               5                  10                  15

Leu Met Ser Ala Gln Glu Ser Trp Ala Ile Lys Glu Glu His Val Ile
            20                  25                  30

Ile Gln Ala Glu Phe Tyr Leu Asn Pro Asp Gln Ser Gly Glu Phe Met
        35                  40                  45

Phe Asp Phe Asp Gly Asp Glu Ile Phe His Val Asp Met Ala Lys Lys
    50                  55                  60

Glu Thr Val Trp Arg Leu Glu Glu Phe Gly Arg Phe Ala Ser Phe Glu
65                  70                  75                  80

Ala Gln Gly Ala Leu Ala Asn Ile Ala Val Asp Lys Ala Asn Leu Glu
                85                  90                  95

Ile Met Thr Lys Arg Ser Asn Tyr Thr Pro Ile Thr Asn Val Pro Pro
           100                 105                 110

Glu Val Thr Val Leu Thr Asn Ser Pro Val Glu Leu Arg Glu Pro Asn
       115                 120                 125

Val Leu Ile Cys Phe Ile Asp Lys Phe Thr Pro Pro Val Val Asn Val
   130                 135                 140

Thr Trp Leu Arg Asn Gly Lys Pro Val Thr Thr Gly Val Ser Glu Thr
145                 150                 155                 160

Val Phe Leu Pro Arg Glu Asp His Leu Phe Arg Lys Phe His Tyr Leu
                165                 170                 175

Pro Phe Leu Pro Ser Thr Glu Asp Val Tyr Asp Cys Arg Val Glu His
            180                 185                 190

Trp Gly Leu Asp Glu Pro Leu Leu Lys His Trp Glu Phe Asp Ala Pro
        195                 200                 205

Ser Pro Leu Pro Glu Thr Thr Glu Glu Phe Gly Gly Ser Gly Gly Ser
    210                 215                 220

Ala Gln Leu Glu Trp Glu Leu Gln Ala Leu Glu Lys Glu Asn Ala Gln
225                 230                 235                 240

Leu Glu Trp Glu Leu Gln Ala Leu Glu Lys Glu Leu Ala Gln Gly Gly
                245                 250                 255

Ser Gly Gly Ser Ala Thr Pro Gln Asn Ile Thr Asp Leu Cys Ala Glu
            260                 265                 270

Tyr His Asn Thr Gln Ile His Thr Leu Asn Asp Lys Ile Phe Ser Tyr
```

```
              275                 280                 285
Thr Glu Ser Leu Ala Gly Lys Arg Glu Met Ala Ile Ile Thr Phe Lys
    290                 295                 300
Asn Gly Ala Thr Phe Gln Val Glu Val Pro Gly Ser Gln His Ile Asp
305                 310                 315                 320
Ser Gln Lys Lys Ala Ile Glu Arg Met Lys Asp Thr Leu Arg Ile Ala
                325                 330                 335
Tyr Leu Thr Glu Ala Lys Val Glu Lys Leu Cys Val Trp Asn Asn Lys
            340                 345                 350
Thr Pro His Ala Ile Ala Ala Ile Ser Met Ala Asn
        355                 360

<210> SEQ ID NO 23
<211> LENGTH: 801
<212> TYPE: DNA
<213> ORGANISM: Artificial Sequence
<220> FEATURE:
<223> OTHER INFORMATION: Description of Artificial Sequence: Synthetic
      fusion construct with human and bacterial
      sequences

<400> SEQUENCE: 23
atggtgtgtc tgaagttccc tggaggctcc tgcatggcag ctctgacagt gacactgatg      60
gtgctgagct ccccactggc tttggctggg acacccgac cacgtttctt ggagcaggtt      120
aaacatgagt gtcatttctt caacgggacg gagcgggtgc ggttcctgga cagatacttc      180
tatcaccaag aggagtacgt gcgcttcgac agcgacgtgg gggagtaccg ggcggtgacg      240
gagctggggc ggcctgatgc cgagtactgg aacagccaga aggacctcct ggagcagaag      300
cgggccgcgg tggacaccta ctgcagacac aactacgggg ttggtgagag cttcacagtg      360
cagcggcgag tctatcctga ggtgactgtg tatcctgcaa agacccagcc cctgcagcac      420
cacaacctcc tggtctgctc tgtgaatggt ttctatccag cagcattga agtcaggtgg      480 gactggacct tccagaccct ggtgatgctg aaacagttc ctcggagtgg agaggtttac      540
acctgccaag tggagcaccc aagcctgacg agccctctca cagtggaatg agagcacgg      600 tctgaatctg cacagagcaa gggcggctcc ggtggtagcg cccagctgaa gaagaaactc      660
caggctctga aaaaaagaa tgcccagctc aagcagaagc tgcaggccct gaagaaaaag      720
ctggctcagg gttccggtgg ttccgcgggt ggtggtttga cgacatcttc gaagctcag      780 aaaatcgaat ggcactaata a                                                801

<210> SEQ ID NO 24
<211> LENGTH: 285
<212> TYPE: PRT
<213> ORGANISM: Artificial Sequence
<220> FEATURE:
<223> OTHER INFORMATION: Description of Artificial Sequence: Synthetic
      fusion construct with human and bacterial
      sequences

<400> SEQUENCE: 24

Met Val Cys Leu Lys Phe Pro Gly Gly Ser Cys Met Ala Ala Leu Thr
1               5                   10                  15
Val Thr Leu Met Val Leu Ser Ser Pro Leu Ala Leu Ala Gly Asp Thr
            20                  25                  30
Arg Pro Arg Phe Leu Glu Gln Val Lys His Glu Cys His Phe Phe Asn
        35                  40                  45
Gly Thr Glu Arg Val Arg Phe Leu Asp Arg Tyr Phe Tyr His Gln Glu
```

-continued

```
                50                  55                  60
Glu Tyr Val Arg Phe Asp Ser Asp Val Gly Glu Tyr Arg Ala Val Thr
65                  70                  75                  80

Glu Leu Gly Arg Pro Asp Ala Glu Tyr Trp Asn Ser Gln Lys Asp Leu
                85                  90                  95

Leu Glu Gln Lys Arg Ala Ala Val Asp Thr Tyr Cys Arg His Asn Tyr
                100                 105                 110

Gly Val Gly Glu Ser Phe Thr Val Gln Arg Arg Val Tyr Pro Gly Val
                115                 120                 125

Thr Val Tyr Pro Ala Lys Thr Gln Pro Leu Gln His His Asn Leu Leu
    130                 135                 140

Val Cys Ser Val Asn Gly Phe Tyr Pro Gly Ser Ile Glu Val Arg Trp
145                 150                 155                 160

Phe Arg Asn Gly Gln Glu Glu Lys Thr Gly Val Val Ser Thr Gly Leu
                165                 170                 175

Ile Gln Asn Gly Asp Trp Thr Phe Gln Thr Leu Val Met Leu Glu Thr
                180                 185                 190

Val Pro Arg Ser Gly Glu Val Tyr Thr Cys Gln Val Glu His Pro Ser
    195                 200                 205

Leu Thr Ser Pro Leu Thr Val Glu Trp Arg Ala Arg Ser Glu Ser Ala
    210                 215                 220

Gln Ser Lys Gly Gly Ser Gly Gly Ser Ala Gln Leu Lys Lys Lys Leu
225                 230                 235                 240

Gln Ala Leu Lys Lys Lys Asn Ala Gln Leu Lys Gln Lys Leu Gln Ala
                245                 250                 255

Leu Lys Lys Lys Leu Ala Gln Gly Ser Gly Gly Ser Ala Gly Gly Gly
                260                 265                 270

Leu Asn Asp Ile Phe Glu Ala Gln Lys Ile Glu Trp His
                275                 280                 285
```